(12) United States Patent
Yamaguchi et al.

(10) Patent No.: US 9,551,928 B2
(45) Date of Patent: *Jan. 24, 2017

(54) ACTINIC-RAY- OR RADIATION-SENSITIVE RESIN COMPOSITION AND METHOD OF FORMING PATTERN THEREWITH

(75) Inventors: Shuhei Yamaguchi, Haibara-gun (JP); Hisamitsu Tomeba, Haibara-gun (JP); Mitsuhiro Fujita, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 681 days.

This patent is subject to a terminal disclaimer.

(21) Appl. No.: 12/754,441

(22) Filed: Apr. 5, 2010

(65) Prior Publication Data
US 2010/0255418 A1 Oct. 7, 2010

(30) Foreign Application Priority Data

Apr. 6, 2009 (JP) ................. 2009-092418
Sep. 1, 2009 (JP) ................. 2009-201948

(51) Int. Cl.
| | | |
|---|---|---|
| G03F 7/004 | (2006.01) |
| G03F 7/38 | (2006.01) |
| C07C 303/32 | (2006.01) |
| C07C 309/14 | (2006.01) |
| C07C 309/00 | (2006.01) |
| C07C 309/10 | (2006.01) |
| C07C 309/17 | (2006.01) |
| C07C 309/42 | (2006.01) |
| C07C 311/09 | (2006.01) |
| C07C 311/48 | (2006.01) |
| C07C 381/12 | (2006.01) |
| C07D 333/46 | (2006.01) |
| C07D 333/76 | (2006.01) |
| G03F 7/039 | (2006.01) |
| G03F 7/20 | (2006.01) |

(52) U.S. Cl.
CPC ........... *G03F 7/0045* (2013.01); *C07C 303/32* (2013.01); *C07C 309/00* (2013.01); *C07C 309/10* (2013.01); *C07C 309/14* (2013.01); *C07C 309/17* (2013.01); *C07C 309/42* (2013.01); *C07C 311/09* (2013.01); *C07C 311/48* (2013.01); *C07C 381/12* (2013.01); *C07D 333/46* (2013.01); *C07D 333/76* (2013.01); *G03F 7/0397* (2013.01); *C07C 2101/08* (2013.01); *C07C 2101/14* (2013.01); *C07C 2102/42* (2013.01); *C07C 2103/18* (2013.01); *C07C 2103/68* (2013.01); *C07C 2103/74* (2013.01); *C07C 2103/86* (2013.01); *C07C 2103/90* (2013.01); *G03F 7/0046* (2013.01); *G03F 7/2041* (2013.01); *G03F 7/38* (2013.01)

(58) Field of Classification Search
CPC ........ G03F 7/0045; G03F 7/0397; G03F 7/38; C07C 303/32; C07C 309/14; C07C 381/12
USPC .... 430/270.1, 326, 330, 910, 919, 920, 921, 430/922; 562/1–6, 30, 36, 37, 40–48, 57, 430/58, 562/66, 67, 125, 126, 400, 104, 562/105, 106; 546/1–40, 141–155; 549/13–78; 568/74, 568/75, 76, 77; 560/149, 227

See application file for complete search history.

(56) References Cited

U.S. PATENT DOCUMENTS

| | | | | |
|---|---|---|---|---|
| 5,525,453 A | * | 6/1996 | Przybilla et al. | ............. 430/170 |
| 7,390,613 B1 | * | 6/2008 | Rahman | ................. C07C 25/18 430/270.1 |
| 7,601,480 B2 | * | 10/2009 | Rahman et al. | ............ 430/270.1 |
| 8,557,499 B2 | * | 10/2013 | Yamaguchi | .......... C07D 285/15 430/270.1 |
| 8,900,794 B2 | * | 12/2014 | Aqad | ................... C07D 313/08 430/270.1 |
| 2002/0076643 A1 | * | 6/2002 | Ohsawa et al. | ............. 430/270.1 |
| 2003/0017411 A1 | * | 1/2003 | Shimada et al. | ............ 430/270.1 |
| 2004/0053158 A1 | | 3/2004 | Yamato et al. | |
| 2004/0234888 A1 | * | 11/2004 | Lamanna | .................... 430/270.1 |
| 2006/0166135 A1 | * | 7/2006 | Wada | .......................... 430/270.1 |
| 2006/0264528 A1 | | 11/2006 | Wada | |
| 2007/0148592 A1 | * | 6/2007 | Wada et al. | ................. 430/270.1 |
| 2007/0224539 A1 | * | 9/2007 | Mizutani | ............... G03F 7/0045 430/270.1 |
| 2009/0111047 A1 | * | 4/2009 | Yamashita | .................. 430/270.1 |
| 2010/0136479 A1 | * | 6/2010 | Yamaguchi | .......... C07C 309/17 430/270.1 |
| 2010/0183980 A1 | * | 7/2010 | Yamaguchi | ................ 430/281.1 |
| 2010/0233629 A1 | | 9/2010 | Wada | |
| 2013/0171567 A1 | * | 7/2013 | Aqad | ................... C07D 493/18 430/285.1 |

FOREIGN PATENT DOCUMENTS

| | | |
|---|---|---|
| JP | 07-333851 A | 12/1995 |
| JP | 2004-177486 A | 6/2004 |
| JP | 2004-526984 A | 9/2004 |
| JP | 2006-330098 A | 12/2006 |
| JP | 2007-507580 A | 3/2007 |
| JP | 2009-98509 A | 5/2009 |
| WO | 2004/107051 A2 | 12/2004 |

OTHER PUBLICATIONS

Japanese Office Action issued in application No. 2010-087299 dated Dec. 3, 2013.

* cited by examiner

*Primary Examiner* — John S Chu
(74) *Attorney, Agent, or Firm* — Sughrue Mion, PLLC

(57) ABSTRACT

According to one embodiment, An actinic-ray- or radiation-sensitive resin composition comprises a basic compound (C) having n basic groups and m groups that when exposed to actinic rays or radiation, generate an acid, provided that n and m satisfy the relationships n≥1, m≥2 and n<m.

15 Claims, 3 Drawing Sheets

(¹H NMR:CDCl₃)

(¹⁹F NMR:CDCl₃)

ACTINIC-RAY- OR RADIATION-SENSITIVE RESIN COMPOSITION AND METHOD OF FORMING PATTERN THEREWITH

CROSS-REFERENCE TO RELATED APPLICATIONS

This application is based upon and claims the benefit of priority from prior Japanese Patent Applications No. 2009-092418, filed Apr. 6, 2009; and No. 2009-201948, filed Sep. 1, 2009, the entire contents of both of which are incorporated herein by reference.

BACKGROUND OF THE INVENTION

1. Field of the Invention

The present invention relates to an actinic-ray- or radiation-sensitive resin composition employed in a semiconductor production process for an IC or the like, a circuit board production process for a liquid crystal, a thermal head or the like and other photofabrication processes, and also relates to a method of forming a pattern with the use of the composition. More particularly, the present invention relates to an actinic-ray- or radiation-sensitive resin composition that is suitable when an electron beam or far-ultraviolet rays of wavelength 250 nm or shorter, preferably 220 nm or shorter, are used as an exposure light source, and also relates to a method of forming a pattern with the use of the composition.

In the present invention, the terms "actinic rays" and "radiation" mean, for example, a mercury lamp bright line spectrum, far-ultraviolet rays as produced by an excimer laser, extreme ultraviolet rays, X-rays, an electron beam and the like; the term "light" means actinic rays or radiation.

2. Description of the Related Art

In photosensitive compositions, such as a chemical-amplification resist composition, for use in semiconductor photolithographic processing, etc., especially when an ArF excimer laser (wavelength: 193 nm) is used as a light source, it is beneficial to employ a resin having an alicyclic hydrocarbon group from the viewpoint of transparency and resistance to dry etching.

Stronger acids are demanded for the photosensitive compositions containing the resin having an alicyclic hydrocarbon group. Thus, use is made of compounds that generate perfluoroalkylsulfonic acids, such as triphenylsulfonium trifluoromethanesulfonate or the like.

However, the perfluoroalkylsulfonic acids exhibit high hydrophobicity, so that the photosensitive compositions containing the acid generators that generate these acids have poor affinity to aqueous developers. Thus, it has been likely to encounter the problems that a decrease of sensitivity is caused by deteriorated developability and development residues (scum) occur.

Patent reference 1 discloses photosensitive compositions each containing a compound that generates a specified acid having a perfluoroalkyl group connected by means of a nitrogen atom.

Patent reference 2 discloses compounds that generate a sulfonic acid having a basic nitrogen atom so as to inhibit any change of pattern line width over time from exposure to radiation to post-baking.

Further improvement of various performances, especially exposure latitude and line edge roughness performances, is demanded in accordance with the further enhancement of pattern fineness.

PRIOR ART LITERATURE

Patent Reference

[Patent reference 1] Jpn. PCT National Publication No. 2007-507580, and
[Patent reference 2] Japanese Patent 3577743.

BRIEF SUMMARY OF THE INVENTION

1. Problem to be Solved by the Invention

It is an object of the present invention to solve the problems of the technology for enhancing the performance of microphotofabrication per se using far-ultraviolet light, EUV, electron beams, etc., especially an ArF excimer laser light. It is a particular object of the present invention to provide an actinic-ray- or radiation-sensitive resin composition that excels in not only developability but also exposure latitude and line edge roughness performances.

2. Means for Solving the Problem

The inventors have conducted extensive and intensive studies with a view toward solving the above problems, and have arrived at the completion of the following present invention.

[1] An actinic-ray- or radiation-sensitive resin composition comprising a basic compound (C) having n basic groups and m groups that when exposed to actinic rays or radiation, generate an acid, provided that n and m satisfy the relationships $n \geq 1$, $m \geq 2$ and $n < m$.

[2] The actinic-ray- or radiation-sensitive resin composition according to [1], further comprising a compound (A) that when exposed to actinic rays or radiation, generates an acid.

[3] The actinic-ray- or radiation-sensitive resin composition according to [1] or [2], further comprising a resin (B) whose dissolution rate in an alkali developer is increased by the action of an acid.

[4] The actinic-ray- or radiation-sensitive resin composition according to any of [1] to [3], wherein basic compound (C) is any of those of general formula (1) below,

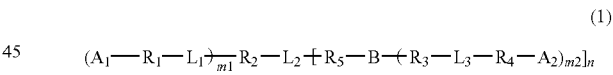

(1)

in which $A_1$ represents either a group that when exposed to actinic rays or radiation, generates an acid or a hydrogen atom; $A_2$ represents a group that when exposed to actinic rays or radiation, generates an acid; B represents a basic group; each of $R_1$, $R_3$, $R_4$ and $R_5$ independently represents a single bond, an alkylene group, a cycloalkylene group or an arylene group; $R_2$ when m1=0 represents a hydrogen atom, an alkyl group, a cycloalkyl group or an aryl group, and when $m1 \geq 1$ represents a 2- to 4-valent connecting group; each of $L_1$ and $L_3$ independently represents either a bivalent connecting group having a heteroatom or a single bond; $L_2$ represents a connecting group; and m1 is an integer of 0 to 3, m2 an integer of 0 to 2 and n an integer of 1 to 3, provided that m being the sum of groups that when exposed to actinic rays or radiation, generate an acid, represented by $A_1$ and $A_2$ is 2 or greater and $n < m$ in which n is the number of basic groups represented by B, and provided that when each of $A_1$, $A_2$, B, $R_1$, $R_3$ and $R_4$ is present in plurality, the plurality of groups may be identical to or different from each other.

[5] The actinic-ray- or radiation-sensitive resin composition according to any of [1] to [4], wherein at least one of the basic groups is an amino group.

[6] The actinic-ray- or radiation-sensitive resin composition according to any of [1] to [5], wherein at least one of the groups that when exposed to actinic rays or radiation, generate an acid is a group with an onium salt structure.

[7] The actinic-ray- or radiation-sensitive resin composition according to any of [1] to [6], wherein at least one of the groups that when exposed to actinic rays or radiation, generate an acid is any of those of general formulae (2-1) to (2-3) below,

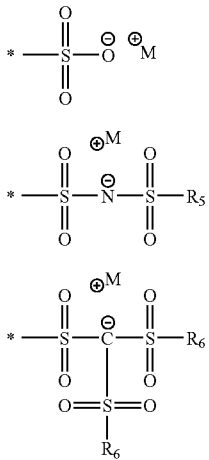

in which M⁺ represents an organic counter-cation; each of $R_5$ and $R_6$ independently represents an optionally substituted alkyl group, an optionally substituted cycloalkyl group or an optionally substituted aryl group; and * represents a site of bonding with a residue of the basic compound (C).

[8] The actinic-ray- or radiation-sensitive resin composition according to any of [1] to [6], wherein at least one of the groups that when exposed to actinic rays or radiation, generate an acid is any of those of general formulae (3-1) to (3-3) below,

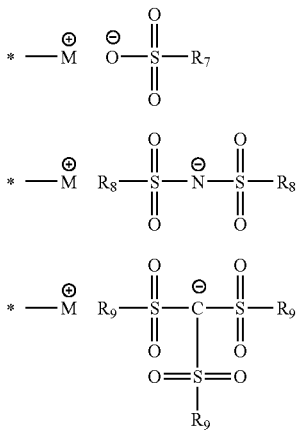

in which M⁺ represents an organic counter-cation; each of $R_7$ to $R_9$ independently represents an optionally substituted alkyl group, an optionally substituted cycloalkyl group or an optionally substituted aryl group; $R_8$ and $R_9$ may be bonded with each other to thereby form a ring; and * represents a site of bonding with a residue of the basic compound (C).

[9] The actinic-ray- or radiation-sensitive resin composition according to any of [1] to [8], wherein resin (B) whose dissolution rate in an alkali developer is increased by the action of an acid contains any of the repeating units of general formula (III) below,

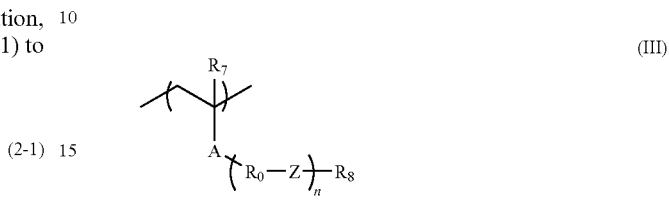

in which
A represents an ester bond (—COO—) or an amido bond (—CONH—);

$R_0$, each independently in the instance of $R_0$s, represents an optionally substituted alkylene group, an optionally substituted cycloalkylene group or a combination thereof;

Z, each independently in the instance of Zs, represents an ether bond; an ester bond, a carbonyl group, an amido bond, a urethane bond or a urea bond;

$R_8$ represents a monovalent organic group with a lactone structure;

n is the number of repetitions of the structure of formula —$R_0$—Z—, being an integer of 1 to 5; and $R_7$ represents a hydrogen atom, a halogen atom or an optionally substituted alkyl group.

[10] The actinic-ray- or radiation-sensitive resin composition according to any of [1] to [9], further comprising a hydrophobic resin (D).

[11] A method of forming a pattern, comprising molding the actinic-ray- or radiation-sensitive resin composition according to any of [1] to [10] into a film, exposing the film and developing the exposed film.

[12] A basic compound having n basic groups and m groups that when exposed to actinic rays or radiation, generate an acid, provided that n and m satisfy the relationships n≥1, m≥2 and n<m.

[13] A compound represented by general formula (1) below,

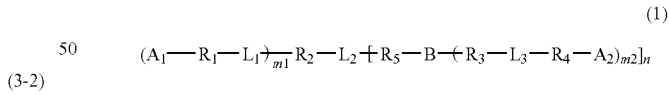

in which $A_1$ represents either a group that when exposed to actinic rays or radiation, generates an acid or a hydrogen atom; $A_2$ represents a group that when exposed to actinic rays or radiation, generates an acid; B represents a basic group; each of $R_1$, $R_3$, $R_4$ and $R_5$ independently represents a single bond, an alkylene group, a cycloalkylene group or an arylene group; $R_2$ when m1=0 represents a hydrogen atom, an alkyl group, a cycloalkyl group or an aryl group, and when m1≥1 represents a 2- to 4-valent connecting group; each of $L_1$ and $L_3$ independently represents either a bivalent connecting group having a heteroatom or a single bond; $L_2$ represents a connecting group; and m1 is an integer of 0 to 3, m2 an integer of 0 to 2 and n an integer of 1 to 3, provided that m being the sum of groups that when exposed to actinic rays or radiation, generate an acid, represented by $A_1$ and $A_2$ is 2 or greater and n<m in which n is the number of basic groups represented by B, and provided that when each of $A_1$, $A_2$, B, $R_1$, $R_3$ and $R_4$ is present in plurality, the plurality of groups may be identical to or different from each other.

The present invention has made it feasible to provide a pattern formed of an actinic-ray- or radiation-sensitive resin composition that excels in developability, exposure latitude and line edge roughness performances even when an ArF excimer laser is used as an exposure light source.

DETAILED DESCRIPTION OF THE INVENTION

Figure 1:
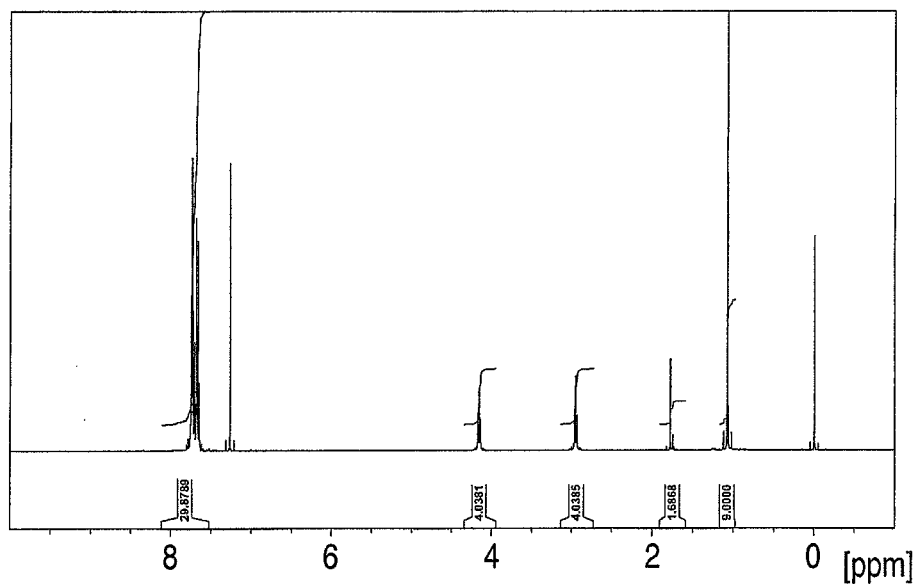
FIG. 1 is the $^1$H-NMR chart of a basic compound C-3 obtained in an Example.

The present invention will be described in detail below.

With respect to the expression of a group (atomic group) used in this specification, the expression even when there is no mention of "substituted and unsubstituted" encompasses groups not only having no substituent but also having substituents. For example, the expression "alkyl groups" encompasses not only alkyls having no substituent (unsubstituted alkyls) but also alkyls having substituents (substituted alkyls).

(C) Basic Compound

Basic compound (C) contained in the actinic-ray- or radiation-sensitive resin composition of the present invention is characterized by having n basic groups and m groups (hereinafter also referred to as "acid generating groups") that when exposed to actinic rays or radiation, generate an acid, provided that n and m satisfy the relationships n≥1, m≥2 and n<m. That is, basic compound (C) is characterized by having one or more basic groups and two or more acid generating groups, provided that the number of acid generating groups is greater than the number of basic groups.

The basic groups are not particularly limited as long as the groups exhibit basicity. An amino group and a phosphine group are preferred.

The acid generating groups are not particularly limited as long as they generate an acid when they are exposed to actinic rays or radiation. As such, use can be made of groups with the structure of an onium salt, a diazo, an oxime or the like to be mentioned hereinafter in connection with compounds (A) that when exposed to actinic rays or radiation, generate an acid. Groups with the structure of an onium salt are preferred.

It is especially preferred for the acid generating group to be any of those with the structure of an onium salt, expressed by general formulae (2-1) to (2-3) and (3-1) to (3-3) below.

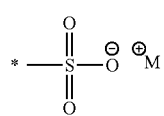

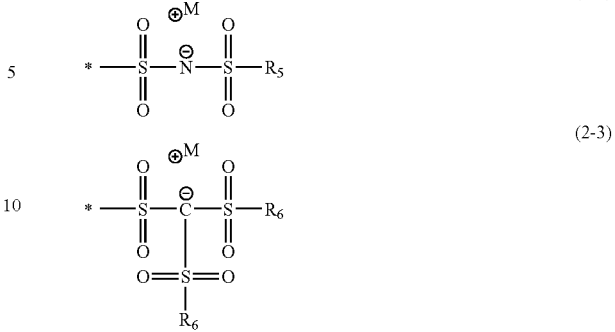

In general formulae (2-1) to (2-3), $M^+$ represents an organic counter-cation; each of $R_5$ and $R_6$ independently represents an alkyl group, a cycloalkyl group or an aryl group; and * represents a site of bonding with a residue of basic compound.

Each of the alkyl groups, cycloalkyl groups and aryl groups represented by $R_5$ and $R_6$ may have a substituent. As the substituent, there can be mentioned a fluorine atom, a sulfonamido group, an alkoxy group, a vinyl group, an acyl group, an acyloxy group or the like. A fluorine atom and a sulfonamido group are especially preferred.

As $M^+$, use can be made of organic counter-cations to be mentioned hereinafter in connection with compounds (A) that when exposed to actinic rays or radiation, generate an acid.

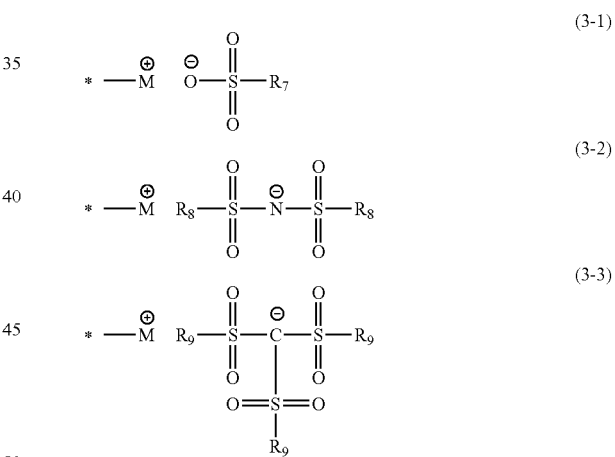

In general formulae (3-1) to (3-3), $M^+$ represents an organic counter-cation; each of $R_7$ to $R_9$ independently represents an alkyl group, a cycloalkyl group or an aryl group; and * represents a site of bonding with a residue of basic compound. $R_8$ and $R_9$ may be bonded with each other to thereby form a ring.

Each of the alkyl group, cycloalkyl group and aryl group represented by each of $R_7$ to $R_9$ may have a substituent. As the substituent, there can be mentioned a fluorine atom, a sulfonamido group, an acyl group, an acyloxy group, an alkoxy group or the like. A fluorine atom and a sulfonamido group are especially preferred.

As $M^+$, use can be made of organic counter-cations to be mentioned hereinafter in connection with compounds (A) that when exposed to actinic rays or radiation, generate an acid.

Specific examples the groups of general formulae (2-1) to (2-3) and (3-1) to (3-3) will be shown below, which however in no way limit the scope of the present invention.
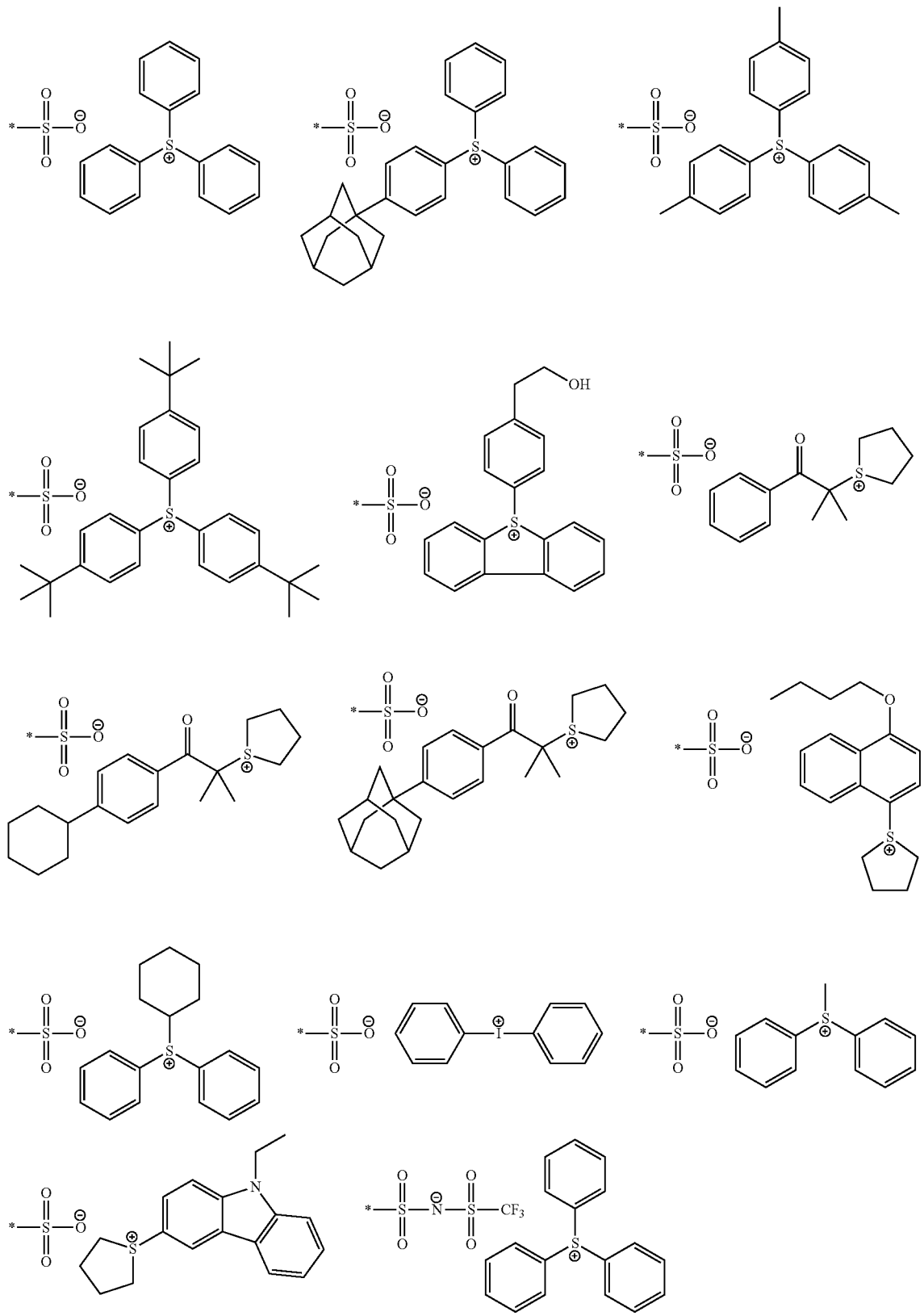

-continued
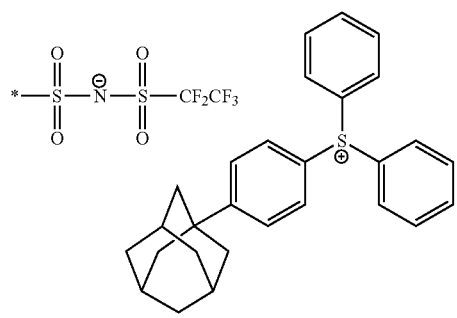
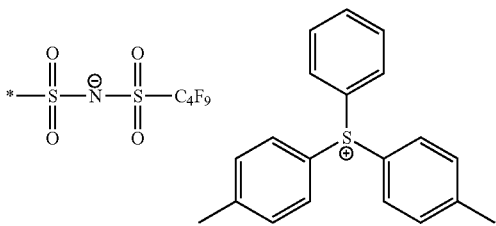
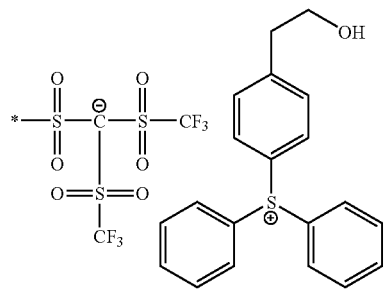
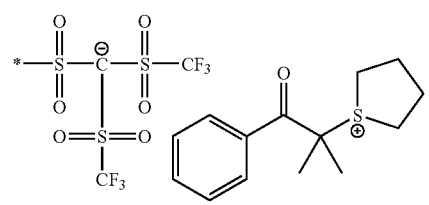
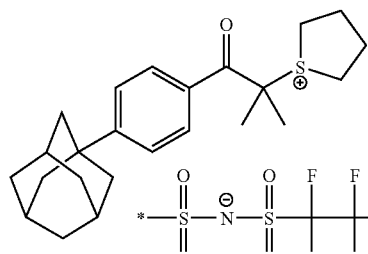
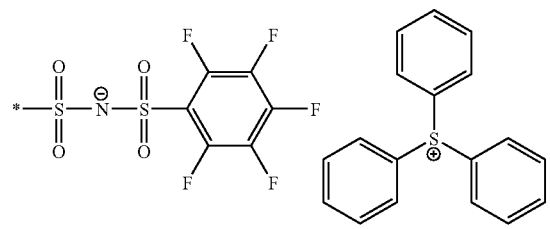
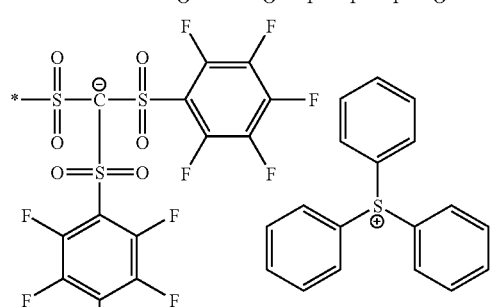
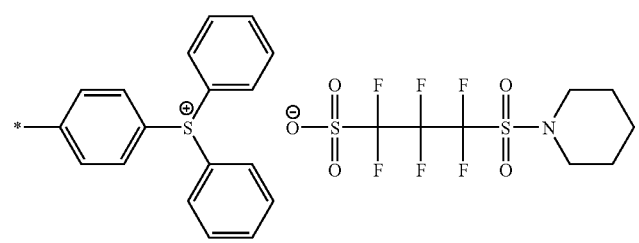
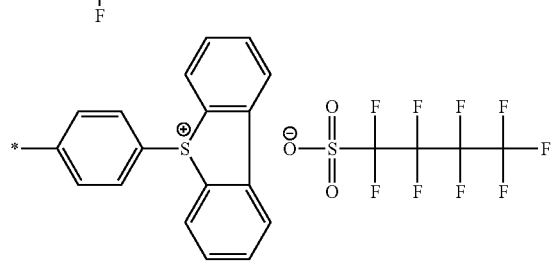
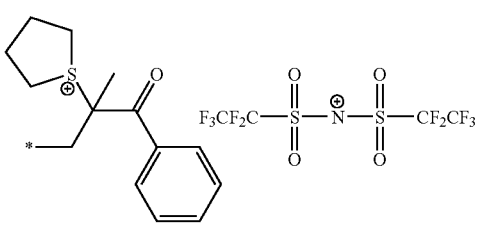
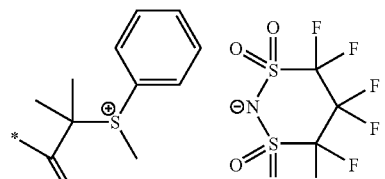
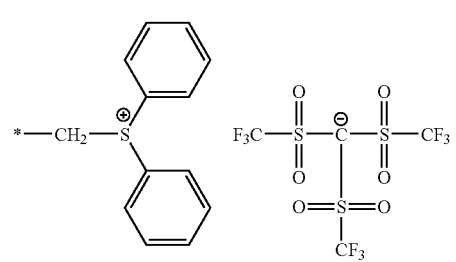

-continued

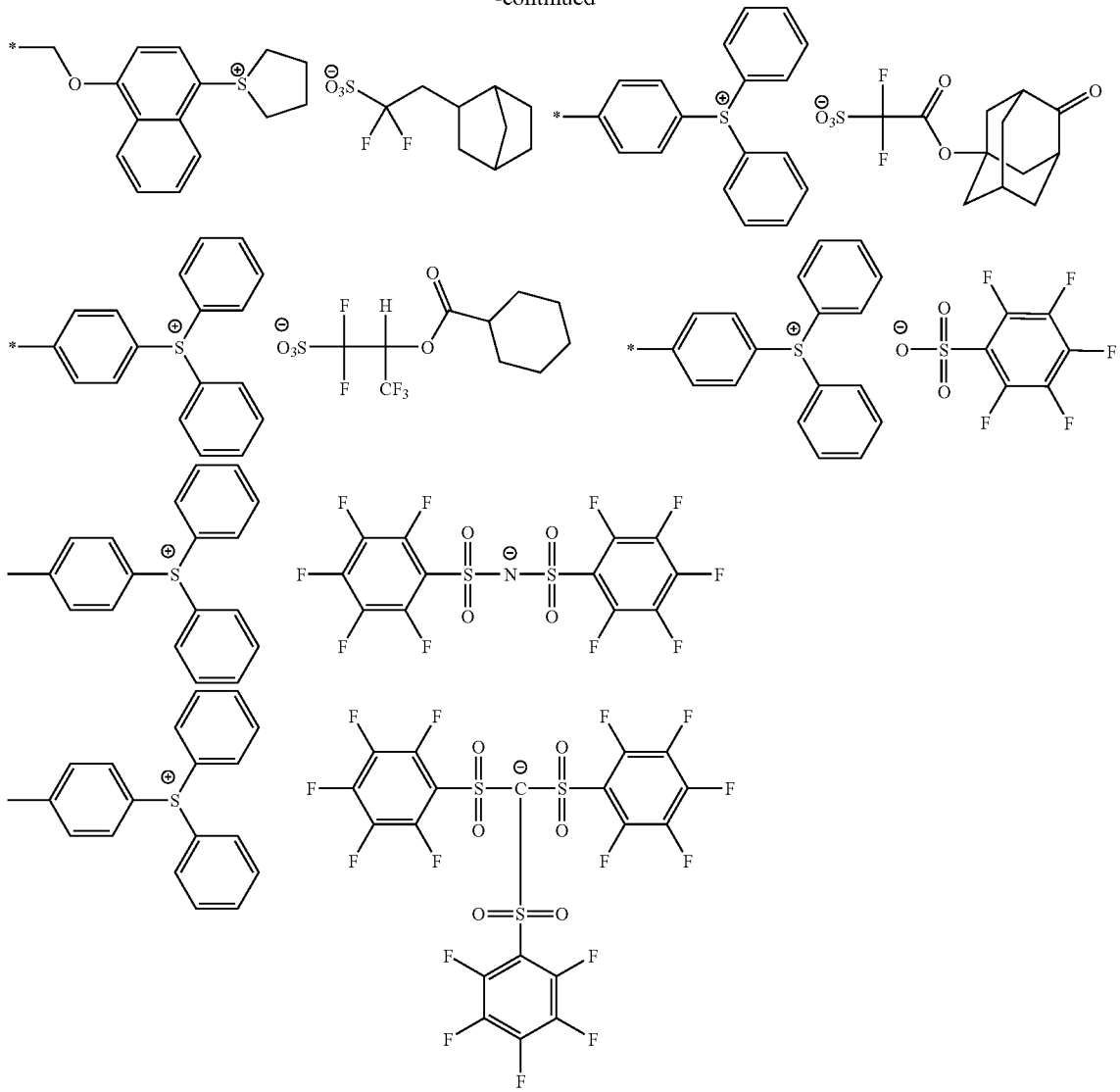

It is preferred for basic compound (C) according to the present invention in its one form to be any of the compounds of general formula (1) below.

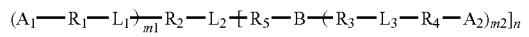

In general formula (1), $A_1$ represents either a group that when exposed to actinic rays or radiation, generates an acid or a hydrogen atom. $A_2$ represents a group that when exposed to actinic rays or radiation, generates an acid. B represents a basic group. Each of $R_1$, $R_3$, $R_4$ and $R_5$ independently represents a single bond, an alkylene group, a cycloalkylene group or an arylene group. $R_2$ when m1=0 represents a hydrogen atom, an alkyl group, a cycloalkyl group or an aryl group, and when m1≥1 represents a 2- to 4-valent connecting group. Each of $L_1$ and $L_3$ independently represents either a bivalent connecting group having a heteroatom or a single bond. $L_2$ represents a connecting group, and m1 is an integer of 0 to 3, m2 an integer of 0 to 2 and n an integer of 1 to 3.

In the general formula, m being the sum of groups that when exposed to actinic rays or radiation, generate an acid, represented by $A_1$ and $A_2$ is 2 or greater and n<m in which n is the number of basic groups represented by B. Further, when each of $A_1$, $A_2$, B, $R_1$, $R_3$ and $R_4$ is present in plurality, the plurality of groups may be identical with or different from each other.

The same description of acid generating groups as made above applies to the acid generating groups represented by $A_1$ and $A_2$.

B is not particularly limited as long as basicity is exhibited by the group. B is preferably an amino group or a phosphine group.

Each of the alkylene group, cycloalkylene group and arylene group represented by each of $R_1$, $R_3$, $R_4$ and $R_5$ may have a substituent. The substituent is preferably an electron withdrawing group. A fluorine atom, a perfluoroalkyl group (for example, a trifluoromethyl group) and the like are preferred.

As the 2- to 4-valent connecting group represented by $R_2$ when m1≥1, there can be mentioned an alkylene group having 1 to 5 carbon atoms or a tertiary or quaternary carbon atom.

The bivalent connecting group having a heteroatom represented by each of $L_1$ and $L_3$ is preferably an oxygen atom, —CO—, —COO—, —CONR—, —SO$_2$NR—, —CONRCO—, —SO$_2$NRCO—, —SO$_2$NRSO$_2$— or —OCONR—. In these formulae, R represents a hydrogen atom, an optionally substituted alkyl group, an optionally substituted cycloalkyl group or an optionally substituted aryl group.

As the connecting group represented by $L_2$, there can be mentioned an alkylene group or a tertiary or quaternary carbon atom. The alkylene group preferably has 1 to 5 carbon atoms.

When A as the acid generating group is any of those of above general formulae (2-1) to (2-3), it is preferred for each of $R_1$ and $R_4$ to have a fluorine atom as its substituent.

Specific examples of compounds (C) will be shown below, which however in no way limit the scope of the present invention.

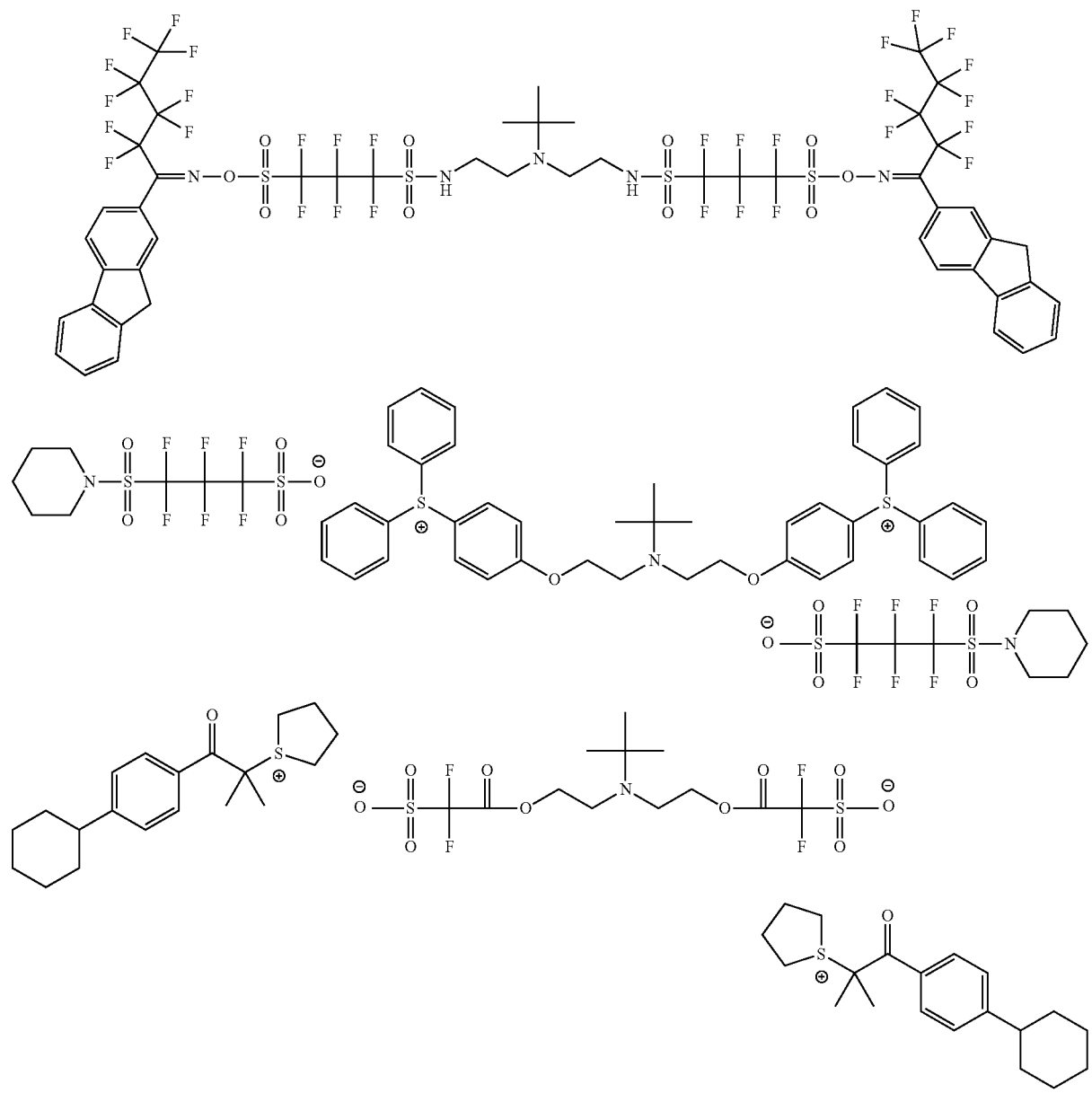

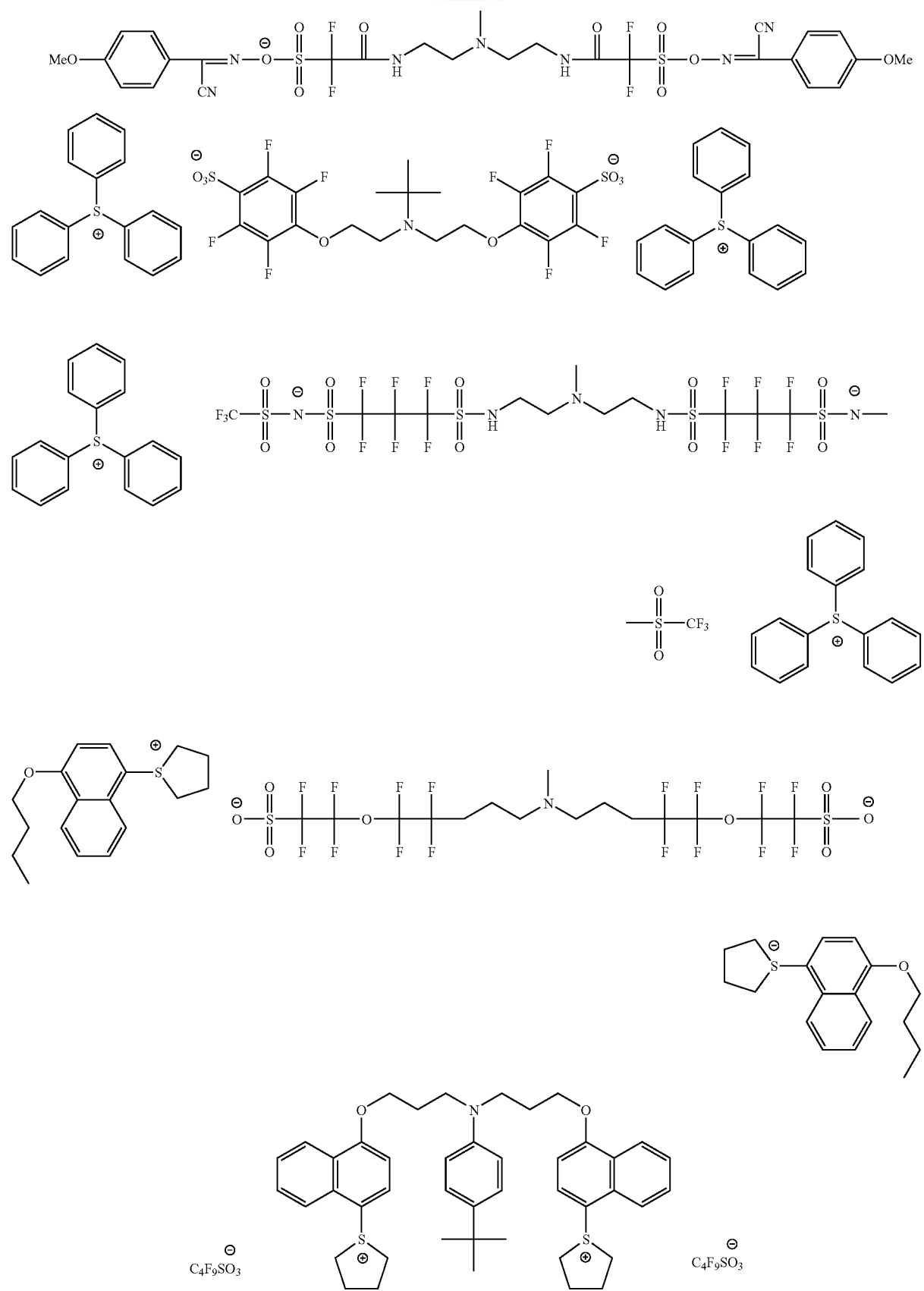

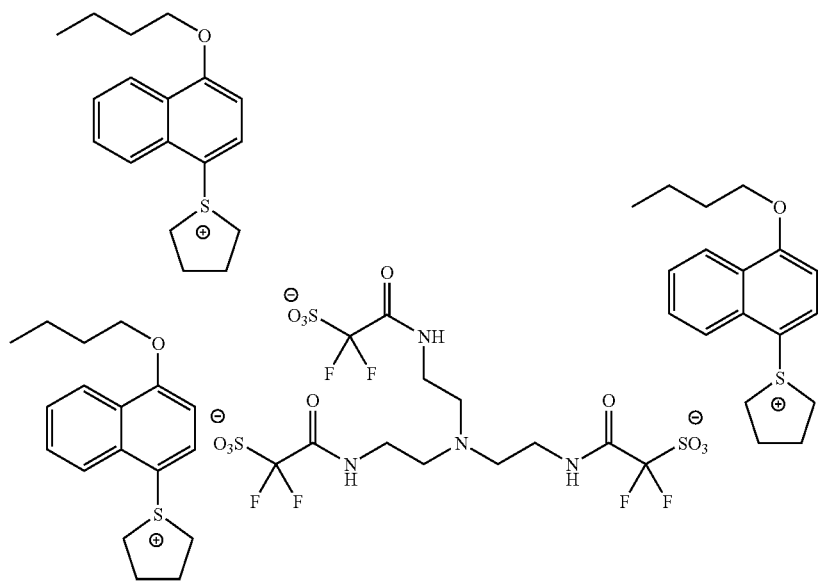
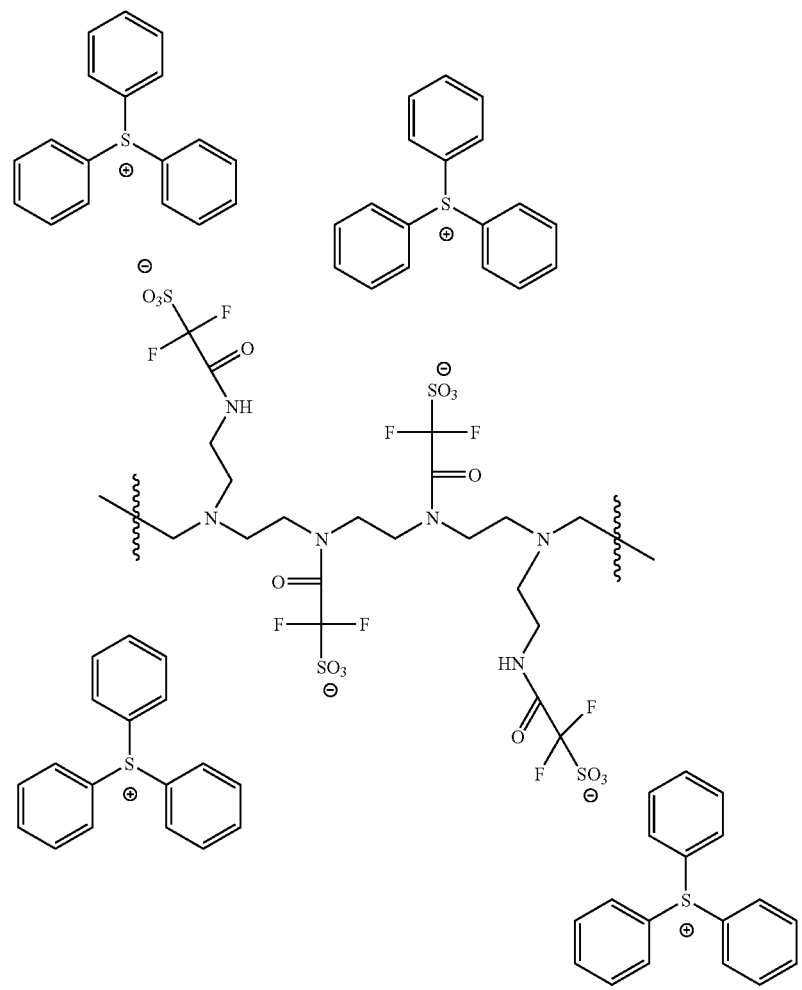
Compound obtained by amidizing a portion of commercially available polyethyleneimine to thereby introduce an acid generating site.

-continued
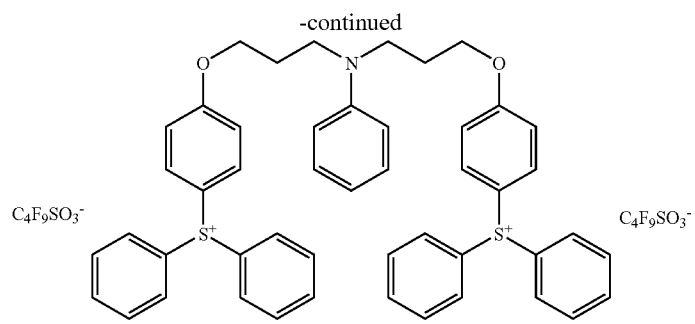
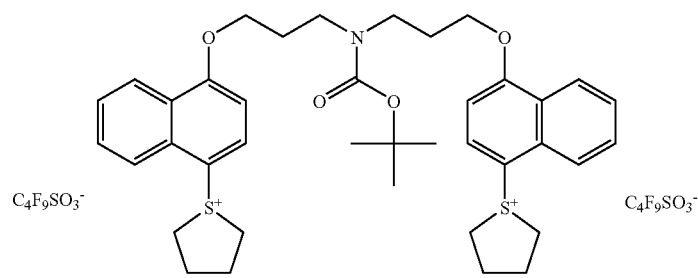
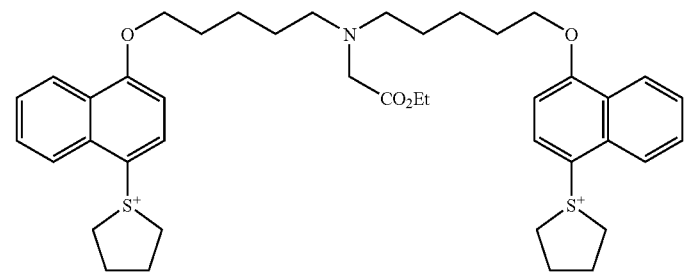
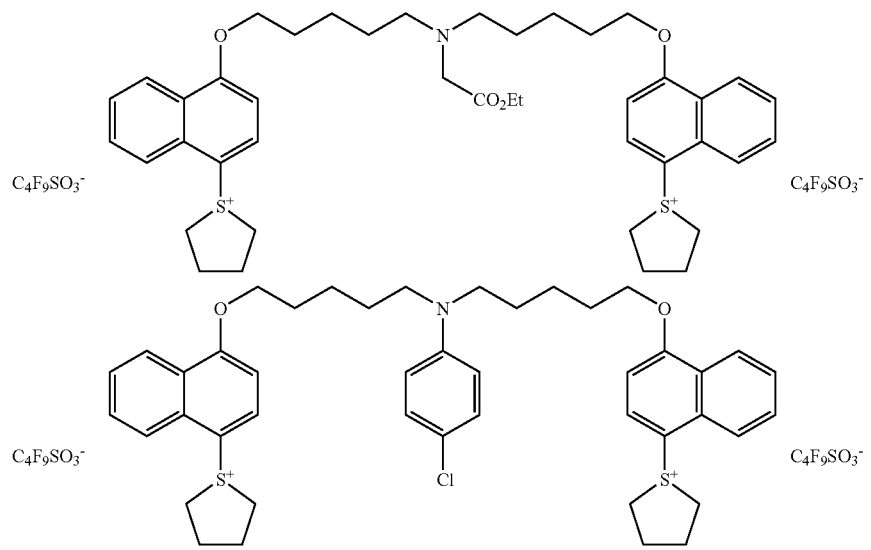

Basic compound (C) is contained in the composition of the present invention in an amount of generally 0.001 to 20 mass %, preferably 0.01 to 15 mass % and especially preferably 0.1 to 10 mass %, based on the total solid of the composition.

(A) Compound that when Exposed to Actinic Rays or Radiation, Generates an Acid

As a compound that when exposed to actinic rays or radiation, generates an acid (hereinafter also referred to as an "acid generator"), use can be made of a member appropriately selected from among a photoinitiator for photocationic polymerization, a photoinitiator for photoradical polymerization, a photo-achromatic agent and photo-discoloring agent for dyes, any of publicly known compounds that when exposed to actinic rays or radiation, generate an acid, employed in microresists, etc., and mixtures thereof.

For example, as the acid generator, there can be mentioned a diazonium salt, a phosphonium salt, a sulfonium salt, an iodonium salt, an imide sulfonate, an oxime sulfonate, diazosulfone, disulfone or o-nitrobenzyl sulfonate.

Further, use can be made of compounds obtained by introducing any of the above groups or compounds that when exposed to actinic rays or radiation, generate an acid in a polymer principal chain or side chain, for example, compounds described in U.S. Pat. No. 3,849,137, DE 3914407, JP-As 63-26653, 55-164824, 62-69263, 63-146038, 63-163452, 62-153853, 63-146029, etc.

Furthermore, use can be made of compounds that when exposed to light, generate an acid described in U.S. Pat. No. 3,779,778 and EP 126,712.

As preferred compounds among the acid generators, there can be mentioned those of the following general formulae (ZI), (ZII) and (ZIII).

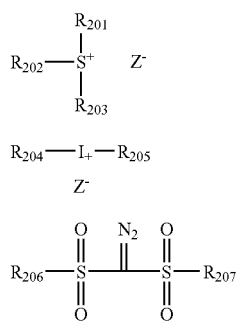

In above general formula (ZI), each of $R_{201}$, $R_{202}$ and $R_{203}$ independently represents an organic group.

The number of carbon atoms of each of the organic groups represented by $R_{201}$, $R_{202}$ and $R_{203}$ is generally in the range of 1 to 30, preferably 1 to 20.

Two of $R_{201}$ to $R_{203}$ may be bonded to each other to thereby form a ring structure, and the ring within the same may contain an oxygen atom, a sulfur atom, an ester bond, an amido bond or a carbonyl group. As the group formed by bonding of two of $R_{201}$ to $R_{203}$, there can be mentioned an alkylene group (for example, a butylene group or a pentylene group).

$Z^-$ represents a normucleophilic anion.

As the normucleophilic anion represented by $Z^-$, there can be mentioned, for example, a sulfonate anion, a carboxylate anion, a sulfonylimido anion, a bis(alkylsulfonyl)imido anion, a tris(alkylsulfonyl)methyl anion or the like.

The normucleophilic anion means an anion whose capability of inducing a nucleophilic reaction is extremely low and is an anion capable of inhibiting any temporal decomposition by intramolecular nucleophilic reaction. This would realize an enhancement of the temporal stability of the resist.

As the sulfonate anion, there can be mentioned, for example, an aliphatic sulfonate anion, an aromatic sulfonate anion, a camphor sulfonate anion or the like.

As the carboxylate anion, there can be mentioned, for example, an aliphatic carboxylate anion, an aromatic carboxylate anion, an aralkyl carboxylate anion or the like.

The aliphatic moiety of the aliphatic sulfonate anion may be an alkyl group or a cycloalkyl group, being preferably an alkyl group having 1 to 30 carbon atoms or a cycloalkyl group having 3 to 30 carbon atoms. As such, there can be mentioned, for example, a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, a boronyl group or the like.

As a preferred aromatic group of the aromatic sulfonate anion, there can be mentioned an aryl group having 6 to 14 carbon atoms, for example, a phenyl group, a tolyl group, a naphthyl group or the like.

The alkyl group, cycloalkyl group and aryl group of the aliphatic sulfonate anion and aromatic sulfonate anion may have a substituent. As the substituent of the alkyl group, cycloalkyl group and aryl group of the aliphatic sulfonate anion and aromatic sulfonate anion, there can be mentioned, for example, a nitro group, a halogen atom (fluorine atom, chlorine atom, bromine atom or iodine atom), a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 2 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), a cycloalkylalkyloxyalkyloxy group (preferably having 8 to 20 carbon atoms) or the like. The aryl group or ring structure of these groups may further have an alkyl group (preferably having 1 to 15 carbon atoms) as its substituent.

As the aliphatic moiety of the aliphatic carboxylate anion, there can be mentioned the same alkyl groups and cycloalkyl groups as mentioned with respect to the aliphatic sulfonate anion.

As the aromatic group of the aromatic carboxylate anion, there can be mentioned the same aryl groups as mentioned with respect to the aromatic sulfonate anion.

As a preferred aralkyl group of the aralkyl carboxylate anion, there can be mentioned an aralkyl group having 6 to 12 carbon atoms, for example, a benzyl group, a phenethyl group, a naphthylmethyl group, a naphthylethyl group, a naphthylbutyl group or the like.

The alkyl group, cycloalkyl group, aryl group and aralkyl group of the aliphatic carboxylate anion, aromatic carboxylate anion and aralkyl carboxylate anion may have a substituent. As the substituent of the alkyl group, cycloalkyl group, aryl group and aralkyl group of the aliphatic carboxylate anion, aromatic carboxylate anion and aralkyl carboxylate anion, there can be mentioned, for example, the same halogen atom, alkyl group, cycloalkyl group, alkoxy group, alkylthio group, etc., as mentioned with respect to the aromatic sulfonate anion.

As the sulfonylimido anion, there can be mentioned, for example, a saccharin anion.

The alkyl group of the bis(alkylsulfonyl)imido anion and tris(alkylsulfonyl)methyl anion is preferably an alkyl group having 1 to 5 carbon atoms. As such, there can be mentioned, for example, a methyl group, an ethyl group, a propyl group, an isopropyl group, an n-butyl group, an isobutyl group, a sec-butyl group, a pentyl group, a neopentyl group or the like. As a substituent of these alkyl groups, there can be mentioned a halogen atom, an alkyl group substituted with a halogen atom, an alkoxy group, an alkylthio group, an alkyloxysulfonyl group, an aryloxysulfonyl group, a cycloalkylaryloxysulfonyl group or the like. An alkyl group substituted with a fluorine atom is preferred.

As the other normucleophilic anions, there can be mentioned, for example, phosphorus fluoride, boron fluoride, antimony fluoride and the like.

The normucleophilic anion represented by $Z^-$ is preferably selected from among an aliphatic sulfonate anion substituted at its α-position of sulfonic acid with a fluorine atom, an aromatic sulfonate anion substituted with a fluorine atom or a group having a fluorine atom, a bis(alkylsulfonyl)imido anion whose alkyl group is substituted with a fluorine atom and a tris(alkylsulfonyl)methide anion whose alkyl group is substituted with a fluorine atom. More preferably, the normucleophilic anion is a perfluorinated aliphatic sulfonate anion having 4 to 8 carbon atoms or a benzene sulfonate anion having a fluorine atom. Still more preferably, the normucleophilic anion is a nonafluorobutane sulfonate anion, a perfluorooctane sulfonate anion, a pentafluorobenzene sulfonate anion or a 3,5-bis(trifluoromethyl)benzene sulfonate anion.

The normucleophilic anion represented by $Z^-$ may have any of the structures of general formulae (Xa) and (Xb) below.

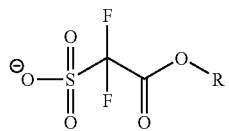

(Xa)

In general formula (Xa), R represents a hydrogen atom or an organic group. R is preferably an organic group having 1 to 40 carbon atoms, more preferably an organic group having 3 to 20 carbon atoms and most preferably any of the organic groups of formula (XI) shown below.

The organic group represented by R essentially has one or more carbon atoms. Preferably, the atom bonded to the oxygen atom of the ester bond appearing in general formula (Xa), <something missing!> is a carbon atom. As the organic groups, there can be mentioned, for example, an alkyl group, a cycloalkyl group, an aryl group, an aralkyl group and a group with a lactone structure. These groups in the chain thereof may have a heteroatom, such as an oxygen atom or a sulfur atom. These groups may be introduced in each other as substituents, and they may have a substituent, such as a hydroxyl group, an acyl group, an acyloxy group, an oxy group (=O) or a halogen atom.

(XI)

In formula (XI), Rc represents a cyclic organic group of a single ring or multiple rings having 3 to 30 carbon atoms that may contain a cyclic ether, cyclic thioether, cyclic ketone, cyclic carbonic ester, lactone or lactam structure. Y represents a hydroxyl group, a halogen atom, a cyano group, a carboxyl group, a hydrocarbon group having 1 to 10 carbon atoms, a hydroxyalkyl group having 1 to 10 carbon atoms, an alkoxy group having 1 to 10 carbon atoms, an acyl group having 1 to 10 carbon atoms, an alkoxycarbonyl group having 2 to 10 carbon atoms, an acyloxy group having 2 to 10 carbon atoms, an alkoxyalkyl group having 2 to 10 carbon atoms, or a halogenated alkyl group having 1 to 8 carbon atoms. In the formula, m is 0 to 6. In the instance of multiple Ys, they may be identical to or different from each other. Further, n is 0 to 10.

The sum of carbon atoms constructing each of groups R of formula (XI) is preferably 40 or less.

Preferably, n is 0 to 3, and it is preferred for Rc to be a monocyclic or polycyclic organic group having 7 to 16 carbon atoms.

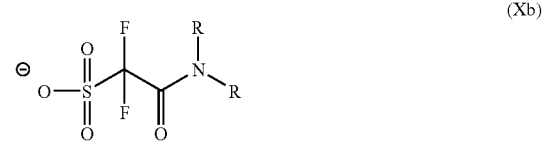

(Xb)

In general formula (Xb), each of Rs represents a hydrogen atom or an organic group without any polycyclic skeleton. Preferably, each of Rs represents a hydrogen atom or an organic group without any polycyclic skeleton having 1 to 40 carbon atoms. More preferably, each of Rs represents a hydrogen atom or an organic group without any polycyclic skeleton having 3 to 20 carbon atoms. Rs may be different from each other, and may be bonded to each other to thereby form a ring. The organic group represented by Rs essentially has one or more carbon atoms. Preferably, the atom bonded to the nitrogen atom of the amido bond appearing in general formula (Xb) is a carbon atom. As the organic groups, there can be mentioned, for example, an alkyl group, cycloalkyl group, aryl group, aralkyl group and group with a lactone structure each having no polycyclic skeleton. The organic groups in the chain thereof may have a heteroatom, such as an oxygen atom or a sulfur atom. These groups may be introduced in each other as substituents, and they may have a substituent, such as a hydroxyl group, an acyl group, an acyloxy group, an oxy group (=O) or a halogen atom.

The molecular weight of each of the normucleophilic anion moieties of general formulae (Xa) and (Xb) is generally in the range of 300 to 1000, preferably 400 to 800 and more preferably 500 to 700.

As the organic groups represented by $R_{201}$, $R_{202}$ and $R_{203}$, there can be mentioned, for example, corresponding groups of the following compounds (ZI-1), (ZI-2) and (ZI-3).

Appropriate use may be made of compounds with two or more of the structures of general formula (ZI). For example, use may be made of compounds having a structure wherein at least one of $R_{201}$ to $R_{203}$ of a compound of general formula (ZI) is bonded to at least one of $R_{201}$ to $R_{203}$ of another compound of general formula (ZI).

As preferred (ZI) components, there can be mentioned the following compounds (ZI-1), (ZI-2), (ZI-3) and (ZI-4).

Compounds (ZI-1) are arylsulfonium compounds of general formula (ZI) wherein at least one of $R_{201}$ to $R_{203}$ is an aryl group, namely, compounds containing an arylsulfonium as a cation.

In the arylsulfonium compounds, all of the $R_{201}$ to $R_{203}$ may be aryl groups. It is also appropriate that the $R_{201}$ to $R_{203}$ are partially an aryl group and the remainder is an alkyl group or a cycloalkyl group.

As the arylsulfonium compounds, there can be mentioned, for example, a triarylsulfonium compound, a diarylalkylsulfonium compound, an aryldialkylsulfonium compound, a diarylcycloalkylsulfonium compound and an aryldicycloalkylsulfonium compound.

The aryl group of the arylsulfonium compounds is preferably a phenyl group or a naphthyl group, more preferably a phenyl group. The aryl group may be one having a heterocyclic structure containing an oxygen atom, a nitrogen atom, a sulfur atom or the like. As the aryl group having a heterocyclic structure, there can be mentioned, for example, a pyrrole residue (group formed by the loss of one hydrogen atom from pyrrole), a furan residue (group formed by the loss of one hydrogen atom from furan), a thiophene residue (group formed by the loss of one hydrogen atom from thiophene), an indole residue (group formed by the loss of one hydrogen atom from indole), a benzofuran residue (group formed by the loss of one hydrogen atom from benzofuran), a benzothiophene residue (group formed by the loss of one hydrogen atom from benzothiophene) or the like. When the arylsulfonium compound has two or more aryl groups, the two or more aryl groups may be identical to or different from each other.

The alkyl group or cycloalkyl group contained in the arylsulfonium compound according to necessity is preferably a linear or branched alkyl group having 1 to 15 carbon atoms or a cycloalkyl group having 3 to 15 carbon atoms. As such, there can be mentioned, for example, a methyl group, an ethyl group, a propyl group, an n-butyl group, a sec-butyl group, a t-butyl group, a cyclopropyl group, a cyclobutyl group, a cyclohexyl group or the like.

The aryl group, alkyl group or cycloalkyl group represented by $R_{201}$ to $R_{203}$ may have as its substituent an alkyl group (for example, 1 to 15 carbon atoms), a cycloalkyl group (for example, 3 to 15 carbon atoms), an aryl group (for example, 6 to 14 carbon atoms), an alkoxy group (for example, 1 to 15 carbon atoms), a halogen atom, a hydroxyl group or a phenylthio group.

Preferred substituents are a linear or branched alkyl group having 1 to 12 carbon atoms, a cycloalkyl group having 3 to 12 carbon atoms and a linear, branched or cyclic alkoxy group having 1 to 12 carbon atoms. More preferred substituents are an alkyl group having 1 to 4 carbon atoms and an alkoxy group having 1 to 4 carbon atoms. The substituents may be contained in any one of the three $R_{201}$ to $R_{203}$, or alternatively may be contained in all three of $R_{201}$ to $R_{203}$. When $R_{201}$ to $R_{203}$ represent an aryl group, the substituent preferably lies at the p-position of the aryl group.

Now, compounds (ZI-2) will be described.

Compounds (ZI-2) are compounds of formula (ZI) wherein each of $R_{201}$ to $R_{203}$ independently represents an organic group having no aromatic ring. The aromatic rings include an aromatic ring having a heteroatom.

The organic group having no aromatic ring represented by $R_{201}$ to $R_{203}$ generally has 1 to 30 carbon atoms, preferably 1 to 20 carbon atoms.

Preferably, each of $R_{201}$ to $R_{203}$ independently represents an alkyl group, a cycloalkyl group, an allyl group or a vinyl group. More preferred groups are a linear or branched 2-oxoalkyl group, a 2-oxocycloalkyl group and an alkoxycarbonylmethyl group. Especially preferred is a linear or branched 2-oxoalkyl group.

As preferred alkyl groups and cycloalkyl groups represented by $R_{201}$ to $R_{203}$, there can be mentioned a linear or branched alkyl group having 1 to 10 carbon atoms (for example, a methyl group, an ethyl group, a propyl group, a butyl group or a pentyl group) and a cycloalkyl group having 3 to 10 carbon atoms (a cyclopentyl group, a cyclohexyl group or a norbornyl group). As more preferred alkyl groups, there can be mentioned a 2-oxoalkyl group and an alkoxycarbonylmethyl group. As more preferred cycloalkyl group, there can be mentioned a 2-oxocycloalkyl group.

The 2-oxoalkyl group may be linear or branched. A group having $>C=O$ at the 2-position of the alkyl group is preferred.

The 2-oxocycloalkyl group is preferably a group having $>C=O$ at the 2-position of the cycloalkyl group.

As preferred alkoxy groups of the alkoxycarbonylmethyl group, there can be mentioned alkoxy groups having 1 to 5 carbon atoms (a methoxy group, an ethoxy group, a propoxy group, a butoxy group and a pentoxy group).

The $R_{201}$ to $R_{203}$ may be further substituted with a halogen atom, an alkoxy group (for example, 1 to 5 carbon atoms), a hydroxyl group, a cyano group or a nitro group.

Compounds (ZI-3) are those represented by the following general formula (ZI-3) which have a phenacylsulfonium salt structure.

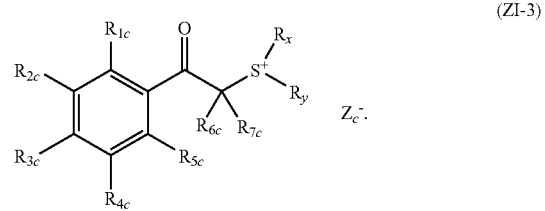

(ZI-3)

In general formula (ZI-3), each of $R_{1c}$ to $R_{5c}$ independently represents a hydrogen atom, an alkyl group, a cycloalkyl group, an alkoxy group, a halogen atom or a phenylthio group.

Each of $R_{6c}$ and $R_{7c}$ independently represents a hydrogen atom, an alkyl group, a cycloalkyl group, a halogen atom, a cyano group or an aryl group.

Each of $R_x$ and $R_y$ independently represents an alkyl group, a cycloalkyl group, a 2-oxoalkyl group, a 2-oxocycloalkyl group, an alkoxycarbonylalkyl group, an allyl group or a vinyl group.

Any two or more of $R_{1c}$ to $R_{5c}$, and $R_{6c}$ and $R_{7c}$, and $R_x$ and $R_y$, may be bonded to each other to thereby form a ring structure. This ring structure may contain an oxygen atom, a sulfur atom, an ester bond or an amido bond. As the group formed by bonding of any two or more of $R_{1c}$ to $R_{5c}$, and $R_{6c}$ and $R_{7c}$, and $R_x$ and $R_y$, there can be mentioned a butylene group, a pentylene group or the like.

$Z_c^-$ represents a normucleophilic anion. There can be mentioned the same normucleophilic anions as mentioned with respect to the $Z^-$ of general formula (ZI).

The alkyl group represented by $R_{1c}$ to $R_{7c}$ may be linear or branched. As such, there can be mentioned, for example, an alkyl group having 1 to 20 carbon atoms, preferably a linear or branched alkyl group having 1 to 12 carbon atoms (for example, a methyl group, an ethyl group, a linear or branched propyl group, a linear or branched butyl group or a linear or branched pentyl group). As the cycloalkyl group, there can be mentioned, for example, a cycloalkyl group having 3 to 8 carbon atoms (for example, a cyclopentyl group or a cyclohexyl group).

The alkoxy group represented by $R_{1c}$ to $R_{5c}$ may be linear, or branched, or cyclic. As such, there can be mentioned, for example, an alkoxy group having 1 to 10 carbon atoms, preferably a linear or branched alkoxy group having 1 to 5 carbon atoms (for example, a methoxy group, an ethoxy group, a linear or branched propoxy group, a linear or branched butoxy group, or a linear or branched pentoxy group) and a cycloalkoxy group having 3 to 8 carbon atoms (for example, a cyclopentyloxy group or a cyclohexyloxy group).

Preferably, any one of $R_{1c}$ to $R_{5c}$ is a linear or branched alkyl group, a cycloalkyl group or a linear, branched or cyclic alkoxy group. More preferably, the sum of carbon atoms of $R_{1c}$ to $R_{5c}$ is in the range of 2 to 15. Accordingly, there can be attained an enhancement of solvent solubility and inhibition of particle generation during storage.

Each of the aryl groups represented by $R_{6c}$ and $R_{7c}$ preferably has 5 to 15 carbon atoms. As such, there can be mentioned, for example, a phenyl group or a naphthyl group.

When $R_{6c}$ and $R_{7c}$ are bonded to each other to thereby form a ring, the group formed by the bonding of $R_{6c}$ and $R_{7c}$ is preferably an alkylene group having 2 to 10 carbon atoms. As such, there can be mentioned, for example, an ethylene group, a propylene group, a butylene group, a pentylene group, a hexylene group or the like. Further, the ring formed by the bonding of $R_{6c}$ and $R_{7c}$ may have a heteroatom, such as an oxygen atom, in the ring.

As the alkyl groups and cycloalkyl groups represented by $R_x$ and $R_y$, there can be mentioned the same alkyl groups and cycloalkyl groups as set forth above with respect to $R_{1c}$ to $R_{7c}$.

As the 2-oxoalkyl group and 2-oxocycloalkyl group, there can be mentioned the alkyl group and cycloalkyl group represented by $R_{1c}$ to $R_{7c}$ having >C=O at the 2-position of the groups.

With respect to the alkoxy group of the alkoxycarbonylalkyl group, there can be mentioned the same alkoxy groups as mentioned above with respect to $R_{1c}$ to $R_{5c}$. As the alkyl group thereof, there can be mentioned, for example, an alkyl group having 1 to 12 carbon atoms, preferably a linear alkyl group having 1 to 5 carbon atoms (e.g., a methyl group or an ethyl group).

The allyl groups are not particularly limited. However, preferred use is made of an unsubstituted allyl group or an allyl group substituted with a cycloalkyl group of a single ring or multiple rings.

The vinyl groups are not particularly limited. However, preferred use is made of an unsubstituted vinyl group or a vinyl group substituted with a cycloalkyl group of a single ring or multiple rings.

As the ring structure that may be formed by the mutual bonding of $R_x$ and $R_y$, there can be mentioned a 5-membered or 6-membered ring, especially preferably a 5-membered ring (namely, a tetrahydrothiophene ring), formed by bivalent $R_x$ and $R_y$ (for example, a methylene group, an ethylene group, a propylene group or the like) in cooperation with the sulfur atom of general formula (ZI-3).

Each of $R_x$ and $R_y$ is preferably an alkyl group or cycloalkyl group having preferably 4 or more carbon atoms. The alkyl group or cycloalkyl group has more preferably 6 or more carbon atoms and still more preferably 8 or more carbon atoms.

Specific examples of the cations of the compounds of general formula (ZI-3) will be shown below.

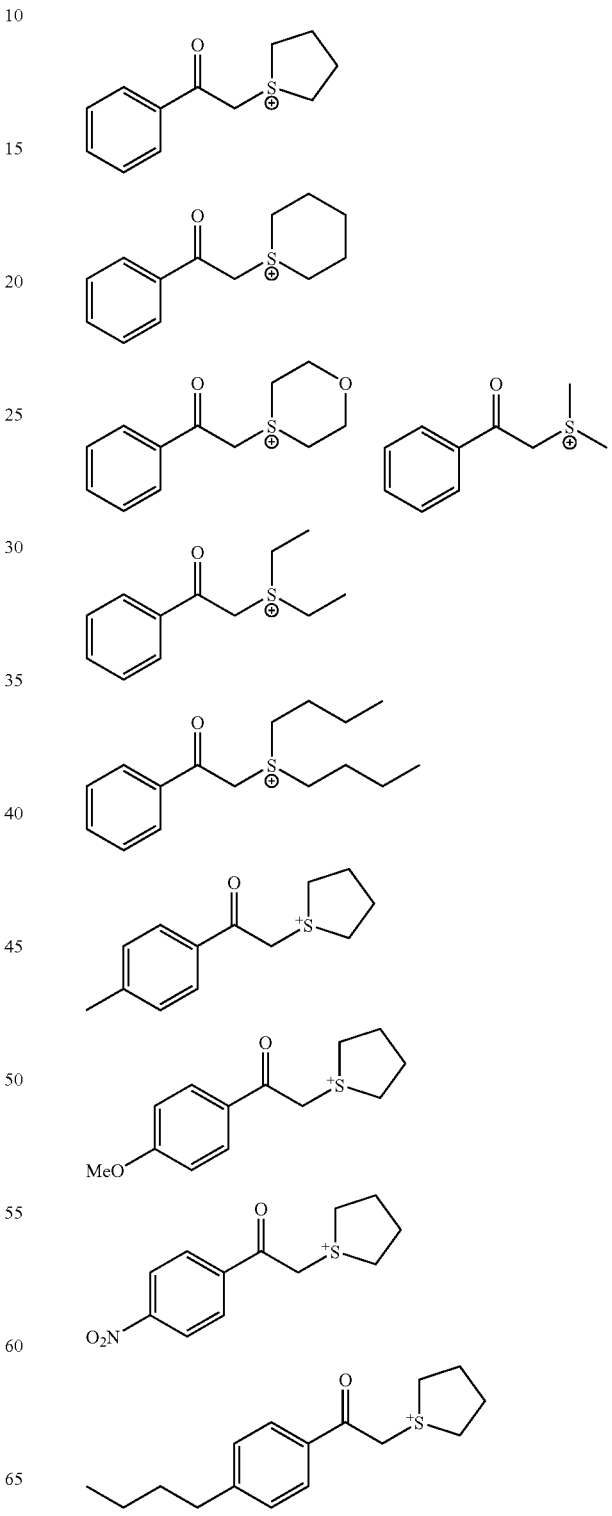

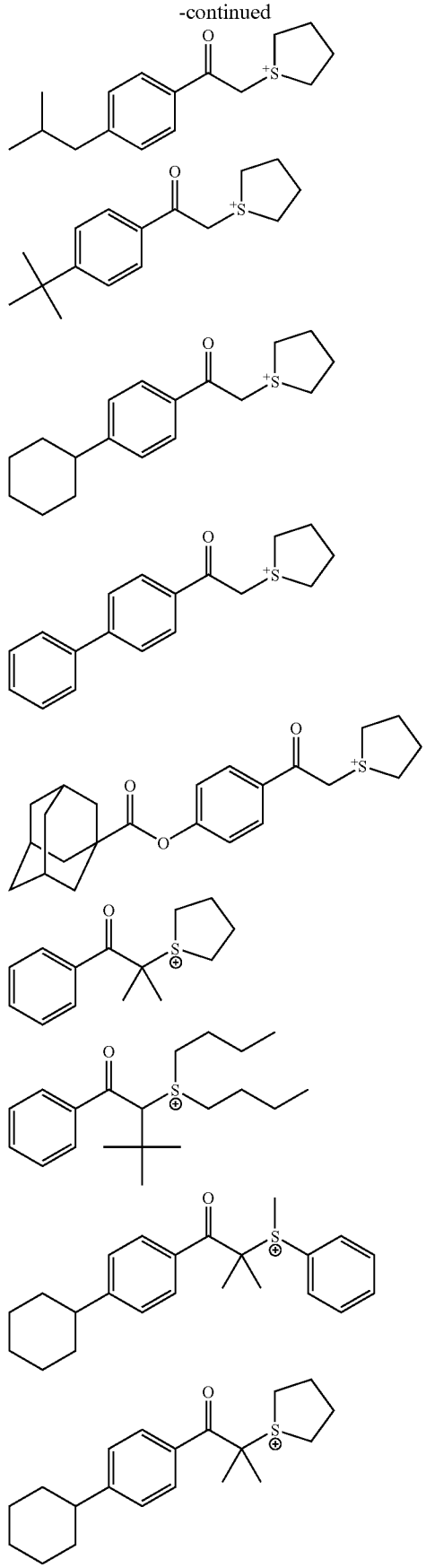
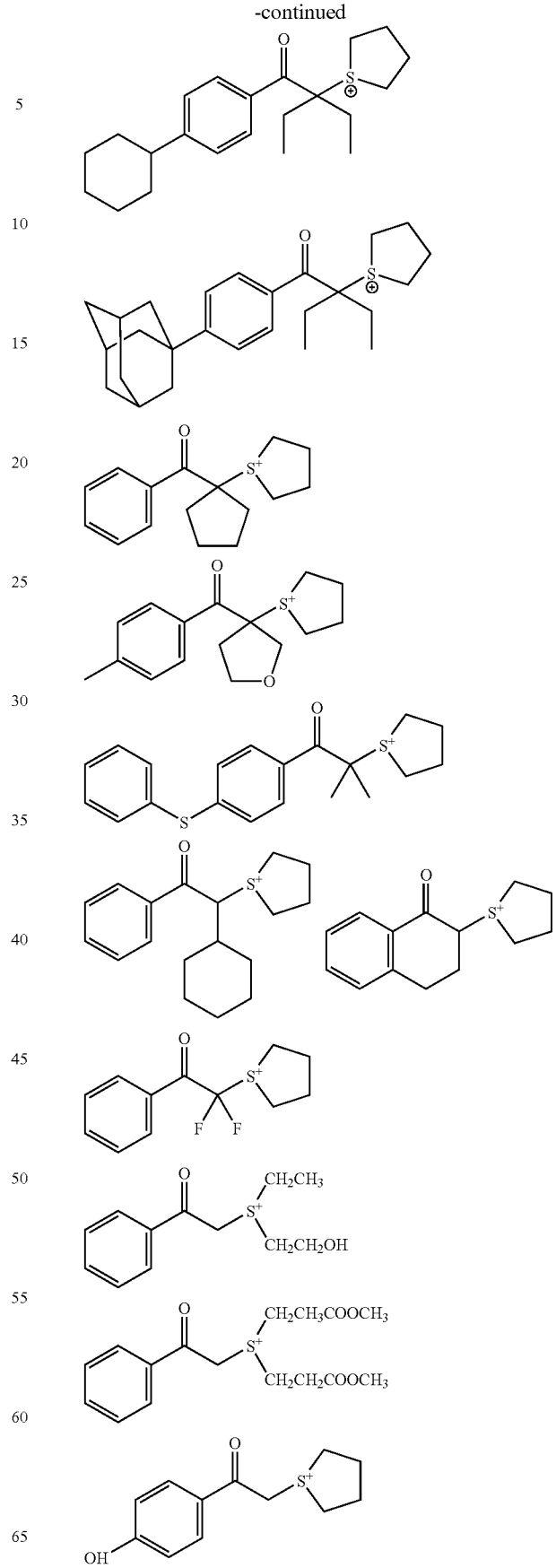

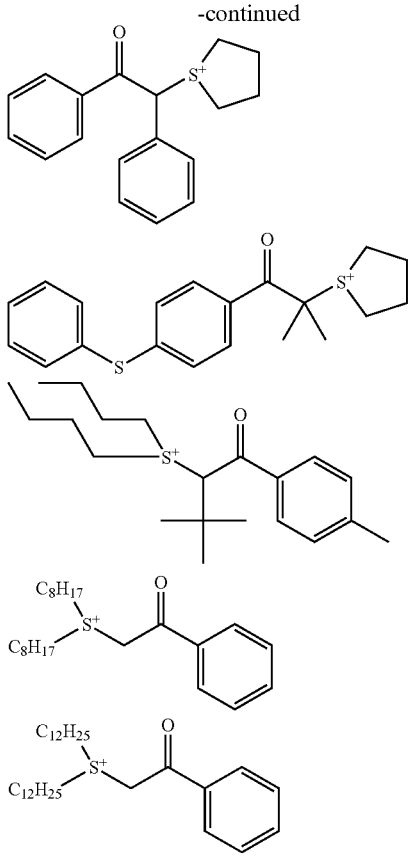

The compounds of general formula (ZI-4) below are preferred.

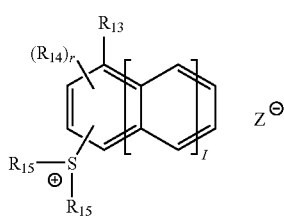

In general formula (ZI-4),

R$_{13}$ represents any of a hydrogen atom, a fluorine atom, a hydroxyl group, an alkyl group, a cycloalkyl group, an alkoxy group, an alkoxycarbonyl group and a group with a cycloalkyl skeleton of a single ring or multiple rings. These groups may have substituents.

R$_{14}$, each independently in the instance of R$_{14}$s, represents any of an alkyl group, a cycloalkyl group, an alkoxy group, an alkoxycarbonyl group, an alkylcarbonyl group, an alkylsulfonyl group, a cycloalkylsulfonyl group and a group with a cycloalkyl skeleton of a single ring or multiple rings. These groups may have substituents.

Each of R$_{15}$s independently represents any of an alkyl group, a cycloalkyl group and a naphthyl group, provided that two of the R$_{15}$s may be bonded to each other to thereby form a ring. These groups may have substituents.

In the formula, l is an integer of 0 to 2.

r is an integer of 0 to 8.

Z$^-$ represents a normucleophilic anion. As such, there can be mentioned any of the same normucleophilic anions as mentioned with respect to the Z$^-$ of the general formula (ZI).

In general formula (ZI-4), the alkyl groups represented by R$_{13}$, R$_{14}$ and R$_{15}$ may be linear or branched and preferably each have 1 to 10 carbon atoms. As such, there can be mentioned a methyl group, an ethyl group, an n-propyl group, an i-propyl group, an n-butyl group, a 2-methylpropyl group, a 1-methylpropyl group, a t-butyl group, an n-pentyl group, a neopentyl group, an n-hexyl group, an n-heptyl group, an n-octyl group, a 2-ethylhexyl group, an n-nonyl group, an n-decyl group and the like. Of these alkyl groups, a methyl group, an ethyl group, an n-butyl group, a t-butyl group and the like are preferred.

As the cycloalkyl groups represented by R$_{13}$, R$_{14}$ and R$_{15}$, there can be mentioned a monocyclic alkyl group such as a cyclopropyl group, a cyclobutyl group, a cyclopentyl group, a cyclohexyl group, a cycloheptyl group, a cyclooctyl group, a cyclododecanyl group, a cyclopentenyl group, a cyclohexenyl group or a cyclooctadienylgroup, and a polycyclic alkyl group such as a norbornyl group, a tricyclodecanyl group, a tetracyclodecanyl group or an adamanty group. Cyclopropyl, cyclopentyl, cyclohexyl and cyclooctyl are especially preferred.

The alkoxy groups represented by R$_{13}$ and R$_{14}$ may be linear or branched and preferably each have 1 to 10 carbon atoms. As such, there can be mentioned, for example, a methoxy group, an ethoxy group, an n-propoxy group, an i-propoxy group, an n-butoxy group, a 2-methylpropoxy group, a 1-methylpropoxy group, a t-butoxy group, an n-pentyloxy group, a neopentyloxy group, an n-hexyloxy group, an n-heptyloxy group, an n-octyloxy group, a 2-ethylhexyloxy group, an n-nonyloxy group, an n-decyloxy group and the like. Of these alkoxy groups, a methoxy group, an ethoxy group, an n-propoxy group, an n-butoxy group and the like are preferred.

The alkoxycarbonyl groups represented by R$_{13}$ and R$_{14}$ may be linear or branched and preferably has 2 to 11 carbon atoms. As such, there can be mentioned, for example, a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, an n-pentyloxycarbonyl group, a neopentyloxycarbonyl group, an n-hexyloxycarbonyl group, an n-heptyloxycarbonyl group, an n-octyloxycarbonyl group, a 2-ethylhexyloxycarbonyl group, an n-nonyloxycarbonyl group, an n-decyloxycarbonyl group and the like. Of these alkoxycarbonyl groups, a methoxycarbonyl group, an ethoxycarbonyl group, an n-butoxycarbonyl group and the like are preferred.

As the groups with a cycloalkyl skeleton of a single ring or multiple rings represented by R$_{13}$ and R$_{14}$, there can be mentioned, for example, a cycloalkyloxy group of a single ring or multiple rings and an alkoxy group with a cycloalkyl group of a single ring or multiple rings. These groups may further have substituents.

With respect to each of the cycloalkyloxy groups of a single ring or multiple rings represented by R$_{13}$ and R$_{14}$, the sum of carbon atoms thereof is preferably 7 or greater, more preferably in the range of 7 to 15. Further, having a cycloalkyl skeleton of a single ring is preferred. The cycloalkyloxy group of a single ring of which the sum of carbon atoms is 7 or greater is one composed of a cycloalkyloxy group, such as a cyclopropyloxy group, a cyclobutyloxy group, a cyclopentyloxy group, a cyclohexyloxy group, a cycloheptyloxy group, a cyclooctyloxy group or a cyclododecanyloxy group, optionally having a substituent selected from among an alkyl group such as methyl, ethyl, propyl, butyl, pentyl, hexyl, heptyl, octyl, dodecyl, 2-ethylhexyl, isopropyl, sec-butyl, t-butyl or isoamyl, a hydroxyl group, a halogen atom (fluorine, chlorine, bromine or iodine), a nitro group, a cyano group, an amido group, a sulfonamido group, an alkoxy group such as methoxy, ethoxy, hydroxyethoxy, propoxy, hydroxypropoxy or butoxy, an alkoxycarbonyl group such as methoxycarbonyl or ethoxycarbonyl, an acyl group such as formyl, acetyl or benzoyl, an acyloxy group such as acetoxy or butyryloxy, a carboxyl group and the like, provided that the sum of carbon atoms thereof including those of any optional substituent introduced in the cycloalkyl group is 7 or greater.

As the cycloalkyloxy group of multiple rings of which the sum of carbon atoms is 7 or greater, there can be mentioned a norbornyloxy group, a tricyclodecanyloxy group, a tetracyclodecanyloxy group, an adamantyloxy group and the like. These may have the above substituents.

With respect to each of the alkyloxy groups having a cycloalkyl skeleton of a single ring or multiple rings represented by $R_{13}$ and $R_{14}$, the sum of carbon atoms thereof is preferably 7 or greater, more preferably in the range of 7 to 15. Further, the alkoxy group having a cycloalkyl skeleton of a single ring is preferred. The alkoxy group having a cycloalkyl skeleton of a single ring of which the sum of carbon atoms is 7 or greater is one composed of an alkoxy group, such as methoxy, ethoxy, propoxy, butoxy, pentyloxy, hexyloxy, heptoxy, octyloxy, dodecyloxy, 2-ethylhexyloxy, isopropoxy, sec-butoxy, t-butoxy or isoamyloxy, substituted with the above optionally substituted cycloalkyl group of a single ring, provided that the sum of carbon atoms thereof including those of the substituents is 7 or greater. For example, there can be mentioned a cyclohexylmethoxy group, a cyclopentylethoxy group, a cyclohexylethoxy group or the like. A cyclohexylmethoxy group is preferred.

As the alkoxy group having a cycloalkyl skeleton of multiple rings of which the sum of carbon atoms is 7 or greater, there can be mentioned a norbornylmethoxy group, a norbornylethoxy group, a tricyclodecanylmethoxy group, a tricyclodecanylethoxy group, a tetracyclodecanylmethoxy group, a tetracyclodecanylethoxy group, an adamantylmethoxy group, an adamantylethoxy group and the like. Of these, a norbornylmethoxy group and a norbornylethoxy group are preferred. These may have the above substituents.

With respect to the alkyl group of the alkylcarbonyl group represented by $R_{14}$, there can be mentioned the same specific examples as mentioned above with respect to the alkyl groups represented by $R_{13}$ to $R_{15}$.

The alkylsulfonyl and cycloalkylsulfonyl groups represented by $R_{14}$ may be linear, branched or cyclic and preferably each have 1 to 10 carbon atoms. As such, there can be mentioned, for example, a methanesulfonyl group, an ethanesulfonyl group, an n-propanesulfonyl group, an n-butanesulfonyl group, a tert-butanesulfonyl group, an n-pentanesulfonyl group, a neopentanesulfonyl group, an n-hexanesulfonyl group, an n-heptanesulfonyl group, an n-octanesulfonyl group, a 2-ethylhexanesulfonyl group, an n-nonanesulfonyl group, an n-decanesulfonyl group, a cyclopentanesulfonyl group, a cyclohexanesulfonyl group and the like. Of these alkylsulfonyl and cycloalkylsulfonyl groups, a methanesulfonyl group, an ethanesulfonyl group, an n-propanesulfonyl group, an n-butanesulfonyl group, a cyclopentanesulfonyl group, a cyclohexanesulfonyl group and the like are preferred.

Each of the $R_{13}$, $R_{14}$ and $R_{15}$ groups may have a substituent. As such a substituent, there can be mentioned, for example, a halogen atom (e.g., a fluorine atom), a hydroxyl group, a carboxyl group, a cyano group, a nitro group, an alkoxy group, an alkoxyalkyl group, an alkoxycarbonyl group, an alkoxycarbonyloxy group or the like.

As the alkoxy group, there can be mentioned, for example, a linear, branched or cyclic alkoxy group having 1 to 20 carbon atoms, such as a methoxy group, an ethoxy group, an n-propoxy group, an i-propoxy group, an n-butoxy group, a 2-methylpropoxy group, a 1-methylpropoxy group, a t-butoxy group, a cyclopentyloxy group or a cyclohexyloxy group.

As the alkoxyalkyl group, there can be mentioned, for example, a linear, branched or cyclic alkoxyalkyl group having 2 to 21 carbon atoms, such as a methoxymethyl group, an ethoxymethyl group, a 1-methoxyethyl group, a 2-methoxyethyl group, a 1-ethoxyethyl group or a 2-ethoxyethyl group.

As the alkoxycarbonyl group, there can be mentioned, for example, a linear, branched or cyclic alkoxycarbonyl group having 2 to 21 carbon atoms, such as a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, a cyclopentyloxycarbonyl group or a cyclohexyloxycarbonyl group.

As the alkoxycarbonyloxy group, there can be mentioned, for example, a linear, branched or cyclic alkoxycarbonyloxy group having 2 to 21 carbon atoms, such as a methoxycarbonyloxy group, an ethoxycarbonyloxy group, an n-propoxycarbonyloxy group, an i-propoxycarbonyloxy group, an n-butoxycarbonyloxy group, a t-butoxycarbonyloxy group, a cyclopentyloxycarbonyloxy group or a cyclohexyloxycarbonyloxy group.

As the ring structure that may be formed by the mutual bonding of two $R_{15}$s, there can be mentioned a 5-membered or 6-membered ring, especially preferably a 5-membered ring (namely, a tetrahydrothiophene ring), formed by two bivalent $R_{15}$s in cooperation with the sulfur atom of general formula (ZI-4). The ring structure may be condensed with an aryl group or a cycloalkyl group. Each of the bivalent $R_{15}$s may have a substituent. As the substituent, there can be mentioned, for example, a hydroxyl group, a carboxyl group, a cyano group, a nitro group, an alkoxy group, an alkoxyalkyl group, an alkoxycarbonyl group, an alkoxycarbonyloxy group or the like. Each of the $R_{15}$s of general formula (ZI-4) is preferably a methyl group, an ethyl group, a naphthyl group, a bivalent group adapted to form a tetrahydrothiophene ring structure by the mutual bonding of two $R_{15}$s in cooperation with the sulfur atom, or the like.

The substituent that can be introduced in $R_{13}$ and $R_{14}$ is preferably a hydroxyl group, an alkoxy group, an alkoxycarbonyl group or a halogen atom (especially a fluorine atom).

In the formula, 1 is preferably 0 or 1, more preferably 1.

r is preferably 0 to 2.

Specific examples of the cations of the compounds of general formula (ZI-4) are shown below.

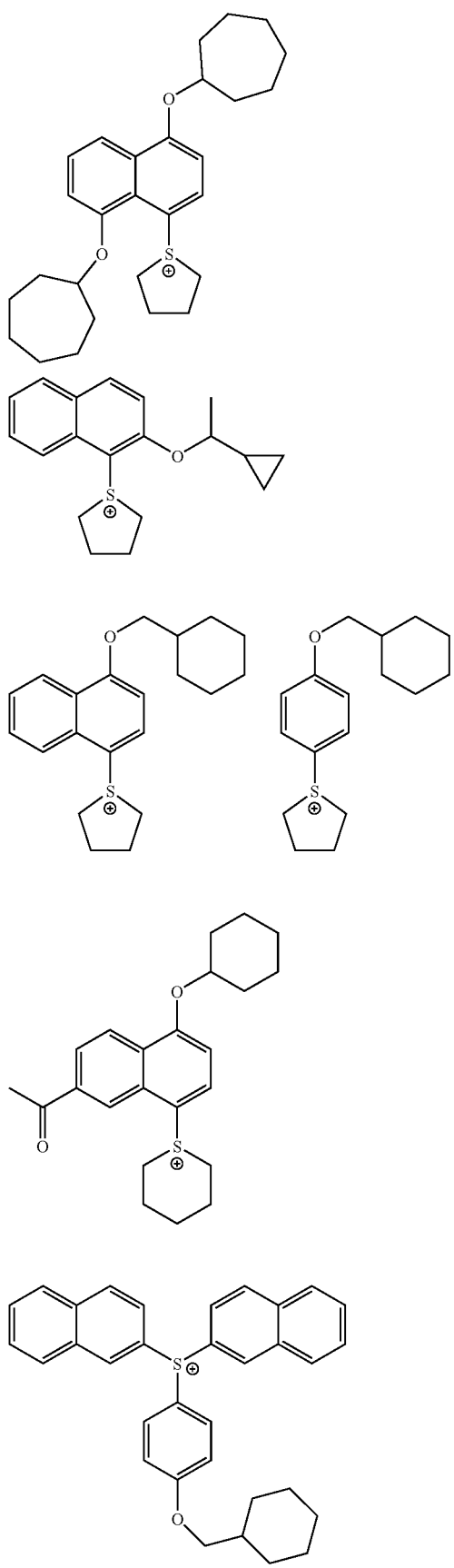
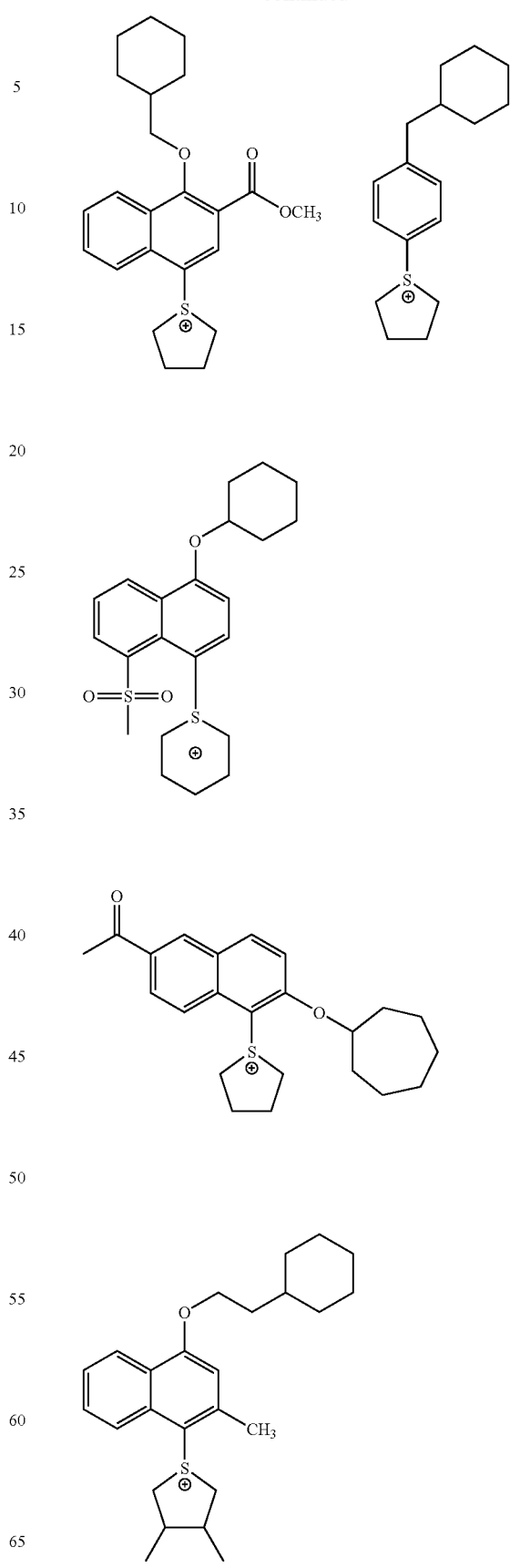

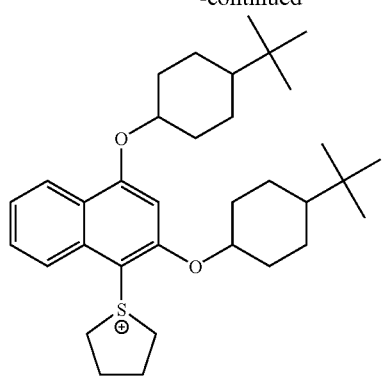
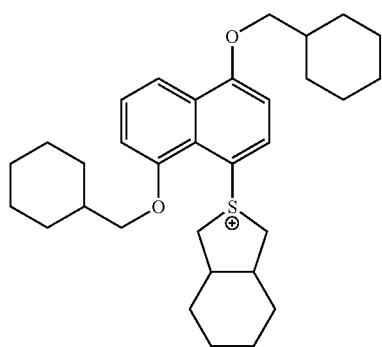
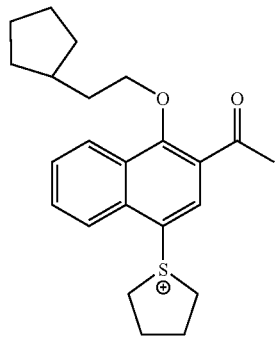
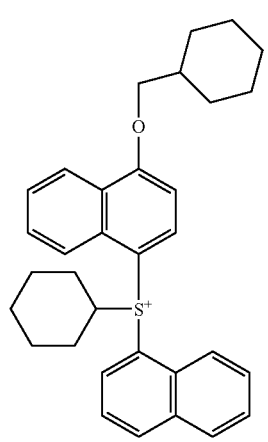
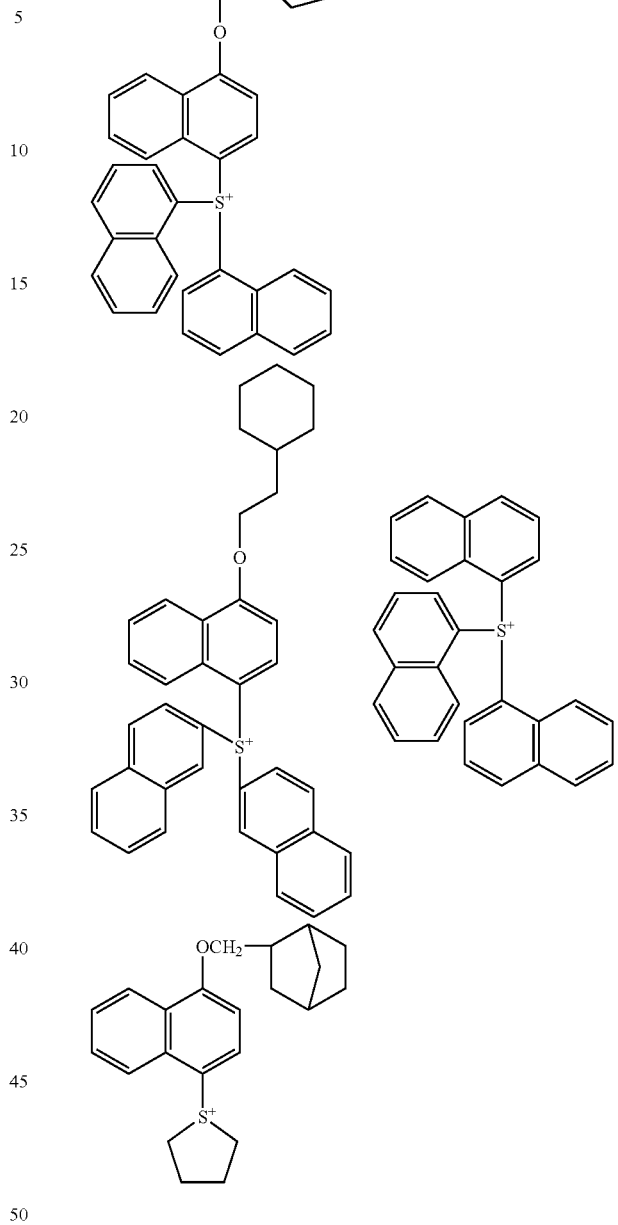

In the general formulae (ZII) and (ZIII), each of $R_{204}$ to $R_{207}$ independently represents an aryl group, an alkyl group or a cycloalkyl group.

The aryl group represented by $R_{204}$ to $R_{207}$ is preferably a phenyl group or a naphthyl group, more preferably a phenyl group. The aryl group represented by $R_{204}$ to $R_{207}$ may be one having a heterocyclic structure containing an oxygen atom, nitrogen atom, sulfur atom or the like. As the aryl group having a heterocyclic structure, there can be mentioned, for example, a pyrrole residue (group formed by loss of one hydrogen atom from pyrrole), a furan residue (group formed by loss of one hydrogen atom from furan), a thiophene residue (group formed by loss of one hydrogen atom from thiophene), an indole residue (group formed by loss of one hydrogen atom from indole), a benzofuran residue (group formed by loss of one hydrogen atom from benzofuran), a benzothiophene residue (group formed by loss of one hydrogen atom from benzothiophene) or the like.

As preferred alkyl groups and cycloalkyl groups represented by $R_{204}$ to $R_{207}$, there can be mentioned a linear or branched alkyl group having 1 to 10 carbon atoms (for example, a methyl group, an ethyl group, a propyl group, a butyl group or a pentyl group) and a cycloalkyl group having 3 to 10 carbon atoms (a cyclopentyl group, a cyclohexyl group or a norbornyl group).

The aryl group, alkyl group and cycloalkyl group represented by $R_{204}$ to $R_{207}$ may have a substituent. As a possible substituent on the aryl group, alkyl group and cycloalkyl group represented by $R_{204}$ to $R_{207}$, there can be mentioned, for example, an alkyl group (for example, 1 to 15 carbon atoms), a cycloalkyl group (for example, 3 to 15 carbon atoms), an aryl group (for example, 6 to 15 carbon atoms), an alkoxy group (for example, 1 to 15 carbon atoms), a halogen atom, a hydroxyl group, a phenylthio group or the like.

$Z^-$ represents a normucleophilic anion. As such, there can be mentioned the same normucleophilic anions as mentioned with respect to the $Z^-$ of the general formula (ZI).

As the acid generators, there can be further mentioned the compounds of the following general formulae (ZIV), (ZV) and (ZVI).

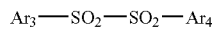

ZIV

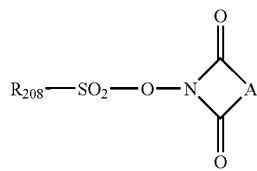

ZV

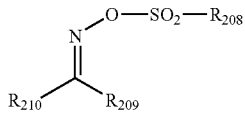

ZVI

In the general formulae (ZIV) to (ZVI), each of $Ar_3$ and $Ar_4$ independently represents an aryl group.

Each of $R_{208}$, $R_{209}$ and $R_{210}$ independently represents an alkyl group, a cycloalkyl group or an aryl group.

A represents an alkylene group, an alkenylene group or an arylene group.

Among the acid generators, the compounds of the general formulae (ZI) to (ZIII) are more preferred.

As a preferred acid generator, there can be mentioned a compound that generates an acid having one sulfonate group or imido group. As a more preferred acid generator, there can be mentioned a compound that generates a monovalent perfluoroalkanesulfonic acid, a compound that generates a monovalent aromatic sulfonic acid substituted with a fluorine atom or fluorine-atom-containing group, or a compound that generates a monovalent imidic acid substituted with a fluorine atom or fluorine-atom-containing group. As a still more preferred acid generator, there can be mentioned any of sulfonium salts of fluorinated alkanesulfonic acid, fluorinated benzenesulfonic acid, fluorinated imidic acid and fluorinated methide acid. With respect to practicable acid generators, it is especially preferred for the generated acid to be a fluorinated alkanesulfonic acid, fluorinated benzenesulfonic acid or fluorinated imidic acid of −1 or below pKa. By the use thereof, an enhancement of sensitivity can be attained.

Especially preferred examples of the acid generators are as follows.

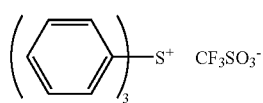

(z1) (z2)

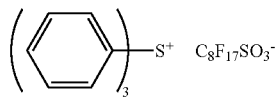

(z3) (z4)

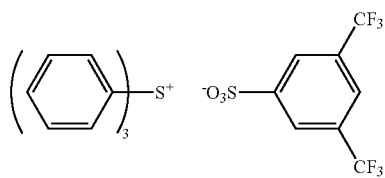

(z5) (z6)

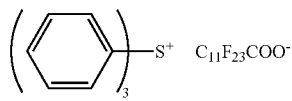

(z7) (z8)

-continued
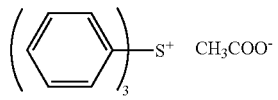 (z9)
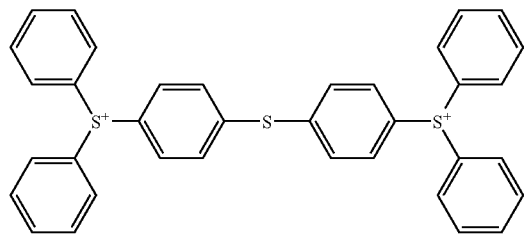 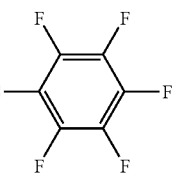 (z10)
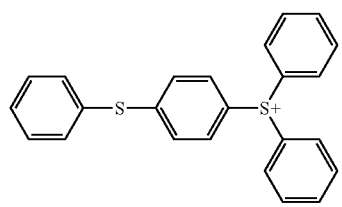 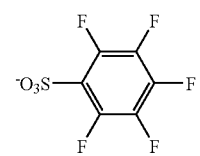 (z11)  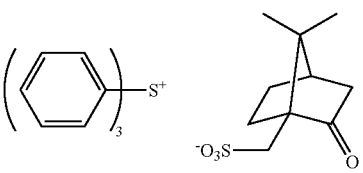 (z12)
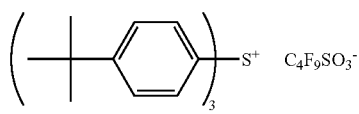 (z13)  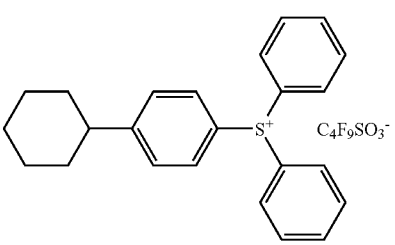 (z14)
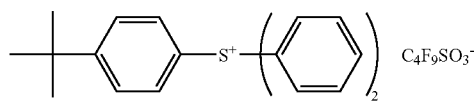 (z15)  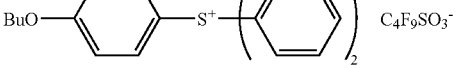 (z16)
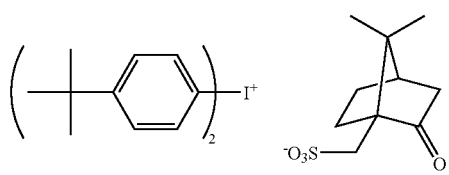 (z17)  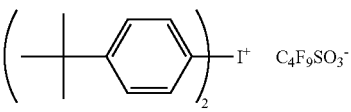 (z18)
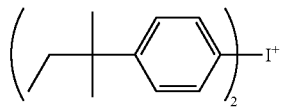 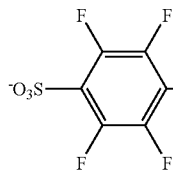 (z19)  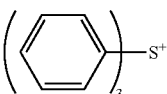 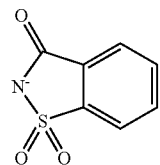 (z20)
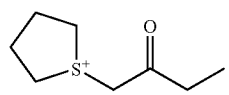 (z21)  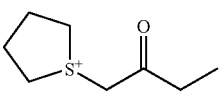  (z22)
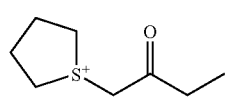 (z23)  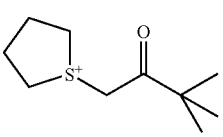  (z24)

-continued

-continued
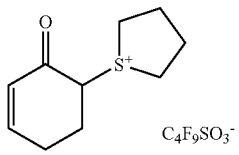 (z41)
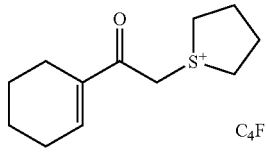 (z42)
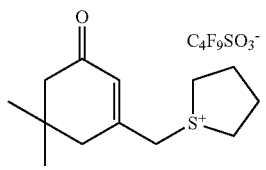 (z43)
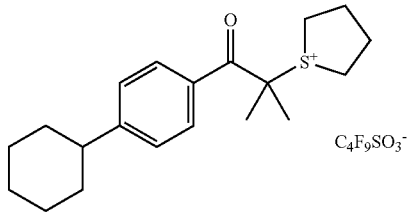 (z44)
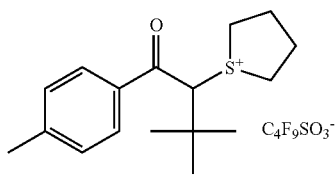 (z45)
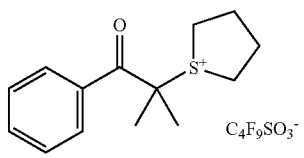 (z46)
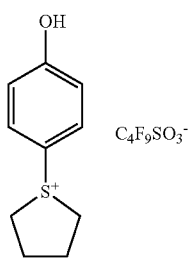 (z47)
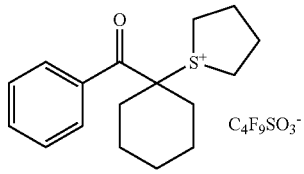 (z48)
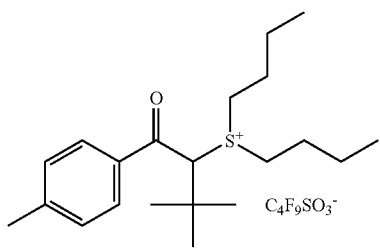 (z49)
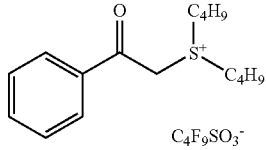 (z50)
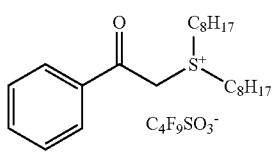 (z51)
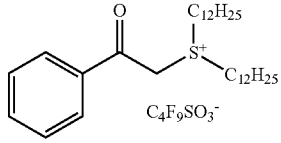 (z52)
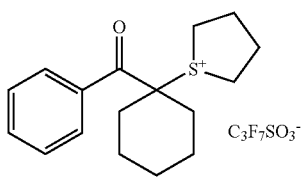 (z53)
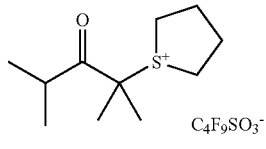 (z54)
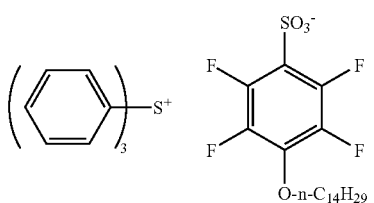 (z55)
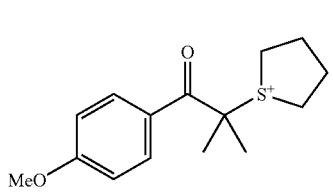 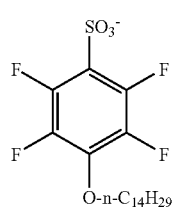 (z56)

-continued
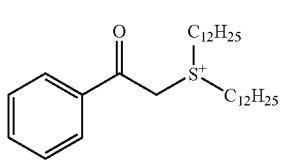 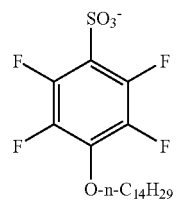 (z57)
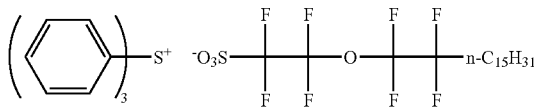 (z58)
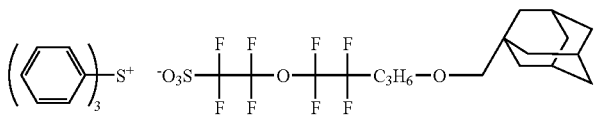 (z59)
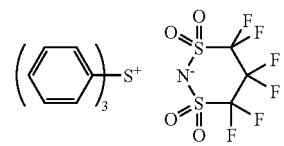 (z60)
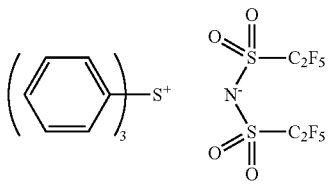 (z61)
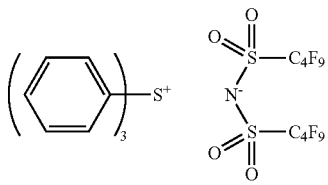 (z62)
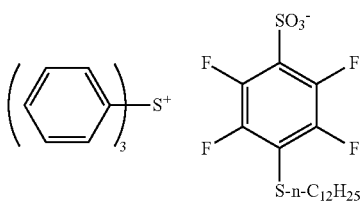 (z63)
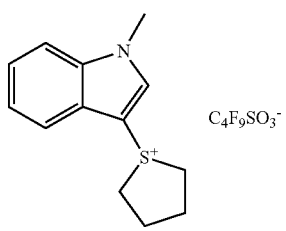 (z64)
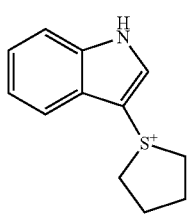 (z65)
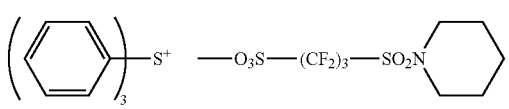 (z66)
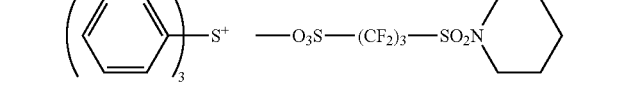 (z67)
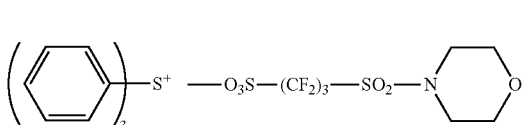 (z68)
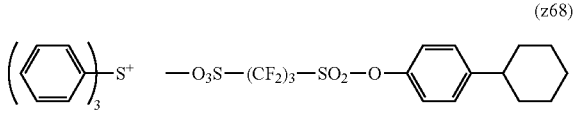 (z69)
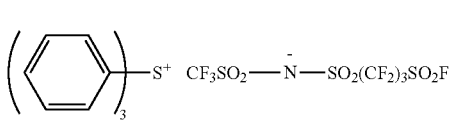 (z70)
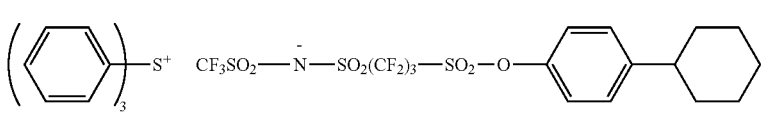

-continued
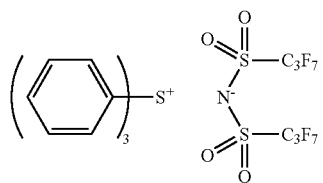 (z71)
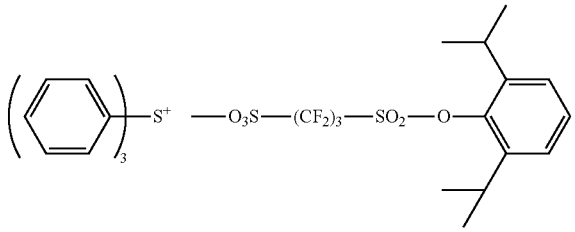 (z72)
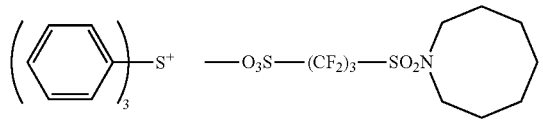 (z73)
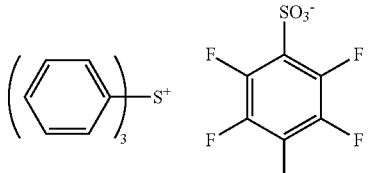 (z74)
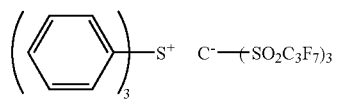 (z75)
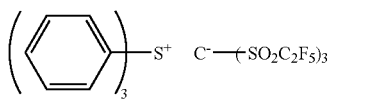 (z76)
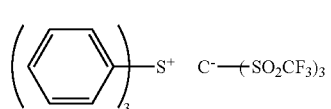 (z77)
 (z78)
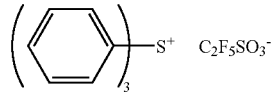 (z79)
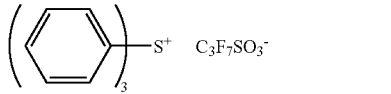 (z80)
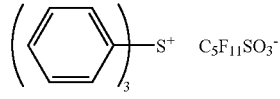 (z81)
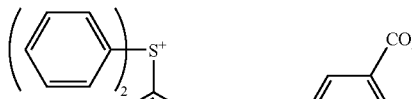 (z82)
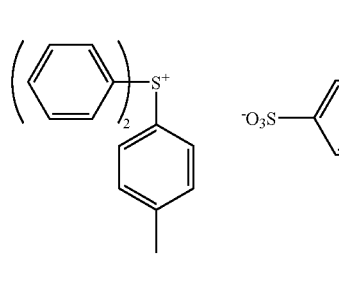 (z83)
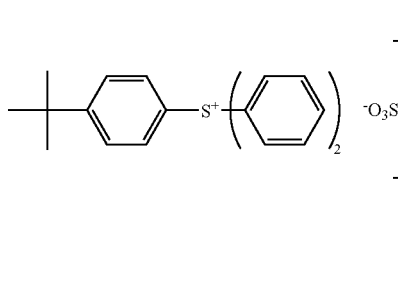 (z84)

-continued
(z85) 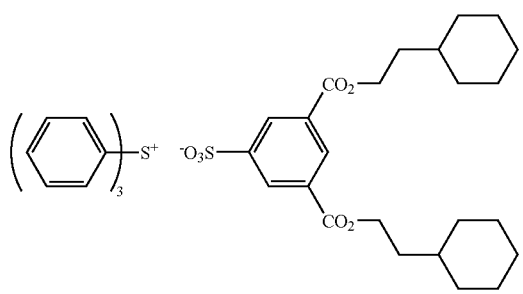
(z86) 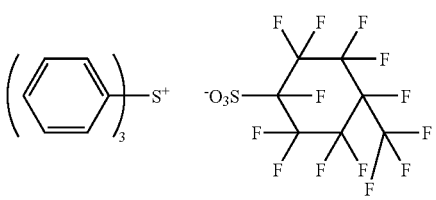
(z87) 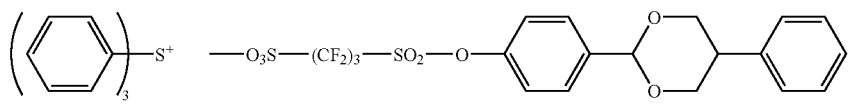
(z88) 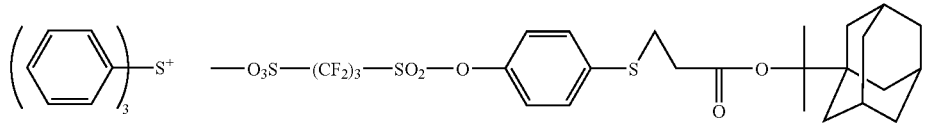
(z89) 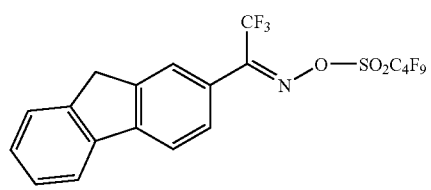
(z90) 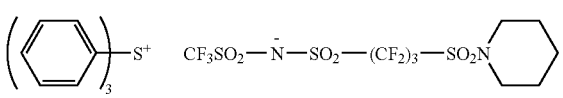
(z91) 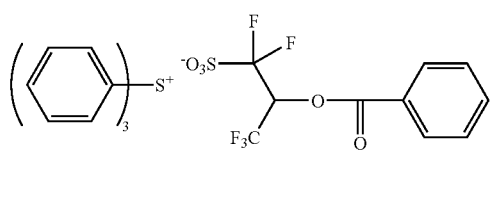
(Y-1) 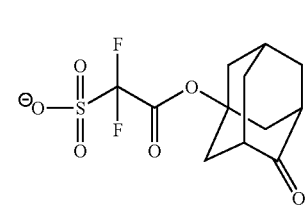
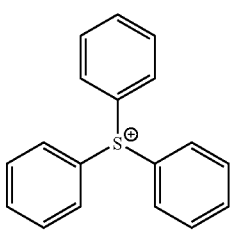
(Y-2) 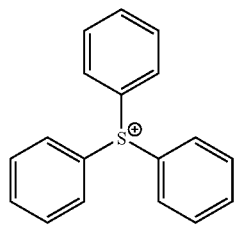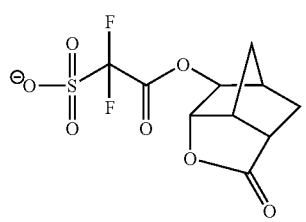
(Y-3) 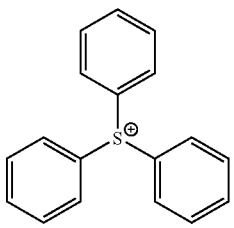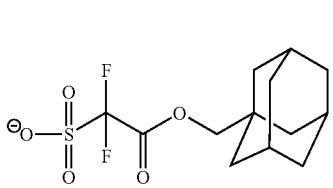
(Y-4) 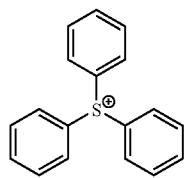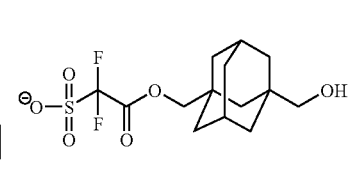
(Y-5) 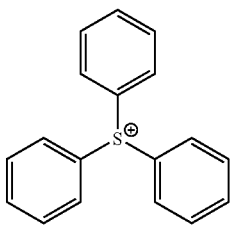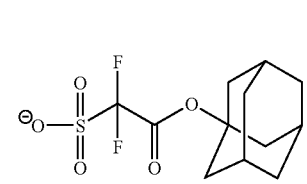

-continued
(Y-6) 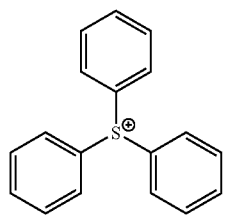
(Y-7) 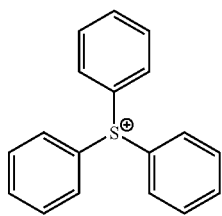
(Y-8) 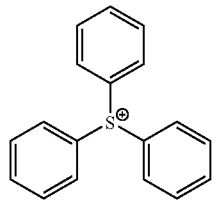
(Y-9) 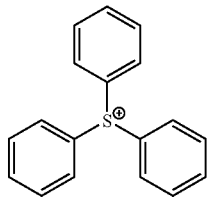
(Y-10) 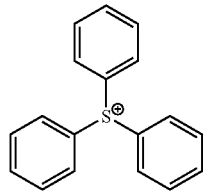
(Y-11) 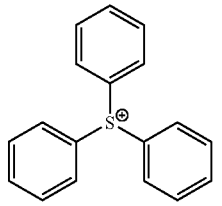
(Y-12) 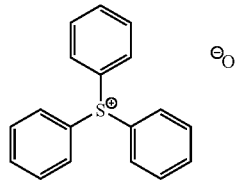
(Y-13) 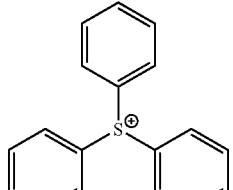
(Y-14) 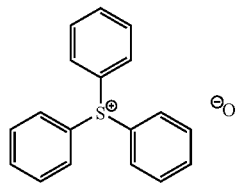
(Y-15) 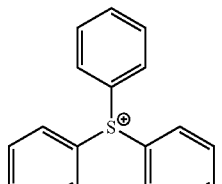
(Y-16) 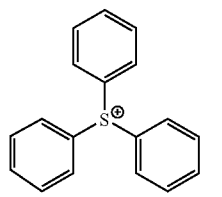
(Y-17) 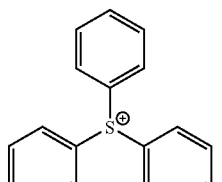
(Y-18) 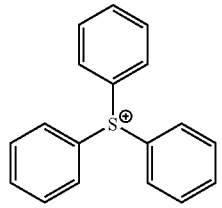
(Y-19) 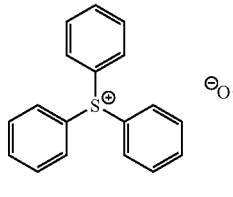

-continued
(Y-20)
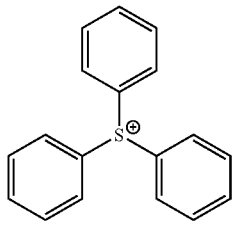 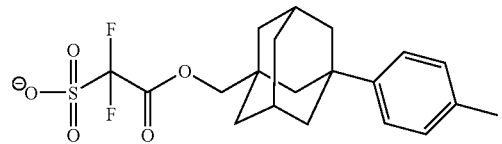
(Y-21)
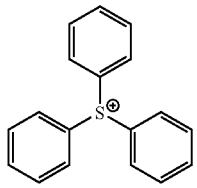 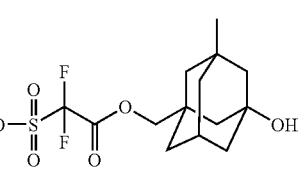
(Y-22)
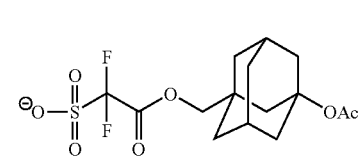
(Y-23)
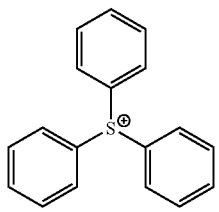 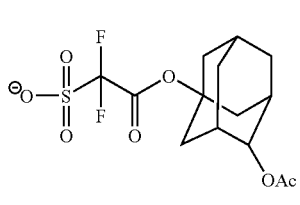
(Y-24)
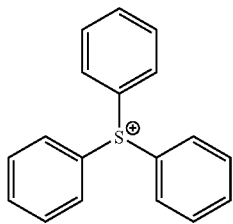 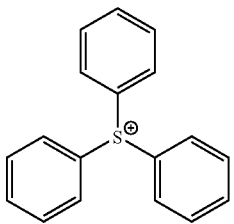
(Y-25)
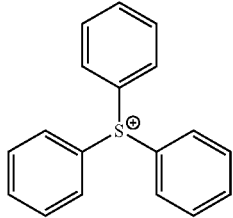 
(Y-26)
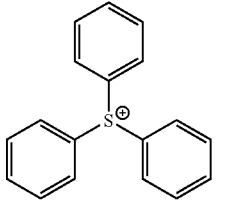
(Y-27)
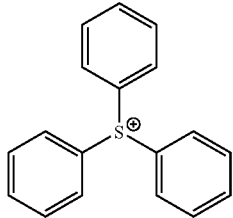 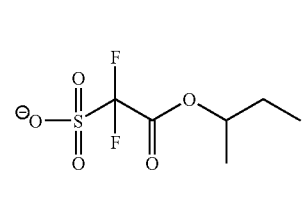
(Y-28)
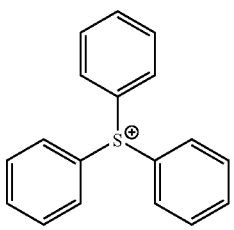

-continued

-continued
(Y-43)
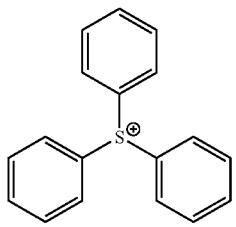 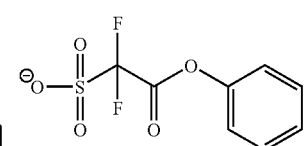
(Y-44)
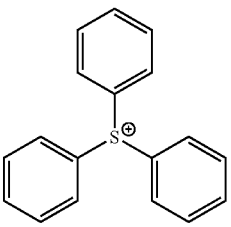 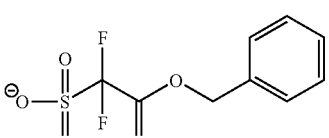
(Y-45)
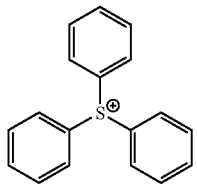 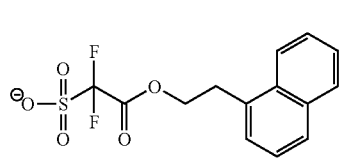
(Y-46)
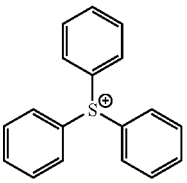 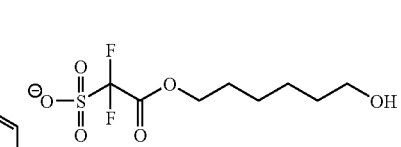
(Y-47)
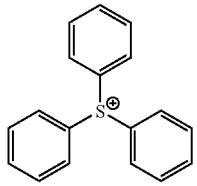 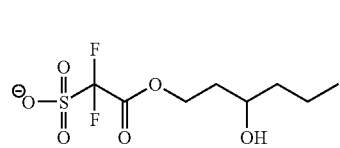
(Y-48)
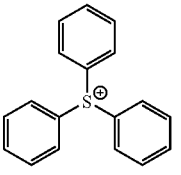 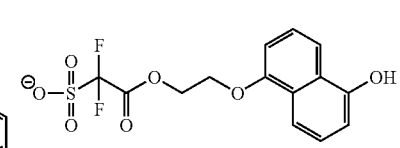
(Y-49)
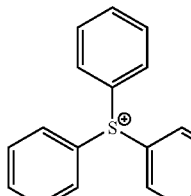 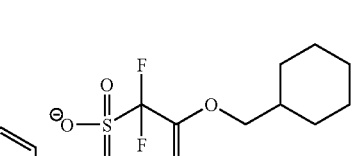
(Y-50)
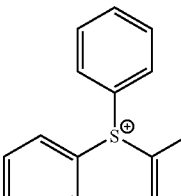 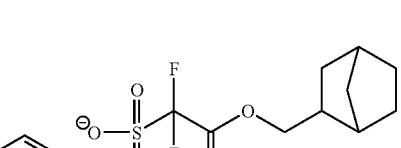
(Y-51)
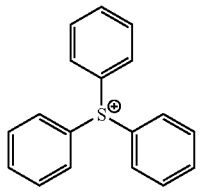 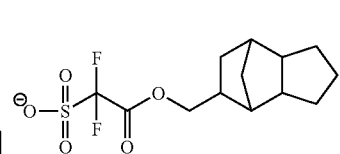
(Y-52)
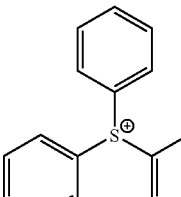 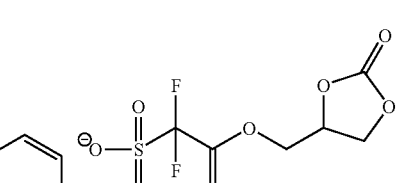
(Y-53)
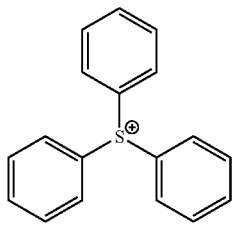 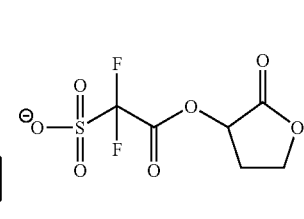
(Y-54)
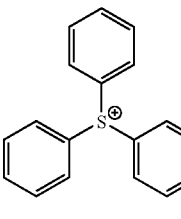 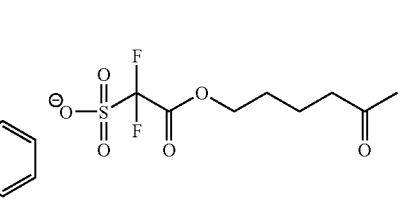

(Y-55)
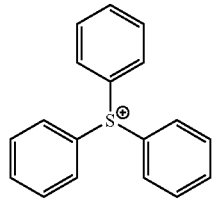 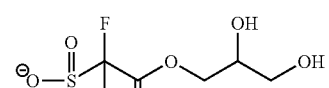
(Y-56)
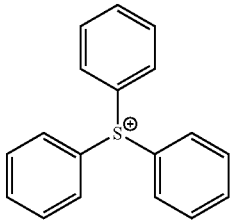 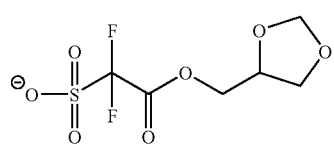
(Y-57)
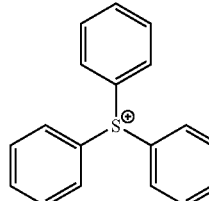 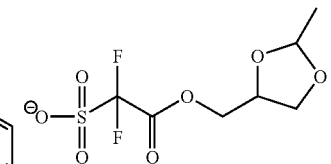
(Y-58)
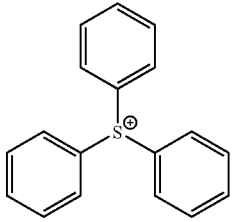 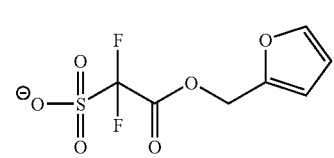
(Y-59)
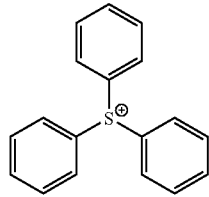 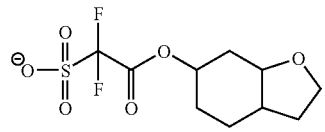
(Y-60)
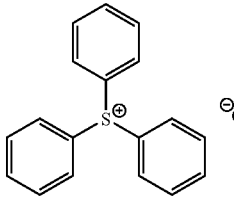 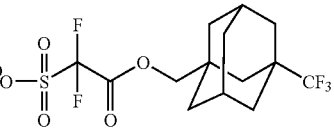
(Y-61)
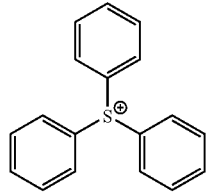 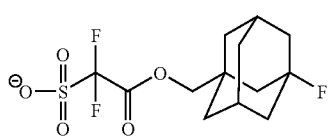
(Y-62)
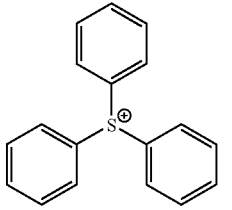 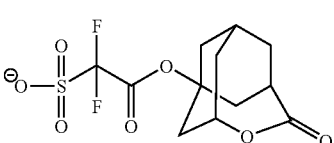
(Y-63)
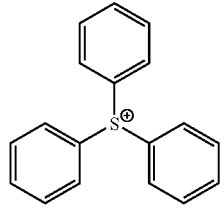 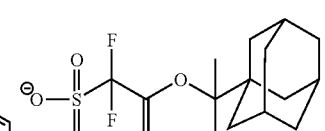
(Y-64)
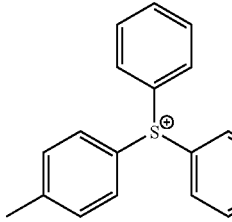 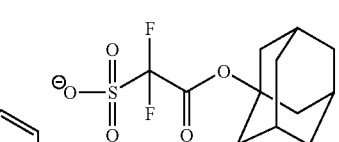
(Y-65)
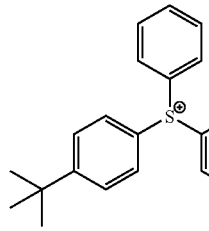 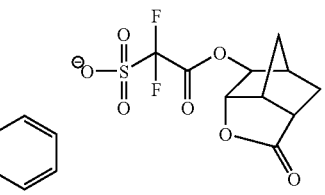
(Y-66)
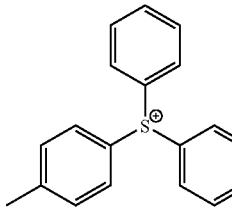 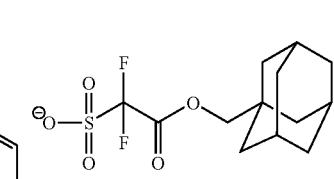

(Y-67)
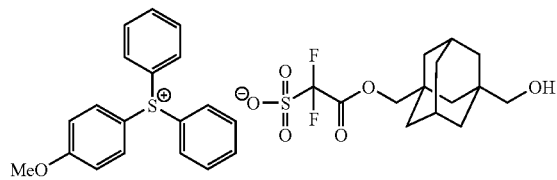
(Y-68)
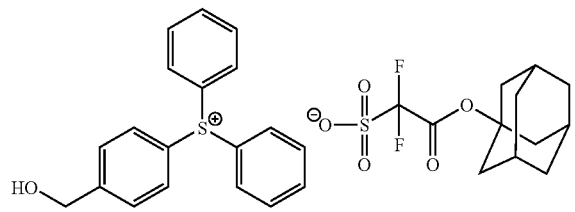
(Y-69)
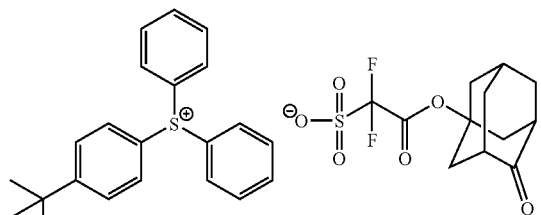
(Y-70)
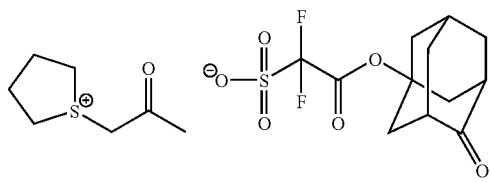
(Y-71)
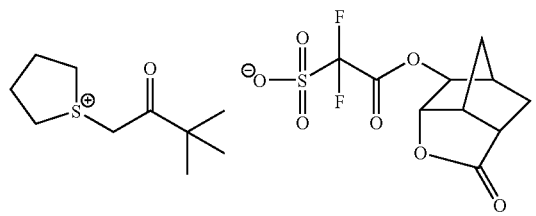
(Y-72)
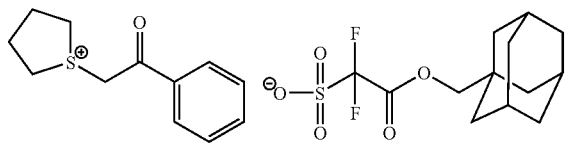
(Y-73)
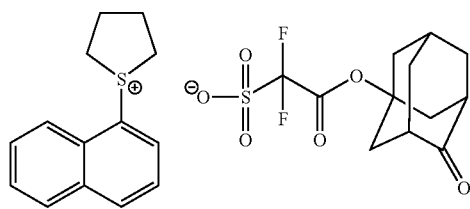
(Y-74)
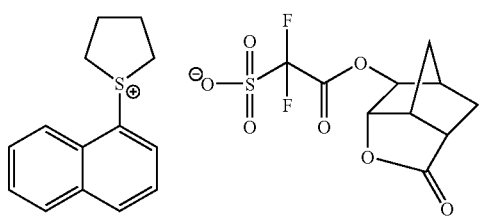
(Y-75)
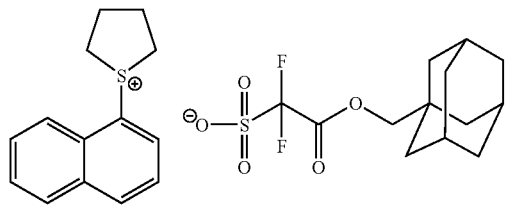
(Y-76)
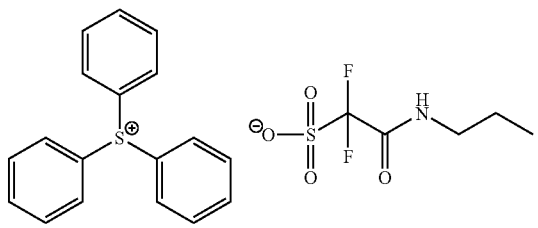
(Y-77)
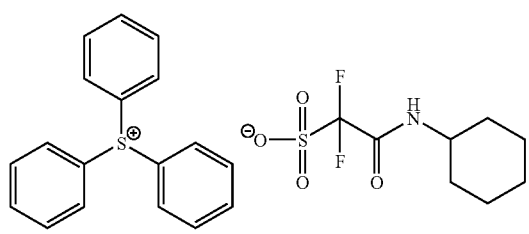
(Y-78)
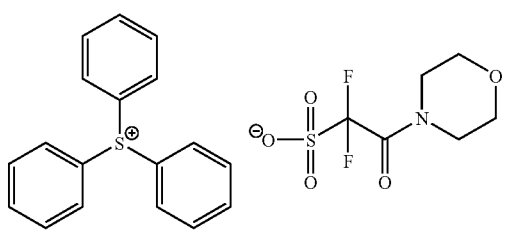

-continued (Y-79)
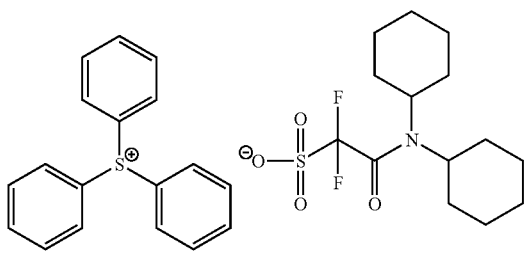
(Y-80)

(Y-81)
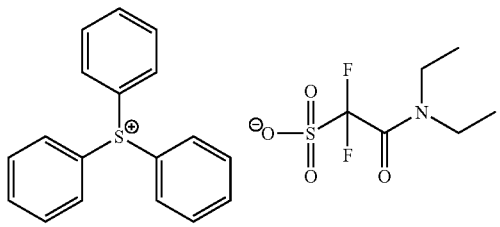
(Y-82)
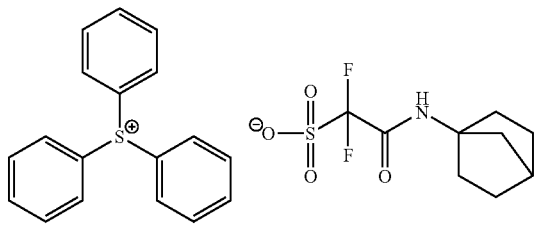

(Y-83)
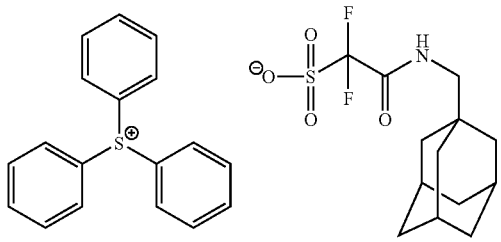
(Y-84)
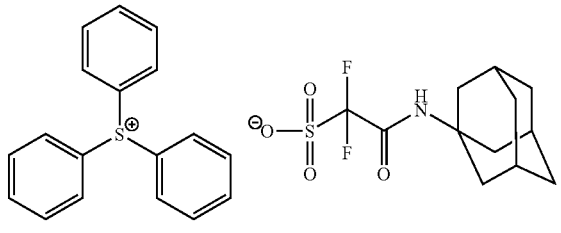

Photo-acid generator (A) can be used either individually or in combination.

The content ratio of photo-acid generator (A) is preferably in the range of 1 to 60 mass %, more preferably 3 to 50 mass % and still more preferably 3 to 35 mass % based on the total solid content of the composition.

(B) Resin Whose Solubility in an Alkali Developer is Increased by the Action of an Acid The composition of the present invention comprises resin (B) whose solubility in an alkali developer is increased by the action of an acid.

The resin whose solubility in an alkali developer is increased by the action of an acid (acid-decomposable resin) has, in its principal chain or side chain, or both of its principal chain and side chain, a group (hereinafter also referred to as "an acid-decomposable group") that is decomposed by the action of an acid to thereby generate an alkali-soluble group.

Resin (B) is preferably insoluble or poorly soluble in alkali developers.

The acid-decomposable group preferably has a structure protected by a group that is decomposed by the action of an acid to thereby eliminate an alkali-soluble group.

As the alkali soluble group, there can be mentioned a phenolic hydroxyl group, a carboxyl group, a fluoroalcohol group, a sulfonate group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, a tris(alkylsulfonyl)methylene group or the like.

As preferred alkali soluble groups, there can be mentioned a carboxyl group, a fluoroalcohol group (preferably hexafluoroisopropanol) and a sulfonate group.

The acid-decomposable group is preferably a group as obtained by substituting the hydrogen atom of any of these alkali soluble groups with an acid eliminable group.

As the acid eliminable group, there can be mentioned, for example, —C($R_{36}$)($R_{37}$)($R_{38}$), —C($R_{36}$)($R_{37}$)($OR_{39}$), —C($R_{01}$)($R_{02}$)($OR_{39}$) or the like.

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded with each other to thereby form a ring structure.

Each of $R_{01}$ to $R_{02}$ independently represents a hydrogen atom, an alkyl group, a cycloalkyl group, an aryl group, an aralkyl group or an alkenyl group.

Preferably, the acid-decomposable group is a cumyl ester group, an enol ester group, an acetal ester group, a tertiary alkyl ester group or the like. A tertiary alkyl ester group is more preferred.

The repeating unit with an acid-decomposable group that may be contained in the resin (B) is preferably any of those of the following general formula (AI).

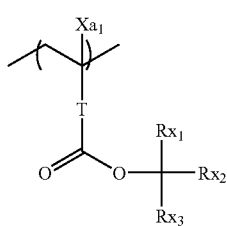

(AI)

In general formula (AI),

Xa₁ represents a hydrogen atom, an optionally substituted methyl group or any of the groups of formula —CH₂—R₉. R₉ represents a hydroxyl group or a monovalent organic group. The monovalent organic group is, for example, an alkyl group having 5 or less carbon atoms or an acyl group. Preferably, the monovalent organic group is an alkyl group having 3 or less carbon atoms, more preferably a methyl group. Xa₁ preferably represents a hydrogen atom, a methyl group, a trifluoromethyl group or a hydroxymethyl group.

T represents a single bond or a bivalent connecting group.

Each of Rx₁ to Rx₃ independently represents an alkyl group (linear or branched) or a cycloalkyl group (monocyclic or polycyclic).

At least two of Rx₁ to Rx₃ may be bonded with each other to thereby form a cycloalkyl group (monocyclic or polycyclic).

As the bivalent connecting group represented by T, there can be mentioned an alkylene group, a group of the formula —COO-Rt-, a group of the formula —O-Rt- or the like. In the formulae, Rt represents an alkylene group or a cycloalkylene group.

T is preferably a single bond or a group of the formula —COO-Rt-. Rt is preferably an alkylene group having 1 to 5 carbon atoms, more preferably a —CH₂— group or —(CH₂)₃— group.

The alkyl group represented by each of Rx₁ to Rx₃ is preferably one having 1 to 4 carbon atoms, such as a methyl group, an ethyl group, an n-propyl group, an isopropyl group, an n-butyl group, an isobutyl group or a t-butyl group.

The cycloalkyl group represented by each of Rx₁ to Rx₃ is preferably a cycloalkyl group of one ring, such as a cyclopentyl group or a cyclohexyl group, or a cycloalkyl group of multiple rings, such as a norbornyl group, a tetracyclodecanyl group, a tetracyclododecanyl group or an adamantyl group.

The cycloalkyl group formed by bonding of at least two of Rx₁ to Rx₃ is preferably a cycloalkyl group of one ring, such as a cyclopentyl group or a cyclohexyl group, or a cycloalkyl group of multiple rings, such as a norbornyl group, a tetracyclodecanyl group, a tetracyclododecanyl group or an adamantyl group.

In a preferred mode, Rx₁ is a methyl group or an ethyl group, and Rx₂ and Rx₃ are bonded with each other to thereby form any of the above-mentioned cycloalkyl groups.

Each of these groups may have a substituent. As the substituent, there can be mentioned, for example, an alkyl group (1 to 4 carbon atoms), a halogen atom, a hydroxyl group, an alkoxy group (1 to 4 carbon atoms), a carboxyl group, an alkoxycarbonyl group (2 to 6 carbon atoms) or the like. The number of carbon atoms of the substituent is preferably 8 or less.

The total content of the repeating units with acid-decomposable groups is preferably in the range of 20 to 70 mol %, more preferably 30 to 50 mol %, based on all the repeating units of the resin (B).

Specific examples of the preferred repeating units with acid-decomposable groups will be shown below, which however in no way limit the scope of the present invention.

In the following formulae, each of Rx and Xa₁ represents a hydrogen atom, CH₃, CF₃ or CH₂OH. Each of Rxa and Rxb represents an alkyl group having 1 to 4 carbon atoms. Z, each independently in the presence of two or more groups, represents a substituent containing a polar group. p represents 0 or a positive integer.

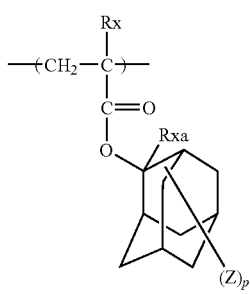

1

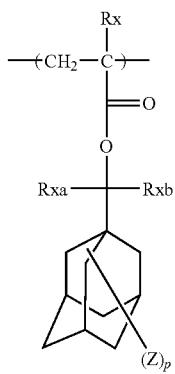

2

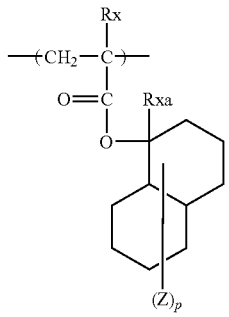

3

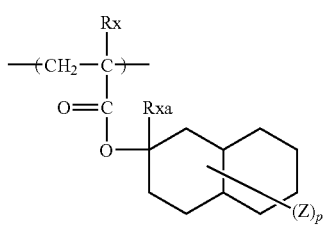

4

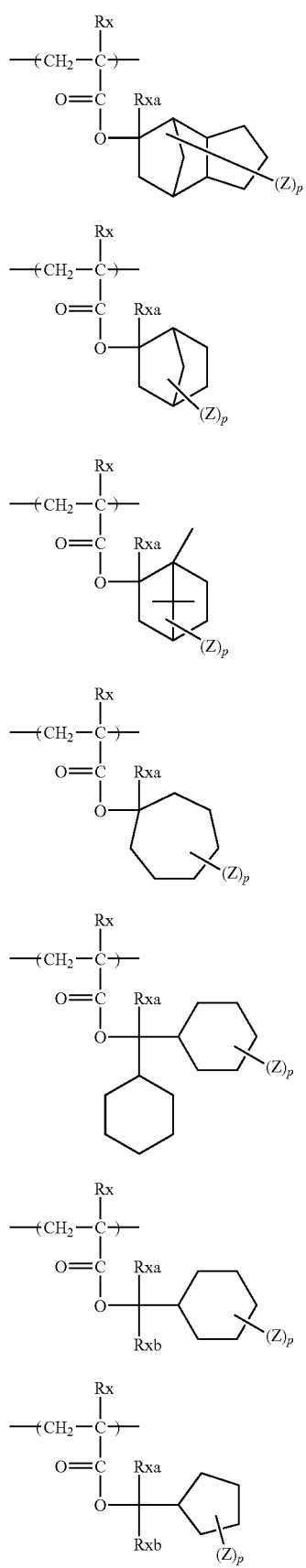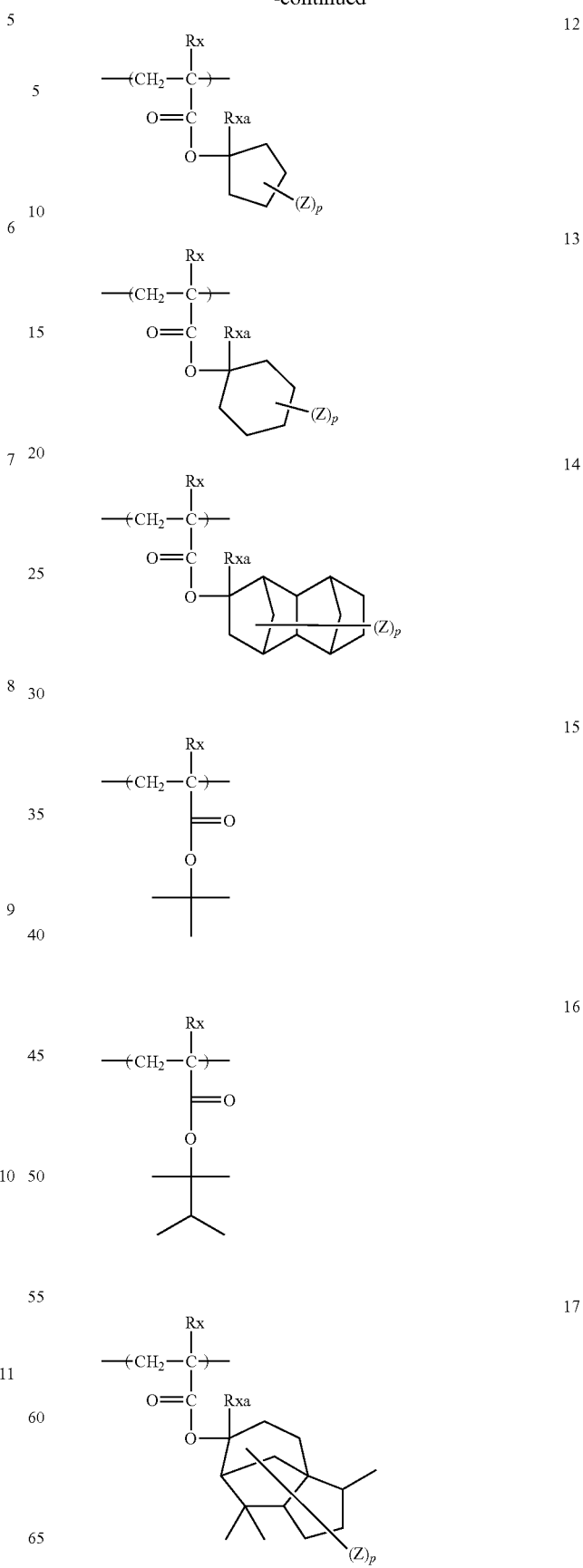

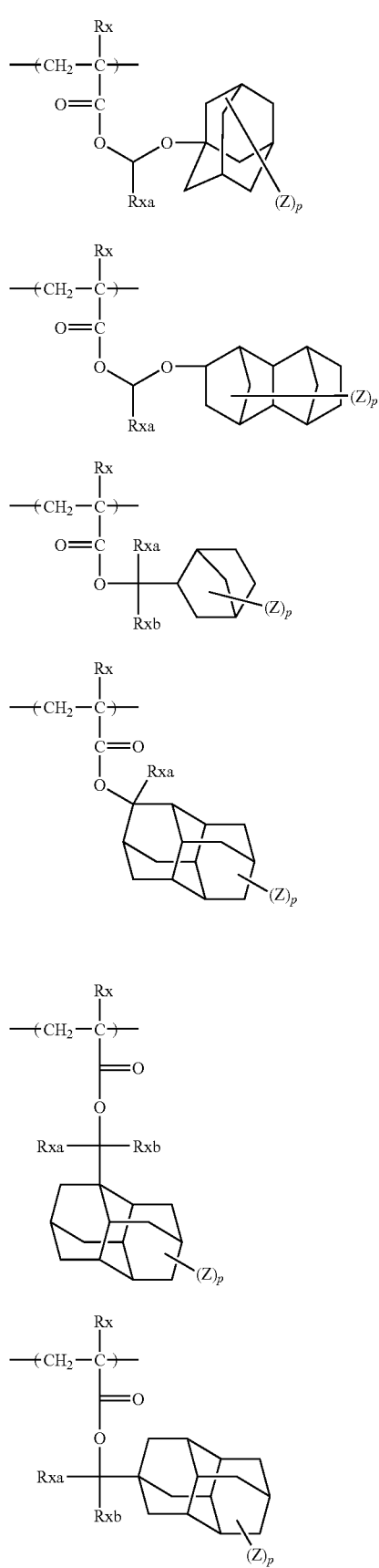
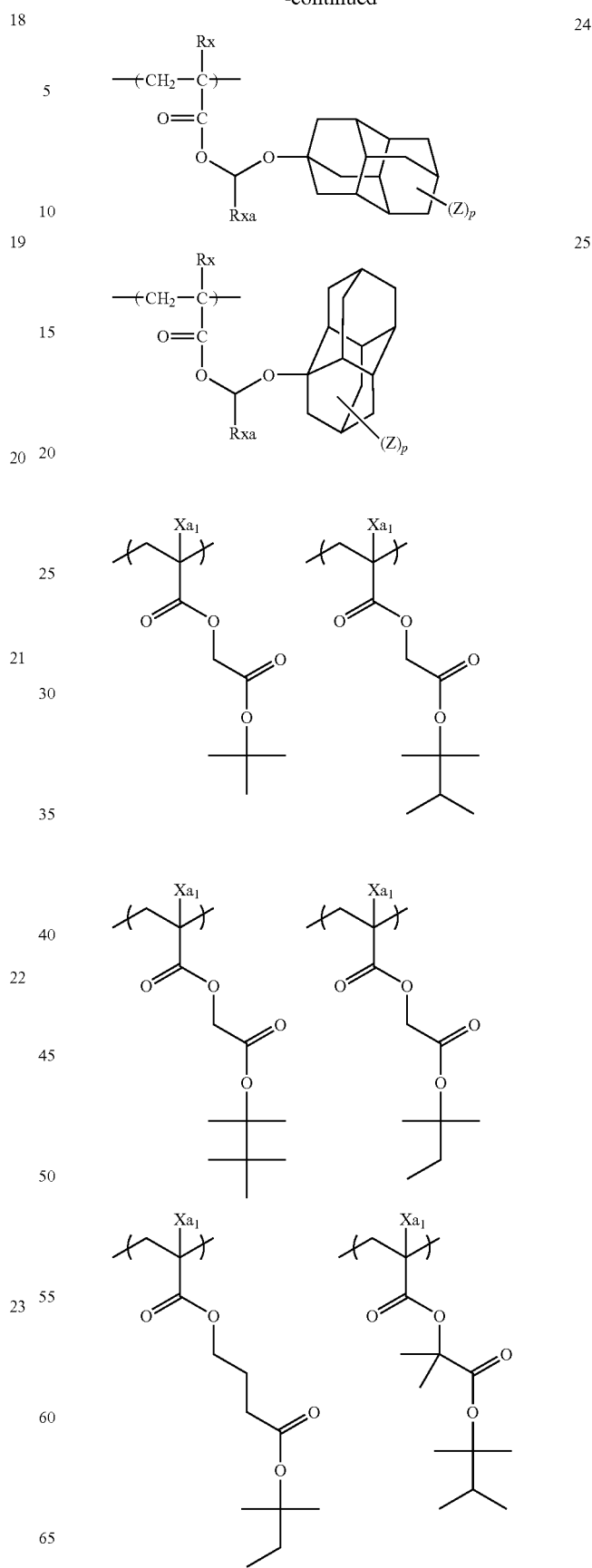

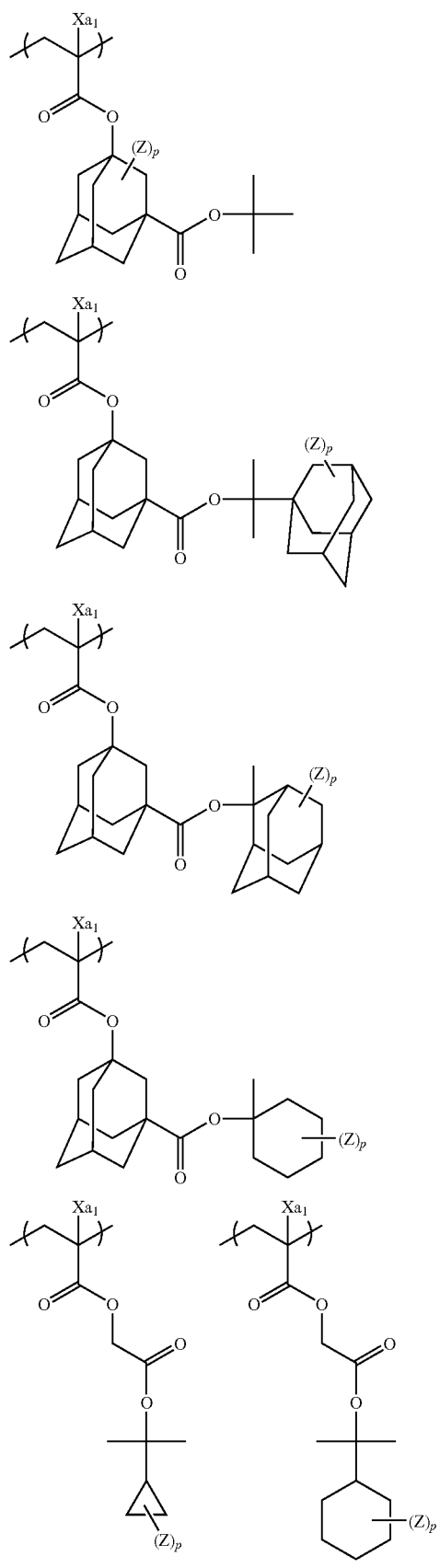
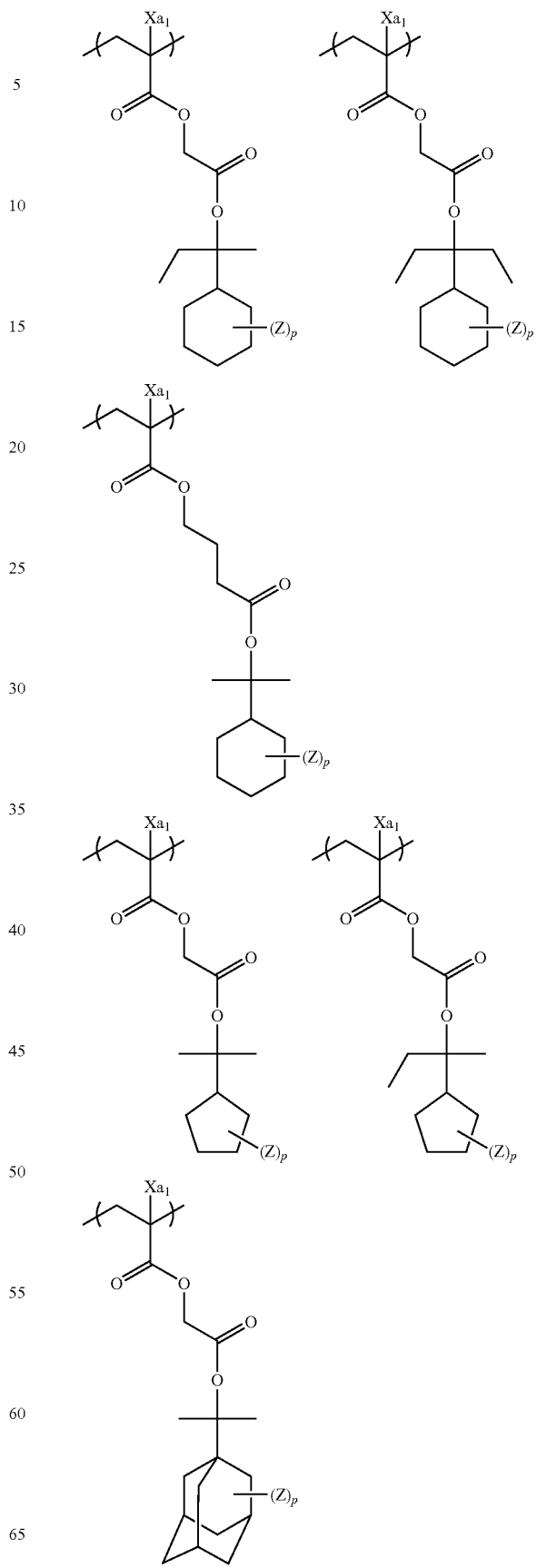

75
-continued
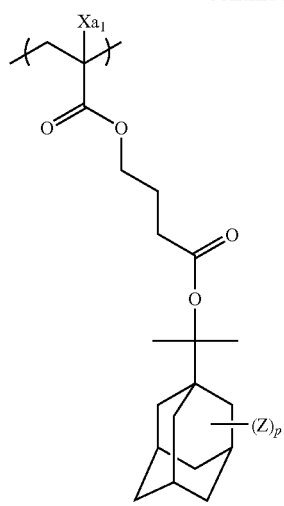
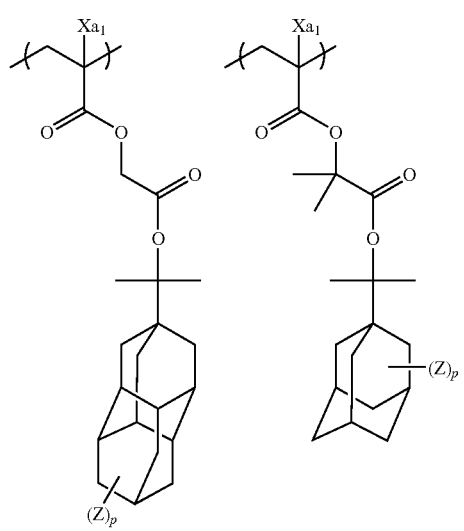
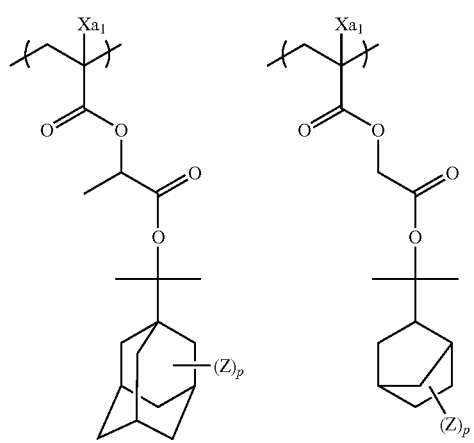
76
-continued
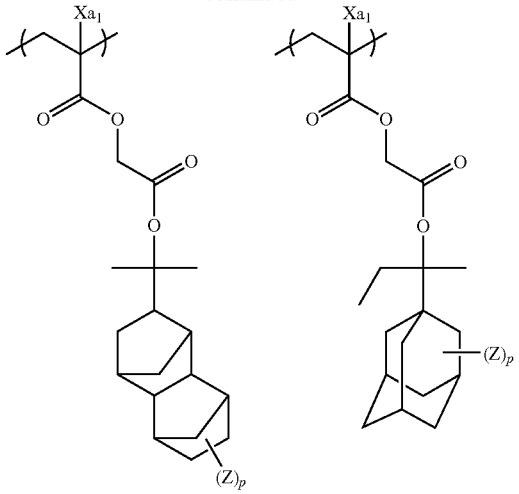
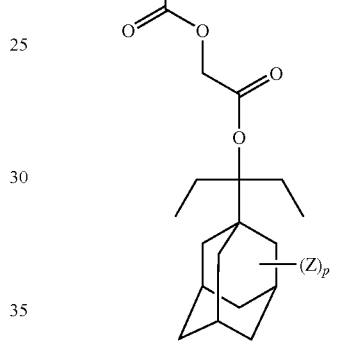
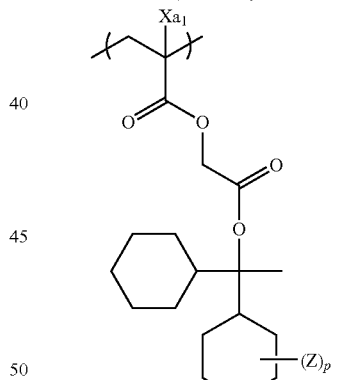
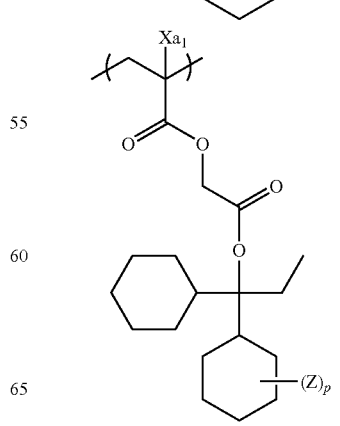

77
-continued
78
-continued
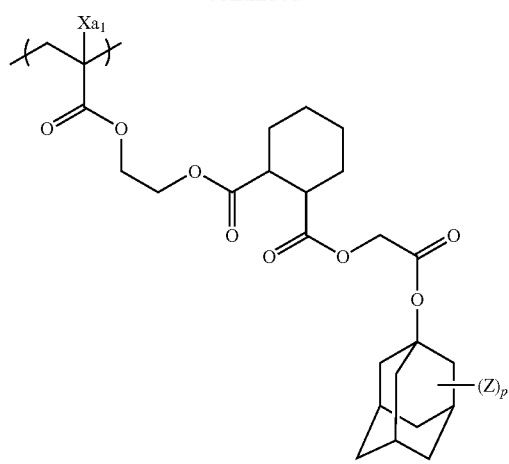
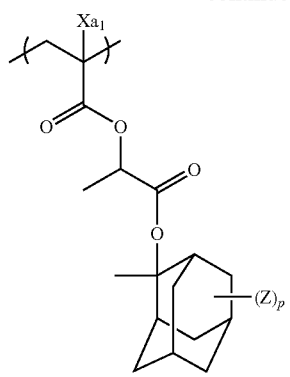
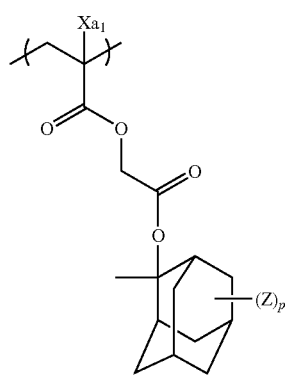
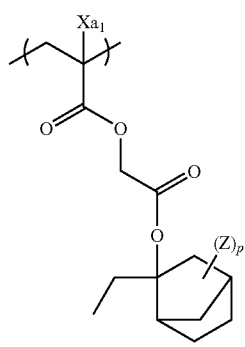
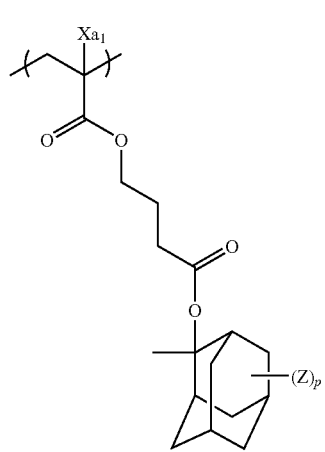
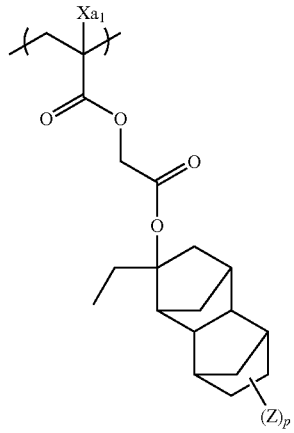
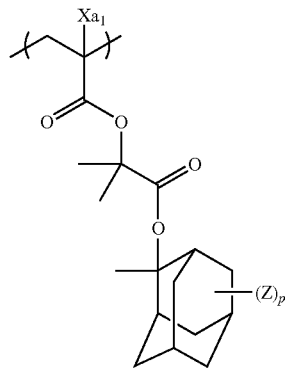
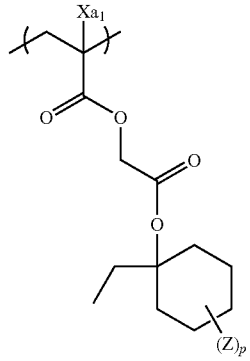 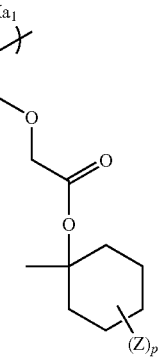

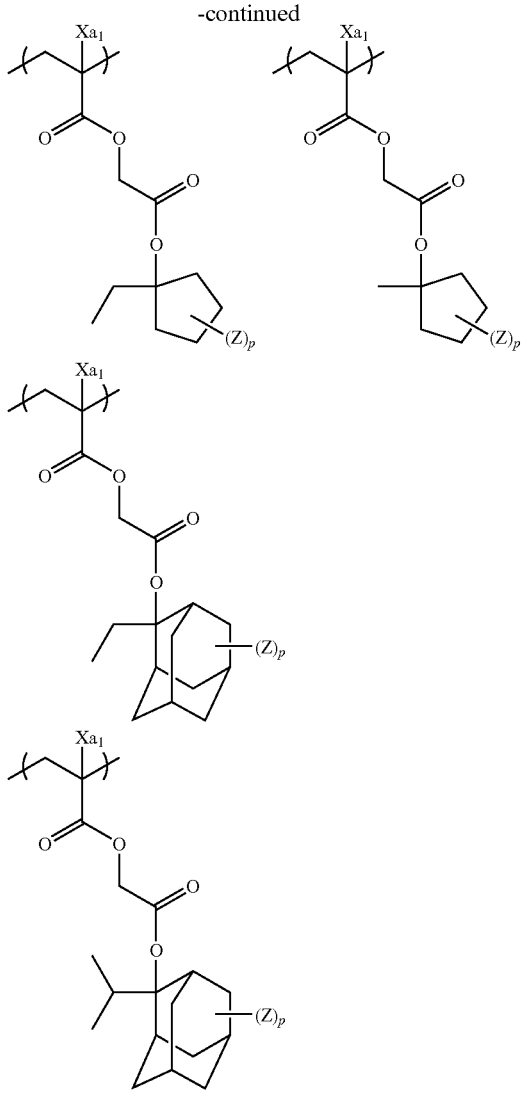

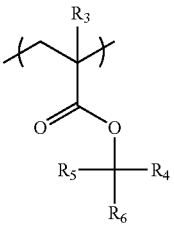

It is more preferred for resin (B) in its one form to be a resin having, as the repeating units of general formula (AI), at least either any of the repeating units of general formula (I) below or any of the repeating units of general formula (II) below. It is more preferred for resin (B) in its other form to be a resin having, as the repeating units of general formula (AI), at least two members of the repeating units of general formula (I) below. It is more preferred for resin (B) in its further form to be a resin having, as the repeating units of general formula (AI), any of the repeating units of general formula (I) below together with any of the repeating units of general formula (II) below.

In general formulae (I) and (II), each of $R_1$ and $R_3$ independently represents a hydrogen atom, an optionally substituted methyl group or any of the groups of formula —$CH_2$—$R_9$. $R_9$ represents a monovalent organic group.

Each of $R_2$, $R_4$, $R_5$ and $R_6$ independently represents an alkyl group or a cycloalkyl group.

R represents an atomic group required for forming an alicyclic structure in cooperation with a carbon atom.

$R_1$ preferably represents a hydrogen atom, a methyl group, a trifluoromethyl group or a hydroxymethyl group.

The alkyl group represented by $R_2$ may be linear or branched, and may have a substituent.

The cycloalkyl group represented by $R_2$ may be monocyclic or polycyclic, and may have a substituent.

$R_2$ preferably represents an alkyl group, more preferably an alkyl group having 1 to 10 carbon atoms, especially 1 to 5 carbon atoms. As examples thereof, there can be mentioned a methyl group and an ethyl group.

R represents an atomic group required for forming an alicyclic structure in cooperation with a carbon atom. The alicyclic structure formed by R is preferably an alicyclic structure of a single ring, and preferably has 3 to 7 carbon atoms, more preferably 5 or 6 carbon atoms.

$R_3$ preferably represents a hydrogen atom or a methyl group, more preferably a methyl group.

Each of the alkyl groups represented by $R_4$, $R_5$ and $R_6$ may be linear or branched, and may have a substituent. The alkyl groups preferably are those each having 1 to 4 carbon atoms, such as a methyl group, an ethyl group, an n-propyl group, an isopropyl group, an n-butyl group, an isobutyl group and a t-butyl group.

Each of the cycloalkyl groups represented by $R_4$, $R_5$ and $R_6$ may be monocyclic or polycyclic, and may have a substituent. The cycloalkyl groups are preferably a cycloalkyl group of a single ring, such as a cyclopentyl group or a cyclohexyl group, and a cycloalkyl group of multiple rings, such as a norbornyl group, a tetracyclodecanyl group, a tetracyclododecanyl group or an adamantyl group.

As the repeating units of general formula (I), there can be mentioned those of general formula (I-1) below.

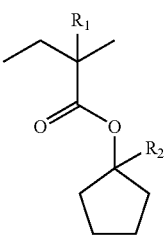

In this formula, $R_1$ and $R_2$ have the same meaning as in general formula (I).

The repeating units of general formula (II) are preferably those of general formula (II-1) below.

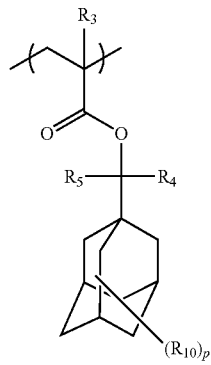

(II-1)

In general formula (II-1), $R_3$ to $R_5$ have the same meaning as in general formula (II).

$R_{10}$ represents a substituent containing a polar group. When a plurality of $R_{10}$s exist, they may be identical to or different from each other. As the substituent containing a polar group, there can be mentioned, for example, a linear or branched alkyl group, or cycloalkyl group, having a hydroxyl group, a cyano group, an amino group, an alkylamido group or a sulfonamido group. An alkyl group having a hydroxyl group is preferred. An isopropyl group is especially preferred as the branched alkyl group.

In the formula, p is an integer of 0 to 15, preferably in the range of 0 to 2, and more preferably 0 or 1.

When a plurality of acid-decomposable repeating units are simultaneously used in resin (B), preferred combinations thereof are shown below. In the following particular examples, R represents a hydrogen atom or an optionally substituted methyl group.

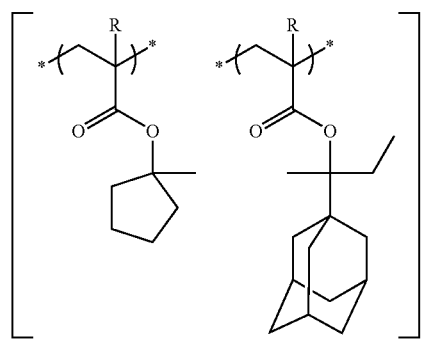

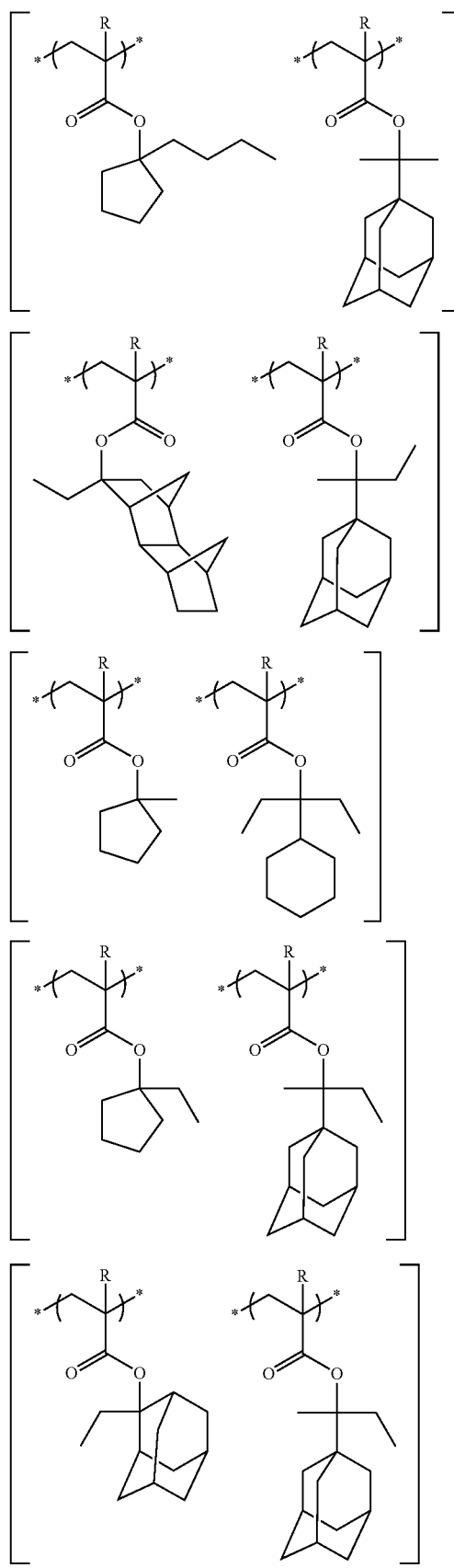

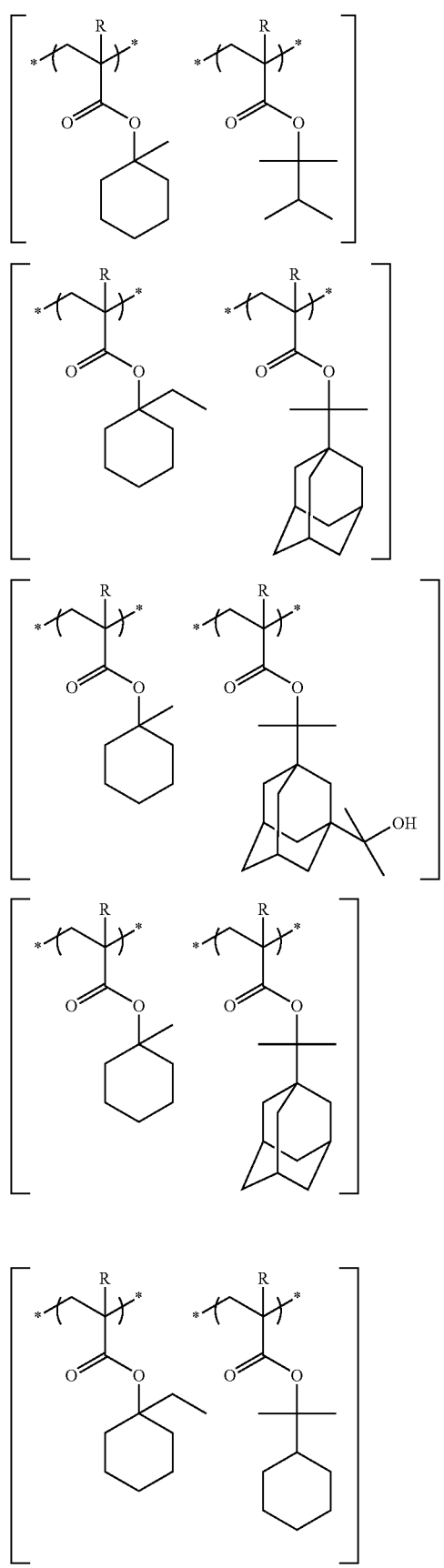
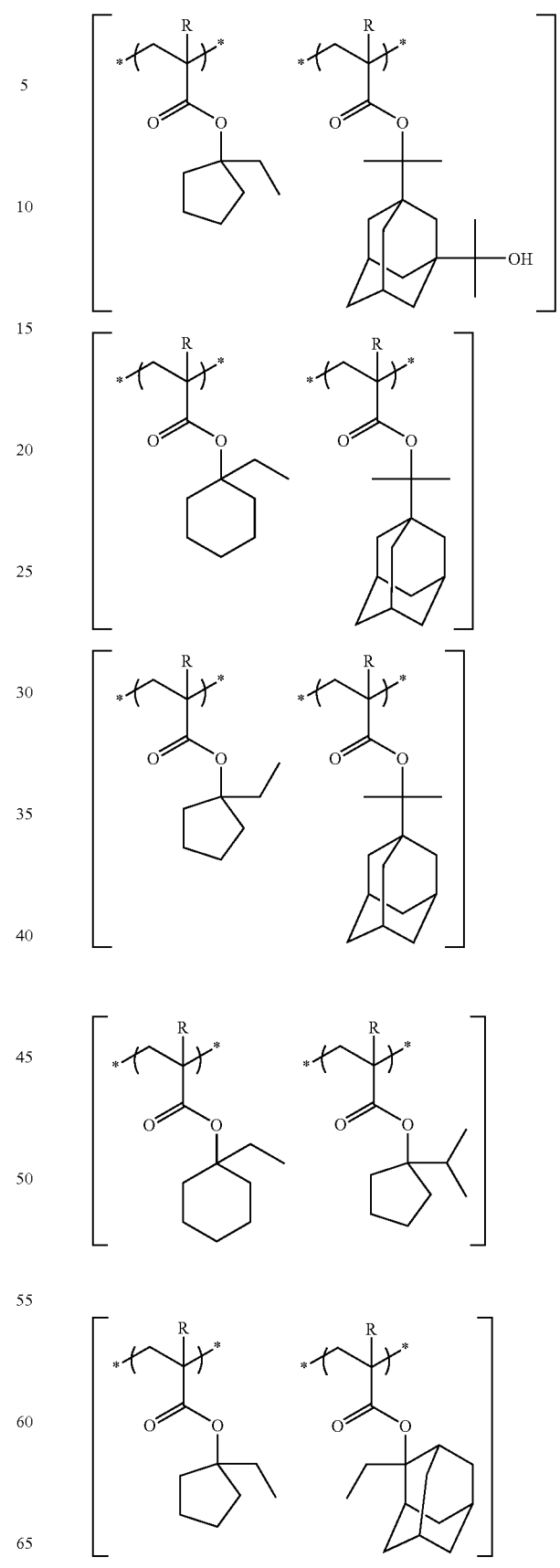

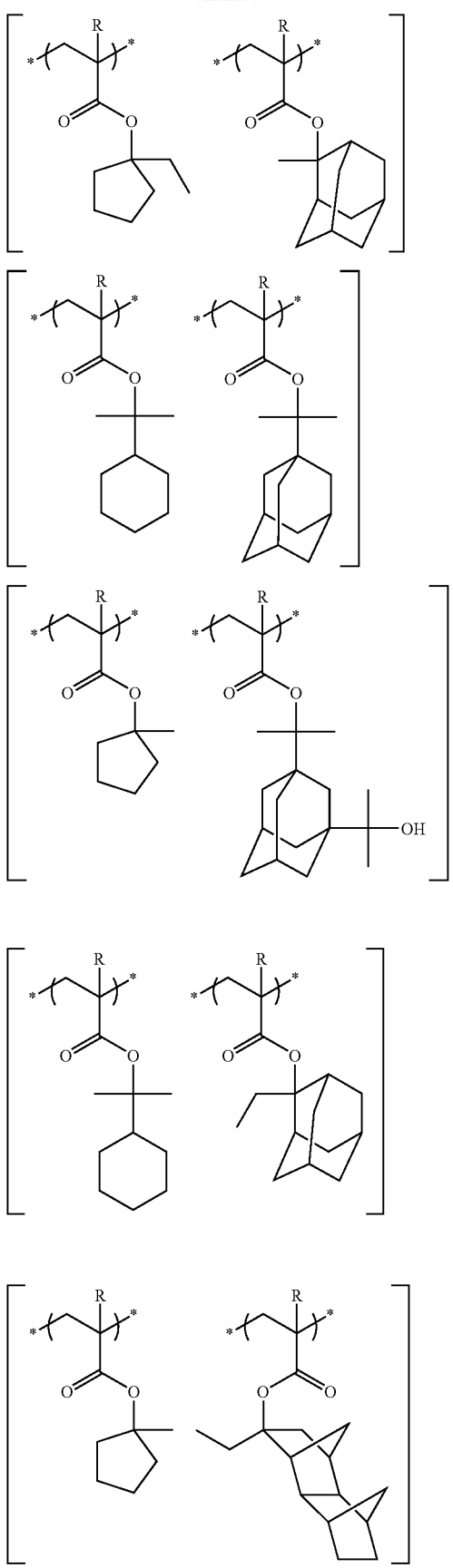

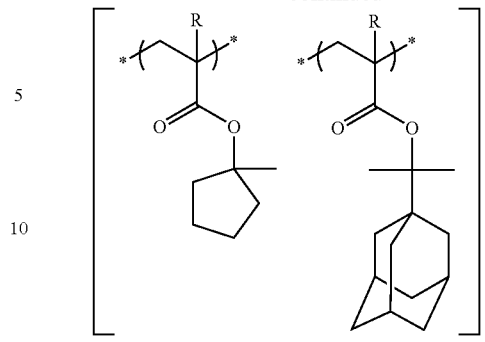

It is preferred for resin (B) to contain any of the repeating units having a lactone group represented by the following general formula (III).

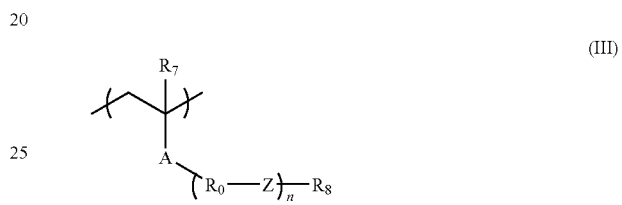

In formula (III),

A represents an ester bond (—COO—) or an amido bond (—CONH—).

$R_0$, each independently in the presence of two or more groups, represents an alkylene group, a cycloalkylene group or a combination thereof.

Z, each independently in the presence of two or more groups, represents an ether bond, an ester bond, a carbonyl group, an amido bond, a urethane bond

or a urea bond

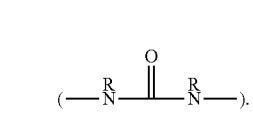

In the formulae, R represents a hydrogen atom, an alkyl group, a cycloalkyl group or an aryl group.

$R_8$ represents a monovalent organic group with a lactone structure.

n represents the number of repetitions of the structure of the formula —$R_0$—Z— and is an integer of 1 to 5.

$R_7$ represents a hydrogen atom, a halogen atom or an alkyl group.

Each of the alkylene group and cycloalkylene group represented by $R_0$ may have a substituent.

Z preferably represents an ether bond or an ester bond, most preferably an ester bond.

The alkyl group represented by $R_7$ is preferably an alkyl group having 1 to 4 carbon atoms, more preferably a methyl group or an ethyl group and most preferably a methyl group. The alkyl group represented by $R_7$ may be substituted. As substituents on $R_7$, there can be mentioned, for example, a halogen atom such as a fluorine atom, a chlorine atom or a bromine atom, a mercapto group, a hydroxyl group, an alkoxy group such as a methoxy group, an ethoxy group, an isopropoxy group, a t-butoxy group or a benzyloxy group, an acyl group such as an acetyl group or a propionyl group, an acetoxy group and the like. $R_7$ preferably represents a hydrogen atom, a methyl group, a trifluoromethyl group or a hydroxymethyl group.

The chain alkylene group represented by $R_0$ is preferably a chain alkylene having 1 to 10 carbon atoms, more preferably 1 to 5 carbon atoms, for example, a methylene group, an ethylene group, a propylene group or the like. The cycloalkylene group is preferably a cycloalkylene having 1 to 20 carbon atoms. As such, there can be mentioned, for example, cyclohexylene, cyclopentylene, norbornylene, adamantylene or the like. The chain alkylene groups are preferred from the viewpoint of the exertion of the effect of the present invention. A methylene group is especially preferred.

The substituent with a lactone structure represented by $R_8$ is not limited as long as the lactone structure is contained. As particular examples thereof, there can be mentioned the lactone structures of general formulae (LC1-1) to (LC1-17) to be shown hereinafter. Of these, the structures of general formula (LC1-4) are most preferred. In general formulae (LC1-1) to (LC1-17), $n_2$ is more preferably 2 or less.

$R_8$ preferably represents a monovalent organic group with an unsubstituted lactone structure or a monovalent organic group with a lactone structure substituted with a methyl group, a cyano group or an alkoxycarbonyl group. More preferably, $R_8$ represents a monovalent organic group with a lactone structure substituted with a cyano group (cyanolactone).

Specific examples of the repeating units having the groups with a lactone structure of general formula (III) will be shown below, which however in no way limit the scope of the present invention.

In the following specific examples, R represents a hydrogen atom, an optionally substituted alkyl group or a halogen atom. Preferably, R represents a hydrogen atom, a methyl group, a hydroxymethyl group or an acetoxymethyl group.

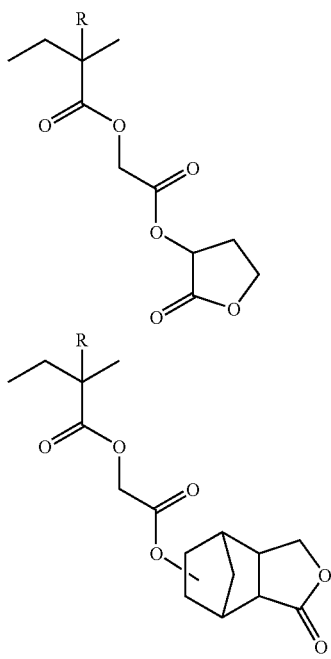

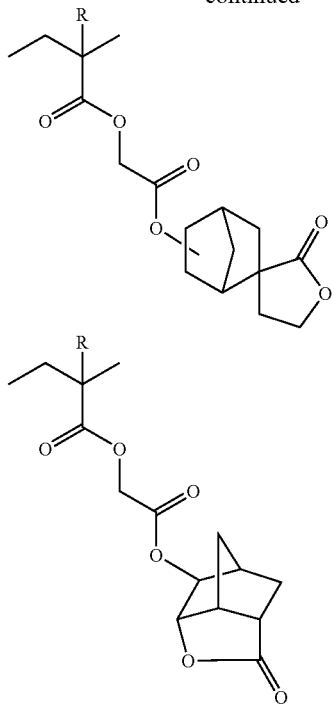

The repeating units of general formula (III-1) below are more preferred as the repeating units with a lactone structure.

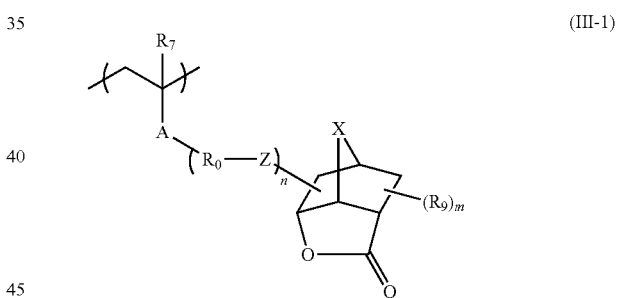

In general formula (III-1), $R_7$, A, $R_0$, Z and n are as defined above with respect to general formula (III).

$R_9$, each independently in the presence of two or more groups, represents an alkyl group, a cycloalkyl group, an alkoxycarbonyl group, a cyano group, a hydroxyl group or an alkoxy group. In the presence of two or more groups, two $R_{9s}$ may be bonded to each other to thereby form a ring.

X represents an alkylene group, an oxygen atom or a sulfur atom, and m is the number of substituents and is an integer of 0 to 5. Preferably, m is 0 or 1.

The alkyl group represented by $R_9$ is preferably an alkyl group having 1 to 4 carbon atoms, more preferably a methyl group or an ethyl group and most preferably a methyl group. As the cycloalkyl group, there can be mentioned a cyclopropyl group, a cyclobutyl group, a cyclopentyl group or a cyclohexyl group. As the alkoxycarbonyl group, there can be mentioned a methoxycarbonyl group, an ethoxycarbonyl group, an n-butoxycarbonyl group, a t-butoxycarbonyl group or the like. These groups may have a substituent. As the substituent therefor, there can be mentioned a hydroxyl group, an alkoxy group such as a methoxy group or an ethoxy group, a cyano group, or a halogen atom such as a fluorine atom. More preferably, $R_9$ represents a methyl group, a cyano group or an alkoxycarbonyl group, still more preferably a cyano group.

As the alkylene group represented by X, there can be mentioned a methylene group, an ethylene group or the like. Preferably, X represents an oxygen atom or a methylene group, more preferably a methylene group.

When m is 1 or greater, the substitution site of at least one $R_9$ is preferably the α-position or β-position of the carbonyl group of the lactone. The substitution at the α-position is especially preferred.

Specific examples of the repeating units having groups with a lactone structure expressed by general formula (III-1) will be shown below, which however in no way limit the scope of the present invention. In the formulae, R represents a hydrogen atom, an optionally substituted alkyl group or a halogen atom, more preferably a hydrogen atom, a methyl group, a hydroxymethyl group or an acetoxymethyl group.

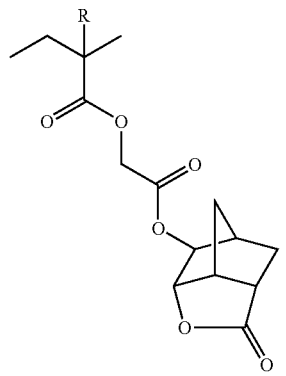

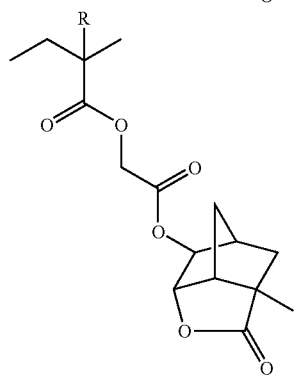

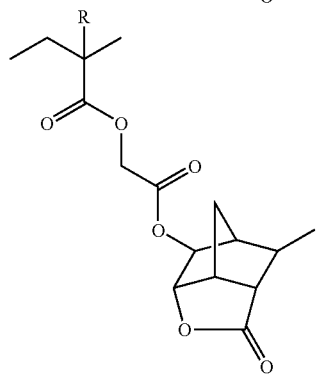

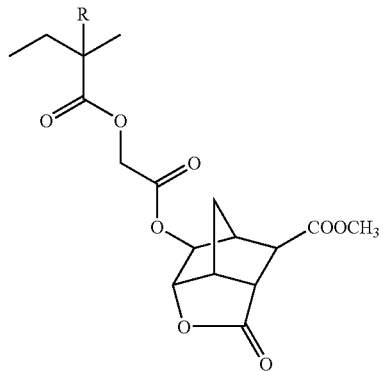

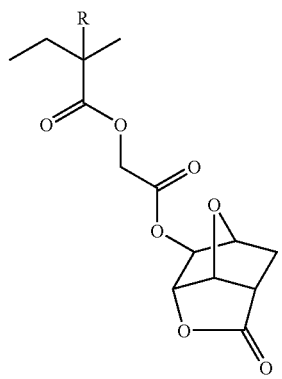

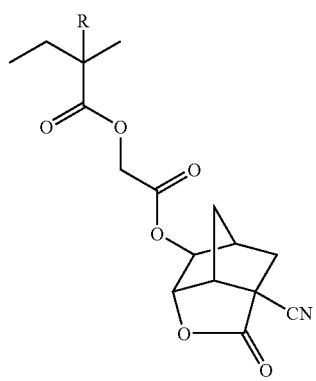

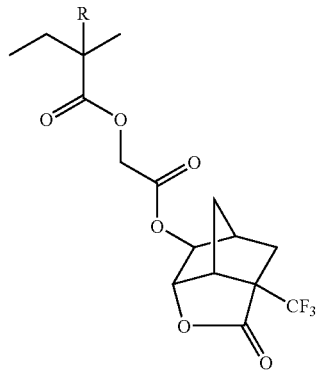

91
-continued
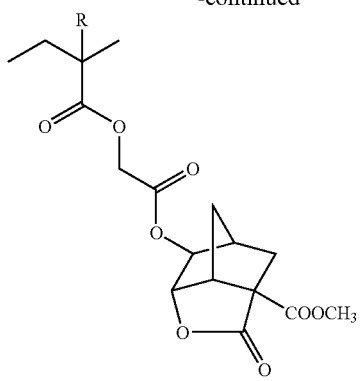
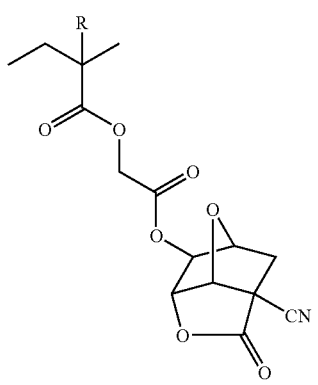
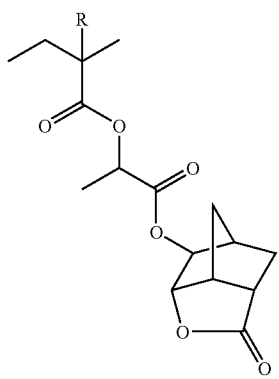
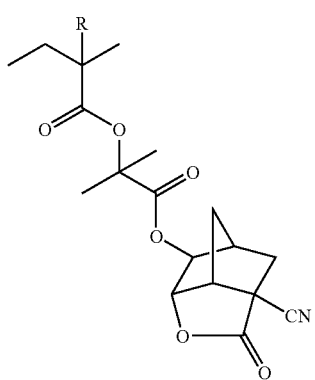
92
-continued
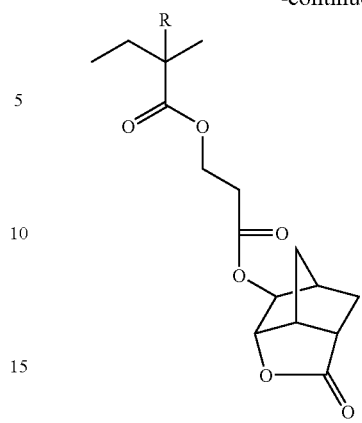
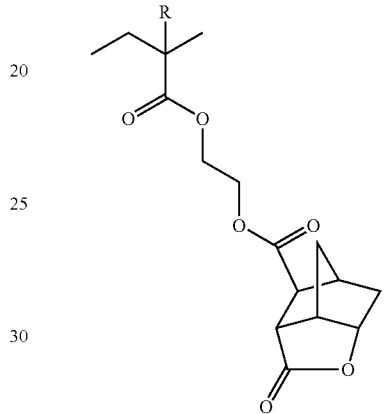
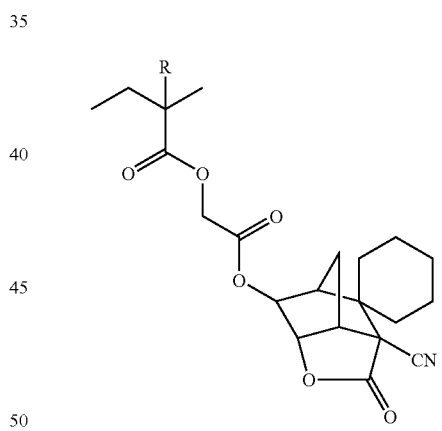
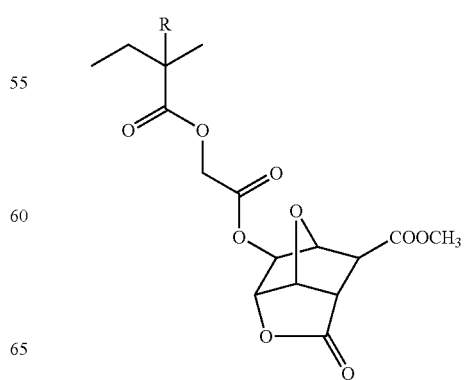

93
-continued
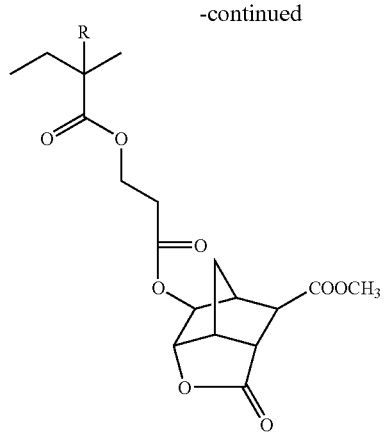
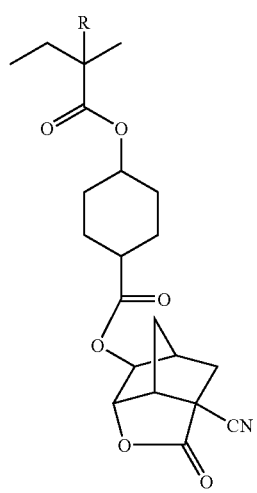
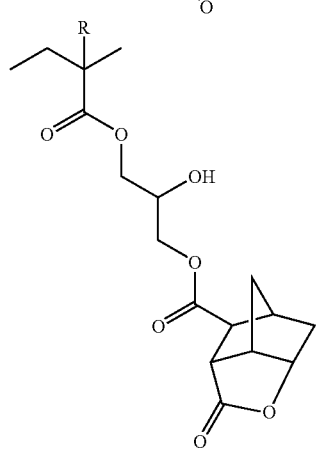
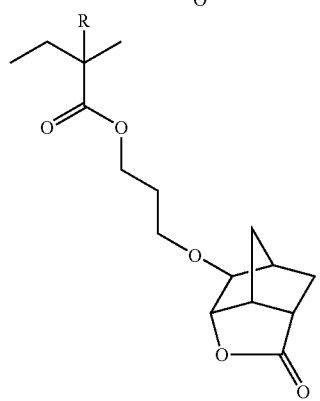
94
-continued
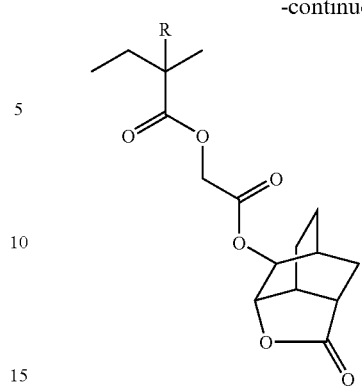
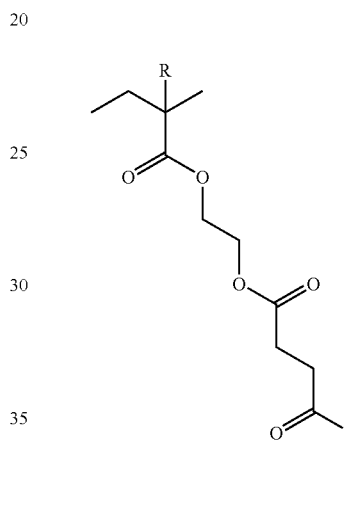
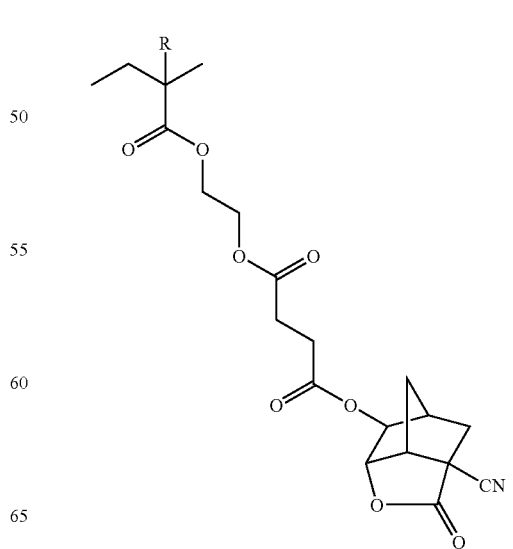

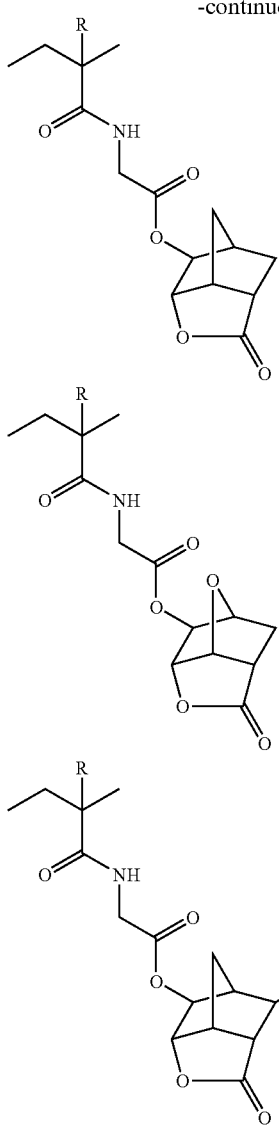

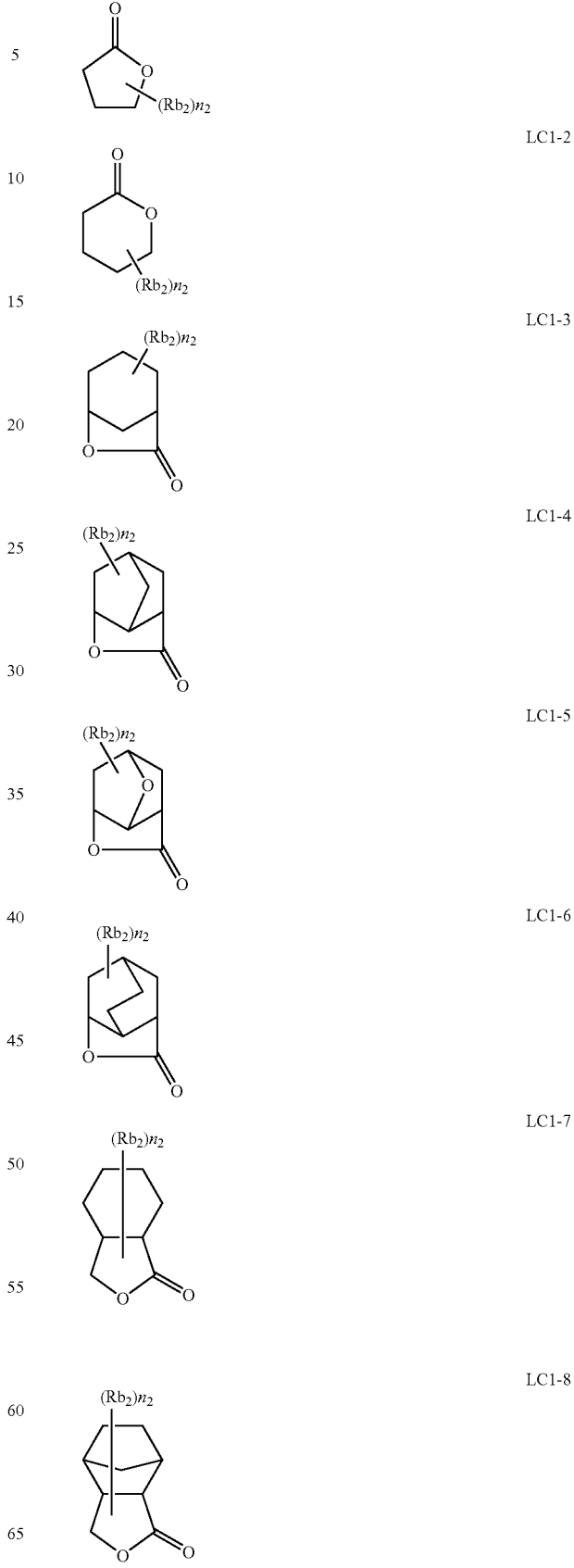

The content of the repeating units of general formula (III), the sum thereof when a plurality of repeating units are contained, is preferably in the range of 15 to 60 mol %, more preferably 20 to 60 mol % and further preferably 30 to 50 mol %, based on all the repeating units contained in the resin.

Resin (B) may contain not only the units of general formula (III) but also repeating units having a lactone group.

Any lactone groups can be employed as long as a lactone structure is possessed therein. However, lactone structures of a 5 to 7-membered ring are preferred, and in particular, those resulting from condensation of lactone structures of a 5 to 7-membered ring with other cyclic structures effected in a fashion to form a bicyclo structure or spiro structure are preferred. The possession of repeating units having a lactone structure represented by any of the following general formulae (LC1-1) to (LC1-17) is more preferred. The lactone structures may be directly bonded to the principal chain of the resin. Preferred lactone structures are those of formulae (LC1-1), (LC1-4), (LC1-5), (LC1-6), (LC1-13), (LC1-14) and (LC1-17). The use of these specified lactone structures would ensure improvement in LWR and development defect.

-continued

LC1-9 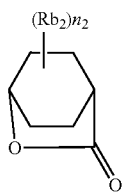

LC1-10 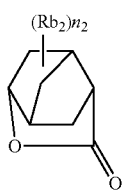

LC1-11 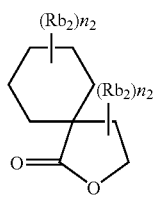

LC1-12 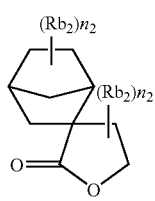

LC1-13 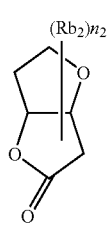

LC1-14 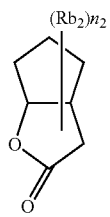

LC1-15 

LC1-16 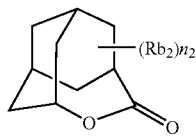

LC1-17 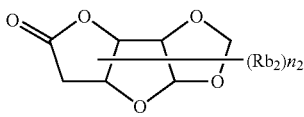

The presence of a substituent ($Rb_2$) on the portion of the lactone structure is optional. As a preferred substituent ($Rb_2$), there can be mentioned an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, an acid-decomposable group or the like. Of these, an alkyl group having 1 to 4 carbon atoms, a cyano group and an acid-decomposable group are more preferred. In the formulae, $n_2$ is an integer of 0 to 4. When $n_2$ is 2 or greater, the plurality of present substituents ($Rb_2$) may be identical to or different from each other. Further, the plurality of present substituents ($Rb_2$) may be bonded to each other to thereby form a ring.

It is also preferred for the repeating units having a lactone structure other than the repeating units of general formula (III) to be the repeating units of the following general formula (AII').

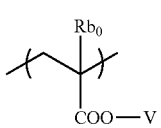 (AII')

In general formula (AII'), $Rb_0$ represents a hydrogen atom, a halogen atom or an optionally substituted alkyl group having 1 to 4 carbon atoms. As a preferred substituent optionally contained in the alkyl group represented by $Rb_0$, there can be mentioned a hydroxyl group or a halogen atom. As the halogen atom represented by $Rb_0$, there can be mentioned a fluorine atom, a chlorine atom, a bromine atom or an iodine atom. The $Ab_0$ is preferably a hydrogen atom, a methyl group, a hydroxymethyl group or a trifluoromethyl group. A hydrogen atom and a methyl group are especially preferred.

V represents a group with a structure represented by any of general formulae (LC1-1) to (LC1-17).

Specific examples of the repeating units having a lactone group other than the repeating units of general formula (III) will now be shown, which however in no way limit the scope of the present invention. In the formulae, Rx represents H, $CH_3$, $CH_2OH$ or $CF_3$.

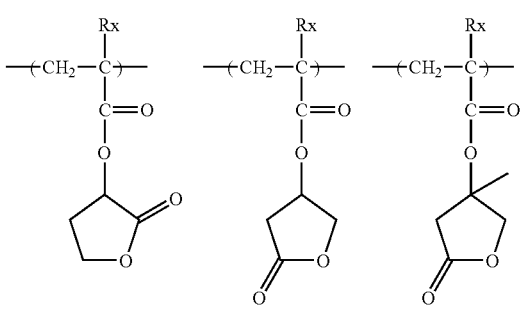

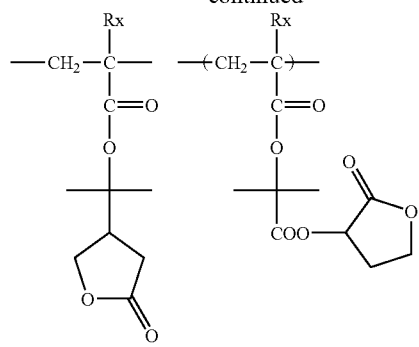
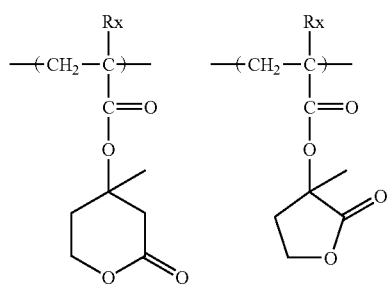
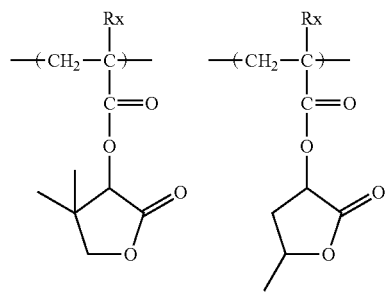
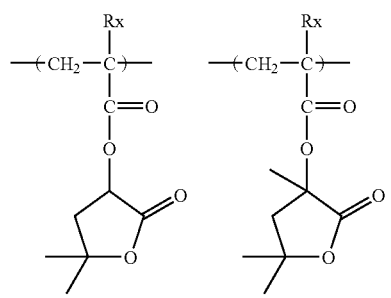
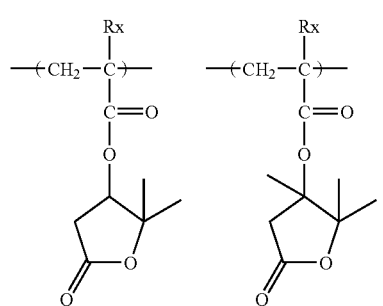
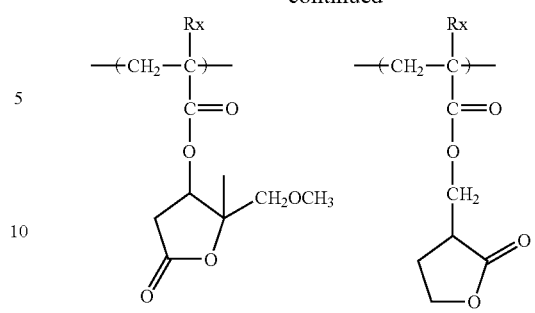
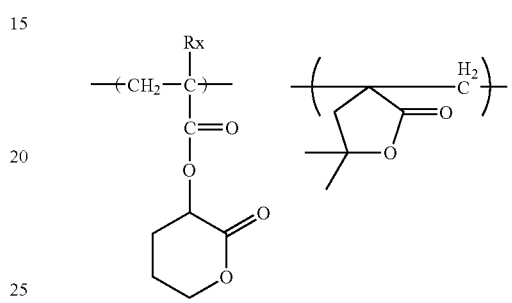
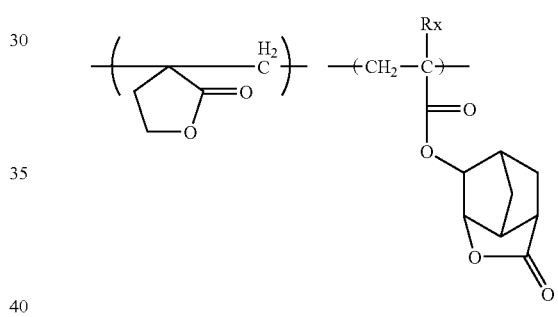
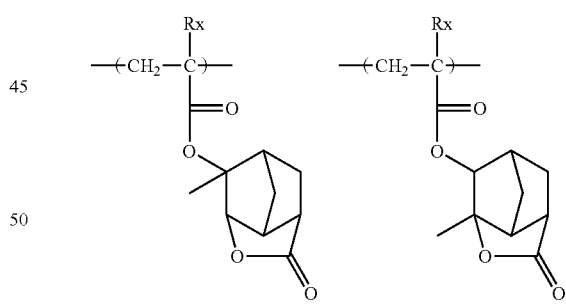
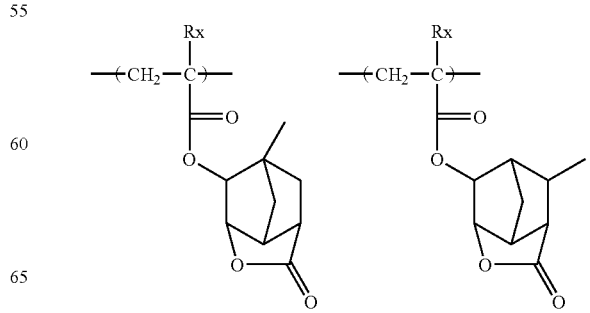

101
-continued
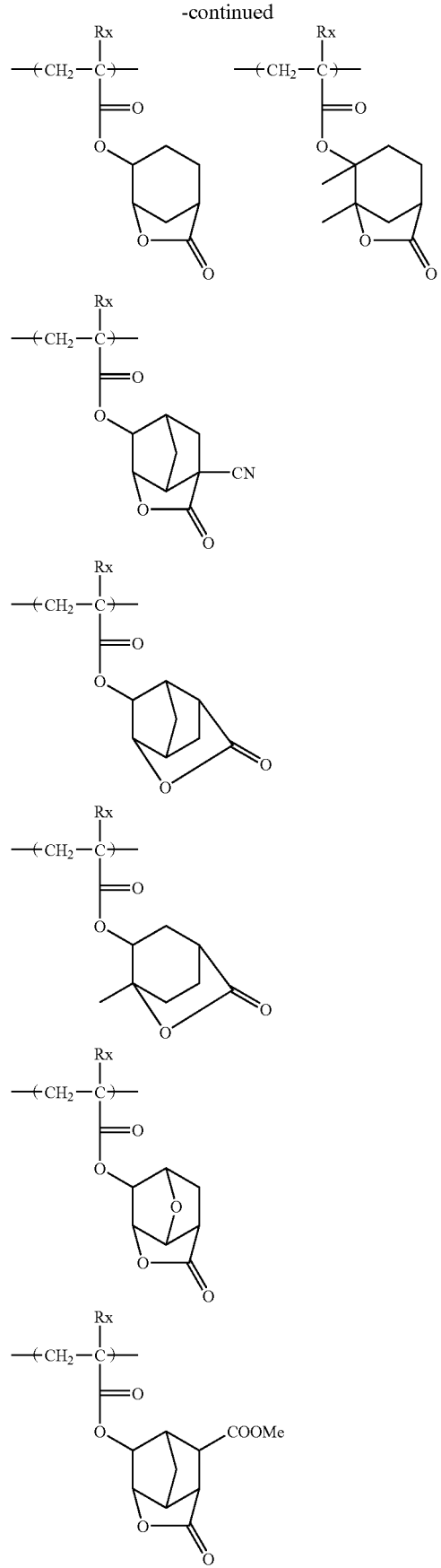
102
-continued
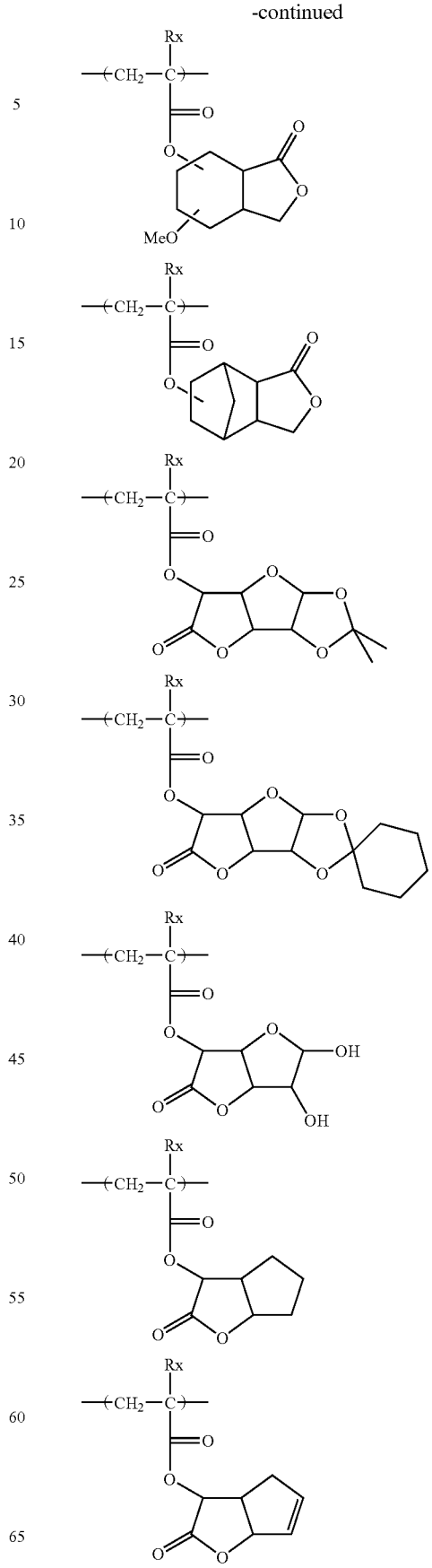

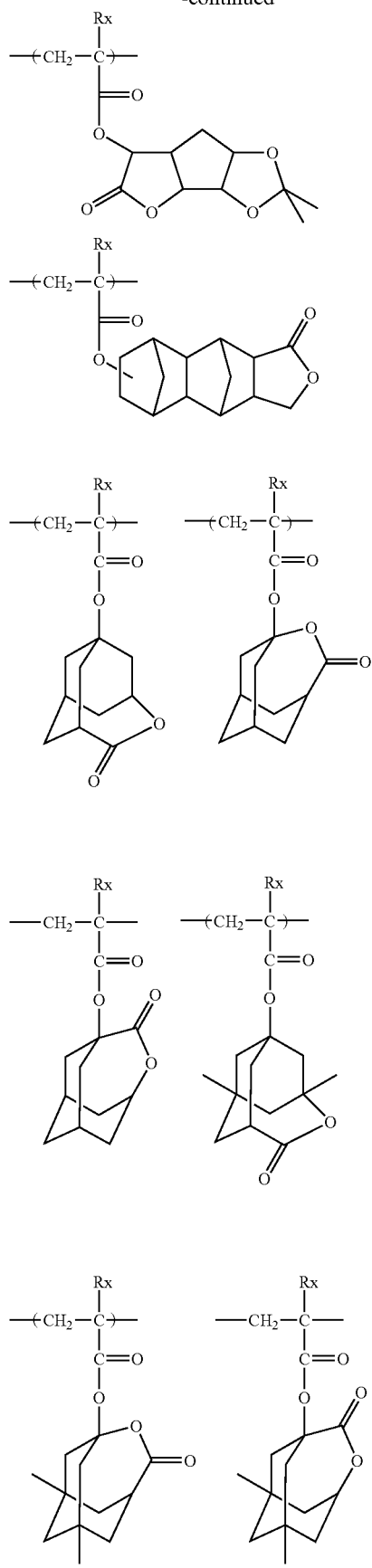
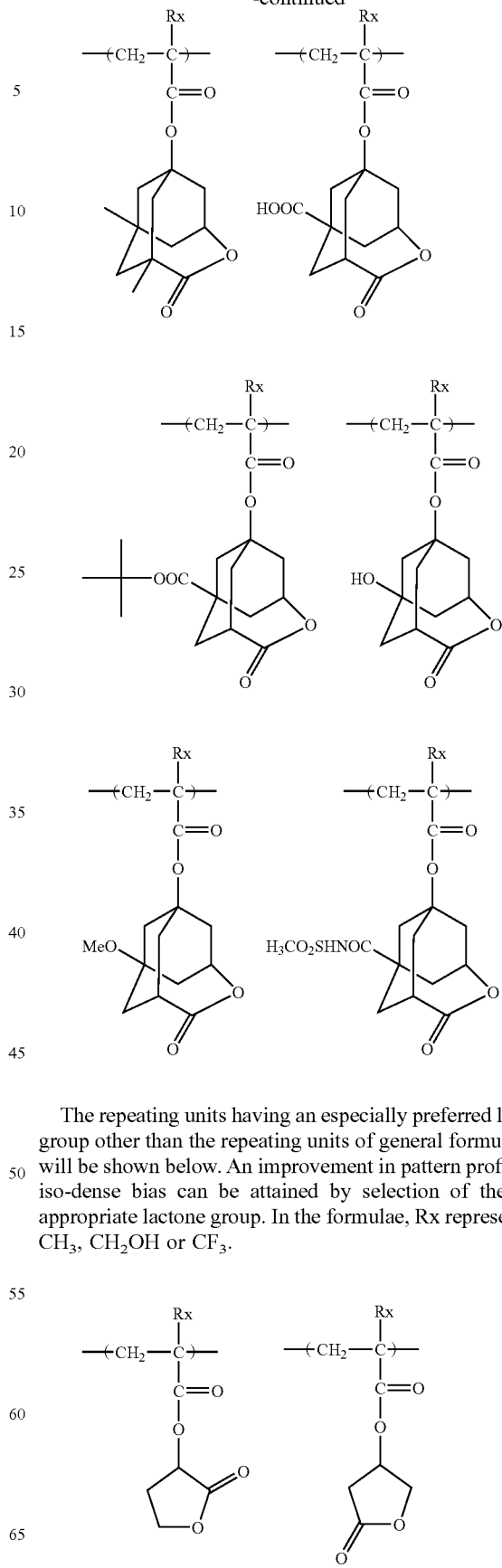
The repeating units having an especially preferred lactone group other than the repeating units of general formula (III) will be shown below. An improvement in pattern profile and iso-dense bias can be attained by selection of the most appropriate lactone group. In the formulae, Rx represents H, $CH_3$, $CH_2OH$ or $CF_3$.

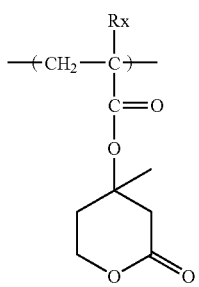

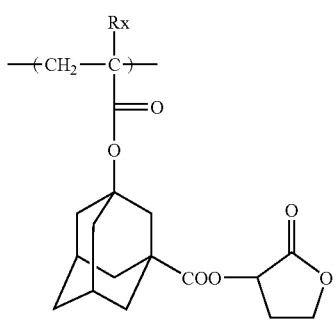

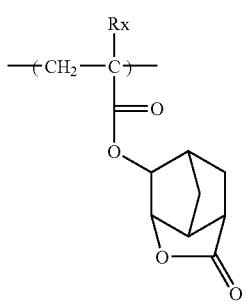

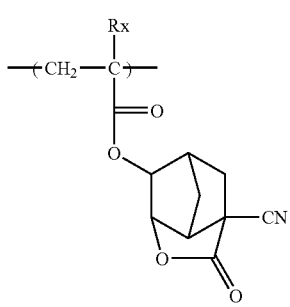

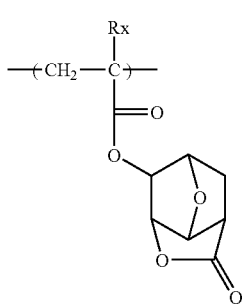

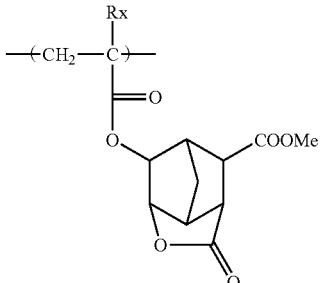

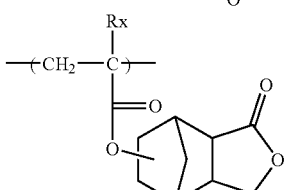

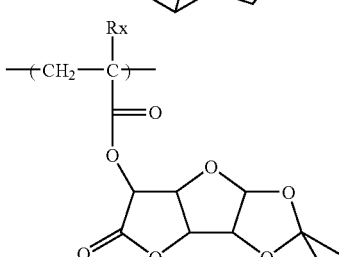

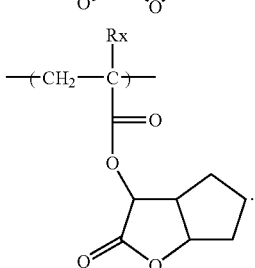

Each of the repeating units having a lactone group is generally present in the form of optical isomers. Any of the optical isomers may be used. It is appropriate to use both a single type of optical isomer alone and a plurality of optical isomers in the form of a mixture. When a single type of optical isomer is mainly used, the optical purity (ee) thereof is preferably 90 or higher, more preferably 95 or higher.

The content ratio of repeating units having a lactone other than the repeating units of general formula (III), the sum thereof when a plurality of repeating units are contained, is preferably in the range of 15 to 60 mol %, more preferably 20 to 50 mol % and further preferably 30 to 50 mol %, based on all the repeating units contained in the resin.

In order to enhance the effect of the present invention, it is practicable to simultaneously employ two or more lactone repeating units selected from among those of general formula (III). In the simultaneous employment, it is preferred to select two or more lactone repeating units from among those of general formula (III) in which n is 1 and simultaneously use them.

It is preferred for resin (B) to have a repeating unit other than the repeating units of general formulae (AI) and (III), having a hydroxyl group or a cyano group. The containment of this repeating unit would realize enhancements of adhesion to substrate and developer affinity. The repeating unit having a hydroxyl group or a cyano group is preferably a repeating unit with a structure of alicyclic hydrocarbon substituted with a hydroxyl group or a cyano group, and preferably has no acid-decomposable group. In the alicyclic hydrocarbon structure substituted with a hydroxyl group or a cyano group, the alicyclic hydrocarbon structure preferably consists of an adamantyl group, a diamantyl group or a norbornane group. As preferred alicyclic hydrocarbon structures substituted with a hydroxyl group or a cyano group, there can be mentioned the partial structures of the following general formulae (VIIa) to (VIId).

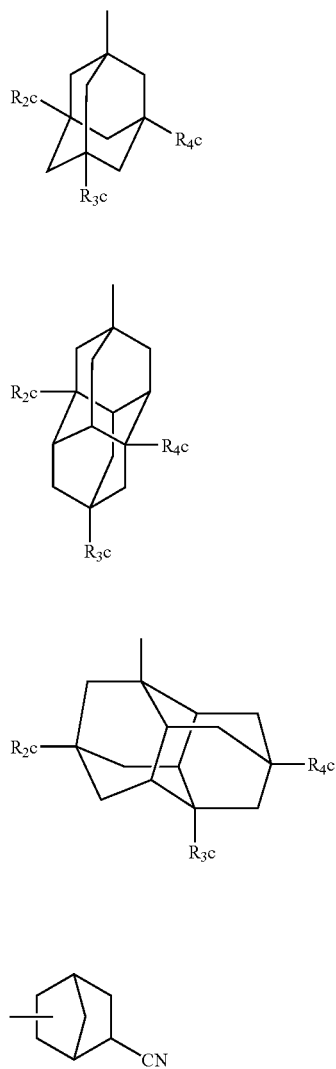

In general formulae (VIIa) to (VIIc), each of $R_2c$ to $R_4c$ independently represents a hydrogen atom, a hydroxyl group or a cyano group, providing that at least one of the $R_2c$ to $R_4c$ represents a hydroxyl group or a cyano group. Preferably, one or two of the $R_2c$ to $R_4c$ are hydroxyl groups and the remainder is a hydrogen atom. In general formula (VIIa), more preferably, two of the $R_2c$ to $R_4c$ are hydroxyl groups and the remainder is a hydrogen atom.

As the repeating units having any of the partial structures of formulae (VIIa) to (VIId), there can be mentioned those of the following general formulae (AIIa) to (AIId).

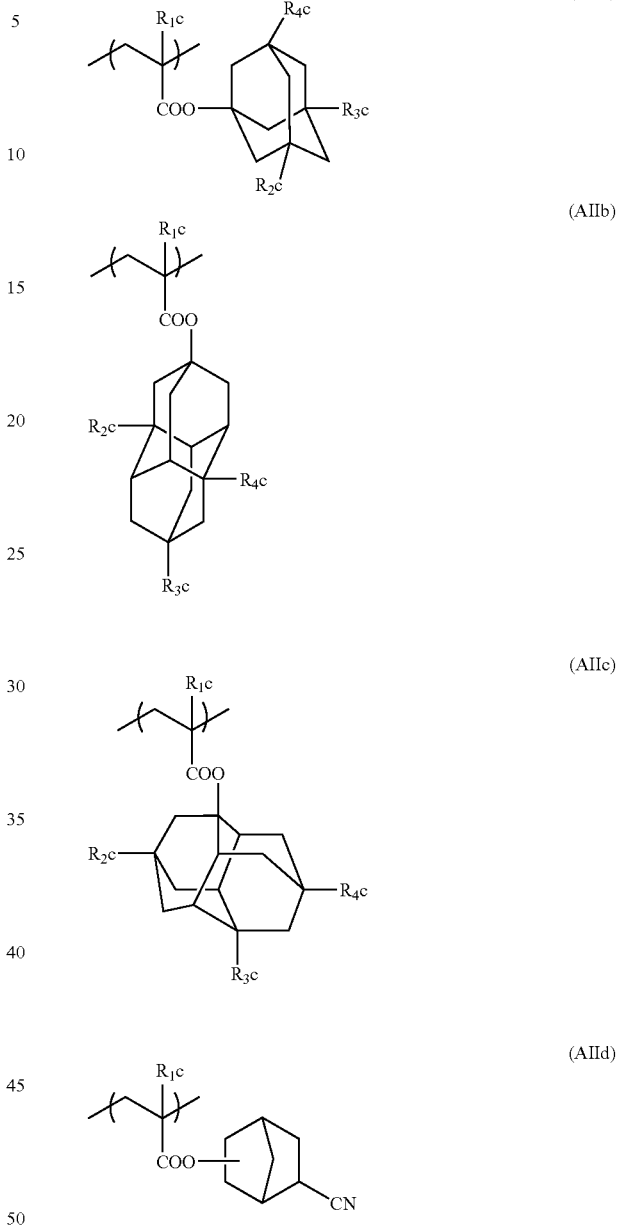

In general formulae (AIIa) to (AIId), $R_1c$ represents a hydrogen atom, a methyl group, a trifluoromethyl group or a hydroxymethyl group.

$R_2c$ to $R_4c$ have the same meaning as those of general formulae (VIIa) to (VIIc).

The content ratio of the repeating unit having a hydroxyl group or a cyano group, based on all the repeating units of resin (B), is preferably in the range of 5 to 40 mol %, more preferably 5 to 30 mol % and still more preferably 10 to 25 mol %.

Specific examples of the repeating units having a hydroxyl group or a cyano group will be shown below, which however in no way limit the scope of the present invention.

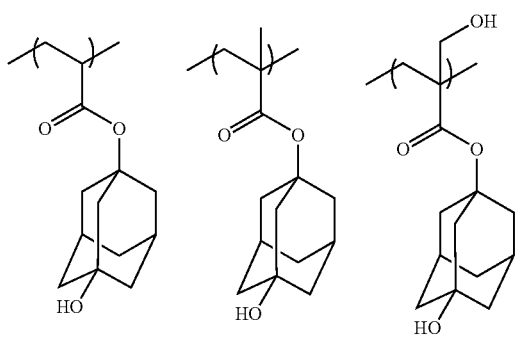
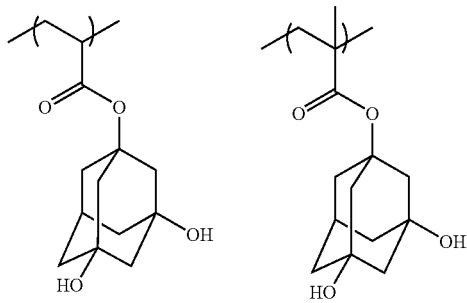
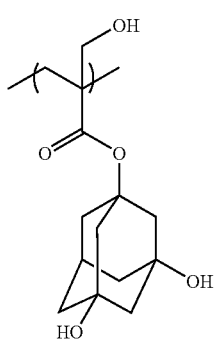
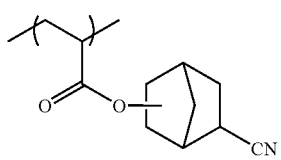
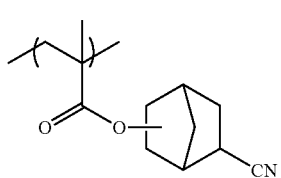
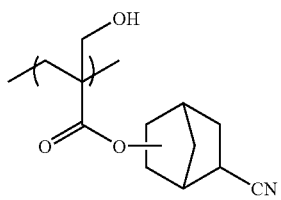

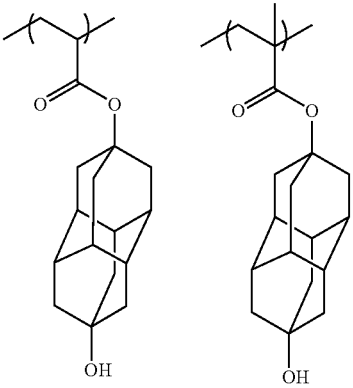

-continued

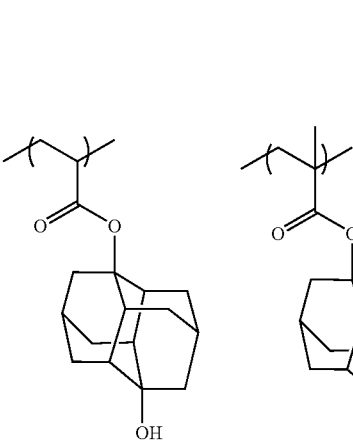

Resin (B) can contain a repeating unit having an alkali-soluble group. As the alkali-soluble group, there can be mentioned a carboxyl group, a sulfonamido group, a sulfonylimido group, a bisulfonylimido group or an aliphatic alcohol substituted at its α-position with an electron-withdrawing group (for example, a hexafluoroisopropanol group). The possession of a repeating unit having a carboxyl group is more preferred. The incorporation of the repeating unit having an alkali-soluble group would increase the resolving power in contact hole usage. The repeating unit having an alkali-soluble group is preferably any of a repeating unit wherein the alkali-soluble group is directly bonded to the principal chain of a resin such as a repeating unit of acrylic acid or methacrylic acid, a repeating unit wherein the alkali-soluble group is bonded via a connecting group to the principal chain of a resin and a repeating unit wherein the alkali-soluble group is introduced in a terminal of a polymer chain by the use of a chain transfer agent or polymerization initiator having the alkali-soluble group in the stage of polymerization. The connecting group may have a monocyclic or polycyclic hydrocarbon structure. The repeating unit of acrylic acid or methacrylic acid is especially preferred.

The content ratio of the repeating unit having an alkali-soluble group based on all the repeating units of resin (B) is preferably in the range of 0 to 20 mol %, more preferably 3 to 15 mol % and still more preferably 5 to 10 mol %.

Specific examples of the repeating units having an alkali-soluble group will be shown below, which however in no way limit the scope of the present invention.

In the formulae, Rx represents H, $CH_3$, $CF_3$, or $CH_2OH$.

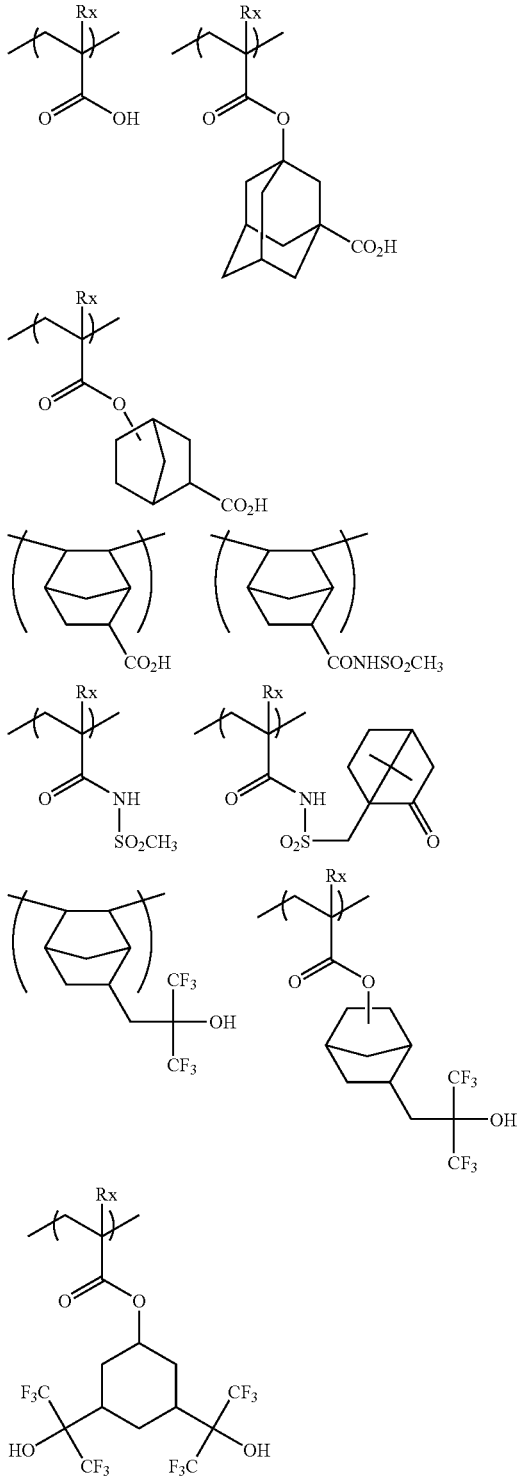

Resin (B) according to the present invention can further contain a repeating unit that has a structure of alicyclic hydrocarbon having no polar group, exhibiting no acid decomposability. As such a repeating unit, there can be mentioned any of the repeating units of general formula (IV) below.

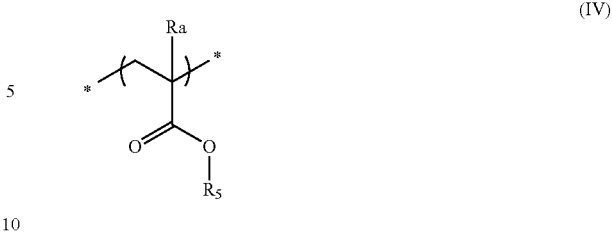

In general formula (IV), $R_5$ represents a hydrocarbon group having at least one cyclic structure in which neither a hydroxyl group nor a cyano group is contained.

Ra represents a hydrogen atom, an alkyl group or a group of the formula —$CH_2$—O—$Ra_2$ in which $Ra_2$ represents a hydrogen atom, an alkyl group or an acyl group. Ra preferably represents a hydrogen atom, a methyl group, a trifluoromethyl group, a hydroxymethyl group or the like, more preferably a hydrogen atom and a methyl group.

The cyclic structures contained in $R_5$ include a monocyclic hydrocarbon group and a polycyclic hydrocarbon group. As the monocyclic hydrocarbon group, there can be mentioned, for example, a cycloalkyl group having 3 to 12 carbon atoms, such as a cyclopentyl group, a cyclohexyl group, a cycloheptyl group or a cyclooctyl group, or a cycloalkenyl group having 3 to 12 carbon atoms, such as a cyclohexenyl group. Preferably, the monocyclic hydrocarbon group is a monocyclic hydrocarbon group having 3 to 7 carbon atoms. A cyclopentyl group and a cyclohexyl group are more preferred.

The polycyclic hydrocarbon groups include ring-assembly hydrocarbon groups and crosslinked-ring hydrocarbon groups. Examples of the ring-assembly hydrocarbon groups include a bicyclohexyl group, a perhydronaphthalene group and the like. As the crosslinked-ring hydrocarbon rings, there can be mentioned, for example, bicyclic hydrocarbon rings, such as pinane, bornane, norpinane, norbornane and bicyclooctane rings (e.g., bicyclo[2.2.2]octane ring or bicyclo[3.2.1]octane ring); tricyclic hydrocarbon rings, such as homobledane, adamantane, tricyclo[5.2.1.0$^{2,6}$]decane and tricyclo[4.3.1.1$^{2,5}$]undecane rings; and tetracyclic hydrocarbon rings, such as tetracyclo[4.4.0.1$^{2,5}$.1$^{7,10}$]dodecane and perhydro-1,4-methano-5,8-methanonaphthalene rings. Further, the crosslinked-ring hydrocarbon rings include condensed-ring hydrocarbon rings, for example, condensed rings resulting from condensation of multiple 5- to 8-membered cycloalkane rings, such as perhydronaphthalene (decalin), perhydroanthracene, perhydrophenanthrene, perhydroacenaphthene, perhydrofluorene, perhydroindene and perhydrophenarene rings.

As preferred crosslinked-ring hydrocarbon rings, there can be mentioned, for example, a norbornyl group, an adamantyl group, a bicyclooctanyl group and a tricyclo[5,2,1,0$^{2,6}$]decanyl group. As more preferred crosslinked-ring hydrocarbon rings, there can be mentioned a norbornyl group and an adamantyl group.

These alicyclic hydrocarbon groups may have substituents. As preferred substituents, there can be mentioned, for example, a halogen atom, an alkyl group, a hydroxyl group protected by a protective group and an amino group protected by a protective group. The halogen atom is preferably a bromine, chlorine or fluorine atom, and the alkyl group is preferably a methyl, ethyl, butyl or t-butyl group. The alkyl group may further have a substituent. As the optional further substituent, there can be mentioned a halogen atom, an alkyl group, a hydroxyl group protected by a protective group or an amino group protected by a protective group.

As the protective group, there can be mentioned, for example, an alkyl group, a cycloalkyl group, an aralkyl group, a substituted methyl group, a substituted ethyl group, an alkoxycarbonyl group or an aralkyloxycarbonyl group. The alkyl group is preferably an alkyl group having 1 to 4 carbon atoms. The substituted methyl group is preferably a methoxymethyl, methoxythiomethyl, benzyloxymethyl, t-butoxymethyl or 2-methoxyethoxymethyl group. The substituted ethyl group is preferably a 1-ethoxyethyl or 1-methyl-1-methoxyethyl group. The acyl group is preferably an aliphatic acyl group having 1 to 6 carbon atoms, such as a formyl, acetyl, propionyl, butyryl, isobutyryl, valeryl or pivaloyl group. The alkoxycarbonyl group is, for example, an alkoxycarbonyl group having 1 to 4 carbon atoms.

The content ratio of any of the repeating units that have a structure of alicyclic hydrocarbon having no polar group, exhibiting no acid decomposability, based on all the repeating units of resin (B), is preferably in the range of 0 to 40 mol %, more preferably 0 to 20 mol %.

Specific examples of the repeating units that have a structure of alicyclic hydrocarbon having no polar group, exhibiting no acid decomposability will be shown below, which however in no way limit the scope of the present invention. In the formulae, Ra represents H, $CH_3$, $CH_2OH$ or $CF_3$.

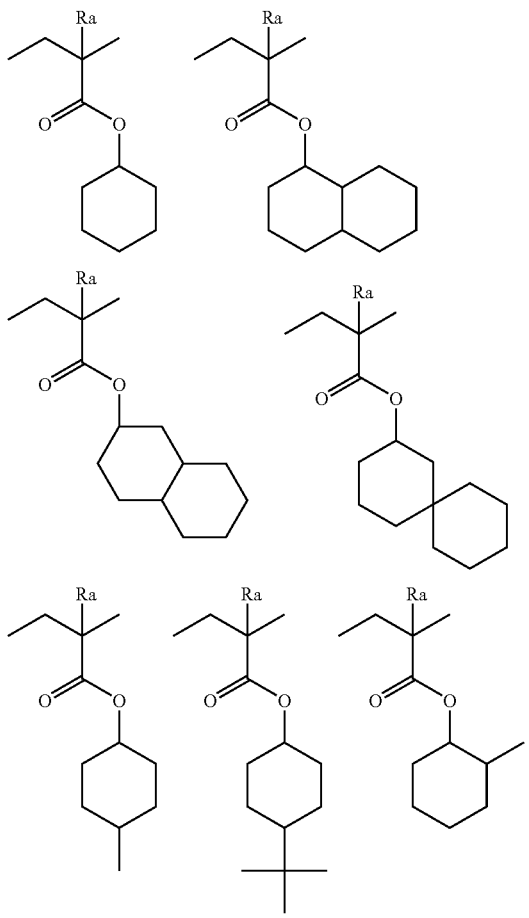

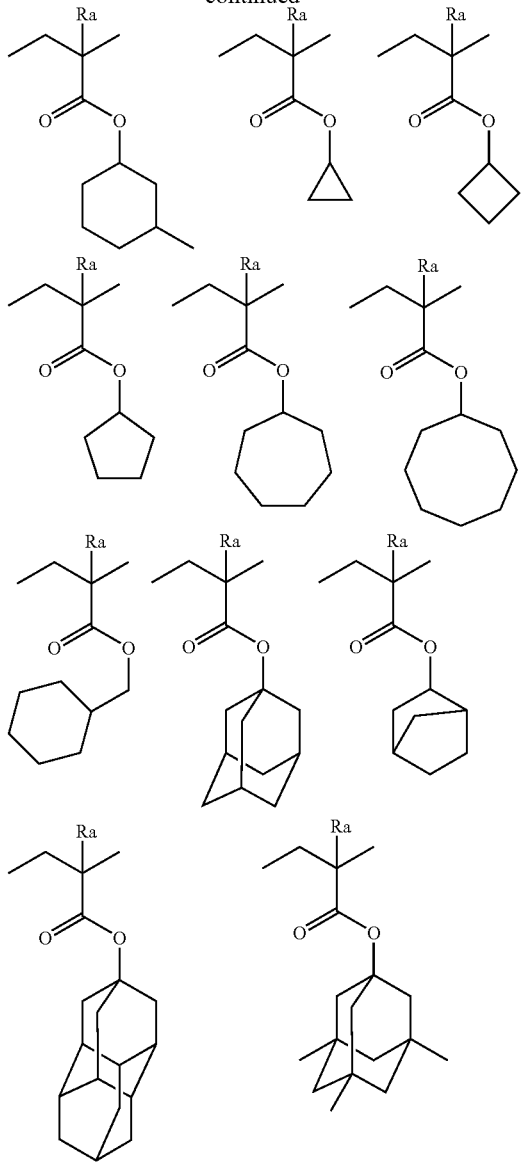

Resin (B) may have, in addition to the foregoing repeating structural units, various repeating structural units for the purpose of regulating the dry etching resistance, standard developer adaptability, substrate adhesion, resist profile and generally required properties of the resist such as resolving power, heat resistance and sensitivity.

As such repeating structural units, there can be mentioned those corresponding to the following monomers, which however are nonlimiting.

The use of such repeating structural units would enable fine regulation of the required properties of resin (A), especially:

(1) solubility in applied solvents,
(2) film forming easiness (glass transition point),
(3) alkali developability,
(4) film thinning (selections of hydrophilicity/hydrophobicity and alkali-soluble group),
(5) adhesion of unexposed area to substrate,
(6) dry etching resistance, etc.

As appropriate monomers, there can be mentioned, for example, a compound having an unsaturated bond capable of addition polymerization, selected from among acrylic esters, methacrylic esters, acrylamides, methacrylamides, allyl compounds, vinyl ethers, vinyl esters and the like.

In addition, any unsaturated compound capable of addition polymerization that is copolymerizable with monomers corresponding to the above various repeating structural units may be copolymerized therewith.

The molar ratios of individual repeating structural units contained in resin (B) are appropriately determined from the viewpoint of regulation of not only the dry etching resistance of the resist but also the standard developer adaptability, substrate adhesion, resist profile and generally required properties of the resist such as the resolving power, heat resistance and sensitivity.

When the composition of the present invention is one for ArF exposure, it is preferred for resin (B) to have no aromatic group from the viewpoint of transparency to ArF beams.

From the viewpoint of the compatibility with hydrophobicresin (I) to be described hereinafter, it is preferred for resin (B) to contain neither a fluorine atom nor a silicon atom.

In resin (B), preferably, all the repeating units consist of (meth)acrylate repeating units. In that instance, use can be made of any of a resin wherein all the repeating units consist of methacrylate repeating units, a resin wherein all the repeating units consist of acrylate repeating units and a resin wherein all the repeating units consist of methacrylate repeating units and acrylate repeating units. However, it is preferred for the acrylate repeating units to account for 50 mol % or less of all the repeating units. It is more preferred to employ a copolymer containing 20 to 50 mol % of (meth)acrylate repeating units having an acid-decomposable group, 20 to 50 mol % of (meth)acrylate repeating units having a lactone group, 5 to 30 mol % of (meth)acrylate repeating units having an alicyclic hydrocarbon structure substituted with a hydroxyl group or a cyano group and 0 to 20 mol % of other (meth)acrylate repeating units.

In the event of exposing the actinic-ray- or radiation-sensitive resin composition of the present invention to KrF excimer laser beams, electron beams, X-rays or high-energy light rays of wavelength 50 nm or less (EUV, etc.), it is preferred for resin (B) to further have hydroxystyrene repeating units. More preferably, resin (B) has hydroxystyrene repeating units, hydroxystyrene repeating units protected by an acid-decomposable group and acid-decomposable repeating units of a (meth)acrylic acid tertiary alkyl ester, etc.

As preferred hydroxystyrene repeating units having an acid-decomposable group, there can be mentioned, for example, repeating units derived from t-butoxycarbonyloxystyrene, a 1-alkoxyethoxystyrene and a (meth)acrylic acid tertiary alkyl ester. Repeating units derived from a 2-alkyl-2-adamantyl(meth)acrylate and a dialkyl(1-adamantyl)methyl(meth)acrylate are more preferred.

Resin (B) of the present invention can be synthesized by conventional techniques (for example, radical polymerization). As general synthetic methods, there can be mentioned, for example, a batch polymerization method in which a monomer species and an initiator are dissolved in a solvent and heated so as to accomplish polymerization and a dropping polymerization method in which a solution of monomer species and initiator is added by dropping to a heated solvent over a period of 1 to 10 hours. The dropping polymerization method is preferred. As a reaction solvent, there can be mentioned, for example, an ether, such as tetrahydrofuran, 1,4-dioxane or diisopropyl ether; a ketone, such as methyl ethyl ketone or methyl isobutyl ketone; an ester solvent, such as ethyl acetate; an amide solvent, such as dimethylformamide or dimethylacetamide; or the solvent capable of dissolving the composition of the present invention, such as propylene glycol monomethyl ether acetate, propylene glycol monomethyl ether or cyclohexanone, to be described hereinafter. It is preferred to perform the polymerization with the use of the same solvent as employed in the actinic-ray- or radiation-sensitive resin composition of the present invention. This would inhibit any particle generation during storage.

The polymerization reaction is preferably carried out in an atmosphere of inert gas, such as nitrogen or argon. The polymerization is initiated by the use of a commercially available radical initiator (azo initiator, peroxide, etc.) as a polymerization initiator. Among the radical initiators, an azo initiator is preferred. An azo initiator having an ester group, a cyano group or a carboxyl group is especially preferred. As preferred initiators, there can be mentioned azobisisobutyronitrile, azobisdimethylvaleronitrile, dimethyl 2,2'-azobis(2-methylpropionate) and the like. According to necessity, a supplementation of initiator or divided addition thereof may be effected. After the completion of the reaction, the reaction mixture is poured into a solvent. The desired polymer is recovered by a method for powder or solid recovery, etc. The concentration during the reaction is in the range of 5 to 50 mass %, preferably 10 to 30 mass %. The reaction temperature is generally in the range of 10° to 150° C., preferably 30° to 120° C. and more preferably 60° to 100° C.

The weight average molecular weight of resin (B) in terms of polystyrene molecular weight as measured by GPC is preferably in the range of 1000 to 200,000, more preferably 2000 to 20,000, still more preferably 3000 to 15,000 and further preferably 5000 to 13,000. The regulation of the weight average molecular weight to 1000 to 200,000 would prevent deteriorations of heat resistance and dry etching resistance and also prevent deterioration of developability and increase of viscosity leading to poor film forming property.

Use is made of the resin whose dispersity (molecular weight distribution) is generally in the range of 1 to 3, preferably 1 to 2.6, more preferably 1 to 2 and most preferably 1.4 to 2.0. The lower the molecular weight distribution, the more excellent the resolving power and resist profile and the smoother the side wall of the resist pattern to thereby attain an excellence in roughness.

In the present invention, the content ratio of resin (B) based on the total solid content of the whole composition is preferably in the range of 30 to 99 mass %, more preferably 60 to 95 mass %.

In the present invention, the resins (B) may be used either individually or in combination.

(D) Simultaneously Usable Basic Compound

From the viewpoint of diminishing any performance change over time from exposure to baking, it is preferred for the actinic-ray- or radiation-sensitive resin composition of the present invention to contain not only above basic compound (C) according to the present invention but also another basic compound (D).

As preferred basic compound (D), there can be mentioned the compounds having the structures of the following formulae (A) to (E).

-continued

—N—C=N—   (B)

=C—N=C—   (C)

=C—N—   (D)

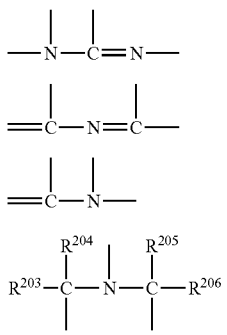   (E)

In general formulae (A) and (E),
$R^{200}$, $R^{201}$ and $R^{202}$ may be identical to or different from each other and each represent a hydrogen atom, an alkyl group (preferably having 1 to 20 carbon atoms), a cycloalkyl group (preferably having 3 to 20 carbon atoms) or an aryl group (having 6 to 20 carbon atoms). $R^{201}$ and $R^{202}$ may be bonded to each other to thereby form a ring.

$R^{203}$, $R^{204}$, $R^{205}$ and $R^{206}$ may be identical to or different from each other and each represent an alkyl group having 1 to 20 carbon atoms.

With respect to this alkyl group, as a preferred substituted alkyl group, there can be mentioned an aminoalkyl group having 1 to 20 carbon atoms, a hydroxyalkyl group having 1 to 20 carbon atoms or a cyanoalkyl group having 1 to 20 carbon atoms.

It is more preferred that in general formulae (A) and (E) the alkyl group be unsubstituted.

As preferred compounds, there can be mentioned guanidine, aminopyrrolidine, pyrazole, pyrazoline, piperazine, aminomorpholine, an aminoalkylmorpholine, piperidine and the like. As more preferred compounds, there can be mentioned compounds with an imidazole structure, a diazabicyclo structure, an onium hydroxide structure, an onium carboxylate structure, a trialkylamine structure, an aniline structure or a pyridine structure, alkylamine derivatives having a hydroxyl group and/or an ether bond, aniline derivatives having a hydroxyl group and/or an ether bond and the like.

As the compounds with an imidazole structure, there can be mentioned imidazole, 2,4,5-triphenylimidazole, benzimidazole, 2-phenylbenzoimidazole and the like. As the compounds with a diazabicyclo structure, there can be mentioned 1,4-diazabicyclo[2,2,2]octane, 1,5-diazabicyclo[4,3,0]non-5-ene, 1,8-diazabicyclo[5,4,0]undec-7-ene and the like. As the compounds with an onium hydroxide structure, there can be mentioned tetrabutylammonium hydroxide, a triarylsulfonium hydroxide, phenacylsulfonium hydroxide, and sulfonium hydroxides having a 2-oxoalkyl group such as triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide and the like. As the compounds with an onium carboxylate structure, there can be mentioned those having a carboxylate at the anion moiety of the compounds with an onium hydroxide structure, for example, an acetate, an adamantane-1-carboxylate, a perfluoroalkyl carboxylate and the like. As the compounds with a trialkylamine structure, there can be mentioned tri(n-butyl)amine, tri(n-octyl)amine and the like. As the aniline compounds, there can be mentioned 2,6-diisopropylaniline, N,N-dimethylaniline, N,N-dibutylaniline, N,N-dihexylaniline and the like. As the alkylamine derivatives having a hydroxyl group and/or an ether bond, there can be mentioned ethanolamine, diethanolamine, triethanolamine, N-phenyldiethanolamine, tris (methoxyethoxyethyl)amine and the like. As the aniline derivatives having a hydroxyl group and/or an ether bond, there can be mentioned N,N-bis(hydroxyethyl)aniline and the like.

As preferred basic compounds, there can be further mentioned an amine compound having a phenoxy group, an ammonium salt compound having a phenoxy group, an amine compound having a sulfonic ester group and an ammonium salt compound having a sulfonic ester group.

As the amine compound, use can be made of any of primary, secondary and tertiary amine compounds. An amine compound having at least one alkyl group bonded to the nitrogen atom thereof is preferred. Among the amine compounds, a tertiary amine compound is more preferred. In the amine compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom. In the amine compounds, it is preferred that the alkyl chain contain an oxygen atom, thereby forming an oxyalkylene group. The number of oxyalkylene groups in each molecule is one or more, preferably 3 to 9 and more preferably 4 to 6. The oxyalkylene group is preferably an oxyethylene group (—$CH_2CH_2O$—) or an oxypropylene group (—$CH(CH_3)CH_2O$— or —$CH_2CH_2CH_2O$—), more preferably an oxyethylene group.

As the ammonium salt compound, use can be made of any of primary, secondary, tertiary and quaternary ammonium salt compounds. An ammonium salt compound having at least one alkyl group bonded to the nitrogen atom thereof is preferred. In the ammonium salt compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom. In the ammonium salt compounds, it is preferred that the alkyl chain contain an oxygen atom, thereby forming an oxyalkylene group. The number of oxyalkylene groups in each molecule is one or more, preferably 3 to 9 and more preferably 4 to 6. The oxyalkylene group is preferably an oxyethylene group (—$CH_2CH_2O$—) or an oxypropylene group (—$CH(CH_3)CH_2O$— or —$CH_2CH_2CH_2O$—), more preferably an oxyethylene group.

As the anion of the ammonium salt compounds, there can be mentioned a halogen atom, a sulfonate, a borate, a phosphate or the like. Of these, a halogen atom and a sulfonate are preferred. Among halogen atoms, chloride, bromide and iodide are especially preferred. Among sulfonates, an organic sulfonate having 1 to 20 carbon atoms is especially preferred. As the organic sulfonate, there can be mentioned an alkyl sulfonate having 1 to 20 carbon atoms and an aryl sulfonate. The alkyl group of the alkyl sulfonate may have a substituent. As the substituent, there can be mentioned, for example, fluorine, chlorine, bromine, an alkoxy group, an acyl group, an aryl group or the like. As specific alkyl sulfonates, there can be mentioned methane sulfonate, ethane sulfonate, butane sulfonate, hexane sulfonate, octane sulfonate, benzyl sulfonate, trifluoromethane sulfonate, pentafluoroethane sulfonate, nonafluorobutane sulfonate and the like. As the aryl group of the aryl sulfonate, there can be mentioned a benzene ring, a naphthalene ring or an anthracene ring. The benzene ring, naphthalene ring or anthracene ring may have a substituent. As preferred substituents, there can be mentioned a linear or branched alkyl group having 1 to 6 carbon atoms and a cycloalkyl group having 3 to 6 carbon atoms. As specific linear or branched alkyl groups and cycloalkyl groups, there can be mentioned methyl, ethyl, n-propyl, isopropyl, n-butyl, i-butyl, t-butyl, n-hexyl, cyclohexyl and the like. As other substituents, there can be mentioned an alkoxy group having 1 to 6 carbon atoms, a halogen atom, cyano, nitro, an acyl group, an acyloxy group and the like.

The amine compound having a phenoxy group or ammonium salt compound having a phenoxy group is one having a phenoxy group at the end of alkyl group of amine compound or ammonium salt compound opposed to the nitrogen atom. The phenoxy group may have a substituent. As the substituent of the phenoxy group, there can be mentioned, for example, an alkyl group, an alkoxy group, a halogen atom, a cyano group, a nitro group, a carboxyl group, a carboxylic ester group, a sulfonic ester group, an aryl group, an aralkyl group, an acyloxy group, an aryloxy group or the like. The substitution position of the substituent may be any of 2- to 6-positions. The number of substituents is optional within the range of 1 to 5.

It is preferred that at least one oxyalkylene group exist between the phenoxy group and the nitrogen atom. The number of oxyalkylene groups in each molecule is one or more, preferably 3 to 9 and further preferably 4 to 6. The oxyalkylene group is preferably an oxyethylene group (—CH$_2$CH$_2$O—) or an oxypropylene group (—CH(CH$_3$)CH$_2$O— or —CH$_2$CH$_2$CH$_2$O—), more preferably an oxyethylene group.

The sulfonic ester group of the amine compound having a sulfonic ester group or ammonium salt compound having a sulfonic ester group may be any of an alkylsulfonic ester, cycloalkylsulfonic ester and arylsulfonic ester. In the alkylsulfonic ester, the alkyl group preferably has 1 to 20 carbon atoms. In the cycloalkylsulfonic ester, the cycloalkyl group preferably has 3 to 20 carbon atoms. In the arylsulfonic ester, the aryl group preferably has 6 to 12 carbon atoms. The alkylsulfonic ester, cycloalkylsulfonic ester and arylsulfonic ester may have substituents. As preferred substituents, there can be mentioned a halogen atom, a cyano group, a nitro group, a carboxyl group, a carboxylic ester group and a sulfonic ester group.

It is preferred that at least one oxyalkylene group exist between the sulfonic ester group and the nitrogen atom. The number of oxyalkylene groups in each molecule is one or more, preferably 3 to 9 and further preferably 4 to 6. The oxyalkylene group is preferably an oxyethylene group (—CH$_2$CH$_2$O—) or an oxypropylene group (—CH(CH$_3$)CH$_2$O— or —CH$_2$CH$_2$CH$_2$O—), more preferably an oxyethylene group.

These basic compounds are used individually or in combination.

The content ratio of basic compound (D) used is generally in the range of 0 to 10 mass %, preferably 0 to 5 mass % based on the total solid content of the composition of the present invention.

(E) Solvent

As the solvent that can be used in the preparation of an actinic-ray- or radiation-sensitive resin composition through dissolution of the above-mentioned components, there can be mentioned, for example, an organic solvent, such as an alkylene glycol monoalkyl ether carboxylate, an alkylene glycol monoalkyl ether, an alkyl lactate, an alkyl alkoxypropionate, a cyclolactone (preferably having 4 to 10 carbon atoms), an optionally cyclized monoketone compound (preferably having 4 to 10 carbon atoms), an alkylene carbonate, an alkyl alkoxyacetate or an alkyl pyruvate.

As preferred alkylene glycol monoalkyl ether carboxylates, there can be mentioned, for example, propylene glycol monomethyl ether acetate, propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate and ethylene glycol monoethyl ether acetate.

As preferred alkylene glycol monoalkyl ethers, there can be mentioned, for example, propylene glycol monomethyl ether, propylene glycol monoethyl ether, propylene glycol monopropyl ether, propylene glycol monobutyl ether, ethylene glycol monomethyl ether and ethylene glycol monoethyl ether.

As preferred alkyl lactates, there can be mentioned, for example, methyl lactate, ethyl lactate, propyl lactate and butyl lactate.

As preferred alkyl alkoxypropionates, there can be mentioned, for example, ethyl 3-ethoxypropionate, methyl 3-methoxypropionate, methyl 3-ethoxypropionate and ethyl 3-methoxypropionate.

As preferred cyclolactones, there can be mentioned, for example, β-propiolactone, β-butyrolactone, γ-butyrolactone, α-methyl-γ-butyrolactone, β-methyl-γ-butyrolactone, γ-valerolactone, γ-caprolactone, γ-octanoic lactone and α-hydroxy-γ-butyrolactone.

As preferred optionally cyclized monoketone compounds, there can be mentioned, for example, 2-butanone, 3-methylbutanone, pinacolone, 2-pentanone, 3-pentanone, 3-methyl-2-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 2-heptanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone and 3-methylcycloheptanone.

As preferred alkylene carbonates, there can be mentioned, for example, propylene carbonate, vinylene carbonate, ethylene carbonate and butylene carbonate.

As preferred alkyl alkoxyacetates, there can be mentioned, for example, acetic acid 2-methoxyethyl ester, acetic acid 2-ethoxyethyl ester, acetic acid 2-(2-ethoxyethoxy)ethyl ester, acetic acid 3-methoxy-3-methylbutyl ester and acetic acid 1-methoxy-2-propyl ester.

As preferred alkyl pyruvates, there can be mentioned, for example, methyl pyruvate, ethyl pyruvate and propyl pyruvate.

As a preferably employable solvent, there can be mentioned a solvent having a boiling point of 130° C. or above measured at ordinary temperature under ordinary pressure. For example, there can be mentioned cyclopentanone, γ-butyrolactone, cyclohexanone, ethyl lactate, ethylene glycol monomethyl ether acetate, propylene glycol monomethyl ether acetate, ethyl 3-ethoxypropionate, ethyl pyruvate, acetic acid 2-ethoxyethyl ester, acetic acid 2-(2-ethoxyethoxy)ethyl ester or propylene carbonate.

In the present invention, these solvents may be used either individually or in combination.

In the present invention, a mixed solvent consisting of a mixture of a solvent having a hydroxyl group in its structure and a solvent having no hydroxyl group may be used as the organic solvent.

As the solvent having a hydroxyl group, there can be mentioned, for example, ethylene glycol, ethylene glycol monomethyl ether, ethylene glycol monoethyl ether, propylene glycol, propylene glycol monomethyl ether, propylene glycol monoethyl ether, ethyl lactate or the like. Of these, propylene glycol monomethyl ether and ethyl lactate are especially preferred.

As the solvent having no hydroxyl group, there can be mentioned, for example, propylene glycol monomethyl ether acetate, ethyl ethoxypropionate, 2-heptanone, γ-butyrolactone, cyclohexanone, butyl acetate, N-methylpyrrolidone, N,N-dimethylacetamide, dimethyl sulfoxide or the like. Of these, propylene glycol monomethyl ether acetate, ethyl ethoxypropionate, 2-heptanone, γ-butyrolactone, cyclohexanone and butyl acetate are especially preferred. Propylene glycol monomethyl ether acetate, ethyl ethoxypropionate and 2-heptanone are most preferred.

The mixing ratio (mass) of a solvent having a hydroxyl group and a solvent having no hydroxyl group is in the range of 1/99 to 99/1, preferably 10/90 to 90/10 and more preferably 20/80 to 60/40. The mixed solvent containing 50 mass % or more of a solvent having no hydroxyl group is especially preferred from the viewpoint of uniform applicability.

It is preferred for the solvent to be a mixed solvent consisting of two or more solvents containing propylene glycol monomethyl ether acetate.

(F) Surfactant

The actinic-ray- or radiation-sensitive resin composition of the present invention preferably further contains a surfactant, and more preferably contains any one, or two or more members, of fluorinated and/or siliconized surfactants (fluorinated surfactant, siliconized surfactant and surfactant containing both fluorine and silicon atoms).

The composition of the present invention when containing the above surfactant would, in the use of an exposure light source of 250 nm or below, especially 220 nm or below, realize a favorable sensitivity and resolving power and produce a pattern of less adhesion and development defects.

As the fluorinated and/or siliconized surfactants, there can be mentioned, for example, those described in JP-As 62-36663, 61-226746, 61-226745, 62-170950, 63-34540, 7-230165, 8-62834, 9-54432, 9-5988 and 2002-277862 and U.S. Pat. Nos. 5,405,720, 5,360,692, 5,529,881, 5,296,330, 5,436,098, 5,576,143, 5,294,511 and 5,824,451. Any of the following commercially available surfactants can be used as is.

As useful commercially available surfactants, there can be mentioned, for example, fluorinated surfactants/siliconized surfactants, such as Eftop EF301 and EF303 (produced by Shin-Akita Kasei Co., Ltd.), Florad FC 430, 431 and 4430 (produced by Sumitomo 3M Ltd.), Megafac F171, F173, F176, F189, F113, F110, F177, F120 and R08 (produced by Dainippon Ink & Chemicals, Inc.), Surflon S-382, SC101, 102, 103, 104, 105 and 106 (produced by Asahi Glass Co., Ltd.), Troy Sol S-366 (produced by Troy Chemical Co., Ltd.), GF-300 and GF-150 (produced by TOAGOSEI CO., LTD.), Sarfron S-393 (produced by SEIMI CHEMICAL CO., LTD.), Eftop EF121, EF122A, EF122B, RF122C, EF125M, EF135M, EF351, EF352, EF801, EF802 and EF601 (produced by JEMCO INC.), PF636, PF656, PF6320 and PF6520 (produced by OMNOVA), and FTX-204G, 208G, 218G, 230G, 204D, 208D, 212D, 218D and 222D (produced by NEOS). Further, polysiloxane polymer KP-341 (produced by Shin-Etsu Chemical Co., Ltd.) can be employed as the siliconized surfactant.

As the surfactant, besides the above publicly known surfactants, use can be made of a surfactant based on a polymer having a fluorinated aliphatic group derived from a fluorinated aliphatic compound produced by a telomerization technique (also called a telomer process) or an oligomerization technique (also called an oligomer process). The fluorinated aliphatic compound can be synthesized by the process described in JP-A-2002-90991.

The polymer having a fluorinated aliphatic group is preferably a copolymer from a monomer having a fluorinated aliphatic group and poly(oxyalkylene) acrylate and/or poly(oxyalkylene)methacrylate, which copolymer may have a random distribution or may result from block copolymerization. As the poly(oxyalkylene) group, there can be mentioned a poly(oxyethylene) group, a poly(oxypropylene) group, a poly(oxybutylene) group or the like. Further, use can be made of a unit having alkylene groups of different chain lengths in a single chain, such as poly(oxyethylene-oxypropylene-oxyethylene block concatenation) or poly(oxyethylene-oxypropylene block concatenation). Moreover, the copolymer from a monomer having a fluorinated aliphatic group and poly(oxyalkylene)acrylate (or methacrylate) is not limited to two-monomer copolymers and may be a three or more monomer copolymer obtained by simultaneous copolymerization of two or more different monomers having a fluorinated aliphatic group, two or more different poly(oxyalkylene)acrylates (or methacrylates), etc.

For example, as a commercially available surfactant, there can be mentioned Megafac F178, F-470, F-473, F-475, F-476 or F-472 (produced by Dainippon Ink & Chemicals, Inc.). Further, there can be mentioned a copolymer from an acrylate (or methacrylate) having a $C_6F_{13}$ group and poly(oxyalkylene)acrylate (or methacrylate), a copolymer from an acrylate (or methacrylate) having a $C_3F_7$ group, poly(oxyethylene)acrylate (or methacrylate) and poly(oxypropylene)acrylate (or methacrylate), or the like.

In the present invention, surfactants other than the fluorinated and/or siliconized surfactants can also be employed. In particular, there can be mentioned, for example, nonionic surfactants consisting of a polyoxyethylene alkyl ether such as polyoxyethylene lauryl ether, polyoxyethylene stearyl ether, polyoxyethylene cetyl ether or polyoxyethylene oleyl ether, a polyoxyethylene alkylaryl ether such as polyoxyethylene octylphenol ether or polyoxyethylene nonylphenol ether, a polyoxyethylene-polyoxypropylene block copolymer, a sorbitan fatty acid ester such as sorbitan monolaurate, sorbitan monopalmitate, sorbitan monostearate, sorbitan monooleate, sorbitan trioleate or sorbitan tristearate, a polyoxyethylene sorbitan fatty acid ester such as polyoxyethylene sorbitan monolaurate, polyoxyethylene sorbitan monopalmitate, polyoxyethylene sorbitan monostearate, polyoxyethylene sorbitan trioleate or polyoxyethylene sorbitan tristearate, or the like.

These surfactants may be used either individually or in combination.

The content ratio of surfactant used is preferably in the range of 0 to 2 mass %, more preferably 0.0001 to 2 mass %, and still more preferably 0.0005 to 1 mass % based on the total mass of the actinic-ray- or radiation-sensitive resin composition (excluding the solvent).

(G) Carboxylic Acid Onium Salt

The actinic-ray- or radiation-sensitive resin composition of the present invention may contain a carboxylic acid onium salt. As the carboxylic acid onium salt, there can be mentioned, for example, a carboxylic acid sulfonium salt, a carboxylic acid iodonium salt, a carboxylic acid ammonium salt or the like. The especially preferred carboxylic acid onium salts are the iodonium salt and the sulfonium salt. It is preferred for the carboxylate residue of the carboxylic acid onium salt for use in the present invention to be one containing neither an aromatic group nor a carbon-carbon double bond. In particular, the especially preferred anion moiety thereof is a linear or branched, monocyclic or polycyclic alkylcarboxylate anion having 1 to 30 carbon atoms. A more preferred anion moiety is an anion of carboxylic acid wherein the alkyl group is partially or wholly fluorinated. The alkyl chain may contain an oxygen atom. Accordingly, transparency to light of wavelength 220 nm or shorter, enhancement of the sensitivity and resolving power, and improvement of the iso-dense bias and exposure margin is attainable.

As the fluorinated carboxylic acid anion, there can be mentioned any of the anions of fluoroacetic acid, difluoroacetic acid, trifluoroacetic acid, pentafluoropropionic acid, heptafulorobutyric acid, nonafluoropentanoic acid, perfluorododecanoic acid, perfluorotridecanoic acid, perfluorocyclohexanecarboxylic acid and 2,2-bistrifluoromethylpropionic acid, or the like.

These carboxylic acid onium salts can be synthesized by reacting a sulfonium hydroxide, an iodonium hydroxide or an ammonium hydroxide and a carboxylic acid with silver oxide in an appropriate solvent.

The content ratio of carboxylic acid onium salt in the composition is generally in the range of 0.1 to 20 mass %, preferably 0.5 to 10 mass % and still more preferably 1 to 7 mass % based on the total solids of the composition.

(H) Dissolution Inhibiting Compound

The composition of the present invention may contain a dissolution inhibiting compound of 3000 or less molecular weight that is decomposed by the action of an acid to thereby increase the solubility in an alkali developer (hereinafter also referred to as "dissolution inhibiting compound"). From the viewpoint of preventing any lowering of 220 nm or shorter transmission, the dissolution inhibiting compound is preferably an alicyclic or aliphatic compound having an acid-decomposable group, such as any of cholic acid derivatives having an acid-decomposable group described in Proceeding of SPIE, 2724, 355 (1996). The acid-decomposable group and alicyclic structure are the same as described with respect to resin (B).

When the actinic-ray- or radiation-sensitive resin composition of the present invention is exposed to a KrF excimer laser or irradiated with electron beams, preferred use is made of one having a structure resulting from substitution of the phenolic hydroxyl group of a phenol compound with an acid-decomposable group. The phenol compound preferably contains 1 to 9 phenol skeletons, more preferably 2 to 6 phenol skeletons.

In the present invention, the molecular weight of each dissolution inhibiting compound is 3000 or less, preferably 300 to 3000 and more preferably 500 to 2500.

The content ratio of dissolution inhibiting compound is preferably in the range of 3 to 50 mass %, more preferably 5 to 40 mass % based on the total solids of the composition.

Specific examples of the dissolution inhibiting compounds will be shown below, which however in no way limit the scope of the present invention.

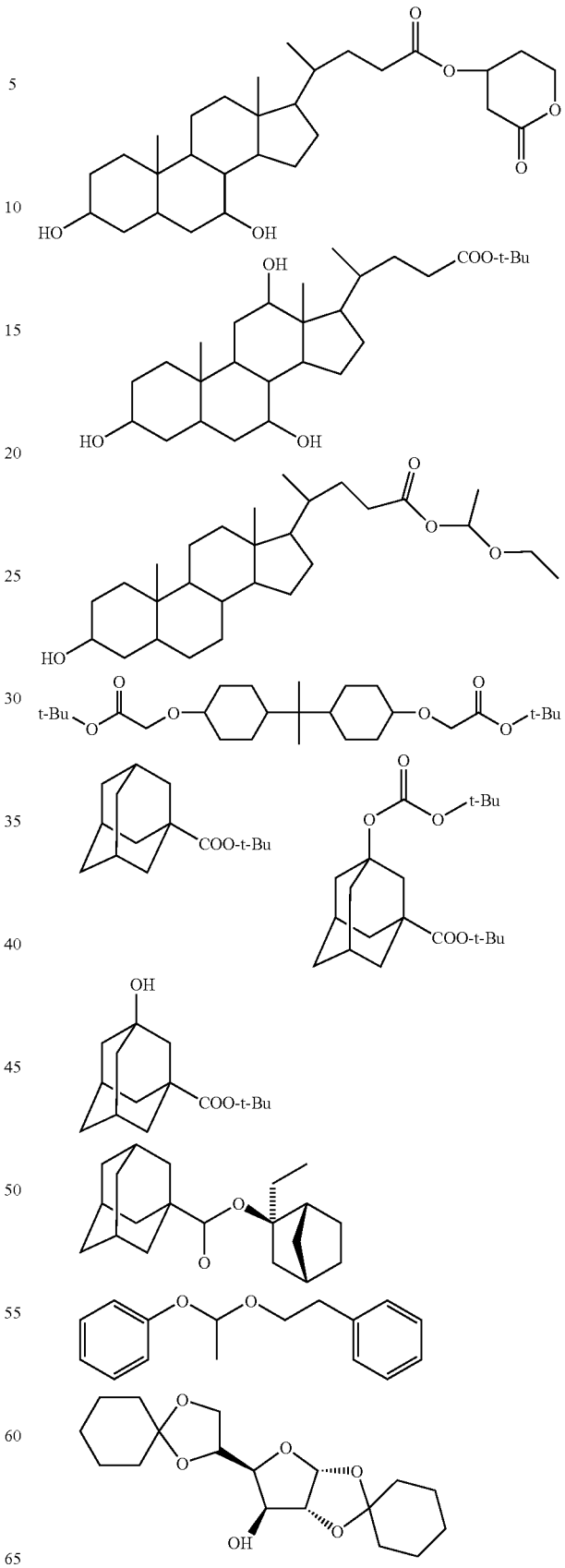

[Other Additives]

The actinic-ray- or radiation-sensitive resin composition of the present invention may further according to necessity contain a dye, a plasticizer, a photosensitizer, a light absorber, a compound capable of increasing the solubility in a developer (for example, a phenolic compound of 1000 or less molecular weight or a carboxylated alicyclic or aliphatic compound), etc.

The above phenolic compound of 1000 or less molecular weight can be easily synthesized by persons of ordinary skill in the art to which the present invention pertains while consulting the processes described in, for example, JP-As 4-122938 and 2-28531, U.S. Pat. No. 4,916,210 and EP 219294.

As the carboxylated alicyclic or aliphatic compound, there can be mentioned, for example, a carboxylic acid derivative of steroid structure such as cholic acid, deoxycholic acid or lithocholic acid, an adamantanecarboxylic acid derivative, adamantanedicarboxylic acid, cyclohexanecarboxylic acid, cyclohexanedicarboxylic acid or the like. These are however nonlimiting.

[Method of Forming Pattern]

From the viewpoint of enhancement of resolving power, it is preferred for the actinic-ray- or radiation-sensitive resin composition of the present invention to be used with a coating thickness of 30 to 250 nm. More preferably, the actinic-ray- or radiation-sensitive resin composition is used with a coating thickness of 30 to 200 nm. This coating thickness can be attained by setting the solid content of the composition within an appropriate range so as to cause the composition to have an appropriate viscosity, thereby improving the applicability and film forming property.

The total solid content of the actinic-ray- or radiation-sensitive resin composition is generally in the range of 1 to 10 mass %, preferably 1 to 8.0 mass % and more preferably 1 to 6.0 mass %.

The actinic-ray- or radiation-sensitive resin composition of the present invention is used in such a manner that the above components are dissolved in a given organic solvent, preferably the above mixed solvent, and filtered and applied onto a given support in the following manner. The filter medium for the filtration preferably consists of a polytetrafluoroethylene, polyethylene or nylon having a pore size of 0.1 μm or less, especially 0.05 μm or less and more especially 0.03 μm or less.

For example, the actinic-ray- or radiation-sensitive resin composition is applied onto a substrate, such as one for use in the production of precision integrated circuit elements (e.g., silicon/silicon dioxide coating), by appropriate application means, such as a spinner or coater, and dried to thereby form a film.

The film is exposed through a given mask to actinic rays or radiation, preferably baked (heated), and developed and rinsed. Accordingly, a desirable pattern can be obtained.

As the exposure light source, there can be mentioned infrared rays, visible light, ultraviolet rays, far-ultraviolet rays, extreme ultraviolet rays, X-rays, electron beams or the like. Among them, preferred use is made of far-ultraviolet rays of wavelength especially 250 nm or less, more especially 220 nm or less and still more especially 1 to 200 nm, such as a KrF excimer laser (248 nm), an ArF excimer laser (193 nm) and an $F_2$ excimer laser (157 nm), as well as X-rays, electron beams and the like. More preferred use is made of an ArF excimer laser, an $F_2$ excimer laser, EUV (13 nm) and electron beams.

Prior to the formation of a film, the substrate may be coated with an antireflection film.

As the antireflection film, use can be made of not only an inorganic film of titanium, titanium dioxide, titanium nitride, chromium oxide, carbon, amorphous silicon or the like but also an organic film composed of a light absorber and a polymer material. Also, as the organic antireflection film, use can be made of commercially available organic antireflection films, such as the DUV30 Series and DUV40 Series produced by Brewer Science Inc. and AR-2, AR-3 and AR-5 produced by Shipley Co., Ltd.

In the development step, an alkali developer is used as follows. As the alkali developer for the actinic-ray- or radiation-sensitive resin composition, use can be made of any of alkaline aqueous solutions of an inorganic alkali such as sodium hydroxide, potassium hydroxide, sodium carbonate, sodium silicate, sodium metasilicate or aqueous ammonia, a primary amine such as ethylamine or n-propylamine, a secondary amine such as diethylamine or di-n-butylamine, a tertiary amine such as triethylamine or methyldiethylamine, an alcoholamine such as dimethylethanolamine or triethanolamine, a quaternary ammonium salt such as tetramethylammonium hydroxide or tetraethylammonium hydroxide, a cycloamine such as pyrrole or piperidine, or the like.

Before the use of the above alkali developer, appropriate amounts of an alcohol and a surfactant may be added thereto.

The alkali concentration of the alkali developer is generally in the range of 0.1 to 20 mass %.

The pH value of the alkali developer is generally in the range of 10.0 to 15.0.

Before the use of the above alkaline aqueous solution, appropriate amounts of an alcohol and a surfactant may be added thereto.

Pure water can be used as the rinse liquid. Before the use, an appropriate amount of surfactant may be added thereto.

The development operation or rinse operation may be followed by the operation for removing any developer or rinse liquid adhering onto the pattern by the use of a supercritical fluid.

[(I) Hydrophobic Resin]

In the exposure of the film of the composition of the present invention via the liquid immersion medium, a hydrophobic resin (I) may be further added according to necessity. This would bring about uneven localization of the hydrophobic resin (I) on the surface layer of the film. When the liquid immersion medium is water, there would be attained an improvement of receding contact angle on the surface of the film with reference to water upon formation of the film, and accordingly an enhancement of the liquid immersion water tracking property. Although the hydrophobic resin (I) is not particularly limited as long as an improvement of receding contact angle on the surface is realized by the addition thereof, it is preferred to employ a resin having at least either a fluorine atom or a silicon atom. The receding contact angle of the film is preferably in the range of 60° to 90°, more preferably 70° or higher. The amount of resin added can be appropriately regulated so that the receding contact angle of the resist film falls within the above range. However, the addition amount is preferably in the range of 0.1 to 10 mass %, more preferably 0.1 to 5 mass % based on the total solids of the composition. Although the hydrophobic resin (I) is unevenly localized on the interface as aforementioned, differing from the surfactant, the hydrophobic resin does not necessarily have to have a hydrophilic group in its molecule and does not need to contribute toward uniform mixing of polar/nonpolar substances.

The receding contact angle refers to a contact angle determined when the contact line at a droplet-substrate interface draws back. It is generally known that the receding contact angle is useful in the simulation of droplet mobility in a dynamic condition. In a simple definition, the receding contact angle can be defined as the contact angle exhibited at the recession of the droplet interface at the time of, after application of a droplet discharged from a needle tip onto a substrate, re-indrawing the droplet into the needle. Generally, the receding contact angle can be measured according to a method of contact angle measurement known as the dilation/contraction method.

In the operation of liquid immersion exposure, it is needed for the liquid for liquid immersion to move on a wafer while tracking the movement of an exposure head involving high-speed scanning on the wafer and thus forming an exposure pattern. Therefore, the contact angle of the liquid for liquid immersion with respect to the resist film in dynamic condition is important, and it is required for the resist to be capable of tracking the high-speed scanning of the exposure head without leaving any droplets.

The fluorine atom or silicon atom of the hydrophobic resin (I) may be present in the principal chain of the resin or may be a substituent on the side chain thereof.

The hydrophobic resin (I) is preferably a resin having an alkyl group containing a fluorine atom, a cycloalkyl group containing a fluorine atom or an aryl group containing a fluorine atom as a partial structure containing a fluorine atom.

The alkyl group containing a fluorine atom (preferably having 1 to 10 carbon atoms, more preferably 1 to 4 carbon atoms) is a linear or branched alkyl group having at least one hydrogen atom thereof substituted with a fluorine atom. Further, other substituents may be possessed.

The cycloalkyl group containing a fluorine atom is a cycloalkyl group of a single ring or multiple rings having at least one hydrogen atom thereof substituted with a fluorine atom. Further, other substituents may be contained.

As the aryl group containing a fluorine atom, there can be mentioned one having at least one hydrogen atom of an aryl group, such as a phenyl or naphthyl group, substituted with a fluorine atom. Further, other substituents may be contained.

As preferred alkyl groups containing a fluorine atom, cycloalkyl groups containing a fluorine atom and aryl groups containing a fluorine atom, there can be mentioned groups of the following general formulae (F2) to (F4), which however in no way limit the scope of the present invention.

(F2)

(F3)

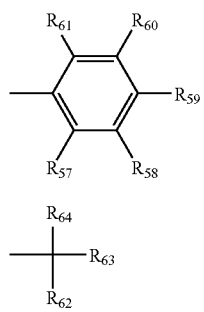

(F4)

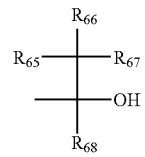

In the general formulae (F2) to (F4), each of $R_{57}$ to $R_{68}$ independently represents a hydrogen atom, a fluorine atom or an alkyl group, provided that at least one of each of $R_{57}$-$R_{61}$, $R_{62}$-$R_{64}$ and $R_{65}$-$R_{68}$ represents a fluorine atom or an alkyl group (preferably having 1 to 4 carbon atoms) having at least one hydrogen atom thereof substituted with a fluorine atom. It is preferred that all of $R_{57}$-$R_{61}$ and $R_{65}$-$R_{67}$ represent fluorine atoms. Each of $R_{62}$, $R_{63}$ and $R_{68}$ preferably represents an alkyl group (especially having 1 to 4 carbon atoms) having at least one hydrogen atom thereof substituted with a fluorine atom, more preferably a perfluoroalkyl group having 1 to 4 carbon atoms. $R_{62}$ and $R_{63}$ may be bonded with each other to thereby form a ring.

Specific examples of the groups of the general formula (F2) include a p-fluorophenyl group, a pentafluorophenyl group, a 3,5-di(trifluoromethyl)phenyl group and the like.

Specific examples of the groups of the general formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-t-butyl group, a perfluoroisopentyl group, a perfluorooctyl group, a perfluoro(trimethyl)hexyl group, a 2,2,3,3-tetrafluorocyclobutyl group, a perfluorocyclohexyl group and the like. Of these, a hexafluoroisopropyl group, a heptafluoroisopropyl group, a hexafluoro(2-methyl)isopropyl group, an octafluoroisobutyl group, a nonafluoro-t-butyl group and a perfluoroisopentyl group are preferred. A hexafluoroisopropyl group and a heptafluoroisopropyl group are more preferred.

Specific examples of the groups of the general formula (F4) include —C(CF$_3$)$_2$OH, —C(C$_2$F$_5$)$_2$OH, —C(CF$_3$)(CF$_3$)OH, —CH(CF$_3$)OH and the like. —C(CF$_3$)$_2$OH is preferred.

Specific examples of the repeating units having a fluorine atom will be shown below, which however in no way limit the scope of the present invention.

In the specific examples, $X_1$ represents a hydrogen atom, —CH$_3$, —F or —CF$_3$.

$X_2$ represents —F or —CF$_3$.

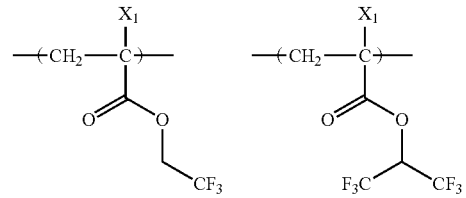

129
-continued
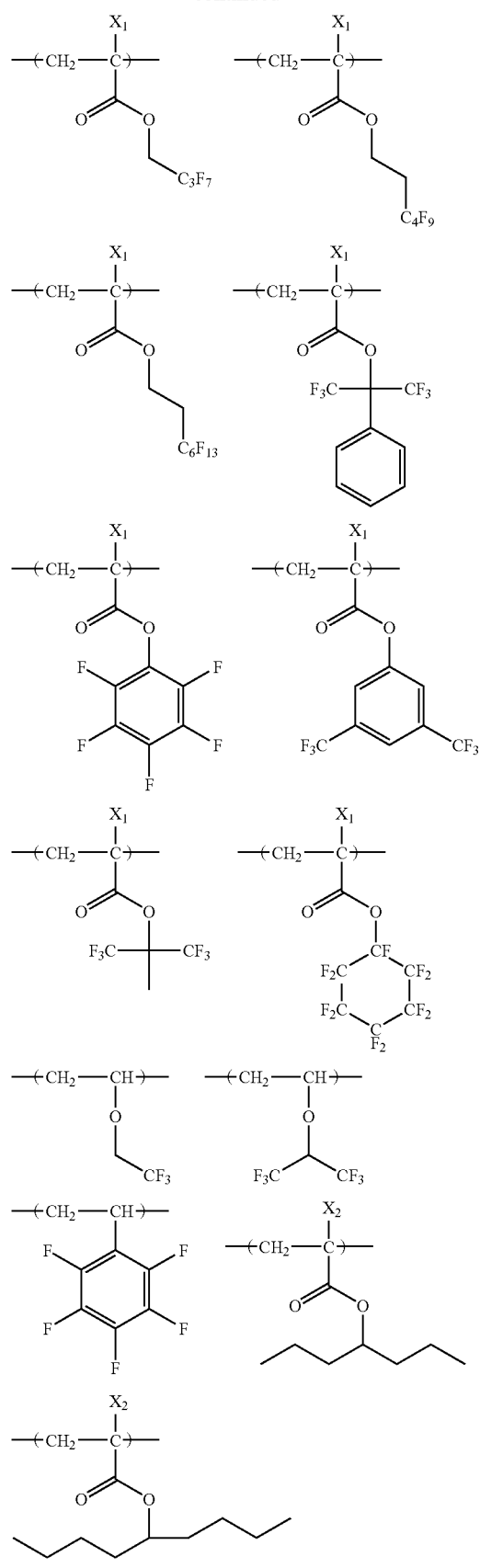
130
-continued
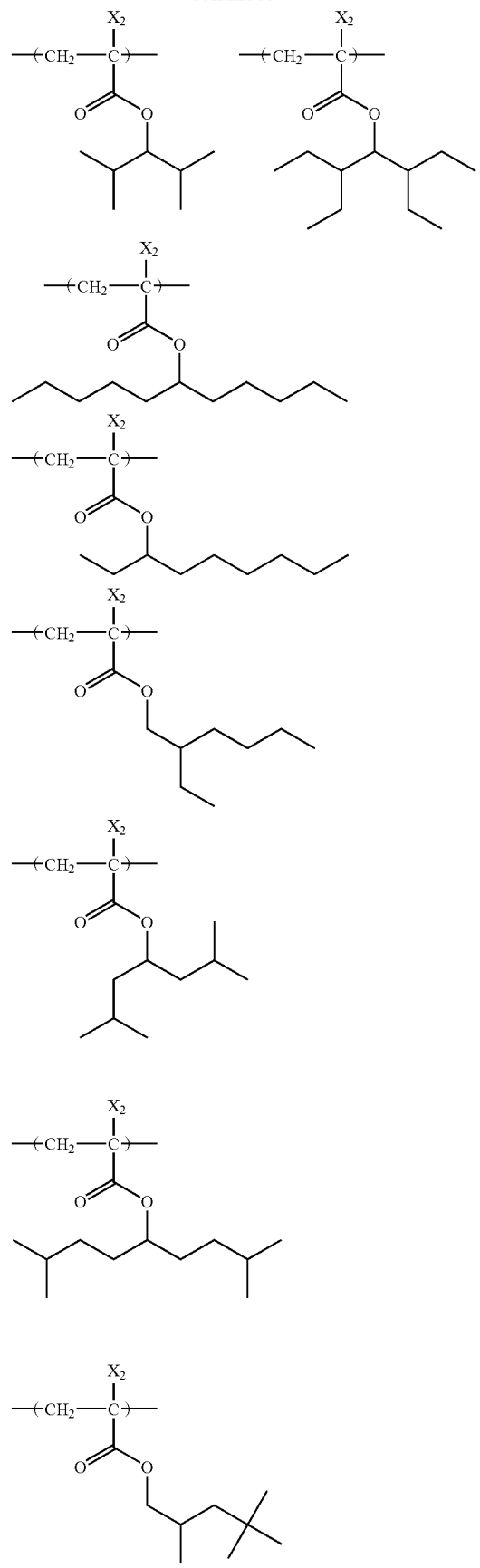

-continued

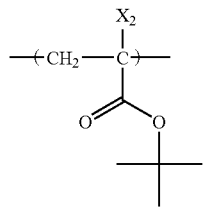

The hydrophobic resin (I) is preferably a resin having an alkylsilyl structure (preferably a trialkylsilyl group) or a cyclosiloxane structure as a partial structure having a silicon atom.

As the alkylsilyl structure or cyclosiloxane structure, there can be mentioned, for example, any of the groups of the following general formulae (CS-1) to (CS-3) or the like.

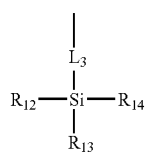
(CS-1)

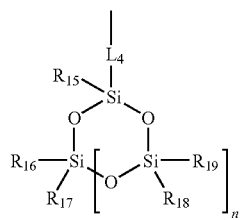
(CS-2)

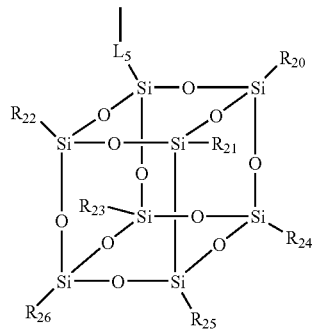
(CS-3)

In the general formulae (CS-1) to (CS-3), each of $R_{12}$ to $R_{26}$ independently represents a linear or branched alkyl group (preferably having 1 to 20 carbon atoms) or a cycloalkyl group (preferably having 3 to 20 carbon atoms).

Each of $L_3$ to $L_5$ represents a single bond or a bivalent connecting group. As the bivalent connecting group, there can be mentioned any one or a combination of two or more groups selected from the group consisting of an alkylene group, a phenylene group, an ether group, a thioether group, a carbonyl group, an ester group, an amido group, a urethane group and a urea group.

In the formulae, n is an integer of 1 to 5.

Specific examples of the repeating units having the groups of the general formulae (CS-1) to (CS-3) will be shown below, which however in no way limit the scope of the present invention. Further, as the specific examples, there can be mentioned the repeating units having silicon atoms contained in the resins (HR-1) to (HR-65) below.

In the specific examples, $X_1$ represents a hydrogen atom, —$CH_3$, —F or —$CF_3$.

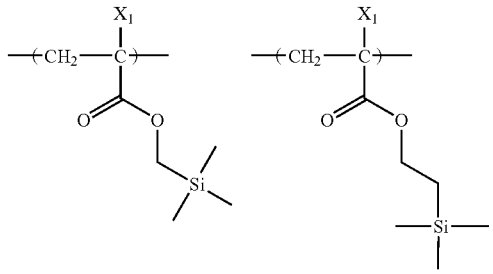

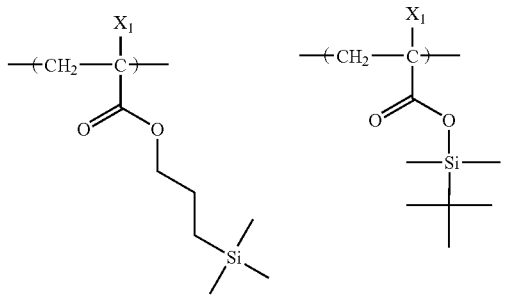

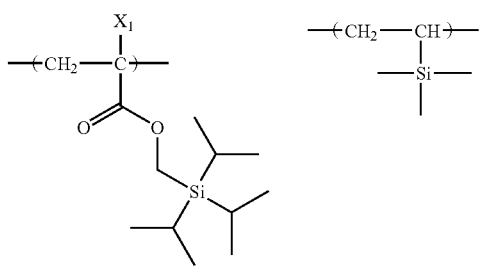

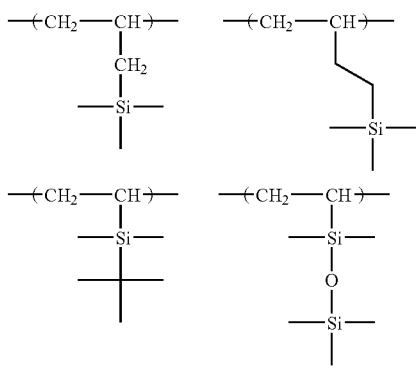

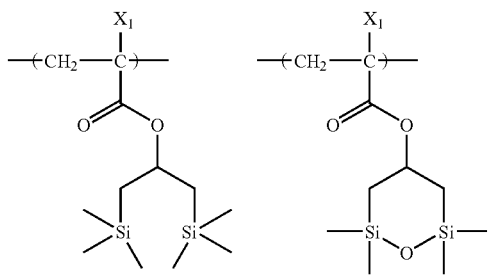

-continued

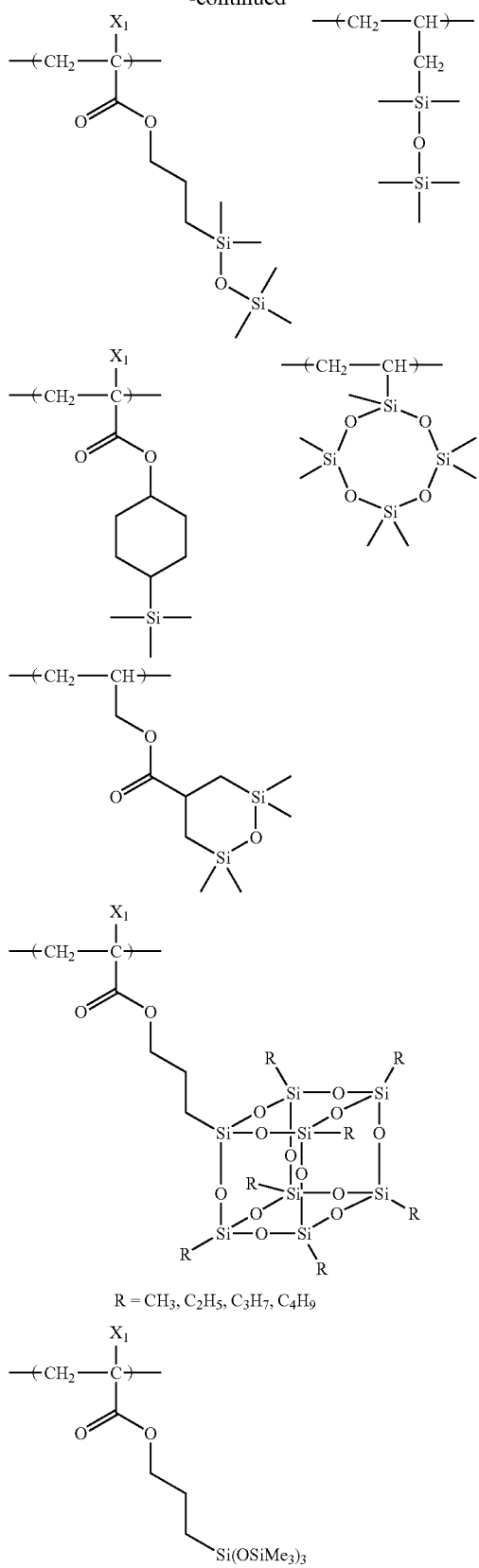

Further, the hydrophobic resin (I) may have a group whose affinity to water is increased by the presence of a base. The group whose affinity to water is increased by the presence of a base, although not particularly limited, is generally:

(x) a group having an active proton, or (y) a group that is decomposed by the action of an alkali developer, resulting in an increase of solubility in the alkali developer.

The group having an active proton (x) is preferably one having a group of 15 or below pKa. As the group having an active proton, there can be mentioned a phenolic hydroxyl group, a carboxylate group, an aliphatic alcohol having its α-position substituted with an electron withdrawing group (for example, a hexafluoroisopropanol group), a sulfonate group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, a tris(alkylsulfonyl)methylene group or the like.

As the repeating unit having the above group having an active proton (x), there can be mentioned a repeating unit wherein an alkali-soluble group is directly bonded to the principal chain of a resin, such as a repeating unit of acrylic acid or methacrylic acid, or a repeating unit wherein the alkali-soluble group is bonded via a connecting group to the principal chain of a resin, or the like. Further, there can be mentioned a repeating unit wherein the alkali-soluble group is introduced in a terminal of a polymer chain by using a chain transfer agent or polymerization initiator having the alkali-soluble group in the stage of polymerization. All these repeating units are preferable.

As the group that is decomposed by the action of an alkali developer, resulting in an increase of solubility in the alkali developer (y), there can be mentioned, for example, an active carboxylic ester group, a group having a lactone structure, an acid anhydride group, an acid imido group or the like. (The above active carboxylic ester group refers to an ester obtained from an alcohol of 13 or below pKa or the like, for example, an ester of phenol, thiol, an aliphatic alcohol having its α-position substituted with an electron withdrawing group (for example, a hexafluoroisopropanol group) or the like.) A group having a lactone structure is preferred.

As the repeating unit having above group (y) that is decomposed by the action of an alkali developer, resulting in an increase of solubility in the alkali developer, there can be mentioned a repeating unit resulting from bonding of group (y) that is decomposed by the action of an alkali developer, resulting in an increase of solubility in the alkali developer, to the principal chain of a resin, such as a repeating unit of an acrylic ester or methacrylic ester, and a repeating unit resulting from polymerization with the use of a chain transfer agent or polymerization initiator having group (y) capable of increasing the solubility in an alkali developer to thereby attain introduction in a polymer chain terminal. Both of these repeating units are preferable.

It is preferred for the hydrophobic resin (I) to contain at least one of the structures of general formulae (i) to (iii) below as the repeating unit having a group whose affinity to water is increased by the presence of a base.

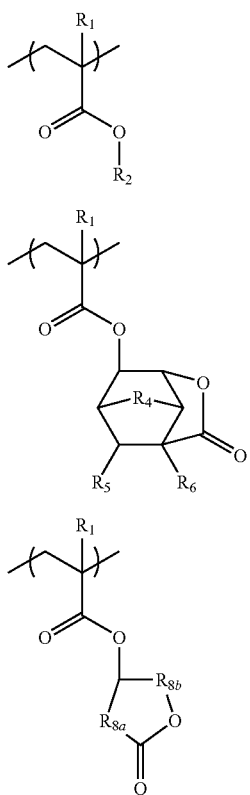

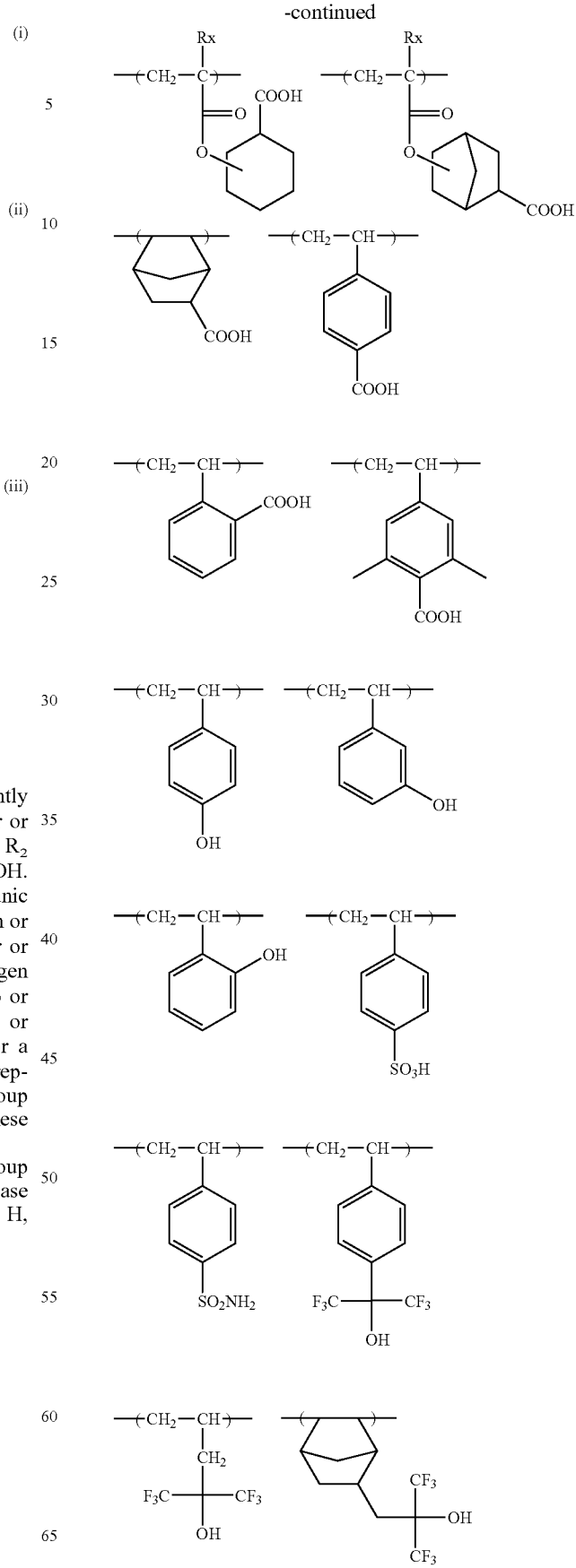

In general formulae (i) to (iii), each of $R_1$s independently represents a hydrogen atom, a fluorine atom or a linear or branched alkyl group having 1 to 4 carbon atoms. $R_2$ represents a hydrogen atom, $-R_3-CO_2H$ or $-R_3-OH$. $R_3$ represents an optionally fluorinated bivalent organic group. $R_4$ represents a methylene group, an oxygen atom or a sulfur atom. $R_5$ represents a hydrogen atom, a linear or branched alkyl group or $-CO_2R_7$. $R_6$ represents a hydrogen atom, a linear or branched alkyl group, a cyano group or $-CO_2R_7$. $R_7$ represents a hydrogen atom, a linear or branched alkyl group having 1 to 20 carbon atoms or a cycloalkyl group. Each of $R_{9a}$ and $R_{8b}$ independently represents a single bond, a linear or branched alkylene group having 1 to 4 carbon atoms or a cycloalkylene group. These groups may further have substituents.

Specific examples of the repeating units having a group whose affinity to water is increased by the presence of a base will be shown below. In the formulae, Rx represents H, $-CH_3$, $-CF_3$ or $CH_2OH$.

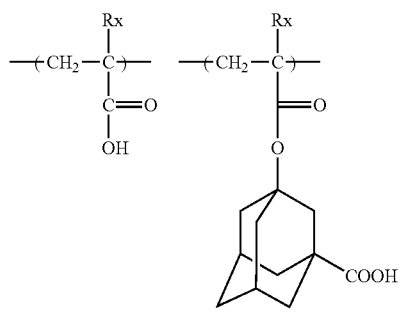

137
-continued
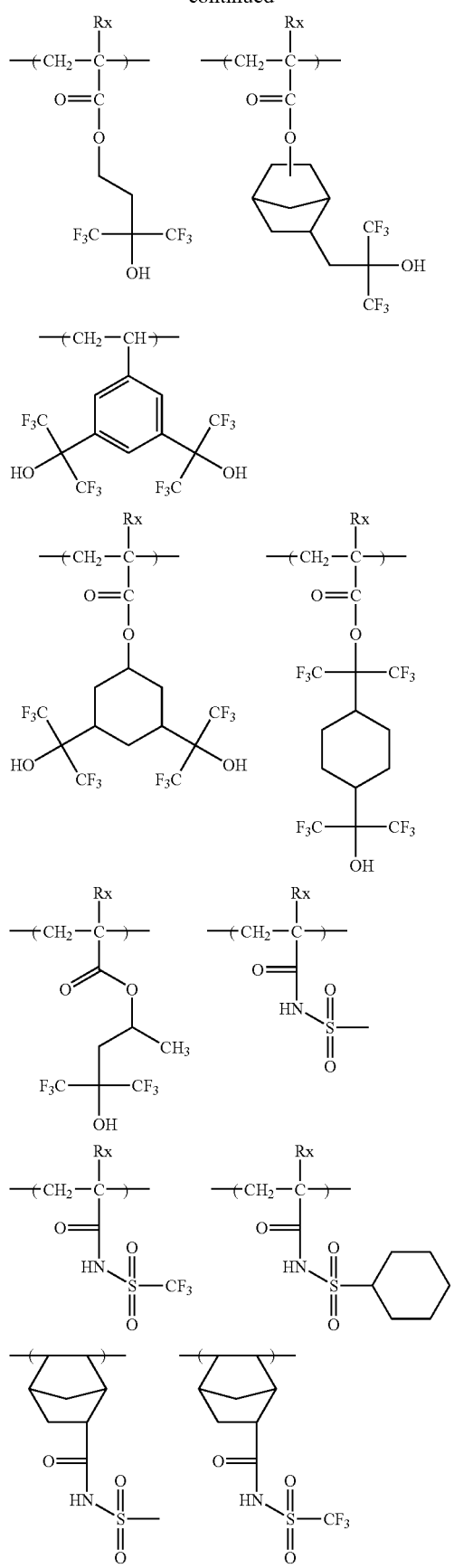
138
-continued
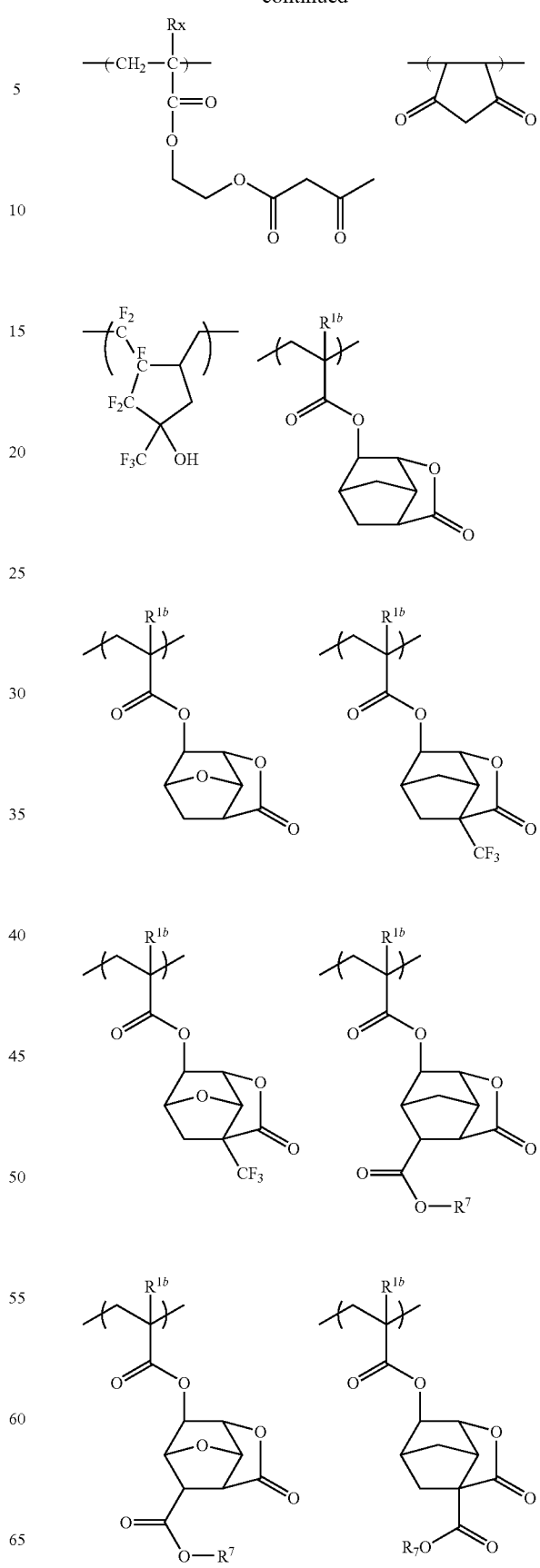

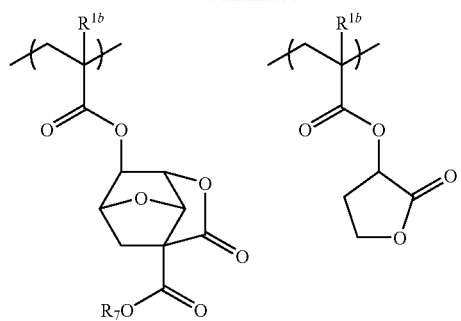
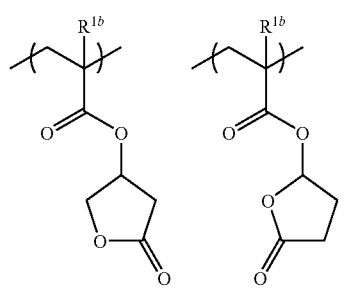
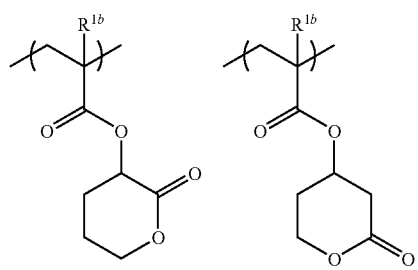
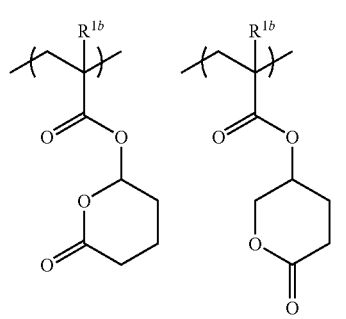
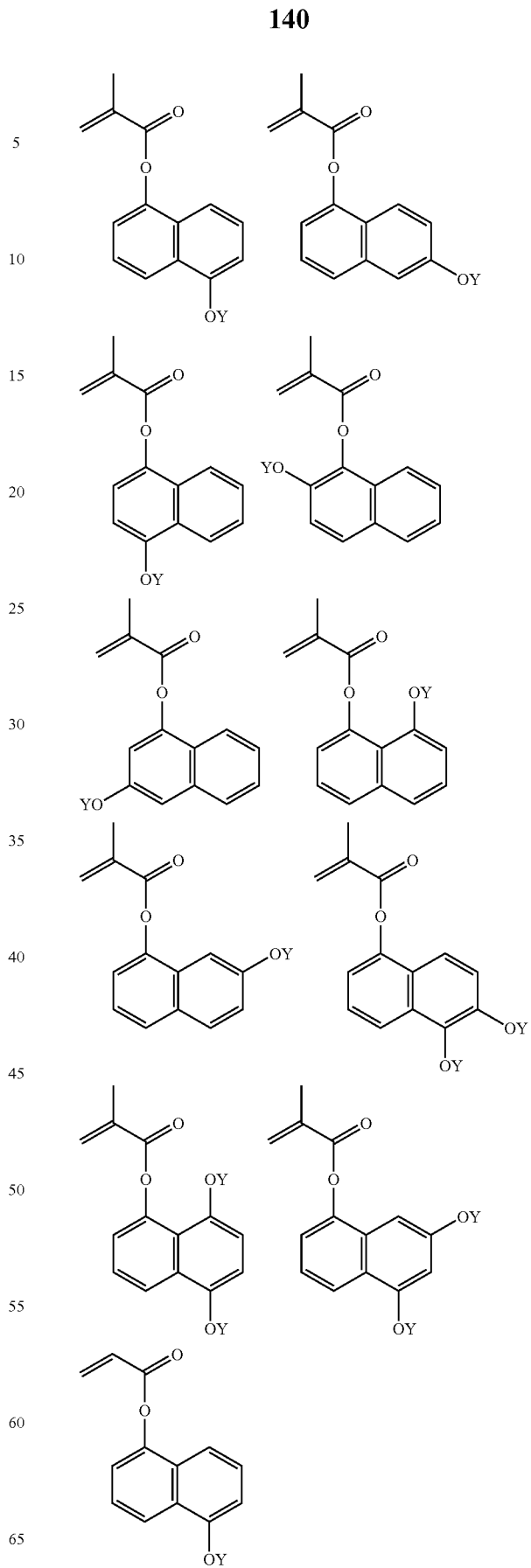

In the formulae, $R^{1b}$ represents a hydrogen atom, a fluorine atom or a linear or branched alkyl group having 1 to 4 carbon atoms. The alkyl group may have a fluorine atom or a hydroxyl group as a substituent. $R_7$ represents a hydrogen atom, a linear or branched alkyl group having 1 to 20 carbon atoms or a cycloalkyl group. Each of the alkyl group and cycloalkyl group represented by $R_7$ may have a fluorine atom as a substituent.

Moreover, specific examples of the monomers capable of providing the repeating unit having a group whose affinity to water is increased by the presence of a base will be shown below. In the specific examples, Y represents a hydrogen atom.

141
-continued
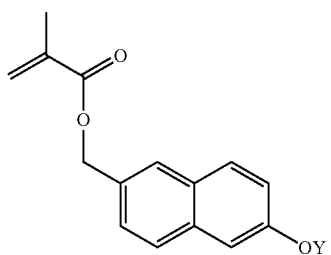
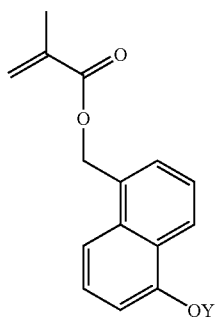
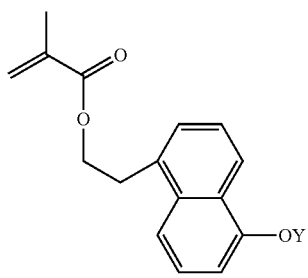
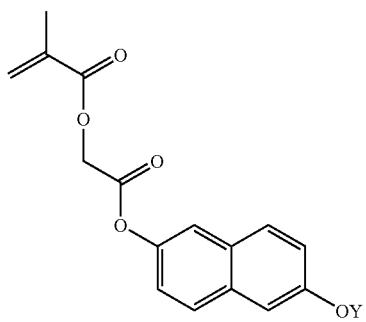
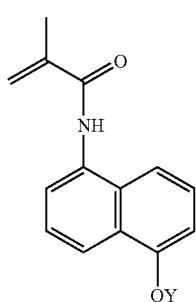
142
-continued
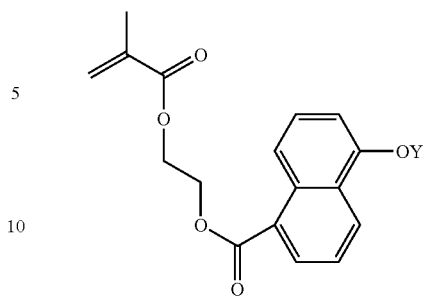
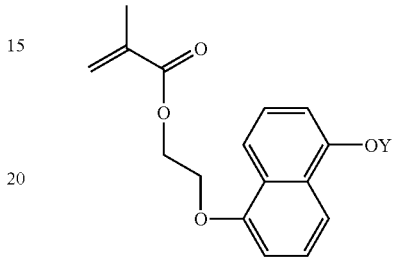
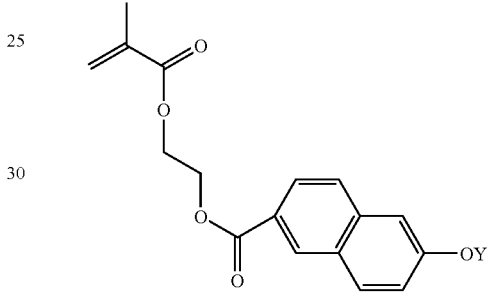
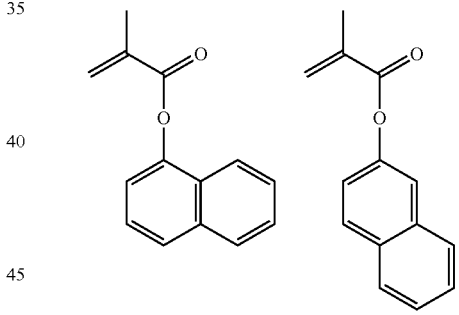
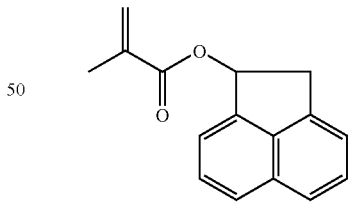
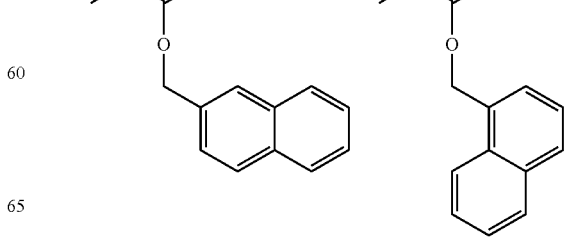

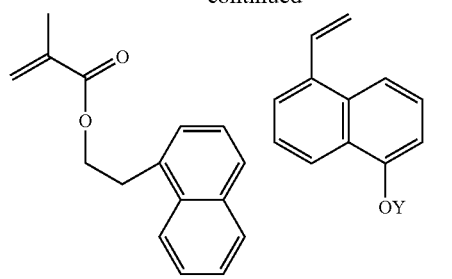
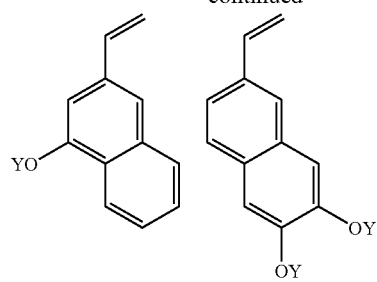
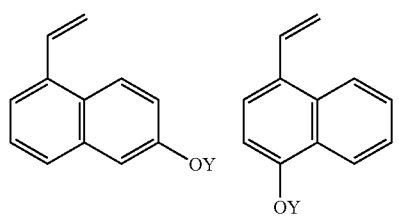
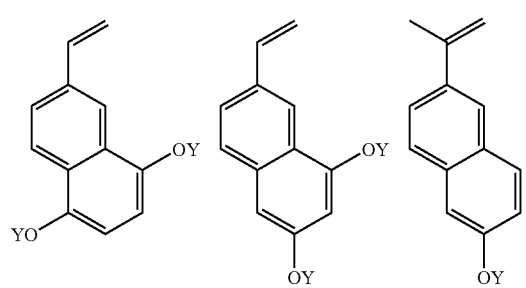
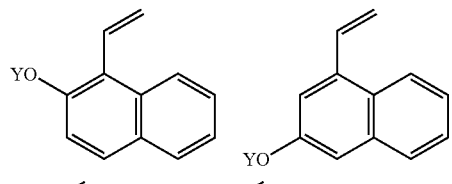
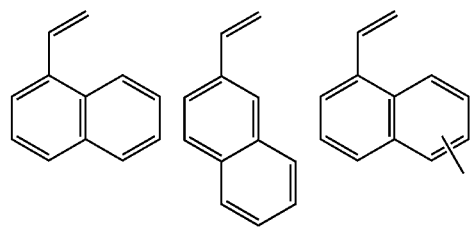
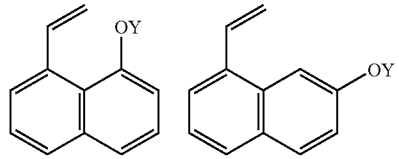
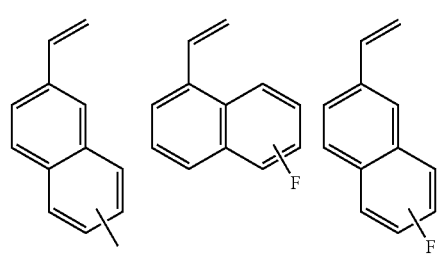
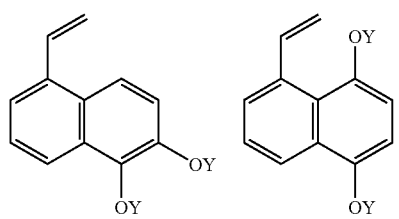
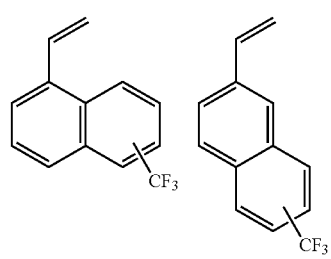
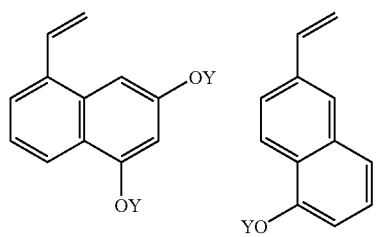
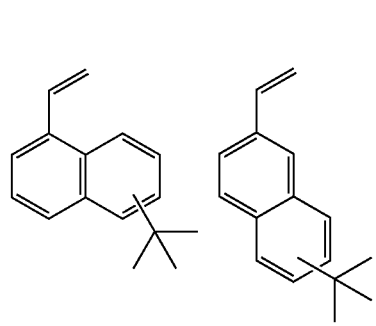
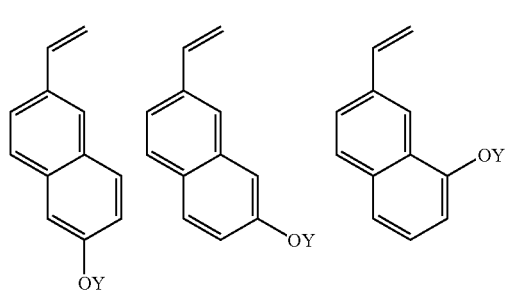

-continued

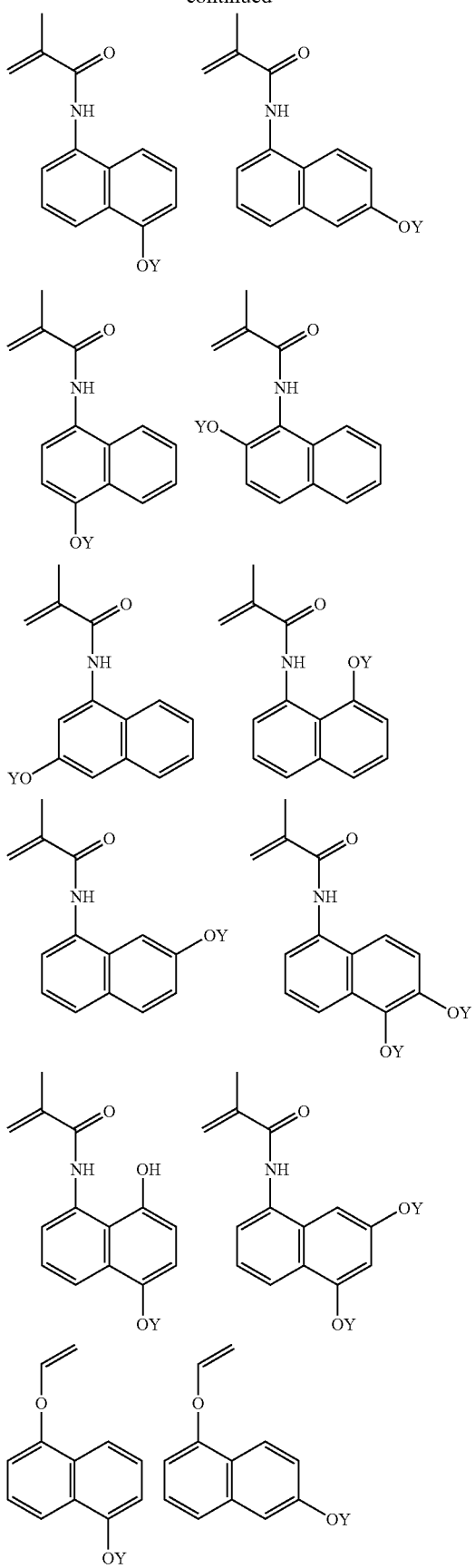
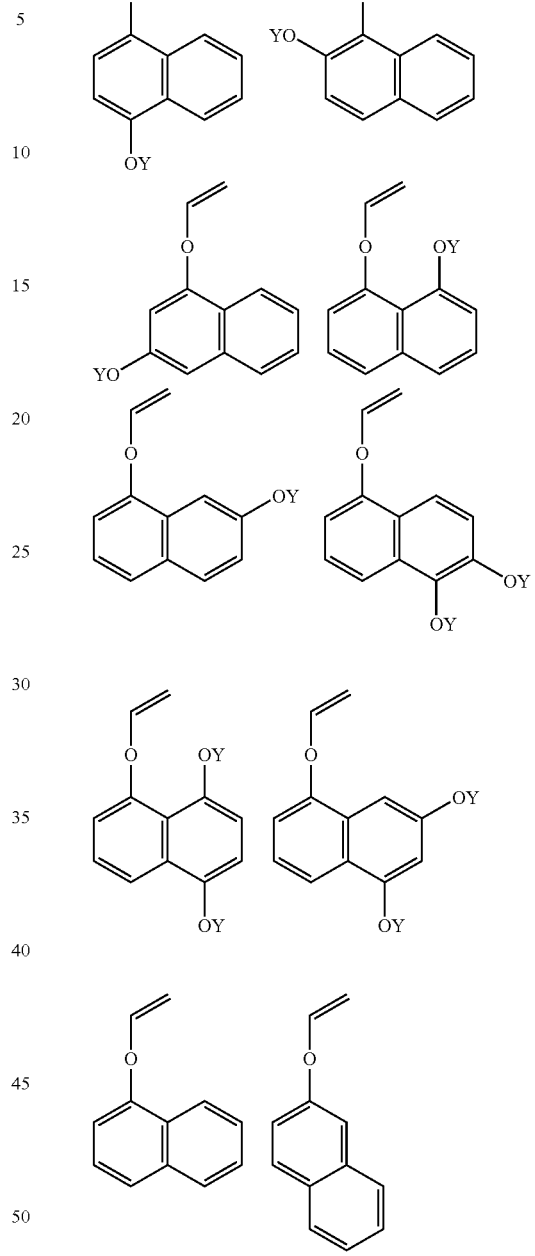

The content of the repeating unit having a group whose affinity to water is increased by the presence of a base is preferably in the range of 1 to 50 mol %, more preferably 3 to 35 mol % and further preferably 5 to 20 mol %, based on all the repeating units contained in the polymer.

The hydrophobic resin (I) may further have a group that is decomposed by the action of an acid (z).

As the repeating unit having the group that is decomposed by the action of an acid (z), contained in the hydrophobic resin (I), there can be mentioned not only those similar to the repeating units having an acid-decomposable group mentioned hereinbefore with respect to the resin as component (B) but also the following specific examples.

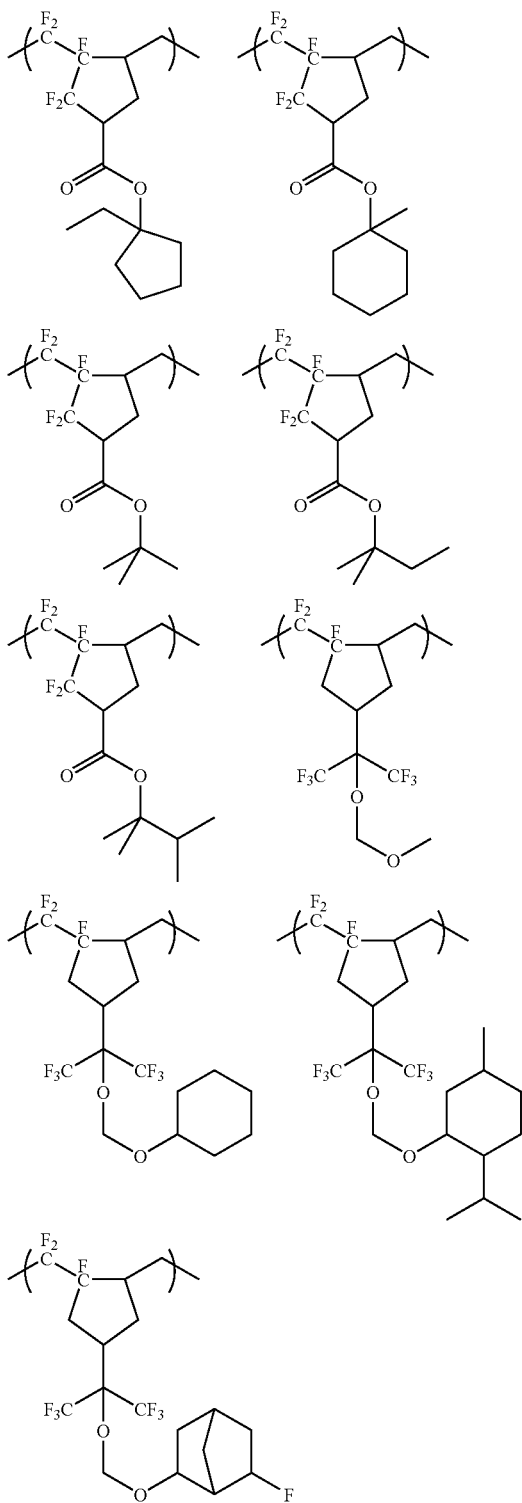

In general formula (iv),

R represents a hydrogen atom, an alkyl group, an alkyl group substituted with a fluorine atom, a cyano group or —$CH_2$—O-$Rac_2$ group, wherein $Rac_2$ represents a hydrogen atom, an alkyl group or an acyl group. R is preferably a hydrogen atom, a methyl group, a hydroxymethyl group or a trifluoromethyl group, especially preferably a hydrogen atom or a methyl group.

$R_4$ represents a group having any of an alkyl group, a cycloalkyl group, an alkenyl group and a cycloalkenyl group.

$L_6$ represents a single bond or a bivalent connecting group.

In general formula (iv), the alkyl group represented by $R_4$ is preferably a linear or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The bivalent connecting group represented by $L_6$ is preferably an alkylene group (preferably having 1 to 5 carbon atoms), an oxy group, a phenylene group or an ester bond (group of the formula —COO—).

When the hydrophobic resin (I) has a fluorine atom, the content ratio of fluorine atom(s) is preferably in the range of 5 to 80 mass %, more preferably 10 to 80 mass %, based on the molecular weight of the hydrophobic resin (I). The repeating unit containing a fluorine atom preferably exists in the hydrophobic resin (I) in an amount of 10 to 100 mass %, more preferably 30 to 100 mass %.

When the hydrophobic resin (I) has a silicon atom, the content ratio of silicon atom(s) is preferably in the range of 2 to 50 mass %, more preferably 2 to 30 mass %, based on the molecular weight of the hydrophobic resin (I). The repeating unit containing a silicon atom preferably exists in the hydrophobic resin (I) in an amount of 10 to 100 mass %, more preferably 20 to 100 mass %.

The weight average molecular weight of the hydrophobic resin (I) in terms of standard polystyrene molecular weight is preferably in the range of 1000 to 100,000, more preferably 1000 to 50,000 and still more preferably 2000 to 15,000.

Impurities, such as metals, should naturally be of low quantity in the hydrophobic resin (I), as for the resin as the component (B). The content ratio of residual monomers and oligomer components is preferably 0 to 10 mass %, more preferably 0 to 5 mass % and still more preferably 0 to 1 mass %. Accordingly, there can be obtained a resist being free from a change of in-liquid foreign matter, sensitivity, etc. over time. From the viewpoint of resolving power, resist profile, side wall of resist pattern, roughness, etc., the molecular weight distribution (Mw/Mn, also referred to as the degree of dispersal) thereof is preferably in the range of 1 to 5, more preferably 1 to 3 and still more preferably 1 to 2.

The content ratio of repeating units having a group (z) that is decomposed by the action of an acid in the hydrophobic resin (I) is preferably in the range of 1 to 80 mol %, more preferably 10 to 80 mol % and still more preferably 20 to 60 mol % based on all the repeating units of the resin (I).

The hydrophobic resin (I) may further have any of the repeating units of general formula (iv) below.

A variety of commercially available products can be used as the hydrophobic resin (I), and also the resin can be synthesized in accordance with conventional methods (for example, radical polymerization). As general synthesizing methods, there can be mentioned, for example, a batch polymerization method in which a monomer species and an initiator are dissolved in a solvent and heated to thereby carry out polymerization, a dropping polymerization method in which a solution of monomer species and initiator is dropped into a hot solvent over a period of 1 to 10 hours, and the like. The dropping polymerization method is preferred. As a reaction solvent, there can be mentioned, for example, an ether such as tetrahydrofuran, 1,4-dioxane or diisopropyl ether, a ketone such as methyl ethyl ketone or methyl isobutyl ketone, an ester solvent such as ethyl acetate, an amide solvent such as dimethylformamide or dimethylacetamide, or the aforementioned solvent capable of dissolving the composition of the present invention, such as propylene glycol monomethyl ether acetate, propylene glycol monomethyl ether or cyclohexanone. Preferably, the polymerization is carried out with the use of the same solvent as that used in the photosensitive composition of the present invention. This would inhibit any particle generation during storage.

The polymerization reaction is preferably carried out in an atmosphere consisting of an inert gas, such as nitrogen or argon. In the initiation of polymerization, a commercially available radical initiator (azo initiator, peroxide, etc.) is used as the polymerization initiator. Among the radical initiators, an azo initiator is preferred, and azo initiators having an ester group, a cyano group and a carboxyl group are more preferred. As specific preferred initiators, there can be mentioned azobisisobutyronitrile, azobisdimethylvaleronitrile, dimethyl 2,2'-azobis(2-methylpropionate) and the like. The reaction concentration is in the range of 5 to 50 mass %, preferably 30 to 50 mass %. The reaction temperature is generally in the range of 10° to 150° C., preferably 30° to 120° C. and more preferably 60° to 100° C.

After the completion of the reaction, the mixture is allowed to stand still to cool to room temperature and purified. In the purification, use is made of routine methods, such as a liquid-liquid extraction method in which residual monomers and oligomer components are removed by water washing or by the use of a combination of appropriate solvents, a method of purification in solution form such as ultrafiltration capable of extraction removal of only components of a given molecular weight or below, a re-precipitation method in which a resin solution is dropped into a poor solvent to thereby coagulate the resin in the poor solvent and thus remove residual monomers, etc. and a method of purification in solid form such as washing of a resin slurry obtained by filtration with the use of a poor solvent. For example, the reaction solution is brought into contact with a solvent wherein the resin is poorly soluble or insoluble (poor solvent) amounting to 10 or less, preferably 10 to 5 times the volume of the reaction solution to thereby precipitate the resin as a solid.

The solvent for use in the operation of precipitation or re-precipitation from a polymer solution (precipitation or re-precipitation solvent) is not limited as long as the solvent is a poor solvent for the polymer. According to the type of polymer, use can be made of any one appropriately selected from among a hydrocarbon, a halogenated hydrocarbon, a nitro compound, an ether, a ketone, an ester, a carbonate, an alcohol, a carboxylic acid, water, a mixed solvent containing these solvents and the like. Of these, it is preferred to employ a solvent containing at least an alcohol (especially methanol or the like) or water as the precipitation or re-precipitation solvent.

The amount of precipitation or re-precipitation solvent used is generally in the range of 100 to 10,000 parts by mass, preferably 200 to 2000 parts by mass and more preferably 300 to 1000 parts by mass per 100 parts by mass of the polymer solution, according to intended efficiency, yield, etc.

The temperature at which the precipitation or re-precipitation is carried out is generally in the range of about 0° to 50° C., preferably about room temperature (for example, about 20° to 35° C.), according to efficiency and operation easiness. The operation of precipitation or re-precipitation can be carried out by a publicly known method, such as a batch or continuous method, with the use of a common mixing vessel, such as an agitation vessel.

The polymer obtained by the precipitation or re-precipitation is generally subjected to common solid/liquid separation, such as filtration or centrifugal separation, and dried before use. The filtration is carried out with the use of a filter medium ensuring solvent resistance, preferably under pressure. The drying is performed at about 30° to 100° C., preferably about 30° to 50° C. at ordinary pressure or reduced pressure (preferably reduced pressure).

Alternatively, after the resin precipitation and separation, the obtained resin may be once more dissolved in a solvent and brought into contact with a solvent wherein the resin is poorly soluble or insoluble. Specifically, the method may include the steps of, after the completion of the radical polymerization reaction, bringing the polymer into contact with a solvent wherein the polymer is poorly soluble or insoluble to thereby precipitate a resin (step a), separating the resin from the solution (step b), re-dissolving the resin in a solvent to thereby obtain a resin solution (A) (step c), thereafter bringing the resin solution (A) into contact with a solvent wherein the resin is poorly soluble or insoluble amounting to less than 10 times (preferably 5 times or less) the volume of the resin solution (A) to thereby precipitate a resin solid (step d) and separating the precipitated resin (step e).

Specific examples of the hydrophobic resins (I) will be shown below. The following Table 1 shows the molar ratio of individual repeating units (corresponding to individual repeating units in order from the left), weight average molecular weight and degree of dispersal with respect to each of the resins.

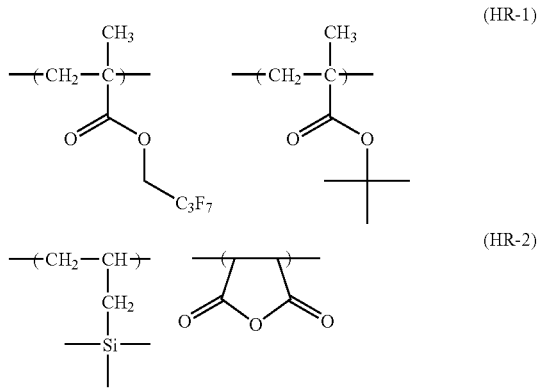

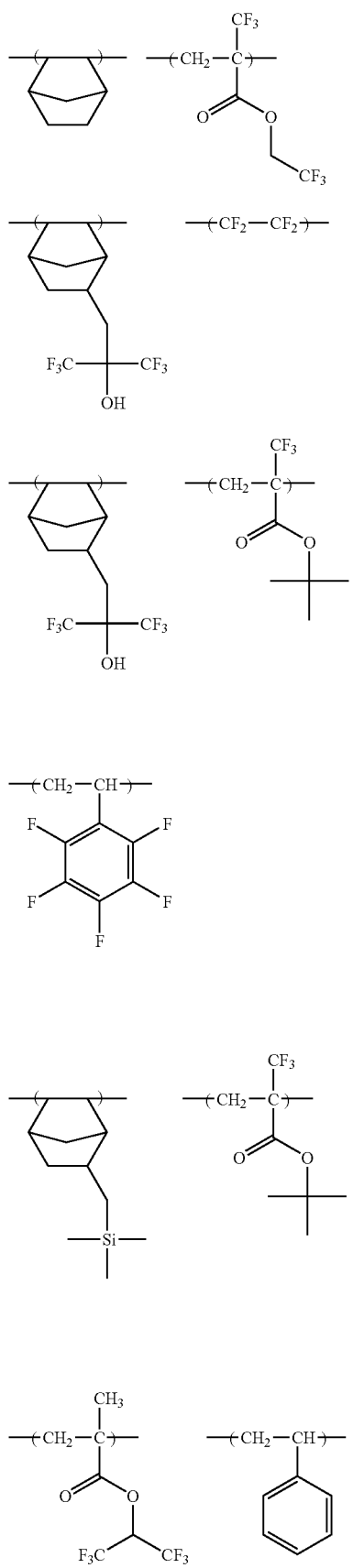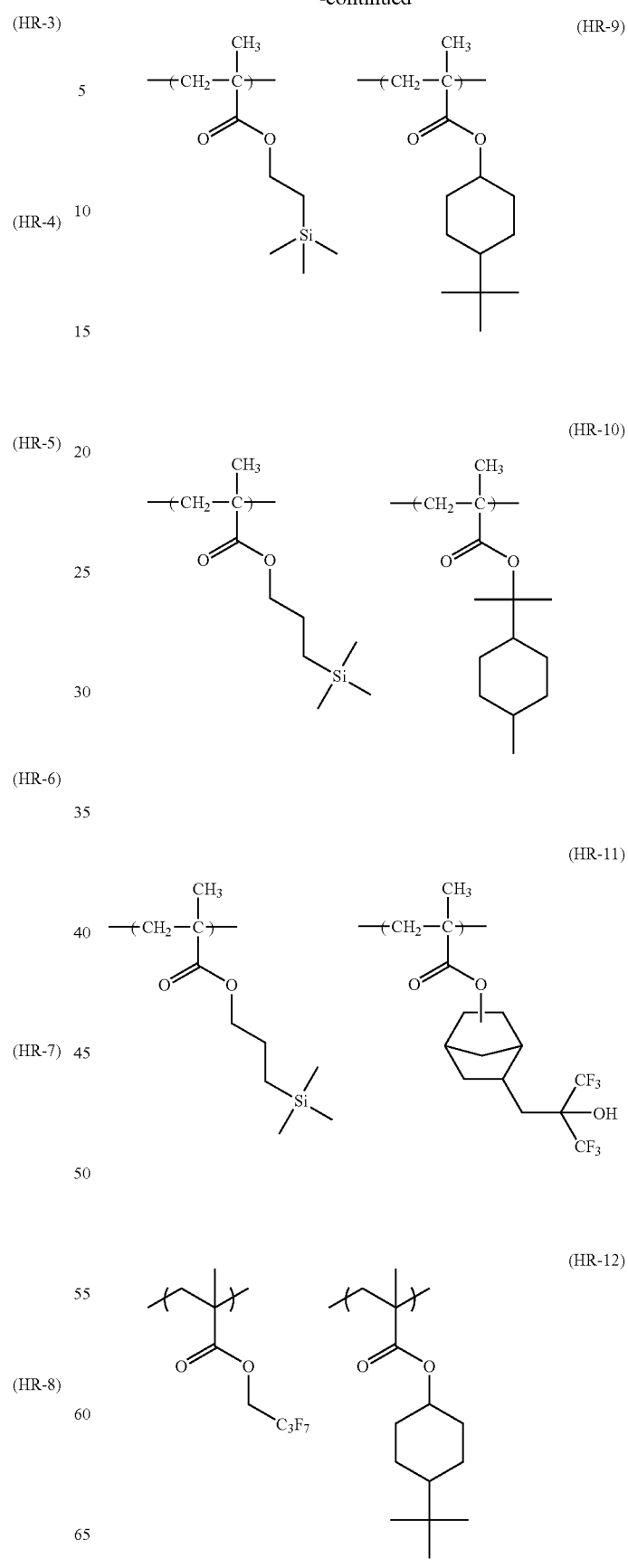

(HR-13)
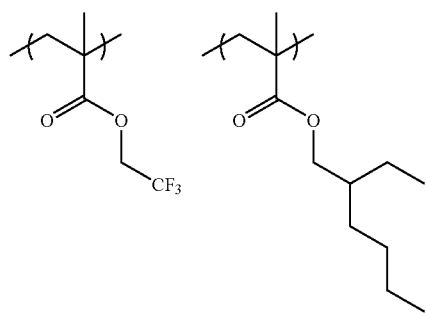
(HR-14)
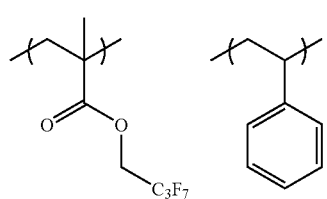
(HR-15)
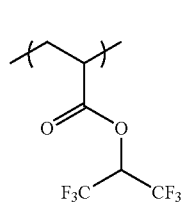
(HR-16)
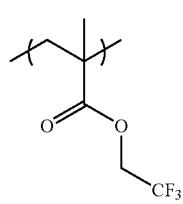
(HR-17)
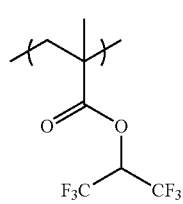
(HR-18)
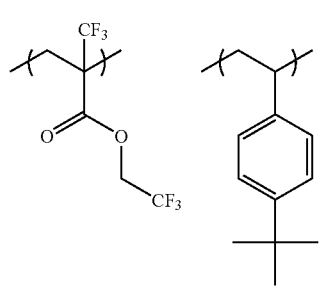
(HR-19)
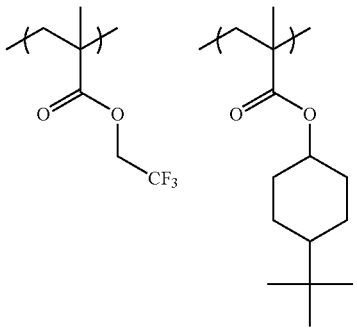
(HR-20)
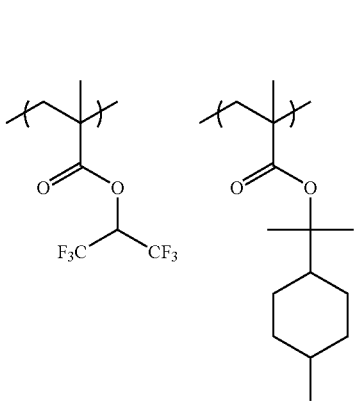
(HR-21)
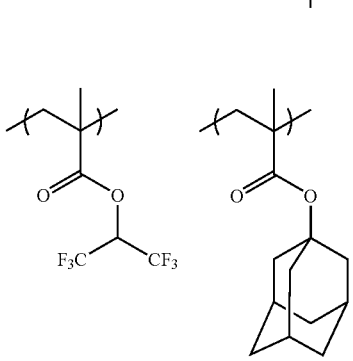
(HR-22)
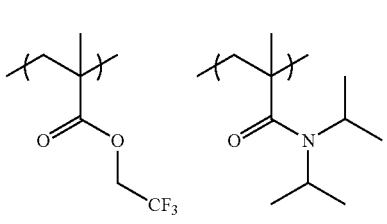
(HR-23)
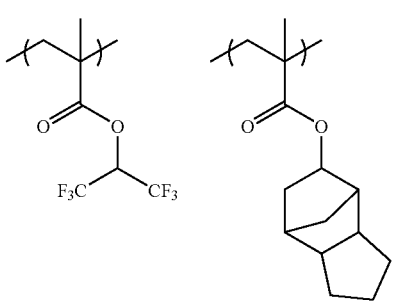

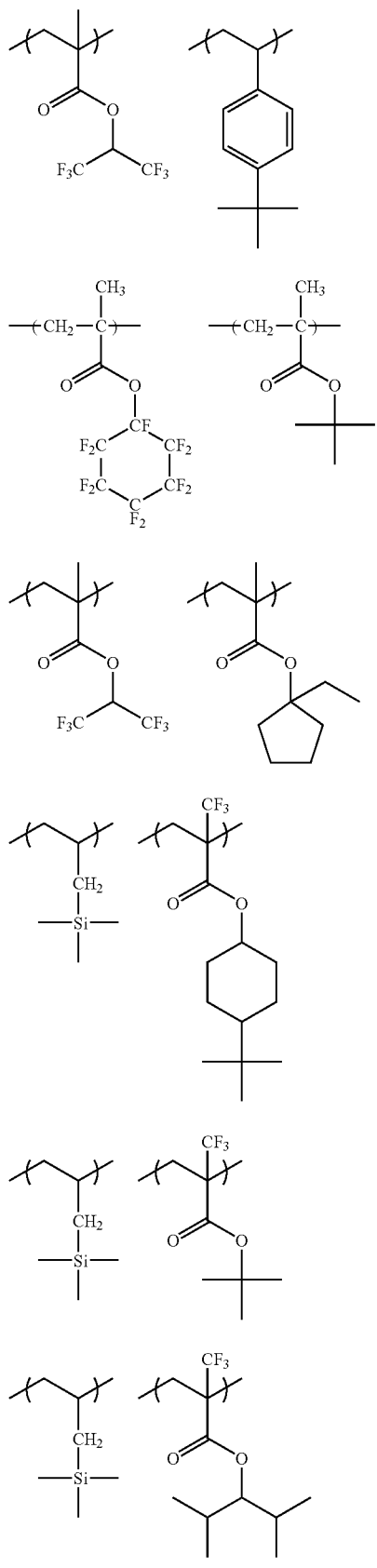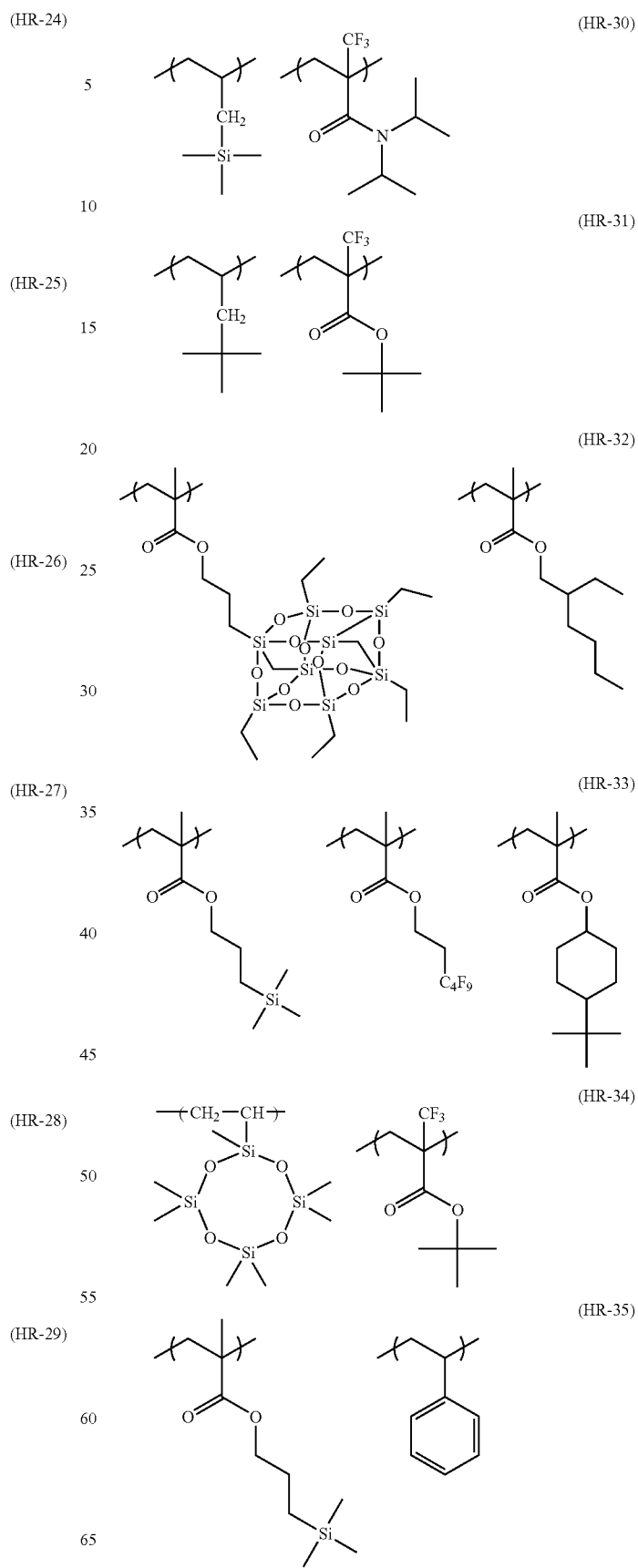

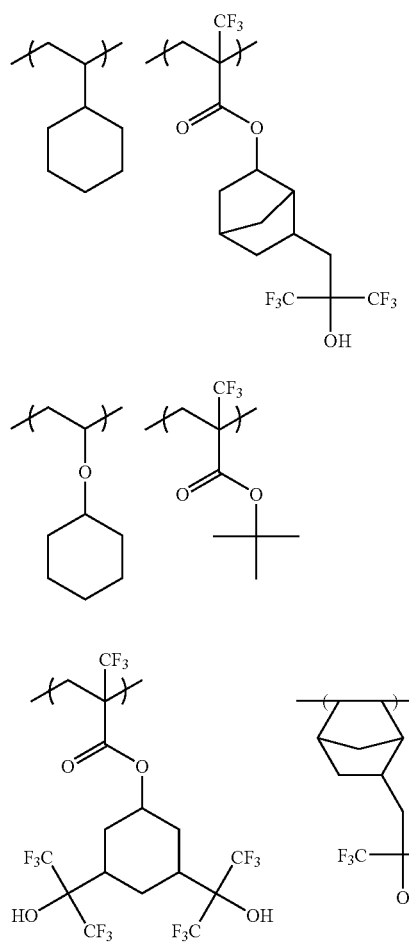 (HR-36)
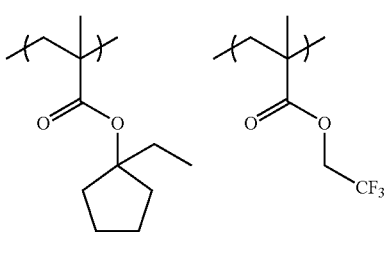 (HR-41)
(HR-37)
(HR-42)
(HR-38)
(HR-43)
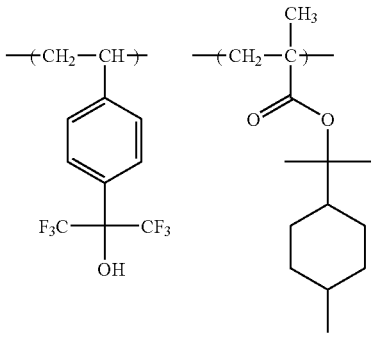
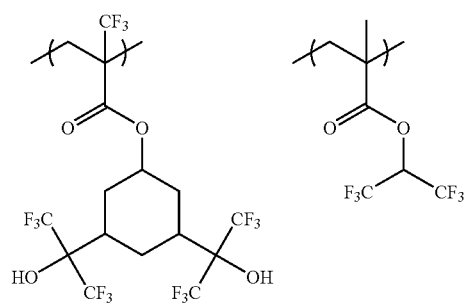 (HR-39)
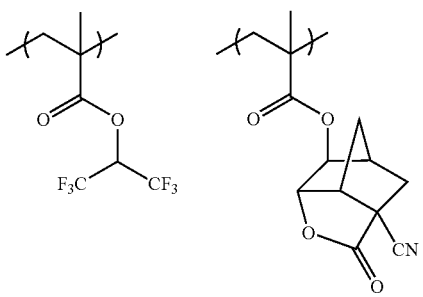 (HR-44)
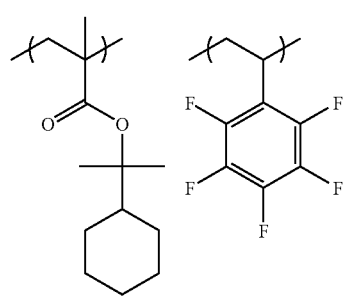 (HR-40)
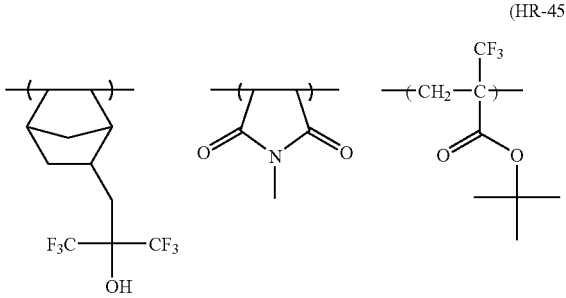 (HR-45)

-continued (HR-68)
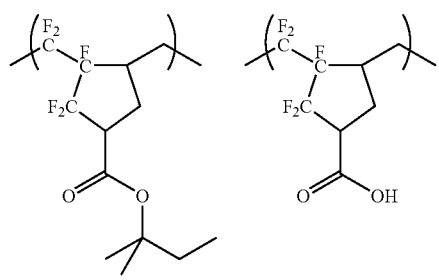
(HR-69)
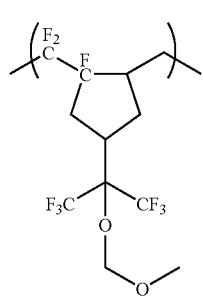
(HR-70)
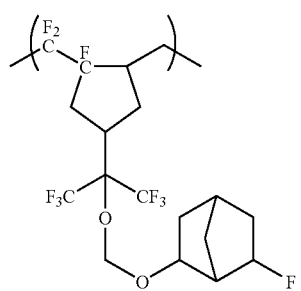
(HR-71)
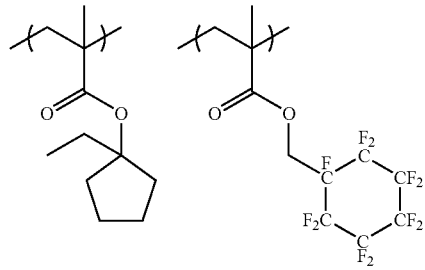
(HR-72)
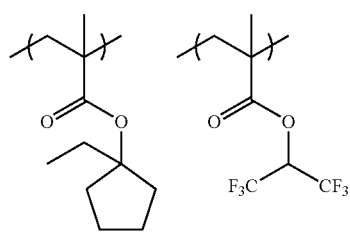
(HR-73)
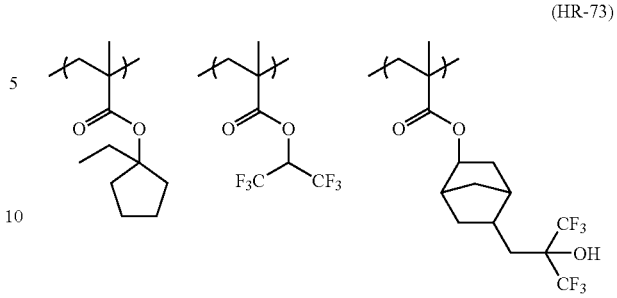
(HR-74)
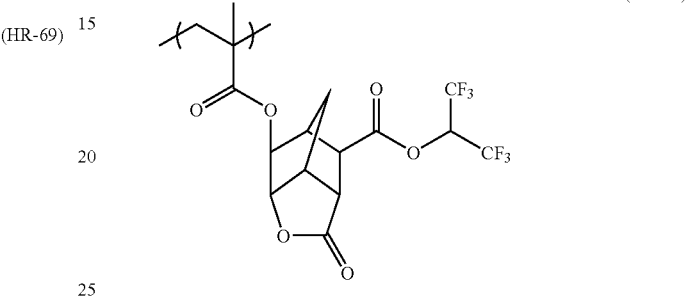
(HR-75)
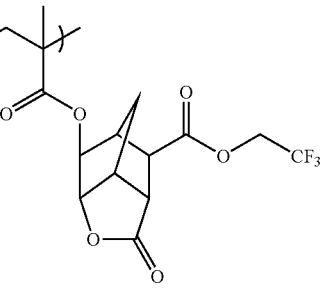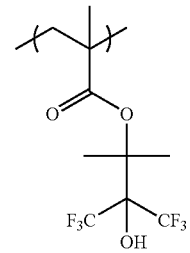
(HR-76)
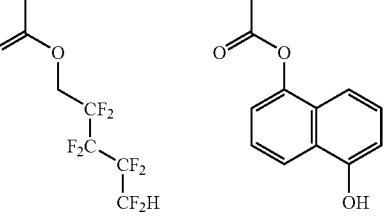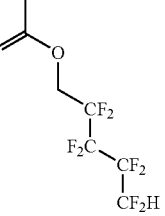
(HR-77)
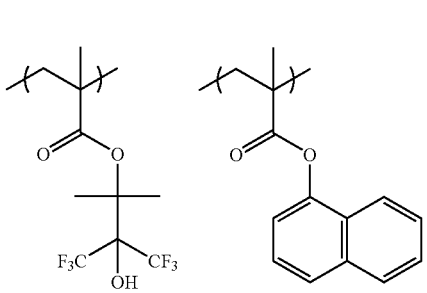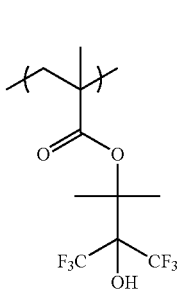

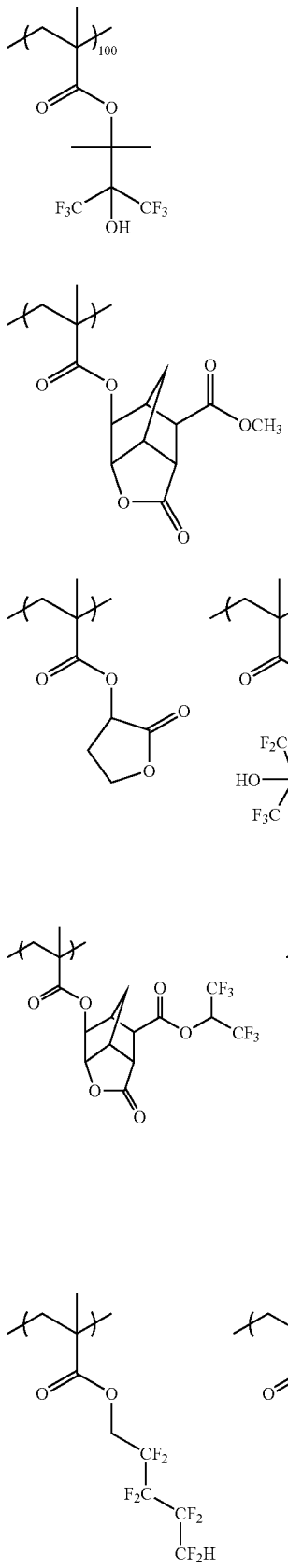
TABLE 1
| Resin | Composition | Mw | Mw/Mn |
|---|---|---|---|
| HR-1 | 50/50 | 4900 | 1.4 |
| HR-2 | 50/50 | 5100 | 1.6 |
| HR-3 | 50/50 | 4800 | 1.5 |
| HR-4 | 50/50 | 5300 | 1.6 |
| HR-5 | 50/50 | 4500 | 1.4 |
| HR-6 | 100 | 5500 | 1.6 |
| HR-7 | 50/50 | 5800 | 1.9 |
| HR-8 | 50/50 | 4200 | 1.3 |
| HR-9 | 50/50 | 5500 | 1.8 |
| HR-10 | 40/60 | 7500 | 1.6 |
| HR-11 | 70/30 | 6600 | 1.8 |
| HR-12 | 40/60 | 3900 | 1.3 |
| HR-13 | 50/50 | 9500 | 1.8 |
| HR-14 | 50/50 | 5300 | 1.6 |
| HR-15 | 100 | 6200 | 1.2 |
| HR-16 | 100 | 5600 | 1.6 |
| HR-17 | 100 | 4400 | 1.3 |
| HR-18 | 50/50 | 4300 | 1.3 |
| HR-19 | 50/50 | 6500 | 1.6 |
| HR-20 | 30/70 | 6500 | 1.5 |
| HR-21 | 50/50 | 6000 | 1.6 |
| HR-22 | 50/50 | 3000 | 1.2 |
| HR-23 | 50/50 | 5000 | 1.5 |
| HR-24 | 50/50 | 4500 | 1.4 |
| HR-25 | 30/70 | 5000 | 1.4 |
| HR-26 | 50/50 | 5500 | 1.6 |
| HR-27 | 50/50 | 3500 | 1.3 |
| HR-28 | 50/50 | 6200 | 1.4 |
| HR-29 | 50/50 | 6500 | 1.6 |
| HR-30 | 50/50 | 6500 | 1.6 |
| HR-31 | 50/50 | 4500 | 1.4 |
| HR-32 | 30/70 | 5000 | 1.6 |
| HR-33 | 30/30/40 | 6500 | 1.8 |
| HR-34 | 50/50 | 4000 | 1.3 |
| HR-35 | 50/50 | 6500 | 1.7 |
| HR-36 | 50/50 | 6000 | 1.5 |
| HR-37 | 50/50 | 5000 | 1.6 |
| HR-38 | 50/50 | 4000 | 1.4 |
| HR-39 | 20/80 | 6000 | 1.4 |
| HR-40 | 50/50 | 7000 | 1.4 |
| HR-41 | 50/50 | 6500 | 1.6 |
| HR-42 | 50/50 | 5200 | 1.6 |
| HR-43 | 50/50 | 6000 | 1.4 |
| HR-44 | 70/30 | 5500 | 1.6 |
| HR-45 | 50/20/30 | 4200 | 1.4 |
| HR-46 | 30/70 | 7500 | 1.6 |
| HR-47 | 40/58/2 | 4300 | 1.4 |
| HR-48 | 50/50 | 6800 | 1.6 |
| HR-49 | 100 | 6500 | 1.5 |
| HR-50 | 50/50 | 6600 | 1.6 |
| HR-51 | 30/20/50 | 6800 | 1.7 |
| HR-52 | 95/5 | 5900 | 1.6 |
| HR-53 | 40/30/30 | 4500 | 1.3 |
| HR-54 | 50/30/20 | 6500 | 1.8 |
| HR-55 | 30/40/30 | 7000 | 1.5 |
| HR-56 | 60/40 | 5500 | 1.7 |
| HR-57 | 40/40/20 | 4000 | 1.3 |
| HR-58 | 60/40 | 3800 | 1.4 |
| HR-59 | 80/20 | 7400 | 1.6 |
| HR-60 | 40/40/15/5 | 4800 | 1.5 |
| HR-61 | 60/40 | 5600 | 1.5 |
| HR-62 | 50/50 | 5900 | 2.1 |
| HR-63 | 80/20 | 7000 | 1.7 |
| HR-64 | 100 | 5500 | 1.8 |
| HR-65 | 50/50 | 9500 | 1.9 |
| HR-66 | 100 | 8000 | 1.4 |
| HR-67 | 100 | 5200 | 1.3 |
| HR-68 | 80/20 | 4500 | 1.5 |
| HR-69 | 100 | 4000 | 1.6 |
| HR-70 | 20/80 | 6400 | 1.4 |
| HR-71 | 60/40 | 5500 | 1.4 |
| HR-72 | 60/40 | 6000 | 1.6 |
| HR-73 | 30/40/30 | 5000 | 1.5 |
| HR-74 | 100 | 4500 | 1.5 |
| HR-75 | 40/60 | 5200 | 1.3 |
| HR-76 | 60/30/10 | 4500 | 1.5 |
| HR-77 | 50/50 | 4000 | 1.6 |
| HR-78 | 100 | 6400 | 1.4 |

TABLE 1-continued

| Resin | Composition | Mw | Mw/Mn |
|---|---|---|---|
| HR-79 | 30/70 | 6000 | 1.6 |
| HR-80 | 40/60 | 8000 | 1.4 |
| HR-81 | 70/30 | 5000 | 1.5 |
| HR-82 | 80/20 | 5500 | 1.4 |

The present invention will be described below with reference to the following Examples, which however in no way limit the scope of the present invention.

<Synthesis of Resin (B)>

[Resin RA-1]

In a nitrogen stream, 65.8 g of cyclohexanone was placed in a three-necked flask and heated at 80° C. A solution obtained by dissolving the following monomer A, monomer B, monomer C and monomer D amounting to 9.84, 4.56, 3.15 and 15.26 g, respectively and further 1.43 g of polymerization initiator V601 (5.0 mol % based on the monomers, produced by Wako Pure Chemical Industries, Ltd.) in 120.86 g of cyclohexanone was dropped thereinto over a period of 6 hours.

After the completion of the dropping, reaction was continued at 80° C. for 2 hours. The reaction liquid was allowed to stand still to cool and was dropped into a mixed liquid consisting of 900 ml of methanol and 100 ml of water over a period of 20 minutes. The thus precipitated powder was collected by filtration and dried, thereby obtaining 18 g of a desired resin (RA-1). The weight average molecular weight of the obtained resin in terms of standard polystyrene molecular weight was 9300 and the dispersity (Mw/Mn) thereof was 1.73.

Monomer A

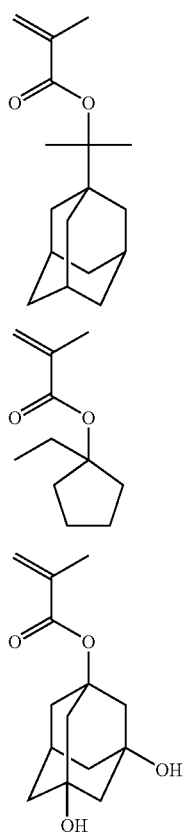

Monomer B

Monomer C

Monomer D

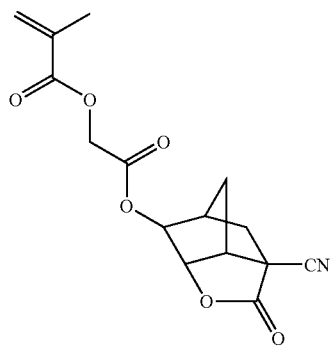

The other resins (RA-2 to RA-4) were synthesized in the same manner. The weight average molecular weight of each of the resins was regulated by changing the amount of initiator added.

The repeating units (molar ratio), weight average molecular weight (Mw) and dispersity (Mw/Mn) of each of the obtained resins are shown below.

(RA-1)

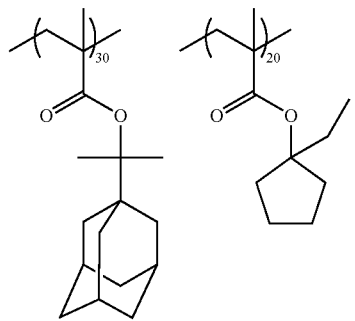

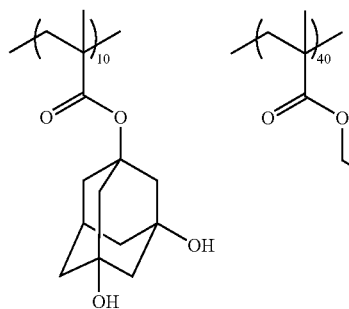

Mw = 9300
Mw/Mn = 1.73

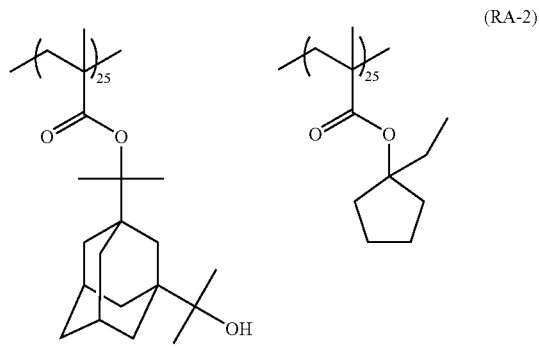
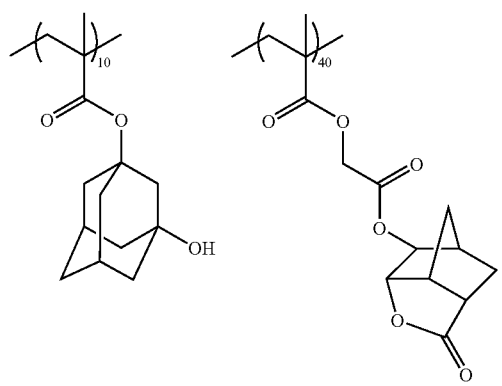
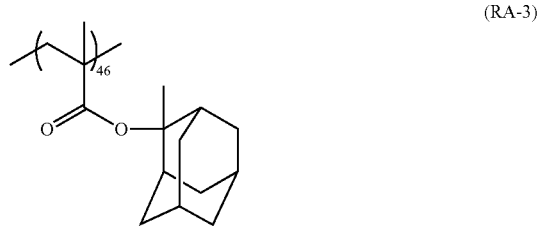
(RA-2)
Mw = 9800
Mw/Mn = 1.86
(RA-3)
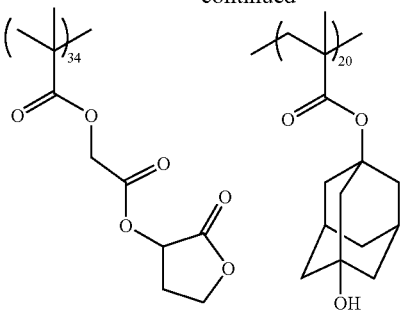
Mw = 12000
Mw/Mn = 1.89
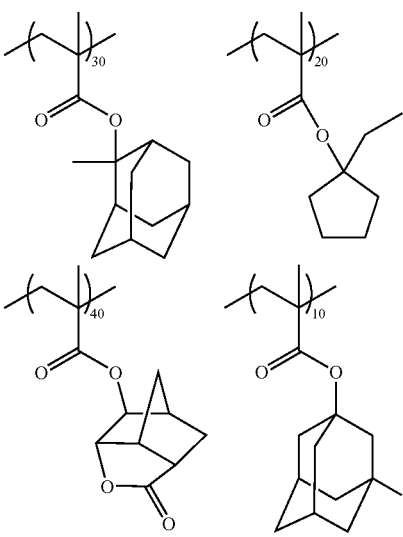
Mw = 11500
Mw/Mn = 1.77
(RA-4)
<Synthesis of Basic Compound (C)>
[Basic Compound C-3]
Compound C-3 was synthesized in accordance with the following synthetic scheme.
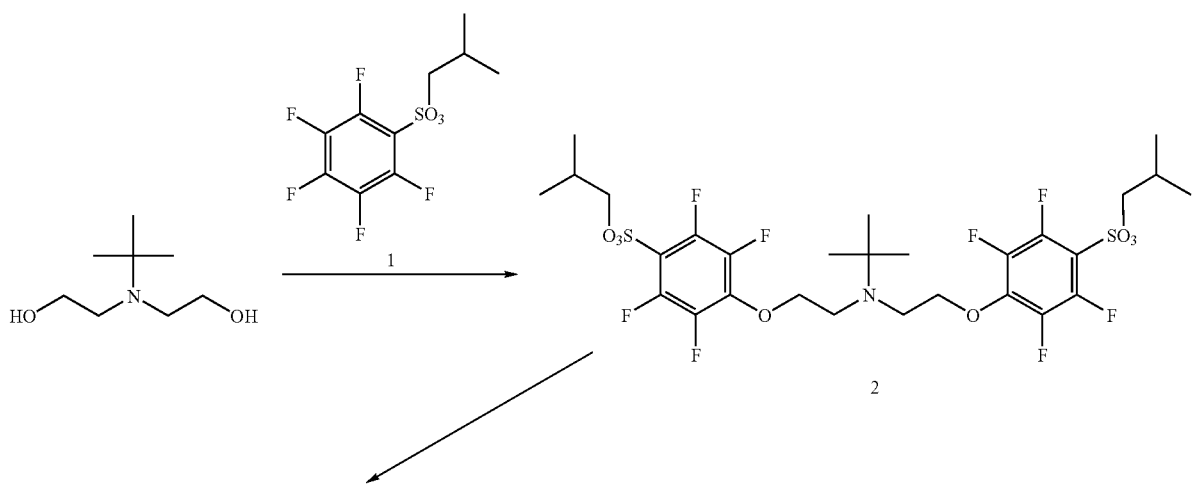

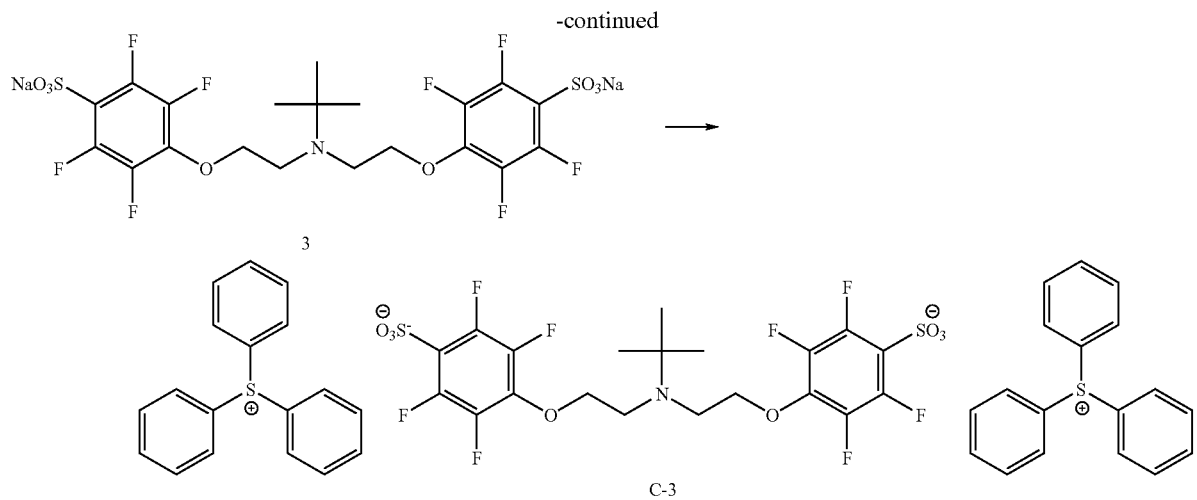

C-3

Synthesis of Compound 1

In a 1 L three-necked flask, 105.9 g of pentafluorobenzenesulfonic acid was dissolved in 100 ml of diisopropyl ether. While cooling with ice, a solution obtained by dissolving 50 g of isobutanol and 50 g of pyridine in 100 ml of diisopropyl ether was dropped into the solution over a period of 30 minutes. After the completion of the dropping, the mixture was agitated at room temperature for 4 hours, and 300 ml of ethyl acetate and 300 ml of 1N hydrochloric acid were added thereto. The resultant organic phase was washed with 300 ml of saturated sodium bicarbonate water and 300 ml of saturated salted water, and dried over sodium sulfate. Thus, 105 g of compound 1 was obtained (yield 88%).

Synthesis of Compound 2

Compound 1 (10 g) was dissolved in 50 ml of 1,2-dichloromethane. While cooling with ice, 2.64 g of N-tert-butyldiethanolamine and a 1N aqueous sodium hydroxide solution were dropped thereinto. After the completion of the dropping, the reaction liquid was agitated at room temperature for 3 hours, and 50 ml of ethyl acetate was added thereto. The resultant organic phase was washed with 100 ml of water. The reaction liquid was concentrated, and purified using column chromatography. Thus, 2.2 g of compound 2 was obtained (yield 19%).

Synthesis of Compound 3

Compound 2 (2.2 g) was dissolved in 10 ml of acetonitrile, and 0.9 g of sodium iodide was added to the solution and agitated for 2 hours. After the agitation, the formed solid was collected by filtration and washed with acetonitrile. Thus, 0.5 g of compound 3 was obtained (yield 25%).

Synthesis of Compound C-3

Figure 2:
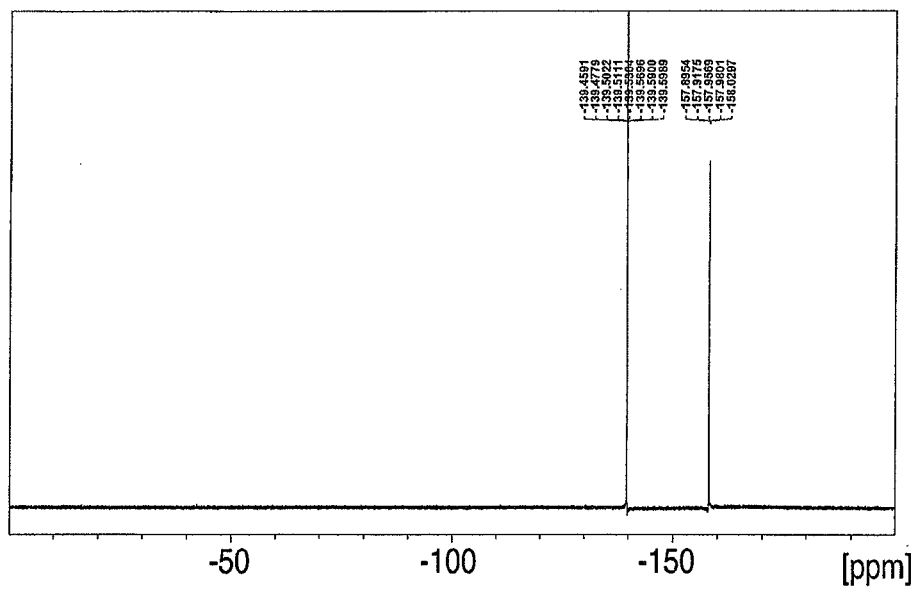
FIG. 2 is the $^{19}$F-NMR chart of a basic compound C-3 obtained in an Example.

Compound 3 (0.5 g) was dissolved in 10 ml of methanol, and 0.7 g of triphenylsulfonium bromide was added to the solution. The reaction solution was concentrated, and 30 ml of chloroform and 30 ml of water were added to the obtained solid and agitated. The resultant organic phase was extracted and washed with 100 ml of water. The washed organic phase was concentrated, thereby obtaining 0.82 g of basic compound C-3 (yield 95%). The NMR charts of the obtained compound C-3 are given in FIGS. 1 and 2.

[Basic Compound C-7]

Basic compound C-7 was synthesized in accordance with the following scheme.

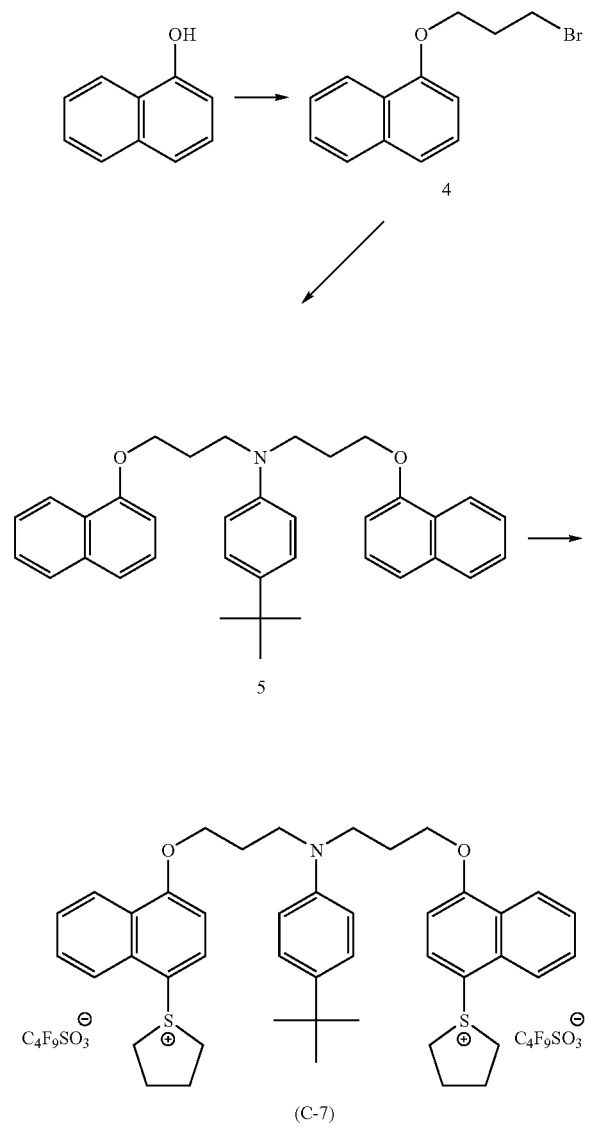

(C-7)

Synthesis of compound 4

In a 1 L three-necked flask, 1-naphthol (10.0 g) and 1,3-dibromopropane (21.0 g) were dissolved in 200 ml of acetonitrile. Potassium carbonate (9.6 g) was added to the solution and heated at 80° C. for 5 hours. The reaction liquid was cooled to room temperature, and 500 ml of hexane and 200 ml of a 1N aqueous sodium hydroxide solution were added thereto. The resultant organic phase was separated and washed with 200 ml of water. The washed organic phase was concentrated. The thus obtained crude product was purified using silica gel column chromatography. Thus, 9.9 g of compound 4 was obtained (yield 58%).

Synthesis of Compound 5

In a 500 ml three-necked flask, 4-t-butylaniline (3.0 g) and compound 4 (9.9 g) were dissolved in 100 g of NMP. Potassium carbonate (5.6 g) was added to the solution and heated at 120° C. for 7 hours. The reaction liquid was cooled to room temperature, and 300 ml of hexane and 200 ml of water were added thereto. The resultant organic phase was separated and washed with 100 ml of a 1N aqueous sodium hydroxide solution and 100 ml of water. The washed organic phase was concentrated. The thus obtained crude product was purified using silica gel column chromatography. Thus, 4.5 g of compound 5 was obtained (yield 43%).

Synthesis of Compound C-7

Figure 3:
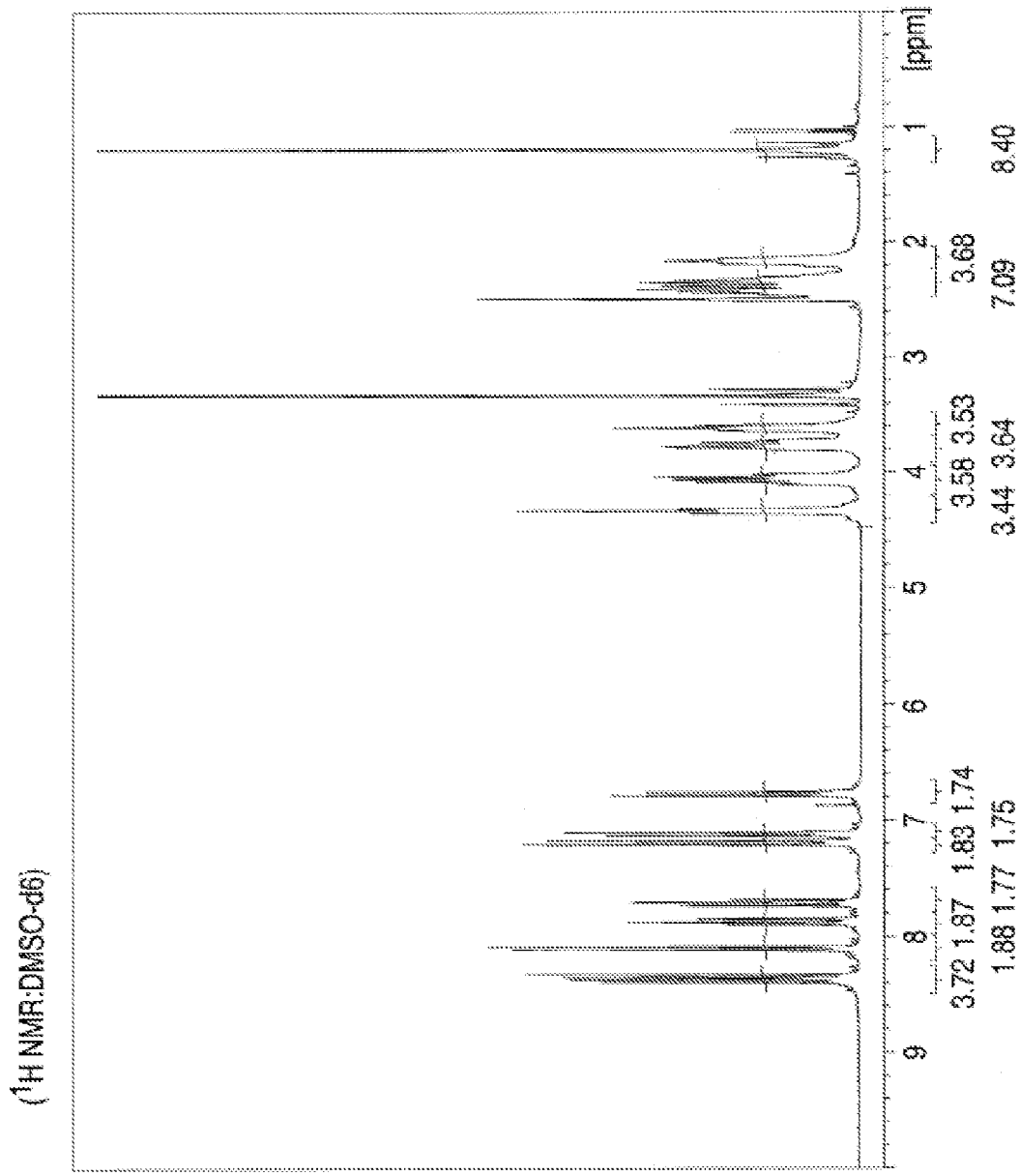
FIG. 3 is the $^1$H-NMR chart of a basic compound C-7 obtained in an Example.
Figure 4:
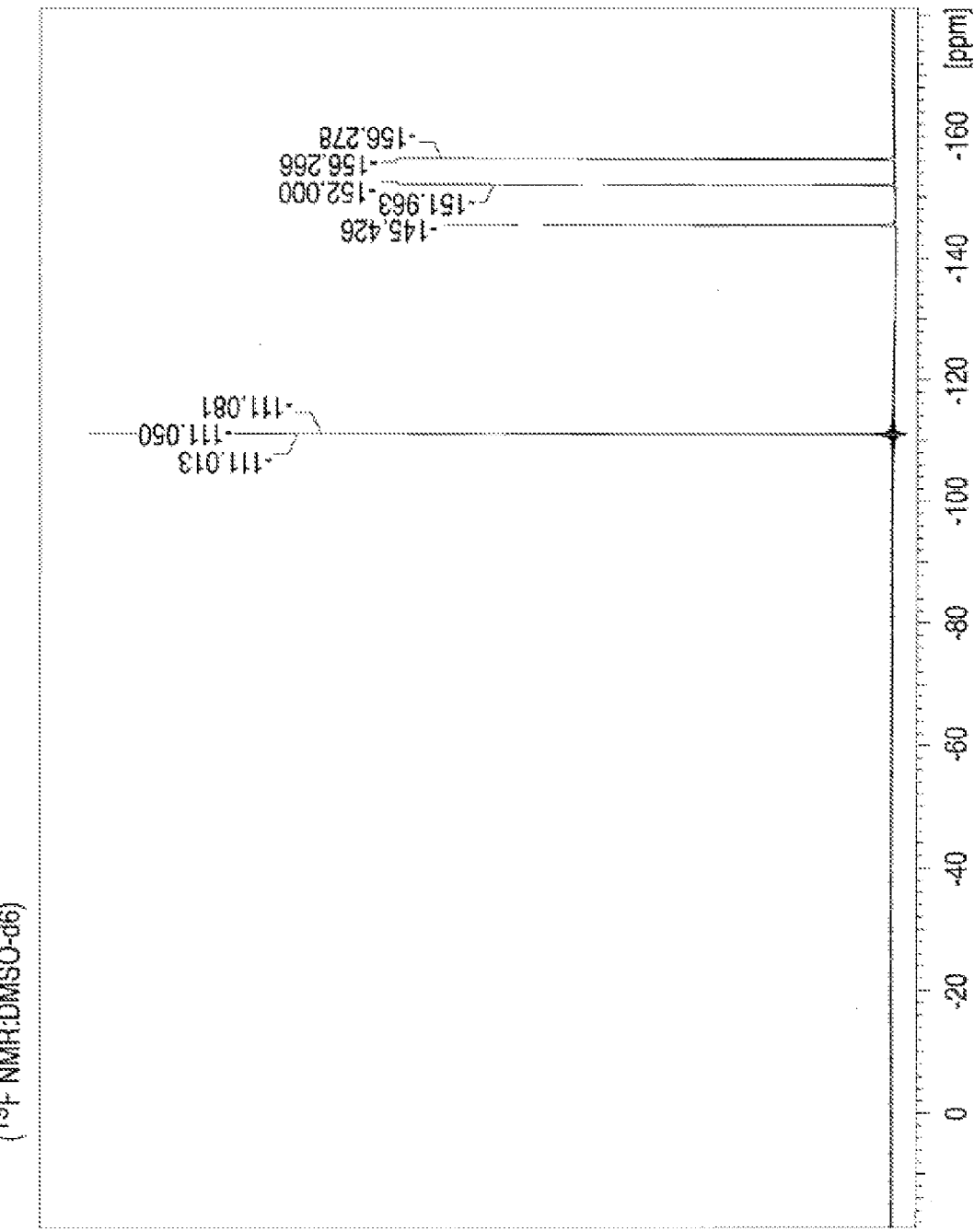
FIG. 4 is the $^{19}$F-NMR chart of a basic compound C-7 obtained in an Example.

In a 300 ml three-necked flask, compound 5 (4.5 g) was dissolved in tetramethylene sulfoxide (3.6 g), and 100 g of Eaton's reagent was added to the solution. The mixture was agitated at room temperature for 3 hours. The reaction liquid was dropped into 200 ml of water, and potassium nonafluorobutanesulfonate (6.7 g) and 200 ml of chloroform were added thereto and vigorously agitated. The resultant organic phase was separated and washed with 200 ml of deionized water five times. The washed organic phase was concentrated. The thus obtained crude crystal was dissolved in ethyl acetate at 50° C., and recrystallized, thereby obtaining 3.1 g of compound C-7 (yield 28%, white solid). The NMR charts of the obtained compound C-7 are given in FIGS. 3 and 4.

Synthesis of Basic Compounds C-8, C-9 and C-10

Basic compounds (C-8) to (C-10) were synthesized in the same manner as described for compound C-7.

H-NMR (300 MHz, DMSO): δ 8.40-8.28 (m, 4H), 8.10 (d, J=8.6 Hz, 2H), 7.92-7.80 (m, 2H), 7.80-7.68 (m, 2H), 7.21 (d, J=8.6 Hz, 2H), 4.28 (t, J=6.1 Hz, 4H), 4.16-3.96 (m, 6H), 3.84-3.68 (m, 4H), 3.40-3.00 (m, 10H), 2.66-2.50 (m, 4H), 2.50-2.24 (m, 8H), 2.00-1.08 (m, 39H)

F-NMR (300 MHz, DMSO): δ −142.0, −144.9, −149.8

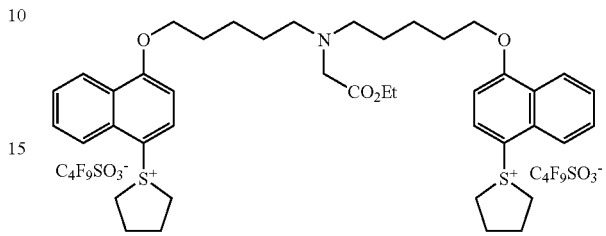

C-9

H-NMR (300 MHz, DMSO): δ 8.40-8.28 (m, 4H), 8.10 (d, J=8.6 Hz, 2H), 7.92-7.80 (m, 2H), 7.80-7.68 (m, 2H), 7.21 (d, J=8.6 Hz, 2H), 4.28 (t, J=6.1 Hz, 4H), 4.16-3.96 (m, 6H), 3.84-3.68 (m, 4H), 3.30 (s, 2H), 2.66-2.50 (m, 4H), 2.50-2.24 (m, 8H), 2.00-1.72 (m, 4H), 1.64-1.36 (m, 8H), 1.18 (t, J=7.1 Hz, 3H)

F-NMR (300 MHz, DMSO): δ −111.0, −145.4, −152.0, −156.3

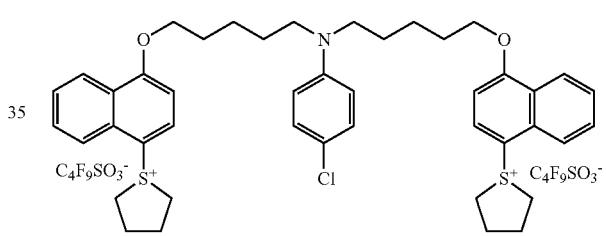

C-10

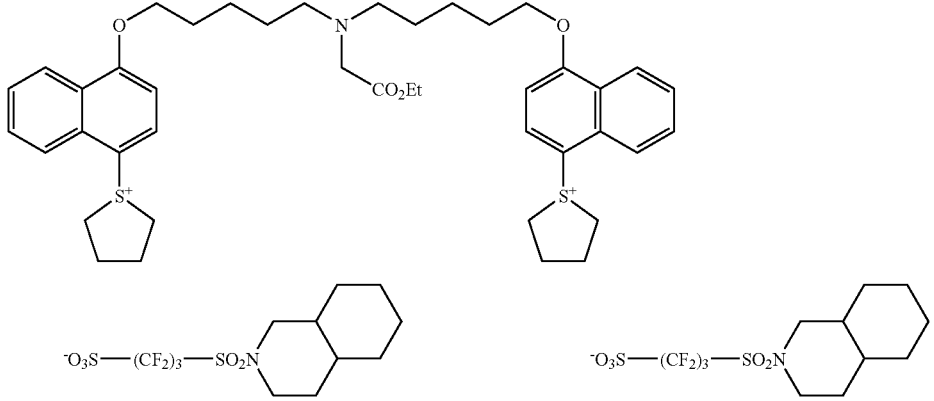

C-8

H-NMR (300 MHz, DMSO): δ8.33 (d, J=9.0 Hz, 4H), 8.10 (d, J=8.6 Hz, 2H), 7.87 (m, 2H), 7.73 (m, 2H), 7.20 (d, J=8.6 Hz, 2H), 7.07 (d, J=8.9 Hz, 2H), 6.64 (d, J=8.8 Hz, 2H), 4.29 (t, J=6.1 Hz, 4H), 4.12-3.98 (m, 4H), 3.83-3.71 (m, 4H), 3.44-3.22 (m, 4H), 2.48-2.26 (m, 8H), 2.05-1.75 (m, 4H), 1.70-1.40 (m, 8H)

F-NMR (300 MHz, DMSO): δ −111.0, −145.4, −152.0, −156.3

<Preparation of Resist>

As indicated in Table 2 below, various components were dissolved in solvents, thereby obtaining solutions of each 5 mass % solid content. These solutions were passed through a polyethylene filter of 0.03 μm pore size, thereby obtaining positive resist solutions. The thus obtained positive resist solutions were evaluated by the following methods. The results are also given in the same table.

<Evaluation of Resist>

(Exposure Condition (1): ArF Dry Exposure)

An organic antireflection film ARC29A (produced by Nissan Chemical Industries, Ltd.) was applied onto a silicon wafer and baked at 205° C. for 60 seconds, thereby forming a 78 nm-thick antireflection film. Each of the prepared positive resist compositions was applied thereonto and baked at 130° C. for 60 seconds, thereby forming a 120 nm-thick resist film. The resultant wafer was exposed through a 6% half-tone mask of 75 nm 1:1 line and space pattern with the use of an ArF excimer laser scanner (manufactured by ASML, PAS 5500/1100, NA 0.75). Thereafter, the exposed wafer was heated at 130° C. for 60 seconds, developed with an aqueous solution of tetramethylammonium hydroxide (2.38 mass %) for 30 seconds, rinsed with pure water and spin dried, thereby obtaining a resist pattern.

[Exposure Latitude]

The optimum exposure intensity was defined as the exposure intensity that reproduced a 75 nm 1:1 line and space mask pattern. The exposure intensity width in which when the exposure intensity was varied, the pattern size allowed 75 nm±10% was measured. The exposure latitude was the quotient of the value of the exposure intensity width divided by the optimum exposure intensity, the quotient expressed by a percentage. The greater the value of the exposure latitude, the less the change of performance by exposure intensity changes and the better the exposure latitude.

[Line Edge Roughness]

In the measurement of line edge roughness, a 75 nm isolated pattern produced at the optimum exposure intensity was observed by means of a critical dimension SEM (model S-9260 manufactured by Hitachi, Ltd.). With respect to a 5 μm range of the longitudinal edge of a line pattern, the distance from a reference line on which edges were to be present was measured on 50 points. The standard deviation of measurements was determined, and 3σ was computed. The smaller the value thereof, the higher the performance exhibited.

[Development Defect]

Random-mode measurement was carried out by means of a defect inspection apparatus KLA2360 (trade name) manufactured by KLA-Tencor Corporation. In the defect inspection apparatus, the pixel size was set at 0.16 μm and the threshold value at 20. Any development defects extracted from differences generated by superimposition between a comparative image and the pixel unit were detected, and the number of development defects per area (cm$^2$) was calculated. The evaluation marks ○, Δ and x were given when the calculated value was less than 0.5, 0.5 to less than 0.8 and 0.8 or greater, respectively. The smaller the value, the higher the performance exhibited.

(Exposure Condition (2): ArF Liquid Immersion Exposure)

An organic antireflection film ARC29A (produced by Nissan Chemical Industries, Ltd.) was applied onto a silicon wafer and baked at 205° C. for 60 seconds, thereby forming a 86 nm-thick antireflection film. Each of the prepared positive resist compositions was applied thereonto and baked at 100° C. for 60 seconds, thereby forming a 100 nm-thick resist film. The resultant wafer was exposed through a 6% half-tone mask of 55 nm 1:1 line and space pattern with the use of an ArF excimer laser liquid immersion scanner (manufactured by ASML, XT1700i, NA 1.20, C-Quad, outer sigma 0.981, inner sigma 0.895, XY deflection). Ultrapure water was used as the liquid for liquid immersion. Thereafter, the exposed wafer was heated at 100° C. for 60 seconds, developed with an aqueous solution of tetramethylammonium hydroxide (2.38 mass %) for 30 seconds, rinsed with pure water and spin dried, thereby obtaining a resist pattern.

[Exposure Latitude]

The optimum exposure intensity was defined as the exposure intensity that reproduced a 65 nm 1:1 line and space mask pattern. The exposure intensity width in which when the exposure intensity was varied, the pattern size allowed 65 nm±10% was measured. The exposure latitude was the quotient of the value of the exposure intensity width divided by the optimum exposure intensity, the quotient expressed by a percentage. The greater the value of the exposure latitude, the less the change of performance by exposure intensity changes and the better the exposure latitude.

[Line Edge Roughness]

In the measurement of line edge roughness, a 120 nm isolated pattern produced at the optimum exposure intensity was observed by means of a critical dimension SEM (model S-9260 manufactured by Hitachi, Ltd.). With respect to a 5 μm range of the longitudinal edge of a line pattern, the distance from a reference line on which edges were to be present was measured on 50 points. The standard deviation of measurements was determined, and 3σ was computed. The smaller the value thereof, the higher the performance exhibited.

[Development Defect]

Random-mode measurement was carried out by means of a defect inspection apparatus KLA2360 (trade name) manufactured by KLA-Tencor Corporation. In the defect inspection apparatus, the pixel size was set at 0.16 μm and the threshold value at 20. Any development defects extracted from differences generated by superimposition between a comparative image and the pixel unit were detected, and the number of development defects per area (cm$^2$) was calculated. The evaluation marks ○, Δ and x were given when the calculated value was less than 0.5, 0.5 to less than 0.8 and 0.8 or greater, respectively. The smaller the value, the higher the performance exhibited.

TABLE 2

| | Acid generator (A) [mass (g)] | Resin (B) [10 g] | Resin (I) [mass (g)] | Basic Compound (C) [mass (g)] | Surfactant [100 ppm] | Solvent [mass ratio] |
|---|---|---|---|---|---|---|
| Ex. 1 | PAG1 [0.2] | RA-1 | HR-1 [0.3] | C-1 [0.03] | W-2 | S1/S3 [60/40] |
| Ex. 2 | PAG2 [0.2] | RA-2 | HR-2 [0.1] | C-2 [0.02] | W-1 | S1/S5 [70/30] |
| Ex. 3 | PAG3 [0.1] | RA-3 | — | C-3 [0.02] | W-1 | S1/S5 [80/20] |
| Ex. 4 | PAG4 [0.2] | RA-4 | HR-3 [0.5] | C-4 [0.04] | W-1 | S1/S2 [80/20] |
| Ex. 5 | PAG1/PAG3 [0.2/0.1] | RA-1 | HR-1 [0.6] | C-3/C-1 [0.03/0.01] | W-2 | S1/S4 [95/5] |
| Ex. 6 | PAG2 [0.2] | RA-2 | HR-1 [0.3] | C-6 [0.04] | W-1 | S1/S2 [80/20] |
| Ex. 7 | PAG1 [0.2] | RA-1/RA-2 [5/5] | HR-3 [0.5] | C-1 [0.03] | W-1 | S1/S2 [80/20] |
| Ex. 8 | — | RA-4 | HR-2 [0.1] | C-6 [0.1] | W-2 | S1/S4 [95/5] |
| Ex. 9 | PAG1 [0.2] | RA-1/RA-2 [5/5] | HR-2 [0.3] | C-7 [0.03] | W-2 | S1/S3 [60/40] |
| Ex. 10 | PAG4 [0.2] | RA-1 | HR-26 [0.3] | C-8 [0.04] | W-1 | S1/S3 [60/40] |
| Ex. 11 | PAG3 [0.2] | RA-4 | HR-1 [0.3] | C-9 [0.03] | W-2 | S1/S4 [95/5] |
| Ex. 12 | PAG2 [0.2] | RA-3 | HR-3 [0.3] | C-10 [0.03] | W-2 | S1/S2 [80/20] |
| Ex. 13 | PAG2 [0.2] | RA-1 | HR-74 [0.3] | D-1 [0.02] | W-1 | S1/S3 [70/30] |
| Ex. 14 | PAG3 [0.2] | RA-2 | — | D-2 [0.02] | W-1 | S1/S3 [70/30] |
| Ex. 15 | PAG4 [0.2] | RA-4 | HR-26 [0.5] | D-3 [0.02] | W-1 | S1/S3 [70/30] |

| | Exposure condition | Exposure latitude (%) | Line edge Roughness (nm) | Development defect |
|---|---|---|---|---|
| Ex. 1 | 2 | 16.9 | 6.2 | ○ |
| Ex. 2 | 2 | 15.9 | 7.1 | ○ |
| Ex. 3 | 1 | 16.5 | 7.0 | ○ |
| Ex. 4 | 2 | 16.6 | 6.6 | ○ |
| Ex. 5 | 2 | 17.0 | 6.5 | ○ |
| Ex. 6 | 2 | 16.9 | 6.6 | ○ |
| Ex. 7 | 2 | 16.8 | 6.1 | ○ |
| Ex. 8 | 2 | 14.9 | 7.5 | ○ |
| Ex. 9 | 2 | 17.0 | 6.1 | ○ |
| Ex. 10 | 2 | 17.2 | 6.6 | ○ |
| Ex. 11 | 2 | 16.5 | 6.2 | ○ |
| Ex. 12 | 2 | 17.4 | 6.7 | ○ |
| Ex. 13 | 2 | 10.6 | 8.5 | x |
| Ex. 14 | 1 | 12.5 | 8.2 | x |
| Ex. 15 | 2 | 13.3 | 7.7 | Δ |

The employed components other than resin (B) are as follows.

[Basic Compound]

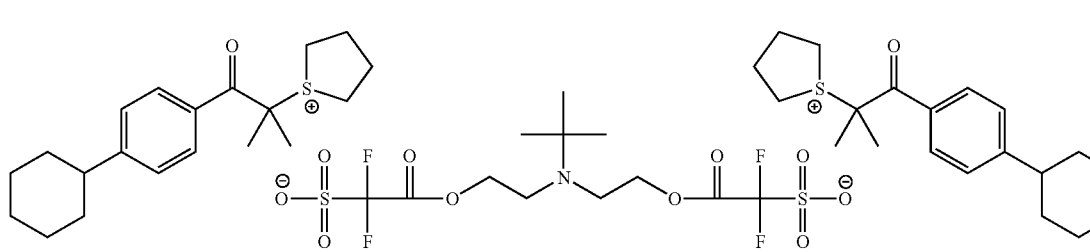

(C-1)

-continued
(C-2)
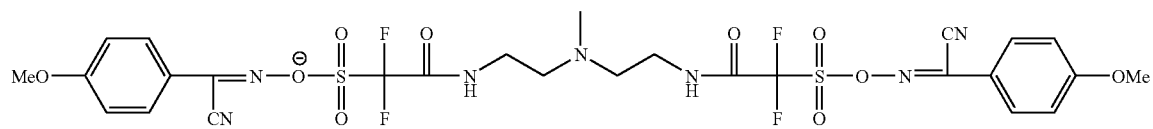
(C-3)
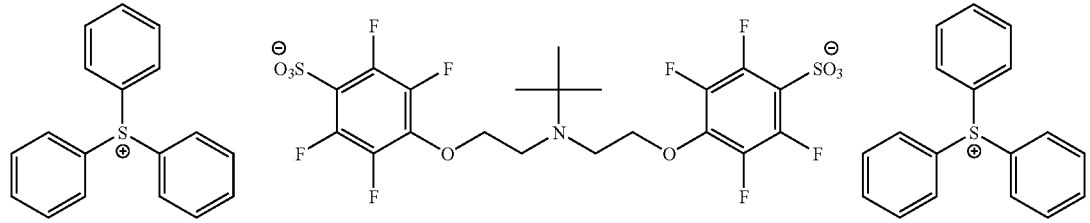
(C-4)
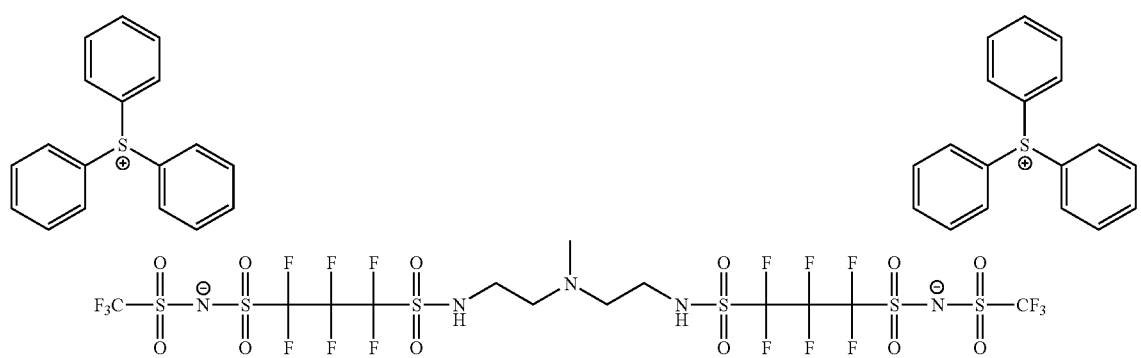
(C-6)
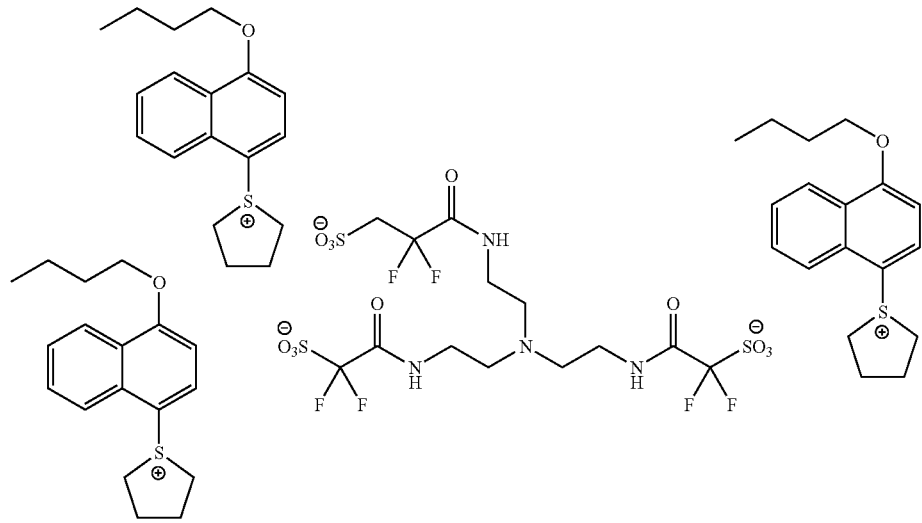
(C-7)
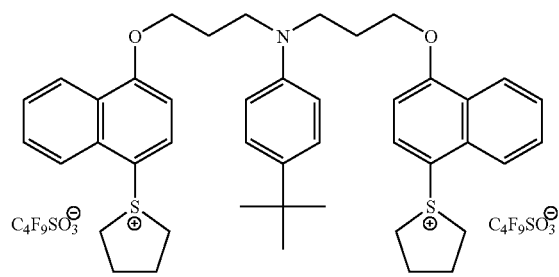

-continued
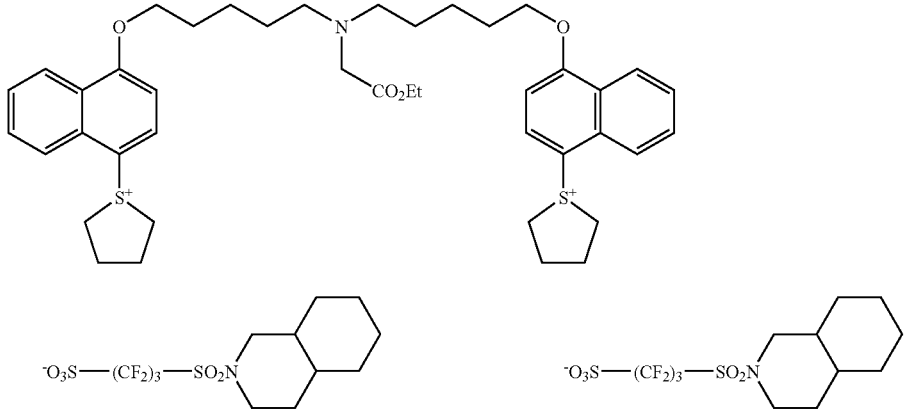
(C-8)
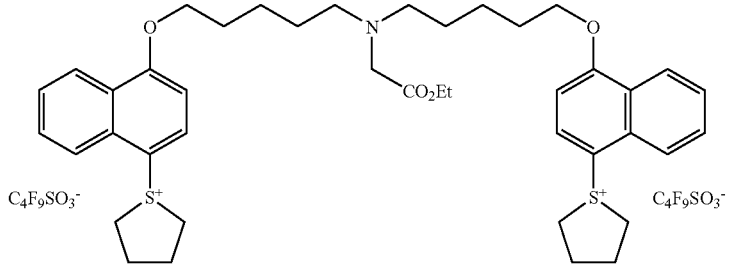
(C-9)
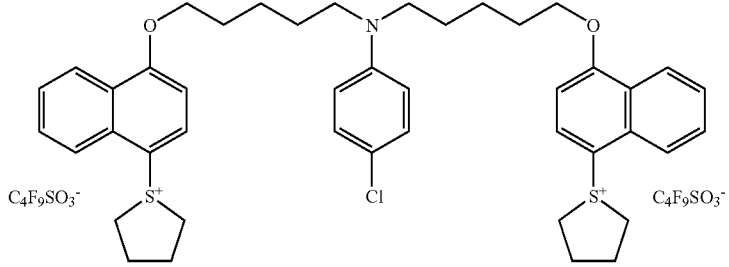
(C-10)
D-1   D-2
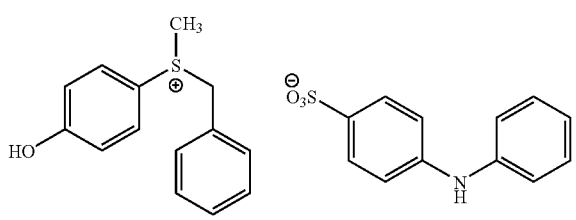
D-3

[Photo-acid generator]

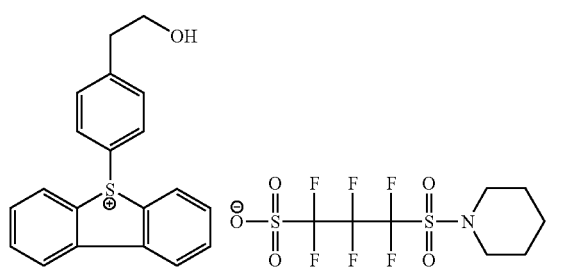 (PAG1)

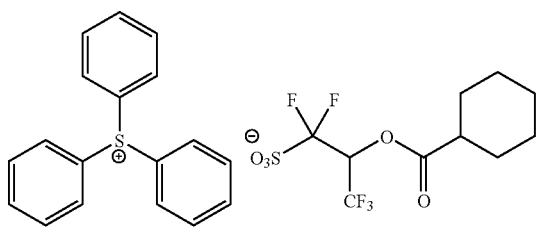 (PAG2)

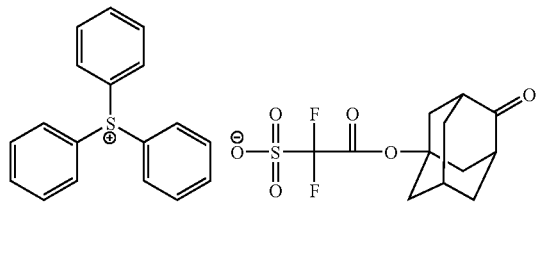 (PAG3)

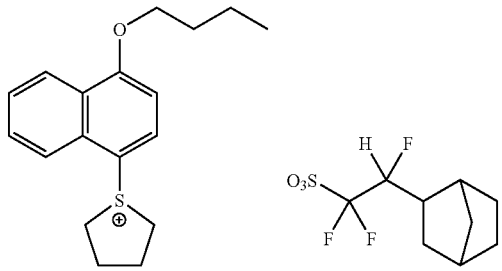 (PAG4)

[Hydrophobic Resin (I)]
Resins HR-1 to 3, HR-26 and HR-74 are those shown hereinbefore by way of examples.

[Surfactant]
W-1: Megafac F176 (produced by Dainippon Ink & Chemicals, Inc.) (fluorinated), and
W-2: Megafac R08 (produced by Dainippon Ink & Chemicals, Inc.) (fluorinated and siliconized).

[Solvent]
S1: propylene glycol methyl ether acetate (PGMEA),
S2: 2-heptanone,
S3: cyclohexanone,
S4: γ-butyrolactone, and
S5: propylene glycol methyl ether (PGME).

What is claimed is:

1. An actinic-ray- or radiation-sensitive resin composition comprising:
a resin (B) whose dissolution rate in an alkali developer is increased by the action of an acid and a basic compound (C) which is any of those of general formula (1) below,

(1)

$$(A_1-R_1-L_1)_{m1}-R_2-L_2+R_5-B+(R_3-L_3-R_4-A_2)_{m2}]_n$$

in which
$A_1$ represents either a group that when exposed to actinic rays or radiation, generates an acid or a hydrogen atom;
$A_2$ represents a group that when exposed to actinic rays or radiation, generates an acid;
provided that at least one of the groups that when exposed to actinic rays or radiation, generates an acid, represented by A1 and/or A2, represents any of those of general formulae (2-1) to (2-3) and (3-1) to (3-3) below;
B represents a basic group selected from an amino group and a phosphine group;

each of $R_1$, $R_3$, and $R_4$ independently represents a single bond, an alkylene group, a cycloalkylene group or an arylene group;
$R_5$ represents an unsubstituted alkylene group;
$R_2$ when m1=0 represents a hydrogen atom, an alkyl group, a cycloalkyl group or an aryl group, and when m1≥1 represents a 2- to 4-valent connecting group;
each of $L_1$ and $L_3$ independently represents either a bivalent connecting group having a heteroatom or a single bond;
$L_2$ represents a connecting group;
and m1 is an integer of 0 to 3, m2 is an integer of 0 to 2 and n is an integer of 1 to 3,
provided that m which is the sum of groups that when exposed to actinic rays or radiation, generate an acid, represented by $A_1$ and $A_2$ is 2 or greater and n<m in which n is the number of basic groups represented by B, and provided that when each of $A_1$, $A_2$, B, $R_1$, $R_3$ and $R_4$ is present in plurality, the plurality of groups may be identical to or different from each other

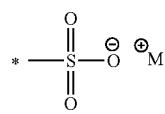 (2-1)

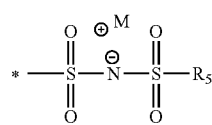 (2-2)

(2-3)

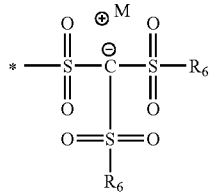

(3-1)

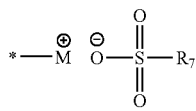

(3-2)

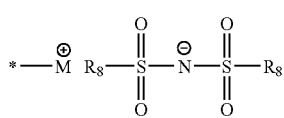

(3-3)

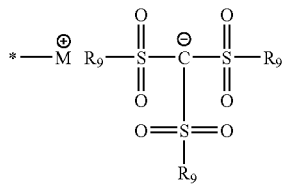

in which M⁺ represents a sulfonium cation, each of $R_5$ to $R_9$ independently represents an optionally substituted alkyl group, an optionally substituted cycloalkyl group or an optionally substituted aryl group; and * represents a site of bonding with a residue of the basic compound (C).

2. The actinic-ray- or radiation-sensitive resin composition according to claim 1, further comprising a compound (A) that when exposed to actinic rays or radiation, generates an acid.

3. The actinic-ray- or radiation-sensitive resin composition according to claim 1, wherein at least one of the basic groups is an amino group.

4. The actinic-ray- or radiation-sensitive resin composition according to claim 1, wherein at least one of the groups that when exposed to actinic rays or radiation, generate an acid is a group with an onium salt structure.

5. The actinic-ray- or radiation-sensitive resin composition according to claim 1, wherein at least one of the groups that when exposed to actinic rays or radiation, generate an acid is any of those of general formulae (2-1) to (2-3) below, (2-1)

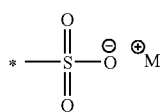

(2-2)

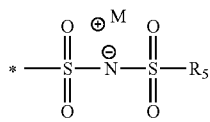

(2-3)

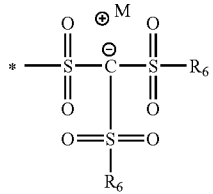

in which M⁺ represents an organic counter-cation; each of $R_5$ and $R_6$ independently represents an optionally substituted alkyl group, an optionally substituted cycloalkyl group or an optionally substituted aryl group; and * represents a site of bonding with a residue of the basic compound (C).

6. The actinic-ray- or radiation-sensitive resin composition according to claim 1, wherein at least one of the groups that when exposed to actinic rays or radiation, generate an acid is any of those of general formulae (3-1) to (3-3) below, (3-1)

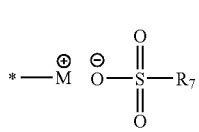

(3-2)

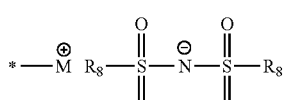

(3-3)

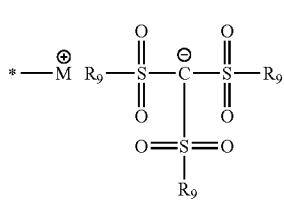

in which M⁺ represents an organic counter-cation; each of $R_7$ to $R_9$ independently represents an optionally substituted alkyl group, an optionally substituted cycloalkyl group or an optionally substituted aryl group; and * represents a site of bonding with a residue of the basic compound (C).

7. The actinic-ray- or radiation-sensitive resin composition according to claim 1, wherein resin (B) whose dissolution rate in an alkali developer is increased by the action of an acid that contains repeating units of general formula (III) below, (III)

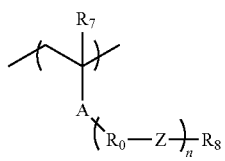

in which

A represents an ester bond (—COO—) or an amido bond (—CONH—);

$R_0$, each independently in the instance of $R_0$s, represents an optionally substituted alkylene group, an optionally substituted cycloalkylene group or a combination thereof;

Z, each independently in the instance of Zs, represents an ether bond, an ester bond, a carbonyl group, an amido bond, a urethane bond or a urea bond;

$R_8$ represents a monovalent organic group with a lactone structure;

n is the number of repetitions of the structure of formula $R_0$—Z—, being an integer of 1 to 5; and $R_7$ represents a hydrogen atom, a halogen atom or an optionally substituted alkyl group.

8. The actinic-ray- or radiation-sensitive resin composition according to claim 1, further comprising a hydrophobic resin (D).

9. A method of forming a pattern, comprising molding the actinic-ray- or radiation-sensitive resin composition according to claim 1 into a film, exposing the film and developing the exposed film.

10. The actinic-ray- or radiation-sensitive resin composition according to claim 1, wherein the resin (B) contains a repeating unit expressed by the below-specified general formula (I),

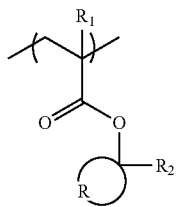

(I)

wherein in general formula (I), $R_1$ represents a hydrogen atom, an optionally substituted methyl group or any of the groups of formula —$CH_2$—$R_9$ $R_9$ represents a monovalent organic group, $R_2$ represents an alkyl group or a cycloalkyl group, R represents an atomic group required for forming an alicyclic structure in cooperation with a carbon atom.

11. The actinic-ray- or radiation-sensitive resin composition according to claim 10, wherein in the general formula (I), the alicyclic structure formed by R is an alicyclic structure of a single ring.

12. The actinic-ray- or radiation-sensitive resin composition according to claim 10, wherein the resin (B) contains at least two repeating units expressed by the general formula (I).

13. The actinic-ray- or radiation-sensitive resin composition according to claim 1, wherein the resin (B) contains a repeating unit expressed by the below-specified general formula (IV)

(IV)

wherein in general formula (IV), $R_5$ represents a hydrocarbon group having at least one cyclic structure in which neither a hydroxyl group nor a cyano group is contained, Ra represents a hydrogen atom, an alkyl group or a group of the formula —$CH_2$—O—$Ra_2$ in which $Ra_2$ represents a hydrogen atom, an alkyl group or an acyl group.

14. The actinic-ray- or radiation-sensitive resin composition according to claim 1, wherein basic compound (C) is contained in the composition in an amount of 0.1 to 10 mass %, based on the total solid of the composition.

15. The actinic-ray- or radiation-sensitive resin composition according to claim 1, wherein the resin (B) has no aromatic group.

* * * * *